US010030027B2

(12) United States Patent
Berger et al.

(10) Patent No.: US 10,030,027 B2
(45) Date of Patent: Jul. 24, 2018

(54) SOLUBLE GUANYLATE CYCLASE STIMULATORS

(71) Applicant: MERCK SHARP & DOHME CORP., Rahway, NJ (US)

(72) Inventors: Raphaelle Berger, New York, NY (US); Yi-Heng Chen, Whippany, NJ (US); Guoqing Li, Belle Mead, NJ (US); Joie Garfunkle, Kriens (CH); Hong-Dong Li, Edison, NJ (US); Shouwu Miao, Edison, NJ (US); Subharekha Raghavan, Teaneck, NJ (US); Cameron J. Smith, Montgomery Village, MD (US); John Stelmach, Westfield, NJ (US); Alan Whitehead, Scotch Plains, NJ (US); Rui Zhang, Plainsboro, NJ (US); Yong Zhang, West Windsor, NJ (US); Jianmin Fu, Beijing (CN); Gang Ji, Beijing (CN); Falong Jiang, Beijing (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/384,429

(22) Filed: Dec. 20, 2016

(65) Prior Publication Data

US 2017/0174693 A1 Jun. 22, 2017

(30) Foreign Application Priority Data

Dec. 22, 2015 (WO) ................ PCT/CN2015/098251

(51) Int. Cl.
*C07D 487/04* (2006.01)
*C07D 519/00* (2006.01)
*A61K 45/06* (2006.01)
*A61K 31/519* (2006.01)

(52) U.S. Cl.
CPC .......... *C07D 487/04* (2013.01); *A61K 31/519* (2013.01); *A61K 45/06* (2013.01); *C07D 519/00* (2013.01)

(58) Field of Classification Search
CPC .... A61K 31/519; A61K 45/06; C07D 487/04; C07D 519/00
See application file for complete search history.

(56) References Cited

U.S. PATENT DOCUMENTS

| 4,845,079 A | 7/1989 | Luly et al. |
| 4,885,292 A | 12/1989 | Ryono et al. |
| 4,894,437 A | 1/1990 | TenBrink |
| 4,980,283 A | 12/1990 | Huang et al. |
| 5,034,512 A | 7/1991 | Hudspeth et al. |
| 5,036,053 A | 7/1991 | Himmelsbach et al. |

(Continued)

FOREIGN PATENT DOCUMENTS

| CN | 103096718 A | 5/2013 |
| DE | 19744027 A1 | 10/1997 |

(Continued)

OTHER PUBLICATIONS

Buchwald, S.L., et al., "Selective Monoarylation of Acetate Esters and Aryl Methyl Ketones Using Aryl Chlorides", Organic Letters, 2009, pp. 1773-1775, vol. 11, No. 8.

Vesely, D.L., et al., et al., "B Complex Vitamins Activate Rat Guanylate Cyclase and Increase Cyclic GMP Levels", Eur. J. Clin. Invest. 1985, pp. 258-262, vol. 15.

Vesely, D.L., et al., "Phencyclidine Stimulates Guanylate Cyclase Activity", Biochem. Biophys. Res. Comm., 1979, pp. 1244-1248, vol. 88.

(Continued)

*Primary Examiner* — Erich A Leeser
(74) *Attorney, Agent, or Firm* — Eric A. Meade; John C. Todaro

(57) ABSTRACT

The invention provides compounds of the Formula (I)

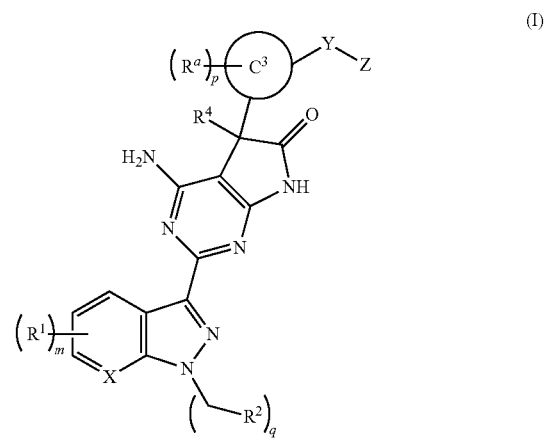

or a pharmaceutically acceptable salts thereof, wherein X, Y, Z, $R^1$, $R^2$, $R^4$, $R^a$, and the subscripts m, p, and q are as described herein. The compounds or their pharmaceutically acceptable salts can modulate the body's production of cyclic guanosine monophosphate ("cGMP"), and are generally suitable for the therapy and prophylaxis of diseases which are associated with a disturbed cGMP balance. The invention also provides pharmaceutical compositions which comprise compounds of Formula (I) or pharmaceutically acceptable salts thereof. The invention also relates to methods for use of the compounds or their pharmaceutically acceptable salts in the therapy and prophylaxis of the abovementioned diseases and for preparing pharmaceuticals for this purpose.

56 Claims, No Drawings

(56) References Cited

U.S. PATENT DOCUMENTS

| | | |
|---|---|---|
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,965 A | 11/1991 | Ocain et al. |
| 5,066,643 A | 11/1991 | Abeles et al. |
| 5,071,837 A | 12/1991 | Doherty et al. |
| 5,075,451 A | 12/1991 | Ocain et al. |
| 5,089,471 A | 2/1992 | Hanson et al. |
| 5,095,119 A | 3/1992 | Ocain et al. |
| 5,098,924 A | 3/1992 | Poss |
| 5,104,869 A | 4/1992 | Albright et al. |
| 5,114,937 A | 5/1992 | Hamby et al. |
| 5,116,835 A | 5/1992 | Ruger et al. |
| 6,743,798 B1 | 6/2004 | Straub et al. |
| 7,173,037 B2 | 2/2007 | Alonso-Alija et al. |
| 8,420,656 B2 | 4/2013 | Follmann et al. |
| 8,455,638 B2 | 6/2013 | Bittner et al. |
| 8,507,512 B2 | 8/2013 | Kim et al. |
| 8,741,910 B2 | 6/2014 | Brockunier et al. |
| 8,859,569 B2 | 10/2014 | Follmann et al. |
| 8,895,583 B2 | 11/2014 | Tan et al. |
| 9,023,849 B2 | 5/2015 | Follmann et al. |
| 9,090,610 B2 | 7/2015 | Follmann et al. |
| 9,216,978 B2 | 12/2015 | Follmann et al. |
| 9,365,574 B2 | 6/2016 | Raghavan et al. |
| 9,611,278 B2 | 4/2017 | Han et al. |
| 2013/0072492 A1* | 3/2013 | Raghavan ............ A61K 31/519 514/248 |
| 2014/0171434 A1 | 6/2014 | Follmann et al. |
| 2014/0228366 A1 | 8/2014 | Follmann et al. |
| 2014/0357637 A1 | 12/2014 | Follmann et al. |
| 2016/0145272 A1 | 5/2016 | Berger et al. |
| 2016/0304537 A1 | 10/2016 | Han et al. |
| 2017/0107236 A1 | 4/2017 | Campbell et al. |

FOREIGN PATENT DOCUMENTS

| | | |
|---|---|---|
| EP | 908456 B1 | 9/1998 |
| WO | 200208188 A1 | 1/2002 |
| WO | 2002060388 A1 | 1/2002 |
| WO | 2004019869 A2 | 3/2004 |
| WO | 2004020408 A1 | 3/2004 |
| WO | 2004020409 A1 | 3/2004 |
| WO | 2004066963 A2 | 8/2004 |
| WO | 2009011836 A1 | 1/2009 |
| WO | 2009042053 A2 | 4/2009 |
| WO | 2009000087 A1 | 12/2009 |
| WO | 2010065275 A1 | 6/2010 |
| WO | 2011149921 A1 | 12/2011 |
| WO | 2015088885 A1 | 6/2015 |
| WO | 2016044446 A1 | 3/2016 |
| WO | 2016081668 A1 | 5/2016 |
| WO | 2016191334 A1 | 12/2016 |
| WO | 2016191335 A1 | 12/2016 |
| WO | 2017106175 A1 | 6/2017 |
| WO | 2017136309 A1 | 8/2017 |

OTHER PUBLICATIONS

Follmann, N. et al., "The Chemistry and Biology of Soluble Guanylate Cyclase Stimulators and Activators", Angewandte Chemie-International Edition, 2013, pp. 9442-9462, vol. 52, Issue 36.

Garigipati, R.S., "An Efficient Conversion of Nitriles to Amidines", Tetrahedron Letters, 1990, pp. 1969-1972, vol. 31, No. 14.

Ignarro, et al., "Regulation of Cytosolic Guanylyl Cyclase by Porphirins and Metalloporphyrins", Adv. Pharmacol, 1994, pp. 35-65, vol. 26.

International Search Report and Written Opinion—PCT/CN2015/098251—dated Sep. 29, 2015; pp. 1-14.

Ko, et al., "YC-1 A Novel Activator of Platelet Guanylate Cyclase", BLOOD, 1994, pp. 4226-4233, vol. 84.

Marcuzzi, F. et al., "Vinyl Cations in Organic Synthesis. A New Route to Disubstituted Alkynes", J. Org. Chem., 1982, pp. 4577-4579, vol. 47.

Notice of Allowance—U.S. Appl. No. 14/945,576 dated Jul. 10, 2017.

Notice of Allowance—U.S. Appl. No. 15/103,148 dated Sep. 6, 2017.

Notice of Allowance—U.S. Appl. No. 15/315,428 dated Jun. 15, 2017.

Pettibone, et al., "A Structurally Novel Stimulator of Guanylate Cyclase With Long-Lasting Hypotensive Activity in The Dog", Eur. J. Pharmacol., 1985, pp. 307-312, vol. 116.

Shen, H.C., et al., "a-Heteroarylation of Esters, Lactones, Amides, and Lactams by Nucleophilic Aroatic Substitution", Organic Letters, 2006, pp. 1447-1450, vol. 8, No. 7.

Wu, et al., "YC-1 Inhibited Human Platelet Aggregation Through no Independent Activation of Soluble Guyanylate Cyclase", Brit. J. Pharmacol., 1995, pp. 1973-1978, vol. 116.

Yang, D.., et al, "Mild a-Halogenation Reactions of 1,3-Dicarbonyl Compounds Catalyzed by Lewis Acids", J. Org. Chem., 2002, pp. 7429-7431, vol. 67.

Yu, et al., "Mechanism of Anti-Proliferation Caused by YC-1, An Indazole Derivative in Cultured Rat A10 Vascular Smooth Muscle Cells", Biochem. J., 1995, pp. 787-792, vol. 306.

Yu, et al., "Vasorelaxant Effect of Isoliquiritigenin, A Novel Soluble Guanylate Cyclase Activator, in Rat Aorta", Brit. J. Pharmacol., 1995, pp. 1587-1594, vol. 114.

* cited by examiner

SOLUBLE GUANYLATE CYCLASE STIMULATORS

CROSS REFERENCE TO RELATED APPLICATIONS

This application is a U.S. Non-Provisional application which claims the benefit of priority of PCT Application No. PCT/CN2015/098251, filed Dec. 22, 2015.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are each composed of an α and a β subunit. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thrombosis, myocardial infarction, strokes or erectile dysfunction results. Pharmacological stimulation of sGC offers a possibility to normalize cGMP production and therefore may make possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons, predominantly only have weak effects on the cGMP formation in cell lysates. D. L. Vesely, *Eur. J. Clin. Invest.*, vol. 15, 1985, p. 258; D. L. Vesely, *Biochem. Biophys. Res. Comm.*, vol. 88, 1979, p. 1244. A stimulation of heme-free guanylate cyclase by protoporphyrin IX was demonstrated by Ignarro et al., *Adv. Pharmacol.*, vol. 26, 1994, p. 35. Pettibone et al., *Eur. J. Pharmacol.*, vol. 116, 1985 p. 307, described an antihypertensive action of diphenyliodonium hexafluorophosphate and attributed this to a stimulation of sGC. According to Yu et al., *Brit. J. Pharmacol*, vol. 114, 1995, p. 1587, isoliquiritigenin, which has a relaxing action on isolated rat aortas, also activates sGC. Ko et al., *Blood* vol. 84, 1994, p. 4226, Yu et al., *Biochem. J.* vol. 306, 1995, p. 787, and Wu et al., *Brit. J. Pharmacol.* vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent No. 908,456 and German Patent Application No. 19,744,027.

It has now been found that the compounds of the present invention effect a strong activation of soluble guanylate cyclase and are therefore may be suitable for the therapy and prophylaxis of disorders which are associated with a low cGMP level.

SUMMARY OF THE INVENTION

The present invention relates to compounds which activate soluble guanylate cyclase and may be valuable pharmaceutically active compounds for the therapy and prophylaxis of diseases, for example for cardiovascular diseases such as hypertension, heart failure, pulmonary hypertension, angina pectoris, diabetes, cardiac insufficiency, thrombosis, chronic kidney disease, fibrosis or atherosclerosis. The compounds of Formula (I)

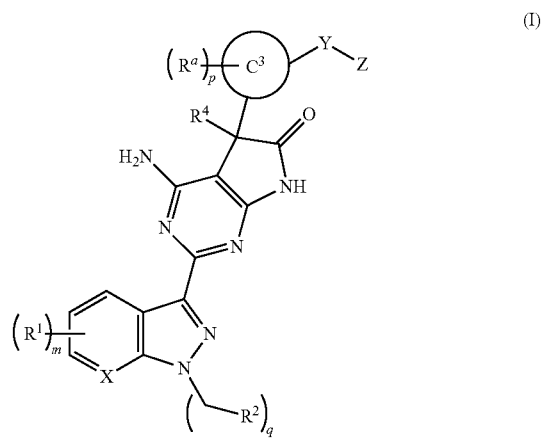

are capable of modulating the body's production of cyclic guanosine monophosphate ("cGMP") and may be suitable for the therapy and prophylaxis of diseases which are associated with a disturbed cGMP balance. The invention furthermore relates to processes for preparing compounds of Formula (I), to the use of such compounds for the therapy and prophylaxis of the above mentioned diseases and for preparing compounds for this purpose, and to pharmaceutical compositions which comprise compounds of Formula (I).

DETAILED DESCRIPTION OF THE INVENTION

In embodiment no. 1, the present invention provides a compound having structural Formula (I):

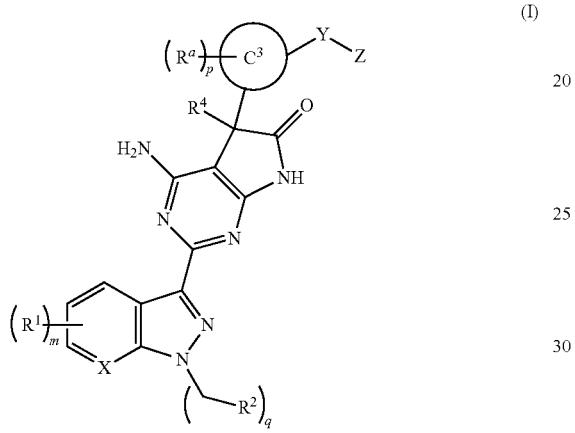

or a pharmaceutically acceptable salt thereof, wherein:
X is C(H) or N;
each $R^1$ is independently halo, hydroxy, $C_1$-$C_3$ alkyl, $C_3$-$C_6$ cycloalkyl or —O—$C_1$-$C_3$ alkyl;
$R^2$ is:
 (a.) $C_1$-$C_6$ alkyl, wherein said $C_1$-$C_6$ alkyl of $R^2$ is unsubstituted or substituted by 1 to 6 moieties independently selected from fluoro or —O—$C_1$-$C_3$ alkyl;
 (b.) ring $C^2$, wherein ring $C^2$ is:
  (i.) $C_3$-$C_{12}$ cycloalkyl;
  (ii.) phenyl;
  (iii.) a 5- or 6-membered monocyclic heteroaryl containing 1 to 2 heteroatoms selected from N, O, or S; or
  (iv.) a 5- or 6-membered monocyclic heterocyclyl containing 1 to 2 heteroatoms selected from N, O, or S;
 wherein ring $C^2$ is unsubstituted or substituted by 1 to 3 moieties independently selected from halo, cyano, $C_1$-$C_3$ alkyl, —O—$C_1$-$C_3$ alkyl, or oxo;
$R^4$ is $C_1$-$C_6$ alkyl, $CF_3$, or $C_3$-$C_6$ cycloalkyl;
ring $C^3$ is:
 (a.) phenyl;
 (b.) a 5- or 6-membered monocyclic heteroaryl or a 9- to 10-membered bicyclic heteroaryl containing 1 to 3 heteroatoms selected from N, O, or S;
 (c.) a 5- or 6-membered monocyclic heterocyclyl containing 1 to 3 heteroatoms selected from N, O, or S; or
 (d.) $C_3$-$C_6$ cycloalkyl;
each $R^a$ is independently selected from halo, cyano, $C_1$-$C_3$ alkyl, —O—$C_1$-$C_3$ alkyl, oxo, or hydroxy;

Y is:
 (a.) a bond;
 (b.) a group of the formula

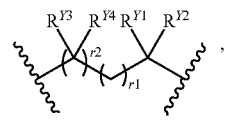

wherein $R^{Y1}$ and $R^{Y2}$ are independently H, $C_1$-$C_3$ alkyl, hydroxy, fluoro, $C_1$-$C_3$ hydroxyalkyl, or amino; or alternatively $R^{Y1}$ and $R^{Y2}$, together with the carbon atom to which they are attached form a $C_3$-$C_6$ cycloalkyl;
 $R^{Y3}$ and $R^{Y4}$ are independently H, $C_1$-$C_3$ alkyl, hydroxy, fluoro, or $C_1$-$C_3$ hydroxyalkyl; or alternatively $R^{Y3}$ and $R^{Y4}$, together with the carbon atom to which they are attached form a $C_3$-$C_6$ cycloalkyl;

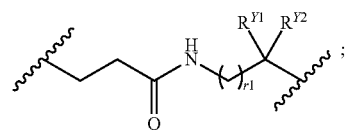

(c.) a group of the formula
 (d.) ring $A^H$, wherein ring $A^H$ is $C_3$-$C_6$ cycloalkyl or phenyl, wherein ring $A^H$ is unsubstituted or substituted by 1 to 3 moieties independently selected from halo or $C_1$-$C_3$ alkyl;
 (e.) a group —CH═CH—; or
 (f.) a group

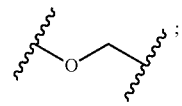 [SMILES: *CO*]

Z is:

(c.)

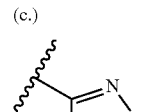

(d.)

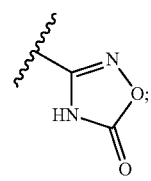

(e.)

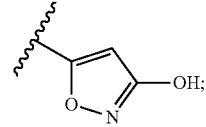

(f.) —SO$_3$H; (g.) —P(=O)(OH)$_2$; or (h.) —C(O)N(H)S(O)$_2$CH$_3$;

the subscript m is 0, 1, or 2;
the subscript p is 0, 1, 2, or 3;
the subscript q is 0 or 1;
the subscript r1 is 0, 1, 2, 3, or 4; and
the subscript r2 is 0 or 1.

In the compounds of Formula (I), when Y is a group of the formula

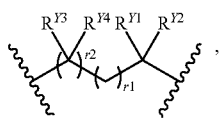

the carbon atom bearing R$^{Y3}$ and R$^{Y4}$ (indicated by the arrow in the structural formula below)

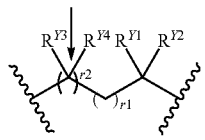

is bonded to a ring atom of ring C$^3$, and the carbon atom bearing R$^{Y1}$ and R$^{Y2}$ is bonded to Z.

Similarly, in the compounds of Formula (I), when Y is a group of the formula

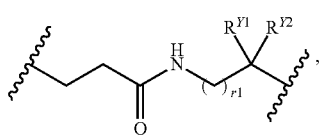

the leftmost carbon atom (indicated by the arrow in the structural formula below)

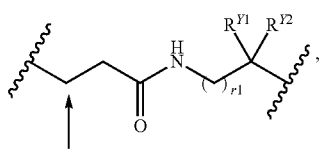

is bonded to a ring atom of ring C$^3$, and the carbon atom bearing R$^{Y1}$ and R$^{Y2}$ is bonded to Z.

Similarly, in the compounds of Formula (I), when Y is a group of the formula

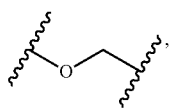 [SMILES: *CO*]

the oxygen atom of the group Y is bonded to a ring atom of ring C$^3$, and the carbon atom in group Y is bonded to Z.

In embodiment no. 2, the present invention provides the compound having structural Formula (I), wherein ring C$^3$ is:
(a.) phenyl;
(b.) a 5- or 6-membered monocyclic heteroaryl containing 1 to 3 heteroatoms selected from N, O, or S;
(c.) a 5- or 6-membered monocyclic heterocyclyl containing 1 to 3 heteroatoms selected from N, O, or S; or
(d.) C$_3$-C$_6$ cycloalkyl;

each R$^a$ is independently selected from halo, cyano, C$_1$-C$_3$ alkyl, —O—C$_1$-C$_3$ alkyl, or oxo;

Y is:
(a.) a bond;
(b.) a group of the formula

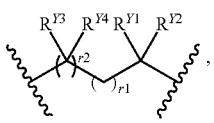

wherein R$^{Y1}$ and R$^{Y2}$ are independently H, C$_1$-C$_3$ alkyl, hydroxy, fluoro, or C$_1$-C$_3$ hydroxyalkyl; or alternatively R$^{Y1}$ and R$^{Y2}$, together with the carbon atom to which they are attached form a C$_3$-C$_6$ cycloalkyl;

R$^{Y3}$ and R$^{Y4}$ are independently H, C$_1$-C$_3$ alkyl, hydroxy, fluoro, or C$_1$-C$_3$ hydroxyalkyl; or alternatively R$^{Y3}$ and R$^{Y4}$, together with the carbon atom to which they are attached form a C$_3$-C$_6$ cycloalkyl;

(c.) a group of the formula or

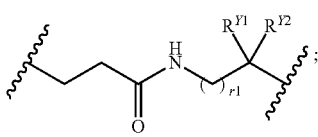

(d.) ring A$^H$, wherein ring A$^H$ is C$_3$-C$_6$ cycloalkyl or phenyl, wherein ring A$^H$ is unsubstituted or substituted by 1 to 3 moieties independently selected from halo or C$_1$-C$_3$ alkyl; and the remaining variables are as set forth in embodiment no. 1.

In embodiment no. 3, the present invention provides the compound having structural Formula (I), wherein the subscript q is 1, and R$^2$ is C$_2$-C$_3$ alkyl which is unsubstituted or substituted by 1 to 5 fluoro; and the remaining variables are as set forth in embodiment no. 2.

In embodiment no. 4, the present invention provides the compound having structural Formula (I), wherein the subscript q is 1, and the group

is selected from —CH$_2$CH$_2$CF$_2$CF$_3$, —CH$_2$CH$_2$CH$_2$CF$_3$, —CH$_2$CH$_2$CH$_3$, —CH$_2$CH$_2$CH$_2$CH$_2$CH$_3$, or —CH$_2$CH$_2$OCH$_3$; and the remaining variables are as set forth in embodiment no. 2.

In embodiment no. 5, the present invention provides the compound having structural Formula (I), wherein the subscript q is 1, and the group

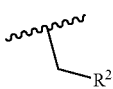

is —$CH_2CH_2CF_2CF_3$; and the remaining variables are as set forth in embodiment no. 2.

In embodiment no. 6, the present invention provides the compound having structural Formula (I), wherein the subscript q is 1;
$R^2$ is ring $C^2$;
  ring $C^2$ is phenyl, cyclohexyl, adamantyl, pyridyl, or tetrahydropyranyl;
    wherein ring $C^2$ is unsubstituted or independently substituted by 1 to 3 fluoro or methyl; and
  the remaining variables are as set forth in embodiment no. 2.

In embodiment no. 7, the present invention provides the compound having structural Formula (I), wherein ring $C^3$ is phenyl, thiazolyl, oxazolyl, oxadiazolyl, triazolyl, or pyridyl; and the remaining variables are as set forth in embodiment no. 2.

In embodiment no. 8, the present invention provides the compound having structural Formula (I), wherein ring $C^3$ is phenyl; and the remaining variables are as set forth in embodiment no. 2.

In embodiment no. 9, the present invention provides the compound having structural Formula (I), wherein ring $C^3$ is thiazolyl; and the remaining variables are as set forth in embodiment no. 2.

In embodiment no. 10, the present invention provides the compound having structural Formula (I), wherein ring $C^3$ is oxazolyl; and the remaining variables are as set forth in embodiment no. 2.

In embodiment no. 11, the present invention provides the compound having structural Formula (I), wherein Y is the group of the formula

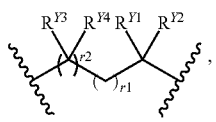

and the remaining variables are as set forth in embodiment no. 2.

In embodiment no. 12, the present invention provides the compound having structural Formula (I), wherein Y is the group of the formula

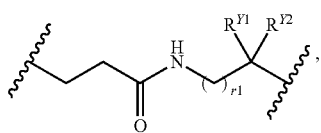

and the remaining variables are as set forth in embodiment no. 2.

In embodiment no. 13, the present invention provides the compound having structural Formula (I), wherein Y is as set forth in embodiment nos. 11 or 12,
  the subscript r1 is 1;
  the subscript r2 is 0 (where present, as in embodiment no. 11);
  $R^{Y1}$ and $R^{Y2}$ are independently H or $C_1$-$C_3$ alkyl;
  the remaining variables are as set forth in embodiment no. 2.

In embodiment no. 14, the present invention provides the compound having structural Formula (I), wherein Z is (a.)
—$CO_2H$;

(b.)
—C(O)N(H)OH;

(c.)
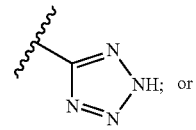

or (d.)
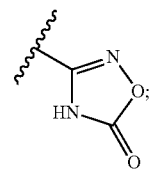

and the remaining variables are as set forth in embodiment no. 2.

In embodiment no. 15, the present invention provides the compound having structural Formula (I), wherein Z is —$CO_2H$, and the remaining variables are as set forth in embodiment no. 2.

In embodiment no. 16, the present invention provides the compound having structural Formula (I), wherein the subscript m is 0 or 1, and the remaining variables are as set forth in embodiment no. 2.

In embodiment no. 17, the present invention provides the compound having structural Formula (I), wherein $R^1$ is chloro or fluoro, and the remaining variables are as set forth in embodiment no. 2.

In embodiment no. 18, the present invention provides the compound having structural Formula (I), wherein X is C(H); and the remaining variables are as set forth in embodiment no. 2.

In embodiment no. 19, the present invention provides the compound having structural Formula (I), wherein X is N; and the remaining variables are as set forth in embodiment no. 2.

In embodiment no. 20, the present invention provides the compound having structural Formula (I), wherein $R^4$ is methyl or cyclopropyl, and the remaining variables are as set forth in embodiment no. 2.

In embodiment no. 21, the present invention provides the compound having structural Formula (I), wherein $R^4$ is methyl, and the remaining variables are as set forth in embodiment no. 2.

In embodiment no. 22, the present invention provides the compound having structural Formula (I), wherein
  $R^2$ is $C_2$-$C_3$ alkyl which is unsubstituted or substituted by 1 to 5 fluoro:
  ring $C^3$ is as set forth as in embodiment no. 7;
  Y is as set forth in embodiment no. 11;
  Z is as set forth in embodiment no. 14;
  $R^1$ is chloro or fluoro;
  X is C(H) or N;

$R^4$ is methyl or cyclopropyl;
the subscript m is 0 or 1;
the subscript q is 1; and
$R^a$, $R^{Y1}$, $R^{Y2}$, $R^{Y3}$, $R^{Y4}$ and the subscripts p, r1, and r2 are as set forth in embodiment no. 2.

In embodiment no. 23, the present invention provides the compound having structural Formula (I), wherein the group

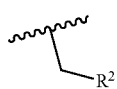

is —$CH_2CH_2CF_2CF_3$:
ring $C^3$ is as set forth as in embodiment no. 8, 9, or 10;
$R^a$ is fluoro, chloro, cyano, methyl, methoxy, or oxo;
Y is

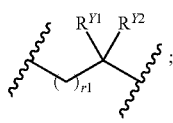

$R^{Y1}$ and $R^{Y2}$ are independently H or $C_1$-$C_3$ alkyl;
Z is —$CO_2H$;
$R^1$ is chloro or fluoro;
X is C(H) or N;
$R^4$ is methyl;
the subscript m is 0 or 1;
the subscript p is 0, 1, or 2;
the subscript q is 1; and
the subscript r1 is 1.

In embodiment no. 24, the compound of the Formula (I) has the Formula (IA)

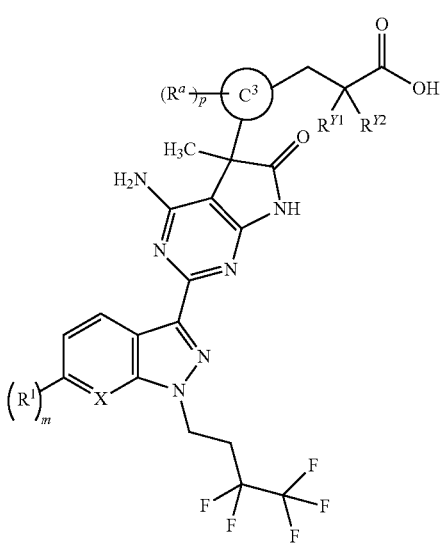

(IA)

wherein
X is C(H) or N;
$R^1$ is methyl or halo;
$C^3$ is phenyl or thiazolyl;
$R^a$ is methyl, cyano, or halo;
$R^{Y1}$ and $R^{Y2}$ are independently H or methyl;
the subscript m is 0 or 1; and
the subscript p is 0 or 1.

In embodiment no. 25, the compound of the Formula (I) has the Formula (IB)

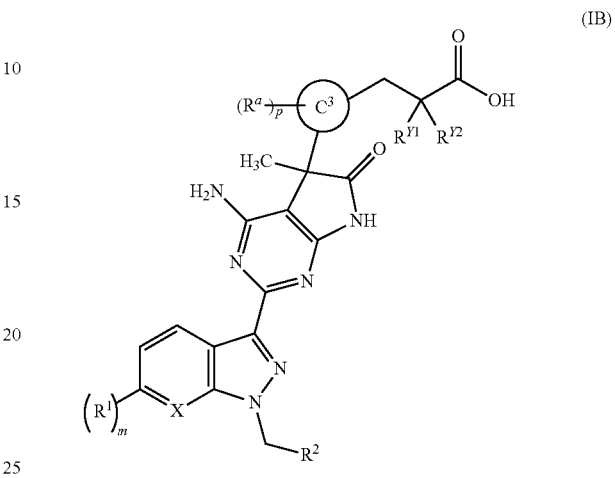

(IB)

wherein
X is C(H) or N;
$R^1$ is methyl or halo;
$R^2$ is ring $C^2$, wherein ring $C^2$ is:
(i.) $C_3$-$C_{12}$ cycloalkyl;
(ii.) phenyl;
(iii.) a 5- or 6-membered monocyclic heteroaryl containing 1 to 2 heteroatoms selected from N, O, or S; or
(iv.) a 5- or 6-membered monocyclic heterocyclyl containing 1 to 2 heteroatoms selected from N, O, or S;
wherein ring $C^2$ is unsubstituted or substituted by 1 to 3 moieties independently selected from halo, cyano, $C_1$-$C_3$ alkyl, —O—$C_1$-$C_3$ alkyl, or oxo;
$C^3$ is phenyl, thiazolyl, or oxazolyl;
$R^a$ is methyl, cyano, or halo;
$R^{Y1}$ and $R^{Y2}$ are independently H or methyl;
the subscript m is 0 or 1; and
the subscript p is 0 or 1.

In embodiment no. 26, the present invention provides a compound having the Formula (IB), wherein
$R^2$ is phenyl which is unsubstituted or substituted by 1 to 3 moieties independently selected from halo, cyano, $C_1$-$C_3$ alkyl, or —O—$C_1$-$C_3$ alkyl; and
the remaining variables are as set forth in embodiment no. 25.

In embodiment no. 27, the present invention provides a compound having the Formula (IA), wherein
$R^1$ is halo;
$C^3$ is phenyl, thiazolyl, oxazolyl, or benzothiazolyl;
$R^{Y1}$ and $R^{Y2}$ are independently H, methyl, or amino; and
X, $R^a$, and the subscripts m and p are as set forth in embodiment no. 24.

In embodiment no. 28, the present invention provides a compound having the Formula (IB), wherein
$R^1$ is halo;
$C^3$ is phenyl, thiazolyl, oxazolyl, or benzothiazolyl;
$R^{Y1}$ and $R^{Y2}$ are independently H, methyl, or amino; and
X, $R^2$, $R^a$, and the subscripts m and p are as set forth in embodiment no. 25.

In embodiment no. 29, the present invention provides the compound having the formula (IB), wherein R² is phenyl and X, R¹, C³, Rᵃ, R^{Y1}, R^{Y2}, the subscripts m and p are as set forth in embodiment no. 25.

In another embodiment, the present invention provides a compound selected from:

3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}oxazol-4-yl)-2,2-dimethylpropanoic acid;

3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl)oxazol-4-yl)-2,2-dimethylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-bromophenyl)propanoic acid;

3-{4-[4-amino-2-{6-chloro-1-[(4-methylcyclohexyl)methyl]-1H-indazol-3-yl}-5-methyl-6-oxo-6,7-dihydro-5H-pyrrolo[2,3-d]pyrimidin-5-yl]phenyl}propanoic acid;

3-{4-[4-amino-2-{6-chloro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]phenyl}propanoic acid;

3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)propanoic acid;

3-(6-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}pyridin-3-yl)-2,2-dimethylpropanoic acid;

3-(4-{4-amino-5-methyl-6-oxo-2-(1-(3,3,4,4,4-pentafluorobutyl)-2,3-dihydro-1H-pyrazolo[3,4-b]pyridin-3-yl)-6,7-dihydro-5H-pyrrolo[2,3-d]pyrimidin-5-yl}phenyl)-2,2-dimethylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid;

3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1H-1,2,3-triazol-1-yl)propanoic acid;

3-(4-{4-amino-2-(1-butyl-6-chloro-1H-pyrazolo[3,4-b]pyridin-3-yl)-5-methyl-6-oxo-6,7-dihydro-5H-pyrrolo[2,3-d]pyrimidin-5-yl}phenyl)propanoic acid;

3-(4-{4-amino-2-(1-butyl-1H-pyrazolo[3,4-b]pyridin-3-yl)-5-methyl-6-oxo-6,7-dihydro-5H-pyrrolo[2,3-d]pyrimidin-5-yl}phenyl)propanoic acid;

3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)propanoic acid;

3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid;

3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2-methylpropanoic acid;

3-(4-{4-amino-2-[5-fluoro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-5-methyl-2-[6-methyl-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}phenyl)propanoic acid;

3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(3-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(3-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}benzoic acid;

3-(3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)acetic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)propanoic acid;

2-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2-methylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoic acid;

1-[(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)methyl]cyclopropanecarboxylic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2-methylpropanoic acid;

2-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}acetic acid;

3-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}propanoic acid;

3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}-2,2-dimethylpropanoic acid;

3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}propanoic acid;

3-(3-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)-2,2-dimethylpropanoic acid;

3-(4-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

3-{4-[4-amino-2-(6-chloro-1-pentyl-1H-indazol-3-yl)-5-methyl-6-oxo-6,7-dihydro-5H-pyrrolo[2,3-d]pyrimidin-5-yl]phenyl}propanoic acid;

3-(4-{4-amino-2-[6-chloro-1-(cyclohexylmethyl)-1H-indazol-3-yl]-5-methyl-6-oxo-6,7-dihydro-5H-pyrrolo[2,3-d]pyrimidin-5-yl}phenyl)propanoic acid;

3-{4-[4-amino-2-(6-chloro-1-hexyl-1H-indazol-3-yl)-5-methyl-6-oxo-6,7-dihydro-5H-pyrrolo[2,3-d]pyrimidin-5-yl]phenyl}propanoic acid;

3-(4-{4-amino-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}phenyl)propanoic acid;

4-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}thiazol-4-yl)butanoic acid;

3-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}oxazol-4-yl)propanoic acid;

2-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}oxazol-4-yl)acetic acid;

3-(4-{4-amino-2-[6-chloro-1-(4,4-dimethylpentyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)propanoic acid;

4-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)butanoic acid;

3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(4-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]phenyl)propanoic acid;

3-(4-[4-amino-2-{6-chloro-1-[(4,4-difluorocyclohexyl)methyl]-1H-indazol-3-yl}-5-methyl-6-oxo-6,7-dihydro-5H-pyrrolo[2,3-d]pyrimidin-5-yl]phenyl)propanoic acid;

3-(4-{4-amino-2-[1-(2-fluorobenzyl)-6-methyl-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(4-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(3-methylbenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4-methylbenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(2-methylbenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}phenyl)propanoic acid;

3-(4-{2-[1-(adamantan-1-ylmethyl)-6-chloro-1H-indazol-3-yl]-4-amino-5-methyl-6-oxo-6,7-dihydro-5H-pyrrolo[2,3-d]pyrimidin-5-yl}phenyl) propanoic acid;

3-(4-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(4-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(2-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}thiazol-4-yl)-2,2-dimethylpropanoic acid;

3-(4-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid;

(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)acetic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-3-methylbutanoic acid;

2-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)cyclopropanecarboxylic acid;

1-[(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)methyl]cyclopropanecarboxylic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid;

(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-4-methyl-1,3-thiazol-5-yl)acetic acid;

3-(2-{4-amino-2-[5-fluoro-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[5-fluoro-1-(3,3,3-trifluoropropyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-{2-[4-amino-2-(1-butyl-1H-pyrazolo[3,4-b]pyridin-3-yl)-5-methyl-6-oxo-6,7-dihydro-5H-pyrrolo[2,3-d]pyrimidin-5-yl]-1,3-thiazol-4-yl}-2,2-dimethylpropanoic acid;

3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid;

3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid;

3-(2-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)benzoic acid;

4-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-5-methyl-1,3-thiazol-4-yl)benzoic acid;

3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-5-cyclopropyl-2-[5-fluoro-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}thiazol-4-yl)-2,2-dimethylpropanoic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-N-hydroxy-2,2-dimethylpropanamide;

[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]acetic acid;

2-[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]-2-methylpropanoic acid;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)glycine;

2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)-2-methylpropanoic acid;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-alanine;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-L-alanine;

(2R)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid;

(2S)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-serine;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-threonine;

N-((2H-tetrazol-5-yl)methyl)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamide;

3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-2H-1,2,3-triazol-2-yl)propanoic acid;

3-(4-{4-amino-2-[6-chloro-1-(2-fluorobenzyl)-5-hydroxy-1H-indazol-3-yl]-5-methyl-6-oxo-6,7-dihydro-5H-pyrrolo[2,3-d]pyrimidin-5-yl}phenyl)propanoic acid;

3-{4-[4-amino-2-(1-butyl-6-methyl-1H-pyrazolo[3,4-b]pyridin-3-yl)-5-methyl-6-oxo-6,7-dihydro-5H-pyrrolo[2,3-d]pyrimidin-5-yl]phenyl}propanoic acid;

4-amino-2-[6-chloro-1-(2-fluorobenzyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one;

4-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)butanoic acid;

(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)acetic acid;

4-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)butanoic acid;

4-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)butanoic acid;

2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)acetic acid;

2-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)acetic acid;

3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)propanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-cyanophenyl)propanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-methylphenyl)propanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-hydroxyphenyl)propanoic acid;

(5S)-3-{2-[4-amino-5-methyl-6-oxo-2-{1-[tetrahydro-2H-pyran-2-ylmethyl]-1H-pyrazolo[3,4-b]pyridin-3-yl}-6,7-dihydro-5H-pyrrolo[2,3-d]pyrimidin-5-yl]-1,3-thiazol-4-yl}-2,2-dimethylpropanoic acid;

3-{2-[4-amino-5-methyl-6-oxo-2-{1-[tetrahydro-2H-pyran-2-ylmethyl]-1H-pyrazolo[3,4-b]pyridin-3-yl}-6,7-dihydro-5H-pyrrolo[2,3-d]pyrimidin-5-yl]-1,3-oxazol-4-yl}-2,2-dimethylpropanoic acid;

(5S)-3-{2-[4-amino-5-methyl-2-{1-[4-methylcyclohexylmethyl]-1H-pyrazolo[3,4-b]pyridin-3-yl}-6-oxo-6,7-dihydro-5H-pyrrolo[2,3-d]pyrimidin-5-yl]-1,3-thiazol-4-yl}-2,2-dimethylpropanoic acid;

3-{2-[4-amino-5-methyl-2-{1-[4-methylcyclohexylmethyl]-1H-pyrazolo[3,4-b]pyridin-3-yl}-6-oxo-6,7-dihydro-5H-pyrrolo[2,3-d]pyrimidin-5-yl]-1,3-oxazol-4-yl}-2,2-dimethylpropanoic acid;

4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-difluorobutanoic acid;

3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-2-yl)-2,2-dimethylpropanoic acid;

3-(6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridin-3-yl)propanoic acid;

2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-benzothiazole-5-carboxylic acid;

3-(6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridin-3-yl)-2,2-dimethylpropanoic acid;

3-{2-[4-amino-2-{6-chloro-1-[4-methylcyclohexylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid;

(5S)-3-{2-[4-amino-2-{6-fluoro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]-1,3-thiazol-4-yl}-2,2-dimethylpropanoic acid;

3-{2-[4-amino-2-{6-fluoro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid;

4-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-difluorobutanoic acid;

(5S)-3-{2-[4-amino-2-{6-fluoro-1-[4-methylcyclohexylmethyl]-1H-indazol-3-yl}-5-methyl-6-oxo-6,7-dihydro-5H-pyrrolo[2,3-d]pyrimidin-5-yl]-1,3-thiazol-4-yl}-2,2-dimethylpropanoic acid;

3-{2-[4-amino-2-{6-fluoro-1-[4-methylcyclohexylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid;

3-(2-{4-amino-2-[6-chloro-1-(2-fluorobenzyl)-1H-indazol-3-yl]-5-cyclopropyl-6-oxo-6,7-dihydro-5H-pyrrolo[2,3-d]pyrimidin-5-yl}-1,3-oxazol-4-yl)-2,2-dimethylpropanoic acid;

3-(2-{4-amino-5-cyclopropyl-2-[6-fluoro-1-(2-fluorobenzyl)-1H-indazol-3-yl]-6-oxo-6,7-dihydro-5H-pyrrolo[2,3-d]pyrimidin-5-yl}-1,3-oxazol-4-yl)-2,2-dimethylpropanoic acid;

3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoic acid;

2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-1,2,3-triazol-1-yl)-2-methylpropanoic acid;

3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-2-yl)-2,2-dimethylpropanoic acid;

4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridine-2-carboxylic acid;

3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1H-pyrazol-1-yl)-2,2-dimethylpropanoic acid;

3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1H-pyrazol-1-yl)-2,2-dimethylpropanoic acid;

4-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)benzoic acid;

4-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)benzoic acid;

3-(4-{4-amino-5-cyclopropyl-2-[1-(2-fluorobenzyl)-1H-pyrazolo[3,4-b]pyridin-3-yl]-6-oxo-6,7-dihydro-5H-pyrrolo[2,3-d]pyrimidin-5-yl}phenyl)propanoic acid;

(S)-3-(2-{4-amino-2-[1-(3-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[1-(3-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[1-(cyclohexylmethyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[1-(cyclohexylmethyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[1-(cyclopentylmethyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[1-(cyclopentylmethyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)-2,2-dimethylpropanoic acid;

4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}benzoic acid;

4-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)benzoic acid;

(2E)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)prop-2-enoic acid;

3-(4-{4-amino-2-[6-chloro-1-(3,3,4,4,4-pentafluorobutyl)-1H-indazol-3-yl]-5-cyclopropyl-6-oxo-6,7-dihydro-5H-pyrrolo[2,3-d]pyrimidin-5-yl}phenyl)propanoic acid;

3-(2-{4-amino-2-[6-chloro-1-(cyclohexylmethyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(4-{4-amino-2-[6-chloro-1-(cyclopentylmethyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[6-chloro-1-(cyclopentylmethyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[6-chloro-1-(cyclopentylmethyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-{4-[4-amino-2-{6-chloro-1-[(3,3-difluorocyclobutyl)methyl]-1H-indazol-3-yl}-5-methyl-6-oxo-6,7-dihydro-5H-pyrrolo[2,3-d]pyrimidin-5-yl]phenyl}propanoic acid;

4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)benzoic acid;

4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)benzoic acid;

4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylbutanoic acid;

4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylbutanoic acid;

2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-benzoxazole-5-carboxylic acid;

3-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}benzoic acid;

3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-5-methyl-1,3-oxazol-4-yl)-2,2-dimethylpropanoic acid;

3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-pyrazol-1-yl)-2,2-dimethylpropanoic acid;

3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-D-alanine;

3-(2-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

3-(2-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}-5-methyl-1,3-oxazol-4-yl)-2,2-dimethylpropanoic acid;

4-(2-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylbutanoic acid;

3-(2-{4-amino-2-[6-chloro-1-(2,4-difluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[6-chloro-1-(2,4-difluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-chloro-1-(2,3-difluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[6-chloro-1-(2,3-difluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-{2-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid;

(S)-3-{2-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]-1,3-thiazol-4-yl}-2,2-dimethylpropanoic acid;

3-(2-{4-amino-2-[6-chloro-1-(3-methylbenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

3-(2-{4-amino-2-[6-chloro-1-(2-fluoro-3-methylbenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[6-chloro-1-(2-fluoro-3-methylbenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-chloro-1-(2,3,6-trifluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[6-chloro-1-(2,3,6-trifluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}benzoic acid;

3-(4-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1H-pyrazol-1-yl)-2,2-dimethylpropanoic acid;

4-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylbutanoic acid;

(S)-3-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

4-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylbutanoic acid;

4-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylbutanoic acid;

3-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-5-methyl-1,3-oxazol-4-yl)-2,2-dimethylpropanoic acid;

(S)-3-(2-{4-amino-2-[1-(2,3-difluorobenzyl)-6-fluoro-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[1-(2,3-difluorobenzyl)-6-fluoro-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[1-(cyclohexylmethyl)-6-fluoro-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[1-(cyclohexylmethyl)-6-fluoro-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(2-{4-amino-2-[1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)acetic acid;

4-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylbutanoic acid;

4-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)-2,2-dimethylbutanoic acid;

4-{2-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylbutanoic acid;

3-(2-{4-amino-2-[6-chloro-1-(3,3-dimethylbutyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}benzoic acid;

(S)-3-(4-{4-amino-2-[1-(3,3-dimethylbutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-2-[6-fluoro-1-(2-fluoro-3-methylbenzyl)-1H-indazol-3-yl]-5-methyl-6-oxo-6,7-dihydro-5H-pyrrolo[2,3-d]pyrimidin-5-yl}-1H-pyrazol-1-yl)-2,2-dimethylpropanoic acid;

3-(2-{4-amino-2-[6-fluoro-1-(2-fluoro-3-methylbenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

3-(2-{4-amino-2-[6-chloro-1-(2-fluoro-5-methylbenzyl)-1H-indazol-3-yl]-5-methyl-6-oxo-6,7-dihydro-5H-pyrrolo[2,3-d]pyrimidin-5-yl}1,3-oxazol-4-yl)-2,2-dimethylpropanoic acid;

(S)-3-(2-{4-amino-2-[6-chloro-1-(2-fluoro-5-methylbenzyl)-1H-indazol-3-yl]-5-methyl-6-oxo-6,7-dihydro-5H-pyrrolo[2,3-d]pyrimidin-5-yl}1,3-thiazol-4-yl)-2,2-dimethylpropanoic acid;

3-(2-{4-amino-2-[6-chloro-1-((3-fluoro-4-methylpyridin-2-yl)methyl)-1H-indazol-3-yl]-5-methyl-6-oxo-6,7-dihydro-5H-pyrrolo[2,3-d]pyrimidin-5-yl}1,3-oxazol-4-yl)-2,2-dimethylpropanoic acid;

(S)-3-(2-{4-amino-2-[6-chloro-1-((3-fluoro-4-methylpyridin-2-yl)methyl)-1H-indazol-3-yl]-5-methyl-6-oxo-6,7-dihydro-5H-pyrrolo[2,3-d]pyrimidin-5-yl}1,3-thiazol-4-yl)-2,2-dimethylpropanoic acid;

(2E)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)prop-2-enoic acid;

(2E)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)prop-2-enoic acid;

2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridine-4-carboxylic acid;

4-(2-{4-amino-2-[1-(2-fluorobenzyl)-1H-indazol-3-yl]-5-methyl-6-oxo-6,7-dihydro-5H-pyrrol o[2,3-d]pyrimidin-5-yl}-1,3-oxazol-4-yl)-2,2-dimethylbutanoic acid;

(S)-3-(4-{4-amino-2-[1-(4-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(2-{4-amino-2-[1-(3-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-5-methyl-6-oxo-2-[1-(2,3,6-trifluorobenzyl)-1H-indazol-3-yl]-6,7-dihydro-5H-pyrrolo[2,3-d]pyrimidin-5-yl}-1,3-thiazol-4-yl)-2,2-dimethylpropanoic acid;

(S)-3-(4-{4-amino-5-methyl-2-[1-(3-methylbenzyl)-1H-indazol-3-yl]-6-oxo-6,7-dihydro-5H-pyrrolo[2,3-d]pyrimidin-5-yl}phenyl)propanoic acid;

3-(2-{4-amino-5-methyl-2-[1-(3-methylbenzyl)-1H-indazol-3-yl]-6-oxo-6,7-dihydro-5H-pyrrolo[2,3-d]pyrimidin-5-yl}-1,3-oxazol-4-yl)-2,2-dimethylpropanoic acid;

(S)-3-(4-{4-amino-2-[1-(cyclopentylmethyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[1-(cyclohexylmethyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(5S)-3-{2-[4-amino-5-methyl-6-oxo-2-{1-[tetrahydro-2H-pyran-2-ylmethyl]-1H-indazol-3-yl}-6,7-dihydro-5H-pyrrolo[2,3-d]pyrimidin-5-yl]-1,3-thiazol-4-yl}-2,2-dimethylpropanoic acid;

3-{2-[4-amino-5-methyl-6-oxo-2-{1-[tetrahydro-2H-pyran-2-ylmethyl]-1H-indazol-3-yl}-6,7-dihydro-5H-pyrrolo[2,3-d]pyrimidin-5-yl]-1,3-oxazol-4-yl}-2,2-dimethylpropanoic acid;

3-{2-[4-amino-5-methyl-2-{1-[-4-methylcyclohexyl methyl]-1H-indazol-3-yl}-6-oxo-6,7-dihydro-5H-pyrrolo[2,3-d]pyrimidin-5-yl]-1,3-oxazol-4-yl}-2,2-dimethylpropanoic acid;

(S)-3-{4-[4-amino-2-{1-[(3-fluoropyridin-2-yl)methyl]-1H-indazol-3-yl}-5-methyl-6-oxo-6,7-dihydro-5H-pyrrolo[2,3-d]pyrimidin-5-yl]phenyl}propanoic acid;

3-(2-{4-amino-2-[1-(2-fluoro-3-methylbenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid;

(S)-3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-D-alanine;

3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-imidazol-4-yl)propanoic acid;

(S)-4-amino-2-[1-(2-fluorobenzyl)-1H-indazol-3-yl]-5-methyl-5-{4-[2-methyl-2-(2H-tetrazol-5-yl)propyl]thiazol-2-yl}-5,7-dihydro-6H-pyrrolo[2,3-d]pyrimidin-6-one;

(S)-4-amino-2-[6-chloro-1-(3,3,4,4,4-pentafluorobutyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one;

(S)-4-amino-2-[6-chloro-1-(2-fluorobenzyl)-1H-indazol-3-yl]-5-methyl-5-{4-[2-methyl-2-(2H-tetrazol-5-yl)propyl]-1,3-thiazol-2-yl}-5,7-dihydro-6H-pyrrolo[2,3-d]pyrimidin-6-one;

4-amino-2-[6-chloro-1-(2-fluorobenzyl)-1H-indazol-3-yl]-5-methyl-5-{4-[2-methyl-2-(2H-tetrazol-5-yl)propyl]-1,3-oxazol-2-yl}-5,7-dihydro-6H-pyrrolo[2,3-d]pyrimidin-6-one;

(S)-4-amino-2-[1-(2-fluorobenzyl)-1H-pyrazolo[3,4-b]pyridin-3-yl]-5-methyl-5-{4-[2-(2H-tetrazol-5-yl)ethyl]phenyl}-5,7-dihydro-6H-pyrrolo[2,3-d]pyrimidin-6-one;

(S)-4-amino-2-[1-(2-fluorobenzyl)-1H-pyrazolo[3,4-b]pyridin-3-yl]-5-methyl-5-{4-[2-methyl-2-(2H-tetrazol-5-yl)propyl]-1,3-thiazol-2-yl}-5,7-dihydro-6H-pyrrolo[2,3-d]pyrimidin-6-one;

(S)-4-amino-2-[1-(2-fluorobenzyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one;

5-[4-(2H-tetrazol-5-yl)pyridin-2-yl]-4-amino-2-[6-chloro-1-(2-fluorobenzyl)-1H-indazol-3-yl]-5-methyl-5,7-dihydro-6H-pyrrolo[2,3-d]pyrimidin-6-one;

5-{4-[(2H-tetrazol-5-yl)methyl]phenyl}-4-amino-2-[6-chloro-1-(2-fluorobenzyl)-1H-indazol-3-yl]-5-methyl-5,7-dihydro-6H-pyrrolo[2,3-d]pyrimidin-6-one;

(S)-5-{4-[2-(2H-tetrazol-5-yl)ethyl]phenyl}-4-amino-2-{1-[(3-fluoropyridin-2-yl)methyl]-1H-indazol-3-yl}-5-methyl-5,7-dihydro-6H-pyrrolo[2,3-d]pyrimidin-6-one;

5-{5-[2-(2H-tetrazol-5-yl)ethyl]pyridin-2-yl}-4-amino-2-[1-(2-fluorobenzyl)-1H-indazol-3-yl]-5-methyl-5,7-dihydro-6H-pyrrolo[2,3-d]pyrimidin-6-one;

5-{5-[2-(2H-tetrazol-5-yl)ethyl]pyridin-2-yl}-4-amino-2-[6-chloro-1-(2-fluorobenzyl)-1H-indazol-3-yl]-5-methyl-5,7-dihydro-6H-pyrrolo[2,3-d]pyrimidin-6-one;

4-amino-2-[1-(2-fluorobenzyl)-1H-indazol-3-yl]-5-methyl-5-{4-[2-methyl-2-(2H-tetrazol-5-yl)propyl]oxazol-2-yl}-5,7-dihydro-6H-pyrrolo[2,3-d]pyrimidin-6-one;

4-amino-2-[6-fluoro-1-(2-fluorobenzyl)-1H-indazol-3-yl]-5-methyl-5-[3-(1H-tetrazol-5-yl)phenyl]-5,7-dihydro-6H-pyrrolo[2,3-d]pyrimidin-6-one;

4-amino-2-[6-fluoro-1-(2-fluorobenzyl)-1H-indazol-3-yl]-5-methyl-5-[4-(1H-tetrazol-5-yl)phenyl]-5,7-dihydro-6H-pyrrolo[2,3-d]pyrimidin-6-one;

4-amino-2-[6-chloro-1-(3,3,4,4,4-pentafluorobutyl)-1H-indazol-3-yl]-5-methyl-5-[3-(1H-tetrazol-5-yl)phenyl]-5,7-dihydro-6H-pyrrolo[2,3-d]pyrimidin-6-one; 4-amino-5-methyl-2-[1-(3,3,4,4,4-pentafluorobutyl)-1H-pyrazolo[3,4-b]pyridin-3-yl]-5-[3-(2H-tetrazol-5-yl)phenyl]-5,7-dihydro-6H-pyrrolo[2,3-d]pyrimidin-6-one;

5-[6-(2H-tetrazol-5-yl)pyridin-2-yl]-4-amino-2-[6-chloro-1-(2-fluorobenzyl)-1H-indazol-3-yl]-5-methyl-5,7-dihydro-6H-pyrrolo[2,3-d]pyrimidin-6-one;

6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridine-3-carboxylic acid;

6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}picolinic acid;

(S)-4-amino-2-[6-chloro-1-(2-fluorobenzyl)-1H-indazol-3-yl]-5-methyl-5-{4-[2-(5-oxo-4,5-dihydro-1,2,4-oxadiazol-3-yl)ethyl]phenyl}-5,7-dihydro-6H-pyrrolo[2,3-d]pyrimidin-6-one;

[2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)ethyl]phosphonic acid;

2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)ethanesulfonic acid;

(S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)-N-(methyl sulfonyl)propanamide;

(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenoxy)acetic acid;

3-[1-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyrrolidin-3-yl]propanoic acid;

3-(1-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}piperidin-4-yl)propanoic acid;

3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)propanoic acid; or a pharmaceutically acceptable salt thereof.

In another embodiment, the present invention provides a compound selected from:

(R)-3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}oxazol-4-yl)-2,2-dimethylpropanoic acid;

(R)-3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(R)-3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl)oxazol-4-yl}-2,2-dimethylpropanoic acid;

(R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-bromophenyl)propanoic acid;

(5R)-3-{4-[4-amino-2-{6-chloro-1-[(4-methylcyclohexyl)methyl]-1H-indazol-3-yl}-5-methyl-6-oxo-6,7-dihydro-5H-pyrrolo[2,3-d]pyrimidin-5-yl]phenyl}propanoic acid;

(R)-3-{4-[4-amino-2-{6-chloro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]phenyl}propanoic acid;

(R)-3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)propanoic acid;

(R)-3-(6-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}pyridin-3-yl)-2,2-dimethylpropanoic acid;

(R)-3-(4-{4-amino-5-methyl-6-oxo-2-(1-(3,3,4,4,4-pentafluorobutyl)-2,3-dihydro-1H-pyrazolo[3,4-b]pyridin-3-yl)-6,7-dihydro-5H-pyrrolo[2,3-d]pyrimidin-5-yl}phenyl)-2,2-dimethylpropanoic acid;

(R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

(R)-3-(3-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid;

(R)-3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1H-1,2,3-triazol-1-yl)propanoic acid;

(R)-3-(4-{4-amino-2-(1-butyl-6-chloro-1H-pyrazolo[3,4-b]pyridin-3-yl)-5-methyl-6-oxo-6,7-dihydro-5H-pyrrolo[2,3-d]pyrimidin-5-yl}phenyl)propanoic acid;

(R)-3-(4-{4-amino-2-(1-butyl-1H-pyrazolo[3,4-b]pyridin-3-yl)-5-methyl-6-oxo-6,7-dihydro-5H-pyrrolo[2,3-d]pyrimidin-5-yl}phenyl)propanoic acid;

(R)-3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)propanoic acid;

(R)-3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid;

(5R)-3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2-methylpropanoic acid;

(R)-3-(4-{4-amino-2-[5-fluoro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(R)-3-(4-{4-amino-5-methyl-2-[6-methyl-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}phenyl)propanoic acid;

(R)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(R)-3-(3-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(R)-3-(4-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(R)-3-(3-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(R)-3-(4-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(R)-3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}benzoic acid;

(R)-3-(3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(R)-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)acetic acid;

(R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)propanoic acid;

(R)-2-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2-methylpropanoic acid;

(R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoic acid;

(R)-1-[(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)methyl]cyclopropanecarboxylic acid;

(R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(5R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2-methylpropanoic acid;

(R)-2-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}acetic acid;

(R)-3-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}propanoic acid;

(R)-3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}-2,2-dimethylpropanoic acid;

(R)-3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}propanoic acid;

(R)-3-(3-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(R)-3-(4-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(R)-3-{4-[4-amino-2-(6-chloro-1-pentyl-1H-indazol-3-yl)-5-methyl-6-oxo-6,7-dihydro-5H-pyrrolo[2,3-d]pyrimidin-5-yl]phenyl}propanoic acid;

(R)-3-(4-{4-amino-2-[6-chloro-1-(cyclohexylmethyl)-1H-indazol-3-yl]-5-methyl-6-oxo-6,7-dihydro-5H-pyrrolo[2,3-d]pyrimidin-5-yl}phenyl)propanoic acid;

(R)-3-{4-[4-amino-2-(6-chloro-1-hexyl-1H-indazol-3-yl)-5-methyl-6-oxo-6,7-dihydro-5H-pyrrolo[2,3-d]pyrimidin-5-yl]phenyl}propanoic acid;

(R)-3-(4-{4-amino-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(3-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}phenyl)propanoic acid;

(R)-4-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}thiazol-4-yl)butanoic acid;

(R)-3-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}oxazol-4-yl)propanoic acid;

(R)-2-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}oxazol-4-yl)acetic acid;

(R)-3-(4-{4-amino-2-[6-chloro-1-(4,4-dimethylpentyl)-1H-indazol-3-yl]-5-methyl-6-oxo-6,7-dihydro-5H-pyrrolo[2,3-d]pyrimidin-5-yl}phenyl)propanoic acid;

(R)-3-(3-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)propanoic acid;

(R)-4-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)butanoic acid;

(R)-3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(R)-3-(4-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]phenyl)propanoic acid;

(R)-3-(4-[4-amino-2-{6-chloro-1-[(4,4-difluorocyclohexyl)methyl]-1H-indazol-3-yl}-5-methyl-6-oxo-6,7-dihydro-5H-pyrrolo[2,3-d]pyrimidin-5-yl]phenyl)propanoic acid;

(R)-3-(4-{4-amino-2-[1-(2-fluorobenzyl)-6-methyl-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(R)-3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(R)-3-(4-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(3-methylbenzyl)-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(4-methylbenzyl)-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(2-methylbenzyl)-1H-indazol-3-yl]-5-methyl-6-oxo-6,7-dihydro-5H-pyrrolo[2,3-d]pyrimidin-5-yl}phenyl)propanoic acid;

(R)-3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(4-{2-[1-(adamantan-1-ylmethyl)-6-chloro-1H-indazol-3-yl]-4-amino-5-methyl-6-oxo-6,7-dihydro-5H-pyrrolo[2,3-d]pyrimidin-5-yl}phenyl) propanoic acid;

(R)-3-(4-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(2-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(R)-3-(4-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(2-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(R)-3-(2-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}thiazol-4-yl)-2,2-dimethylpropanoic acid;

(R)-3-(4-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(R)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid;

(R)-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)acetic acid;

(R)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-3-methylbutanoic acid;

(5R)-2-(2-{-4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)cyclopropanecarboxylic acid;

(R)-1-[(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)methyl]cyclopropanecarboxylic acid;

(R)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid;

(R)-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-4-methyl-1,3-thiazol-5-yl)acetic acid;

(R)-3-(2-{4-amino-2-[5-fluoro-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(R)-3-(2-{4-amino-2-[5-fluoro-1-(3,3,3-trifluoropropyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(R)-3-{2-[4-amino-2-(1-butyl-1H-pyrazolo[3,4-b]pyridin-3-yl)-5-methyl-6-oxo-6,7-dihydro-5H-pyrrolo[2,3-d]pyrimidin-5-yl]-1,3-thiazol-4-yl}-2,2-dimethylpropanoic acid;

(R)-3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid;

(R)-3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid;

(R)-3-(2-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(R)-3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(R)-3-(2-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(R)-3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(R)-3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)benzoic acid;

(R)-4-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-5-methyl-1,3-thiazol-4-yl)benzoic acid;

(R)-3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(R)-3-(2-{4-amino-5-cyclopropyl-2-[5-fluoro-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}thiazol-4-yl)-2,2-dimethylpropanoic acid;

(R)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-N-hydroxy-2,2-dimethylpropanamide;

(R)-[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]acetic acid;

(R)-2-[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]-2-methylpropanoic acid;

(R)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)glycine;

(R)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)-2-methylpropanoic acid;

(5R)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-alanine;

(5R)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-L-alanine;

(5R)-(2R)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid;

(5R)-(2S)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid;

(5R)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-serine;

(5R)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-threonine;

(R)—N-((2H-tetrazol-5-yl)methyl)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamide;

(R)-3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-2H-1,2,3-triazol-2-yl)propanoic acid;

(R)-3-(4-{4-amino-2-[6-chloro-1-(2-fluorobenzyl)-5-hydroxy-1H-indazol-3-yl]-5-methyl-6-oxo-6,7-dihydro-5H-pyrrolo[2,3-d]pyrimidin-5-yl}phenyl)propanoic acid;

(R)-3-{4-[4-amino-2-(1-butyl-6-methyl-1H-pyrazolo[3,4-b]pyridin-3-yl)-5-methyl-6-oxo-6,7-dihydro-5H-pyrrolo[2,3-d]pyrimidin-5-yl]phenyl}propanoic acid;

(R)-4-amino-2-[6-chloro-1-(2-fluorobenzyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one;

(R)-4-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)butanoic acid;

(R)-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)acetic acid;

(R)-4-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)butanoic acid;

(R)-4-(4-{4-amino-5-methyl-6-oxo-2-[1-(3,3,4,4,4-pentafluorobutyl)-1H-pyrazolo[3,4-b]pyridin-3-yl)-6,7-dihydro-5H-pyrrolo[2,3-d]pyrimidin-5-yl}phenyl)butanoic acid;

(R)-2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)acetic acid;

(R)-2-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)acetic acid;

(R)-3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)propanoic acid;

(R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-cyanophenyl)propanoic acid;

(R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-methylphenyl)propanoic acid;

(R)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-hydroxyphenyl)propanoic acid; or a pharmaceutically acceptable salt thereof.

In another embodiment, the present invention provides a compound selected from:

(S)-3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}oxazol-4-yl)-2,2-dimethylpropanoic acid;

(S)-3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(S)-3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl)oxazol-4-yl}-2,2-dimethylpropanoic acid;

(S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-bromophenyl)propanoic acid;

(5S)-3-{4-[4-amino-2-{6-chloro-1-[(4-methylcyclohexyl)methyl]-1H-indazol-3-yl}-5-methyl-6-oxo-6,7-dihydro-5H-pyrrolo[2,3-d]pyrimidin-5-yl]phenyl}propanoic acid;

(S)-3-{4-[4-amino-2-{6-chloro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]phenyl}propanoic acid;

(S)-3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)propanoic acid;

(S)-3-(6-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}pyridin-3-yl)-2,2-dimethylpropanoic acid;

(S)-3-(4-{4-amino-5-methyl-6-oxo-2-(1-(3,3,4,4,4-pentafluorobutyl)-2,3-dihydro-1H-pyrazolo[3,4-b]pyridin-3-yl)-6,7-dihydro-5H-pyrrolo[2,3-d]pyrimidin-5-yl}phenyl)-2,2-dimethylpropanoic acid;

(S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

(S)-3-(3-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid;

(S)-3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1H-1,2,3-triazol-1-yl)propanoic acid;

(S)-3-(4-{4-amino-2-(1-butyl-6-chloro-1H-pyrazolo[3,4-b]pyridin-3-yl)-5-methyl-6-oxo-6,7-dihydro-5H-pyrrolo[2,3-d]pyrimidin-5-yl}phenyl)propanoic acid;

(S)-3-(4-{4-amino-2-(1-butyl-1H-pyrazolo[3,4-b]pyridin-3-yl)-5-methyl-6-oxo-6,7-dihydro-5H-pyrrolo[2,3-d]pyrimidin-5-yl}phenyl)propanoic acid;

(S)-3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)propanoic acid;

(S)-3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid;

(5S)-3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2-methylpropanoic acid;

(S)-3-(4-{4-amino-2-[5-fluoro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(S)-3-(4-{4-amino-5-methyl-2-[6-methyl-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}phenyl)propanoic acid;

(S)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(S)-3-(3-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(S)-3-(4-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(S)-3-(3-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(S)-3-(4-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

(S)-3-{4-[4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}benzoic acid;

(S)-3-(3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(S)-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)acetic acid;

(S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)propanoic acid;

(S)-2-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2-methylpropanoic acid;

(S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoic acid;

(S)-1-[(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)methyl]cyclopropanecarboxylic acid;

(S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(5S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2-methylpropanoic acid;

(S)-2-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}acetic acid;

(S)-3-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}propanoic acid;

(S)-3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}-2,2-dimethylpropanoic acid;

(S)-3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}propanoic acid;

(S)-3-(3-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(S)-3-(4-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(S)-3-{4-[4-amino-2-(6-chloro-1-pentyl-1H-indazol-3-yl)-5-methyl-6-oxo-6,7-dihydro-5H-pyrrolo[2,3-d]pyrimidin-5-yl]phenyl}propanoic acid;

(S)-3-(4-{4-amino-2-[6-chloro-1-(cyclohexylmethyl)-1H-indazol-3-yl]-5-methyl-6-oxo-6,7-dihydro-5H-pyrrolo[2,3-d]pyrimidin-5-yl}phenyl)propanoic acid;

(S)-3-{-4-[4-amino-2-(6-chloro-1-hexyl-1H-indazol-3-yl)-5-methyl-6-oxo-6,7-dihydro-5H-pyrrolo[2,3-d]pyrimidin-5-yl]phenyl}propanoic acid;

(S)-3-(4-{4-amino-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(3-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}phenyl)propanoic acid;

(S)-4-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}thiazol-4-yl)butanoic acid;

(S)-3-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}oxazol-4-yl)propanoic acid;

(S)-2-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}oxazol-4-yl)acetic acid;

(S)-3-(4-{4-amino-2-[6-chloro-1-(4,4-dimethylpentyl)-1H-indazol-3-yl]-5-methyl-6-oxo-6,7-dihydro-5H-pyrrolo[2,3-d]pyrimidin-5-yl}phenyl)propanoic acid;

(S)-3-(3-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)propanoic acid;

(S)-4-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)butanoic acid;

(S)-3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(S)-3-(4-{4-amino-2-[6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]phenyl)propanoic acid;

(S)-3-(4-{4-amino-2-[6-chloro-1-[(4,4-difluorocyclohexyl)methyl]-1H-indazol-3-yl}-5-methyl-6-oxo-6,7-dihydro-5H-pyrrolo[2,3-d]pyrimidin-5-yl]phenyl)propanoic acid;

(S)-3-(4-{4-amino-2-[1-(2-fluorobenzyl)-6-methyl-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(S)-3-(4-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(3-methylbenzyl)-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(4-methylbenzyl)-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(2-methylbenzyl)-1H-indazol-3-yl]-5-methyl-6-oxo-6,7-dihydro-5H-pyrrolo[2,3-d]pyrimidin-5-yl}phenyl)propanoic acid;

(S)-3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(4-{2-[1-(adamantan-1-ylmethyl)-6-chloro-1H-indazol-3-yl]-4-amino-5-methyl-6-oxo-6,7-dihydro-5H-pyrrolo[2,3-d]pyrimidin-5-yl}phenyl) propanoic acid;

(S)-3-(4-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(2-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(S)-3-(4-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(2-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

(S)-3-(2-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}thiazol-4-yl)-2,2-dimethylpropanoic acid;

(S)-3-(4-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

(S)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid;

(S)-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)acetic acid;

(S)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-3-methylbutanoic acid;

(5S)-2-(2-{-4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)cyclopropanecarboxylic acid;

(S)-1-[(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)methyl]cyclopropanecarboxylic acid;

(S)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid;

(S)-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-4-methyl-1,3-thiazol-5-yl)acetic acid;

(S)-3-(2-{4-amino-2-[5-fluoro-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-(2-{4-amino-2-[5-fluoro-1-(3,3,3-trifluoropropyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-{2-[4-amino-2-(1-butyl-1H-pyrazolo[3,4-b]pyridin-3-yl)-5-methyl-6-oxo-6,7-dihydro-5H-pyrrolo[2,3-d]pyrimidin-5-yl]-1,3-thiazol-4-yl}-2,2-dimethylpropanoic acid;

(S)-3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid;

(S)-3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid;

(S)-3-(2-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-(2-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)benzoic acid;

(S)-4-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-5-methyl-1,3-thiazol-4-yl)benzoic acid;

(S)-3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

(S)-3-(2-{4-amino-5-cyclopropyl-2-[5-fluoro-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}thiazol-4-yl)-2,2-dimethylpropanoic acid;

(S)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-N-hydroxy-2,2-dimethylpropanamide;

(S)-[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]acetic acid;

(S)-2-[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]-2-methylpropanoic acid;

(S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)glycine;

(S)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)-2-methylpropanoic acid;

(5S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-alanine;

(5S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-L-alanine;

(5S)-(2R)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid;

(5S)-(2S)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid;

(5S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-serine;

(5S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-threonine;

(S)—N-((2H-tetrazol-5-yl)methyl)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamide;

(S)-3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-2H-1,2,3-triazol-2-yl)propanoic acid;

(S)-3-(4-{4-amino-2-[6-chloro-1-(2-fluorobenzyl)-5-hydroxy-1H-indazol-3-yl]-5-methyl-6-oxo-6,7-dihydro-5H-pyrrolo[2,3-d]pyrimidin-5-yl}phenyl)propanoic acid;

(S)-3-{4-[4-amino-2-(1-butyl-6-methyl-1H-pyrazolo[3,4-b]pyridin-3-yl)-5-methyl-6-oxo-6,7-dihydro-5H-pyrrolo[2,3-d]pyrimidin-5-yl]phenyl}propanoic acid;

(S)-4-amino-2-[6-chloro-1-(2-fluorobenzyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one;

(S)-4-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)butanoic acid;

(S)-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)acetic acid;

(S)-4-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)butanoic acid;

(S)-4-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)butanoic acid;

(S)-2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)acetic acid;

(S)-2-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)acetic acid;

(S)-3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)propanoic acid;

(S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-cyanophenyl)propanoic acid;

(S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-methylphenyl)propanoic acid;

(S)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-hydroxyphenyl)propanoic acid; or a pharmaceutically acceptable salt thereof.

The present invention includes the pharmaceutically acceptable salts of the compounds defined herein, including the pharmaceutically acceptable salts of all structural formulas, embodiments and classes defined herein. Reference to the compounds of structural Formula (I) includes the compounds of other generic structural Formulas and embodiments that fall within the scope of Formula (I), including but not limited to the compounds of Formulas (IA) or (IB).

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkoxy" and "alkyl-O—" are used interchangeably and refer to an alkyl group linked to oxygen.

"Alkyl-NH—" refers to an alkyl group linked to an NH group. Examples of alkyl-NH-include methyl-amino or methyl-NH— and ethyl-amino or ethyl-NH—.

"Aryl" means phenyl or naphthyl.

"Haloalkyl" include mono-substituted as well as multiple halo substituted alkyl groups, up to perhalo substituted alkyl. For example, halomethyl, 1,1-difluoroethyl, trifluoromethyl or 1,1,1,2,2-pentafluorobutyl are included.

"Haloalkoxy" and "haloalkyl-O" are used interchangeably and refer to halo substituted alkyl groups or "haloalkyl" linked through the oxygen atom. Haloalkoxy include mono-substituted as well as multiple halo substituted alkoxy groups, up to perhalo substituted alkoxy. For example, trifluoromethoxy is included.

"Cycloalkyl" means a saturated cyclic hydrocarbon radical having the number of carbon atoms designated if no number of atoms is specified, 3-12 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, adamantyl, decahydronaphthyl, indanyl and the like.

"Cycloalkoxy" and "cycloalkyl-O" are used interchangeably and refer to a cycloalkyl group, as defined above, linked to oxygen.

"Heterocyclyl" "heterocycle" or "heterocyclic" refers to nonaromatic monocyclic ring structures in which one or more atoms in the ring, the heteroatom(s), is an element other than carbon. Such nonaromatic cyclic ring structures can be saturated or unsaturated. Heteroatoms are typically O, S or N atoms. Examples of heterocyclyl groups include: piperidine, piperazinyl, morpholinyl, pyrrolidinyl, tetrahydrofuranyl, azetidinyl, oxiranyl, or aziridinyl, and the like.

"Heteroaryl" refers to an aromatic monocyclic and bicyclic ring structures in which one or more atoms in the ring, the heteroatom(s), is an element other than carbon. Heteroatoms are typically O, S, or N atoms. Examples of heteroaromatic groups include: pyridinyl, pyrimidinyl, pyrrolyl, pyridazinyl, isoxazolyl, thiazolyl, oxazolyl, indolyl, benzoxazolyl, benzothiazolyl, or imidazolyl.

"Halogen" (or "halo") unless otherwise indicated, includes fluorine (fluoro), chlorine (chloro), bromine (bromo) and iodine (iodo). In one embodiment, halo is fluoro (—F) or chloro (—Cl).

When any variable (e.g., $R^1$, $R^2$, etc.) occurs more than one time in any constituent or in Formula (I) or other generic formulas herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e., $R^1$, $R^2$, etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, such as $R^1$ in Formula (I), are permitted on any available carbon atom in the ring to which the variable is attached. When a moiety is noted as being "optionally substituted" in Formula (I) or any embodiment thereof, it means that Formula (I) or the embodiment thereof encompasses compounds that contain the noted substituent (or substituents) on the moiety and also compounds that do not contain the noted substituent (or substituents) on the moiety.

Compounds of Formula (I) may contain one or more asymmetric centers and can thus occur as racemates and racemic mixtures, single enantiomers, diastereoisomeric mixtures and individual diastereoisomers. Centers of asymmetry that are present in the compounds of Formula (I) can all independently of one another have S configuration or R configuration. The compounds of this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereoisomeric forms of the compounds of Formula (I). Where a structural formula or chemical name specifies a particular configuration at a stereocenter, the enantiomer or stereoisomer of the compound resulting from that specified stereocenter is intended. Where a structural formula of the compounds of Formula (I) indicates a straight line at a chiral center, the structural formula includes both the S and R stereoisomers associated with the chiral center and mixtures thereof.

Compounds of Formula (I) may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Vibrational circular dichroism (VCD) may also be used to determine the absolute stereochemistry. Alternatively, any stereoisomer or isomers of a compound of Formula (I) may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula (I) described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formulas I of the present invention.

In the compounds of Formula (I), the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of Formula (I) and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula (I), can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids. If the compounds of Formula (I) simultaneously contain acidic and basic groups in the molecule the invention also includes, in addition to the salt forms mentioned, inner salts or betaines (zwitterions). Salts can be obtained from the compounds of Formula (I) by customary methods which are known to the person skilled in the art, for example, by combination with an organic or inorganic acid or base in a solvent or dispersant, or by anion exchange or cation exchange from other salts. The present invention also includes all salts of the compounds of Formula (I) which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula (I), including the Examples, are intended to be included within the scope of the present invention. In addition, some of the compounds of the instant invention may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

The present invention also relates to processes for the preparation of the compounds of Formula (I) which are described in the following and by which the compounds of the invention are obtainable.

The compounds of Formula (I) according to the invention effect an increase of cGMP concentration via the activation of the soluble guanylate cyclase (sGC), and they therefore may be useful agents for the therapy and prophylaxis of disorders which are associated with a low or decreased cGMP level or which are caused thereby, or for whose therapy or prophylaxis an increase of the present cGMP level is desired. The activation of the sGC by the compounds of Formula (I) can be examined, for example, in the cell-based sGC functional assay described in the Biological Assays below.

The compounds of Formula (I) bind with high potency to sGC. High potency compounds are preferred to enable administration of low human doses. For inhaled delivery applications, high potency compounds may enable use of low human doses, and allow for formulation within the restraints of an inhaled delivery device.

The binding potencies of the compounds of Formula (I) can be determined in a competitive binding assay that uses a labeled sGC ligand. The Biological Assays section below describes an example of a competitive binding assay used to determine the compounds' abilities to displace a radioligand that binds to purified recombinant sGC.

The activity of the compounds in vivo can be assessed in various animal models of hypertension, such as by measuring their acute efficacy in spontaneously hypertensive rats (SHR). In addition, the activity of the compounds can be assessed by measuring the pulmonary and systolic blood pressure in a hypoxia-induced pulmonary hypertension rat model following intratracheal administration of sGC stimulator compounds. In one embodiment, preferred compounds of the Formula (I) achieve a minimum decrease in pulmonary arterial pressure of ≥15 mmHg for the corresponding smaller decrease in systolic blood pressure in the hypoxia-induced pulmonary hypertension rat model. For instance, in one embodiment, preferred compounds of the Formula (I) achieve a minimum decrease in pulmonary arterial pressure of ≥15 mmHg for the corresponding decrease in systolic blood pressure, which decrease is ≤10 mmHg in this assay. The Biological Assays section below describes these in vivo models of hypertension.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. In a preferred embodiment, the term "therapeutically effective amount" means an amount of a pharmaceutical drug that alleviates at least one clinical symptom in a human patient. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. As an example, the dosage a patient receives can be selected so as to achieve the desired reduction in blood pressure; the dosage a patient receives may also be titrated over time in order to reach a target blood pressure. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Disorders and pathological conditions which are associated with a low cGMP level or in which an increase of the cGMP level is desired and for whose therapy and prophylaxis it is possible to use compounds of Formula (I) are, for example, cardiovascular diseases, such as endothelial dysfunction, diastolic dysfunction, atherosclerosis, hypertension, heart failure, pulmonary hypertension (WHO Groups 1-5), which includes pulmonary arterial hypertension (PAH), stable and unstable angina pectoris, thromboses, restenoses, myocardial infarction, strokes, cardiac insufficiency, fibrosis or pulmonary hypertonia, or, for example, erectile dysfunction, asthma (e.g., bronchial asthma), acute respiratory distress syndrome (ARDS), acute lung injury, pulmonary fibrosis, chronic kidney disease, chronic kidney insufficiency, cystic fibrosis, interstitial lung disease, sickle cell anemia, scleroderma, Raynaud's Syndrome, and diabetes. Compounds of Formula (I) can additionally be used in the therapy of cirrhosis of the liver and also for improving a restricted memory performance or ability to learn.

In one embodiment of the invention, the compounds of Formula (I) may be used for treating cardiovascular disease, endothelial dysfunction, diastolic dysfunction, atherosclerosis, hypertension, heart failure, pulmonary hypertension (WHO groups I, II, III, IV), angina pectoris, thrombosis, restenosis, myocardial infarction, stroke, cardiac insufficiency, fibrosis, pulmonary hypertonia, erectile dysfunction, asthma, chronic kidney disease, diabetes, diabetic retinopathy, cirrhosis of the liver, chronic obstructive pulmonary disease (COPD), acute respiratory distress syndrome, acute lung injury, pulmonary fibrosis, cystic fibrosis, or interstitial lung disease.

The compounds of Formula (I) and their pharmaceutically acceptable salts can be administered to animals, preferably to mammals, and in particular to humans, as pharmaceuticals by themselves, in mixtures with one another or in the form of pharmaceutical compositions. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

Subjects of the present invention therefore also are the compounds of Formula (I) and their pharmaceutically acceptable salts for use as pharmaceuticals, their use for activating soluble guanylate cyclase, for normalizing a disturbed cGMP balance and in particular their use in the therapy and prophylaxis of the above mentioned syndromes as well as their use for preparing medicaments for these purposes.

Furthermore, a subject of the present invention is pharmaceutical compositions which comprise as active component an effective dose of at least one compound of Formula (I) and/or a pharmaceutically acceptable salt thereof and a customary pharmaceutically acceptable carrier, i.e., one or more pharmaceutically acceptable carrier substances and/or additives.

Thus, a subject of the invention is, for example, said compound and its pharmaceutically acceptable salts for use as a pharmaceutical, pharmaceutical compositions which comprise as active component an effective dose of the compound of Formula (I) and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceutical compositions according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion.

The pharmaceutical compositions can also be administered by the inhaled route. Dosage forms for inhaled administration may conveniently be formulated as aerosols or dry powders. For compositions suitable and/or adapted for inhaled administration, it is preferred that the compound of Formula (I) is in a particle-size-reduced form, and more preferably the size-reduced form is obtained or obtainable by micronisation.

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

Pharmaceutical compositions suitable for inhaled administration may also take the form of a dry powder inhalable composition. Such a composition can comprise a powder base such as lactose, glucose, trehalose, mannitol or starch, the compound of Formula (I) (preferably in particle-size-reduced form, e.g., in micronised form), and optionally a performance modifier such as L-leucine or another amino acid, and/or metals salts of stearic acid such as magnesium or calcium stearate. In some embodiments, the dry powder inhalable composition comprises a dry powder blend of lactose and the compound of Formula (I) or salt thereof.

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Merck & Co., Inc.), Turbuhaler® (AstraZeneca), Ultrahaler® (Aventis), and the like.

Other suitable administration forms are, for example, percutaneous or topical administration, for example in the form of ointments, tinctures, sprays or transdermal therapeutic systems, or, for example, microcapsules, implants or rods. The preferred administration form depends, for example, on the disease to be treated and on its severity.

The amount of active compound of Formula (I) and/or its pharmaceutically acceptable salts in the pharmaceutical composition normally is from 0.01 to 200 mg, such as from 0.1 to 200 mg, preferably from 1 to 200 mg, per dose, but depending on the type of the pharmaceutical composition it can also be higher. In some embodiments, the amount of active compound of Formula (I) and/or its pharmaceutically acceptable salts in the pharmaceutical composition is from 0.01 to 10 mg per dose. The pharmaceutical compositions usually comprise 0.5 to 90 percent by weight of the compound of Formula (I) and/or their pharmaceutically acceptable salts. The preparation of the pharmaceutical compositions can be carried out in a manner known per se. For this purpose, one or more compounds of Formula (I) and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules, it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically acceptable sodium chloride solution, alcohols such as ethanol, glycerol, polyols, sucrose, invert sugar, glucose, mannitol, vegetable oils, etc. It is also possible to lyophilize the compounds of Formula (I) and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical compositions can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula (I) and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula (I). In general, a daily dose of approximately 0.0001 to 100 mg/kg, in particular, 0.0001 to 0.30 mg/kg or 0.01 to 0.03 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

The compounds of Formula (I) activate soluble guanylate cyclase. Due to this property, apart from use as pharmaceutically active compounds in human medicine and veterinary medicine, they can also be employed as a scientific tool or as an aid for biochemical investigations in which such an effect on soluble guanylate cyclase is intended, and also for diagnostic purposes, for example in the in vitro diagnosis of cell samples or tissue samples. The compounds of Formula (I) and salts thereof can furthermore be employed, as already mentioned above, as intermediates for the preparation of other pharmaceutically active compounds.

One or more additional pharmacologically active agents may be administered in combination with a compound of Formula (I). An additional active agent (or agents) is intended to mean a pharmaceutically active agent (or agents)

that is active in the body, including pro-drugs that convert to pharmaceutically active form after administration, which are different from the compound of Formula (I), and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula (I) in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g., sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazosin, prazosin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); LDL cholesterol lowering agents such as (i) HMG-CoA reductase inhibitors (e.g., simvastatin, lovastatin, pravastatin, cerivastatin, fluvastatin, atorvastatin, and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe); HDL-raising drugs, (e.g., niacin and nicotinic acid receptor agonists, and extended-release versions thereof); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, evacetrapib, and torcetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40; SSTR$^3$ antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, ertugliflozin, canagliflozin, BI-10773, PF-04971729, remogloflozin, TS-071, tofogliflozin, ipragliflozin, and LX-4211); inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR$^5$ receptor (also known as GPBAR$^1$, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formula (I) are also described by the Schemes as follows. In some cases the order of carrying out the steps of reaction schemes may be varied to facilitate the reaction or to avoid unwanted reaction products. The "R" and "X" groups in the Schemes correspond to the variables defined in Formula (I) at the same positions on the structures.

Scheme 1 outlines the general approach to assembling compounds of type S-1d. Starting with an amidine S-1a and coupling with either malononitrile S-1b or lactam S-1c, in the presence of either an inorganic base (e.g., KHCO$_3$) or amine base (e.g., NEt$_3$) respectively, affords pyrimidine containing substrates S-1d.

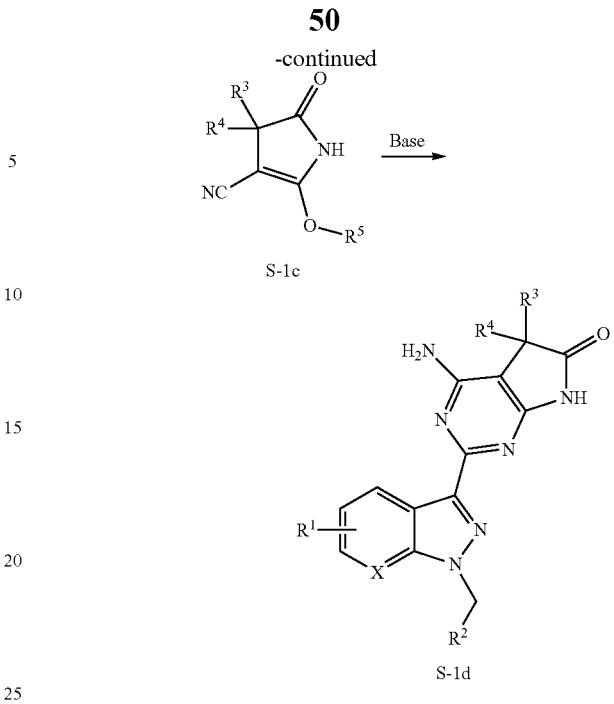

wherein R$^3$=CO$_2$R$^{10}$ or

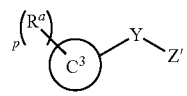

Z' is a Z (e.g., CO$_2$H) or a precursor to Z (CO$_2$H)

Malononitrile type coupling partners can be assembled as outlined in Scheme 2, lines A and B. Intermediate S-2a can either be purchased (R$^4$=Me), or can be generated in one-step from diethyl oxalate through treatment with a Grignard reagent or other organometallic reagents. Condensation of malononitrile with intermediate S-2a, analogous to literature conditions (Hagiwara et. al. *Synthesis* 1974, 9, 669) affords intermediate S-2b. Subsequent 1,4-addition with a Grignard reagent or lithiate in a solvent such as THF at room temperature to −78° C. affords functionalized malononitrile S-1b. An alternate approach to derivatized malononitriles, in which the R$^4$ group is introduced later, is outlined in line B. Starting with a di-alkyl oxalate, condensation with malononitrile analogous to conditions described in the literature (Sentman et. al. *J. Org. Chem.* 1982, 47, 4577) affords intermediate S-2d. Subsequent treatment with an Grignard reagent affords intermediate S-2e, analogous to intermediate S-1b when R$^3$=CO$_2$R$^{10}$.

Scheme 1

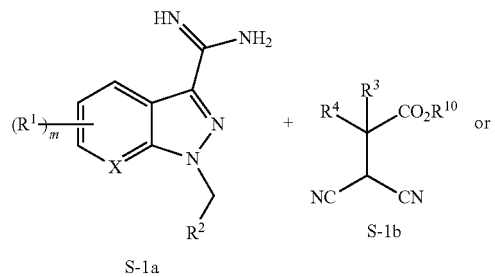

Scheme 2

A.

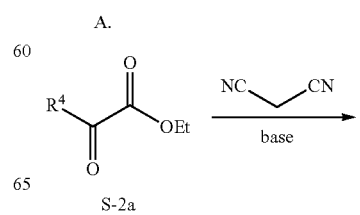

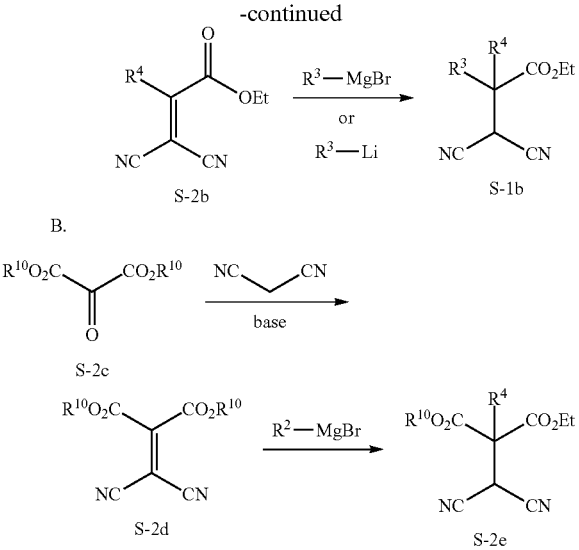

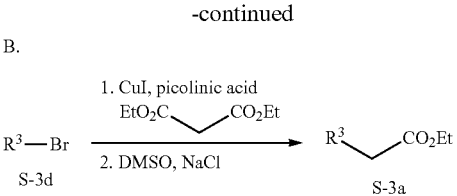

Malononitriles of type S-1b can be cyclized in the presence of alkoxide type bases such as sodium methoxide in methanol or sodium ethoxide in ethanol to form lactams S-1c as shown in Scheme 4. Additionally, functionalized alkyne containing malononitrile S-4a can undergo 1,3-dipolar cycloaddition with functionalized carbon-linked azides in the presence of a copper reagent to afford 1,2,3-triazoles S-4b.

An alternative method for assembling malononitrile type reagents is outlined below in Scheme 3. Functionalized esters S-3a can either be purchased or assembled via copper catalyzed cross-coupling reactions followed by decarboxylation as outlined in line B of Scheme 3. S-3a may also be prepared from the corresponding carboxylic acid by treatment with trimethylsilyl diazomethane or methanol with catalytic sulfuric acid. S-3a may be prepared by the alpha arylation/heteroarylation of esters as described by Buchwald, S. L. et al *Organic Letters* 2009, 11(8), 1773; or by Shen, H. C. et al *Organic Letters* 2006, 8(7), 1447. Additional functionalization of S-3a via alkylation in the presence of a base such as LiHMDS, NaHMDS, NaH or LDA in a solvent such as THF or DMF affords intermediate S-3b. The compound S-3c is prepared by treating compound S-3b with a brominating reagent such as NBS and AIBN in a solvent such as carbon tetrachloride at refluxing temperatures. Alternatively, the compound S-3c may be prepared by reaction with NBS and magnesium perchlorate in acetonitrile solvent at room temperature as described by Yang, D. et al *Journal of Organic Chemistry* 2002, 67(21), 7429. Compound S-3c may also be prepared by treating compound S-3b with a base such as sodium hydride followed by treatment with NBS. Compound S-1b is obtained from S-3c by reaction with malononitrile and a base such as sodium hydride, t-BuOK, $K_2CO_3$ or DBU in a solvent such as THF or DMF at ambient temperature to elevated temperatures.

Scheme 3

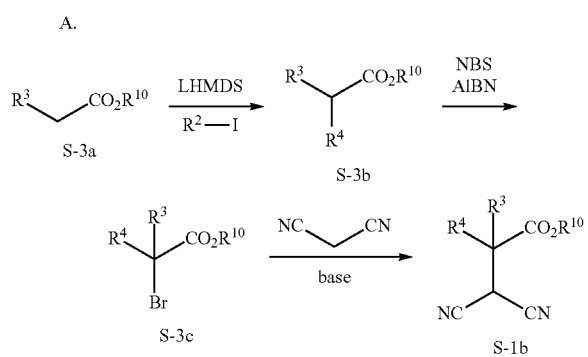

Scheme 4

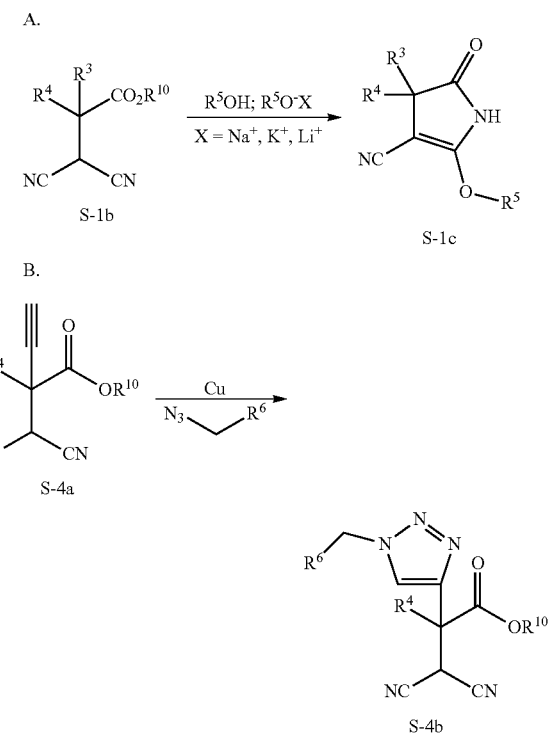

Heterocycles of type S-5e and S-5h can be generated as outlined in Scheme 5, lines A and B. S-5e can be prepared as outlined in line A starting from commercially available ethyl 2-cyanopropanoate S-5a, in which treatment with chlorotrimethyl silane in water affords amide S-5b. Subsequent cyclization with a functionalized α-bromoketone reagent such as S-5c in the presence of silver triflate leads to S-5d. From here, bromination with NBS and LiHMDS, followed by treatment with malononitrile, affords target substrates such as S-5e. S-5h can be accessed as outlined in line B, starting from commercially available thioamide S-5f. Treatment with α-bromoketones such as S-5c, followed by bromination with KBr and hydrogen peroxide and followed lastly by treatment with malononitrile affords substrates of type S-5h.

Scheme 5

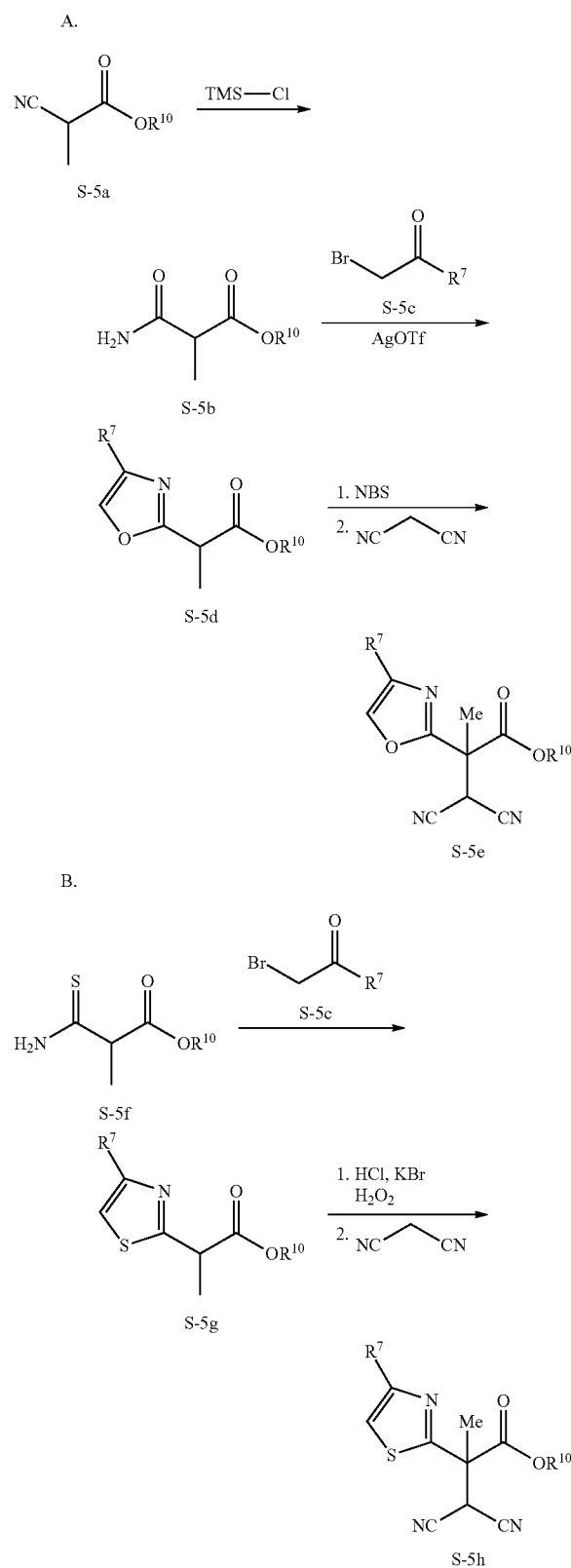

Scheme 6

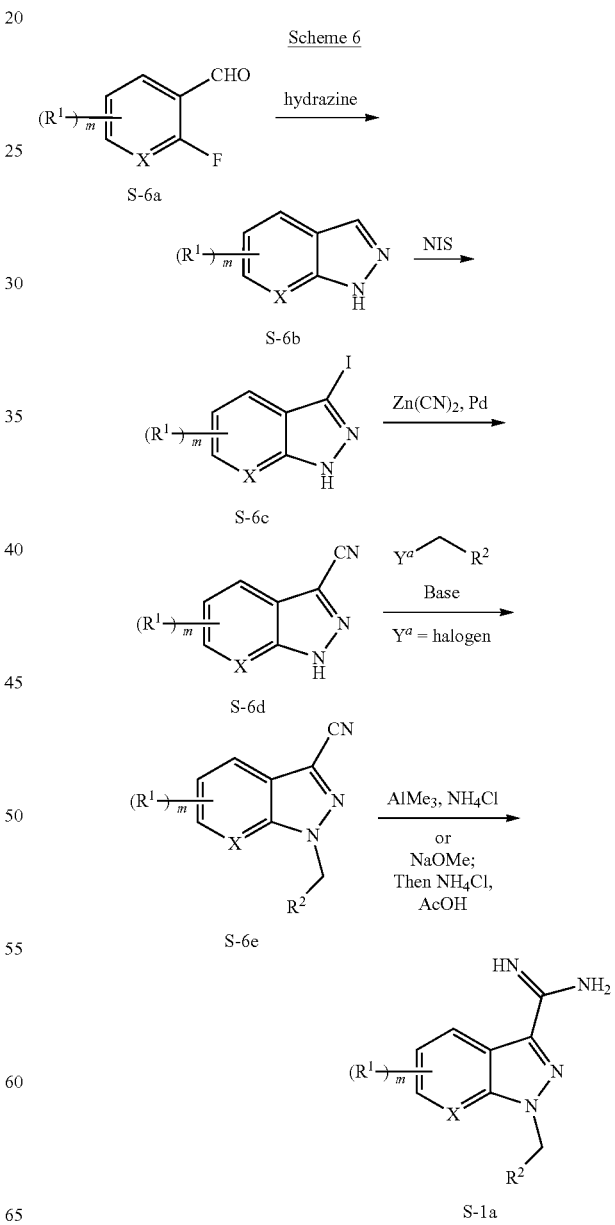

aldehyde S-6a, condensation with hydrazine while heating in a solvent such as DMA affords the indazole S-6b. Subsequent iodination with an iodination reagent such as NIS in a solvent such as DCM or DMA, followed by palladium catalyzed cross coupling with zinc cyanide using a catalyst such as $Pd_2(dba)_3$ and DPPF in a solvent such as DMA affords the nitrile intermediate S-6d. Alkylation of the indazole with bromo or iodo halide using a base such as cesium carbonate, sodium hydride or $K_2CO_3$ in a solvent such as DMF, DMA or acetonitrile at ambient temperature to 100° C. gives S-6e. Conversion of the nitrile to amidines of type S-1a can be accomplished with a reagent such as amino(chloro)methylaluminum, prepared from trimethylaluminum and ammonium chloride, in a non-polar solvent such as toluene while heating as described by Garigipati, R. S. et al. *Tetrahedron Letters* 1990, 31(14), 1969. Alternative conditions utilize sodium methoxide followed by treatment with ammonium chloride in the presence of acetic acid.

The general approach to amidines S-1a is outlined in Scheme 6 below. Starting with generic type 2-fluorobenz- As described in Scheme 7, aza-indazole substrates S-7a can be further functionalized by oxidation of the pyridine with mCPBA in acetic acid solvent to afford the N-oxide, followed by treatment with POCl₃ to afford the alpha-chloro substituted intermediate S-7c that can be subsequently converted to amidine S-7d.

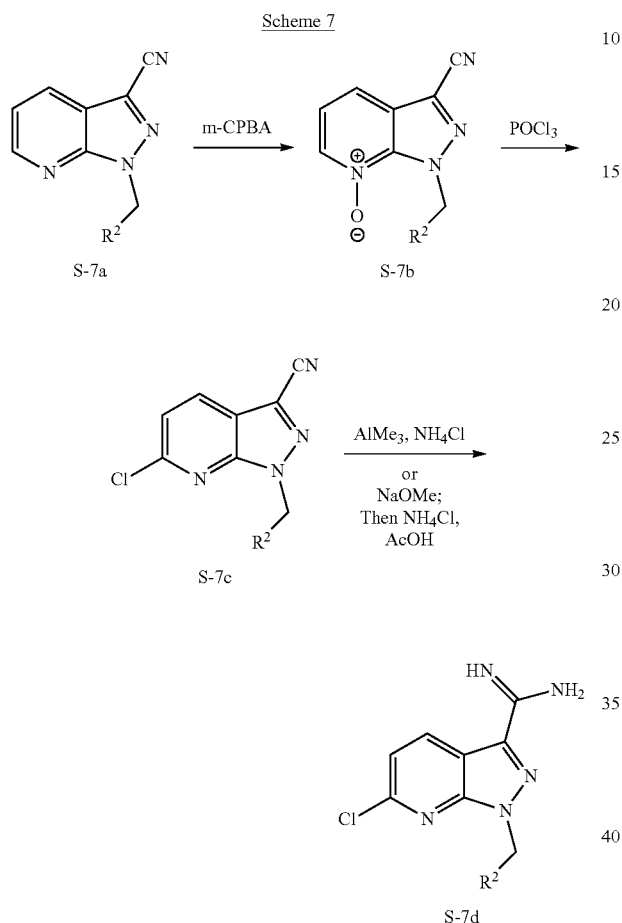

Some common routes for final compound synthesis are outlined in the Schemes 8, 9 and 10 below. One approach as generically outlined in Scheme 8, is coupling of functionalized malononitrile S-8c or lactam S-8b with amidines to afford intermediates of type S-8d bearing an ester. Amidine coupling with malonontrile reagents of type S-8c, typically are performed in an alcohol solvent such as tBuOH at RT to 80° C. and utilize a base such as KHCO₃, though reactions can also be run in the absence of base. Amidine couplings with activated lactam structures such as S-8b are typically ran in solvents such as THF at room temperature to 80° C. with an alkyl amine base such as Et₃N. Subsequent hydrolysis with a base such as lithium hydroxide in a solvent mixture containing a polar organic solvent such as dioxane or acetonitrile in combination with water affords final products S-8e. Chiral resolution of enantiomers can occur at any of the stages up to and including post hydrolysis formation of S-8e. This resolution includes chiral resolution of functionalized malonitriles S-8c or lactams S-8b or post condensation with amidines at the ester intermediate S-8d or post hydrolysis resolution of acid S-8e.

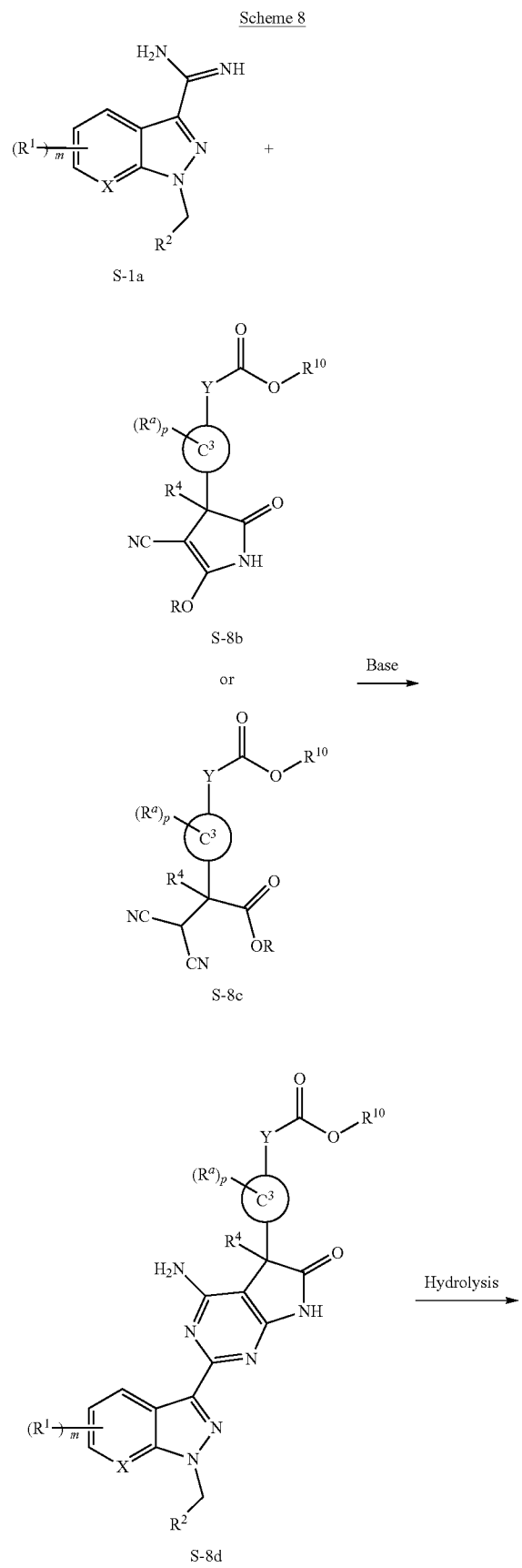

-continued

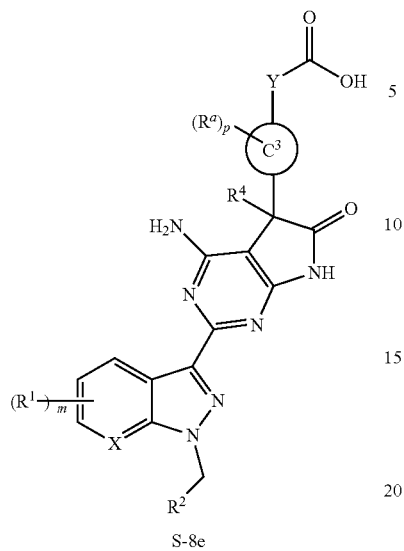

S-8e

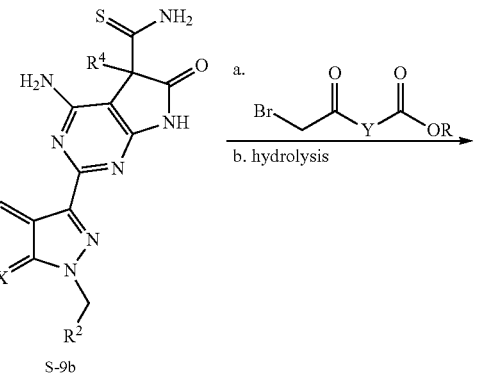

S-9b

Another method for the synthesis of functionalized acids linked to thiazoles is outlined in Scheme 9. Starting from either chiral or racemic S-9a (assembled as generally outlined in Scheme 1), conversion to the amide with ammonia in methanol, followed by treatment with Lawesson's reagent in toluene at elevated temperatures affords thioamide intermediate S-9b. Coupling with bromo-functionalized β-keto esters in an alcohol such as ethanol at elevated temperatures followed by hydrolysis affords acid S-9c. In addition to generating chiral S-9a through use of chiral reagents of type S-1c or resolution of ester S-9a, chiral resolution can occur at thioamide S-9b or the subsequent ester or acid S-9c.

Scheme 9

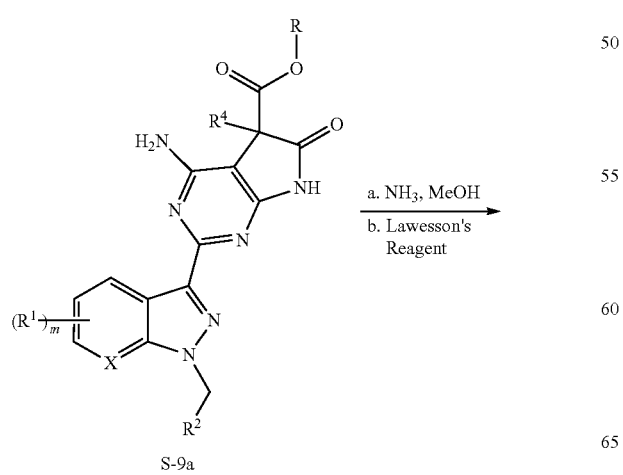

S-9a

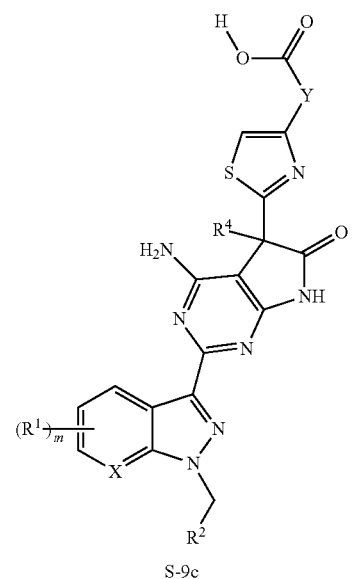

S-9c

Additionally, compounds of type S-10b can be formed from the more active single enantiomers of type S-8e (general synthesis outlined in Scheme 8) using common coupling reagents such as O-(benzotriazol-1-yl)-N,N,N',N'-tetramethyluronium tetrafluoroborate to couple with amino-esters. The ester intermediate S-10a can then be hydrolyzed to provide S-10b.

Scheme 10

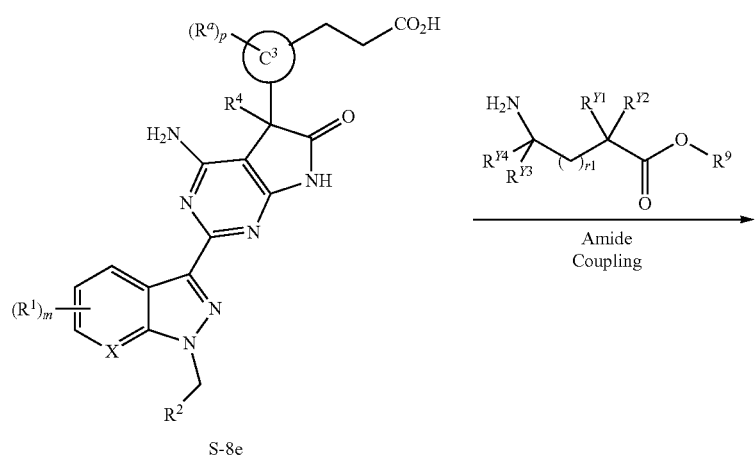

S-8e

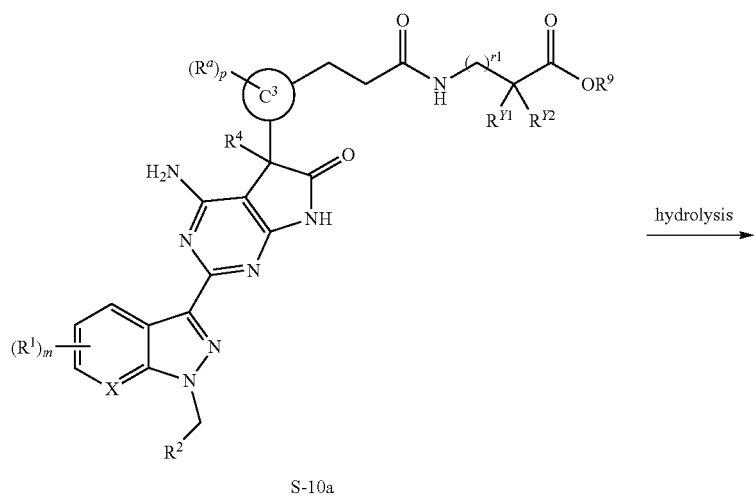

S-10a

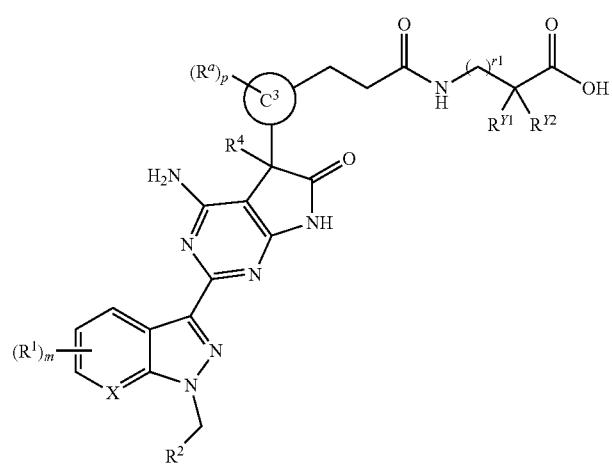

S-10b

Compounds of type S-11b can be formed from type S-8e (general synthesis outlined in Scheme 8). The nitrile compounds type S-11a can be formed by conversion of the carboxylic acid to the corresponding amide using reagent such as Boc anhydride and TFA, followed by dehydration of the amide to form the nitrile with reagents such as trifluoroacetic anhydride. Treatment of compounds of type S-11a with sodium azide or TMS-azide provides tetrazole compounds type S-11b.

Scheme 11

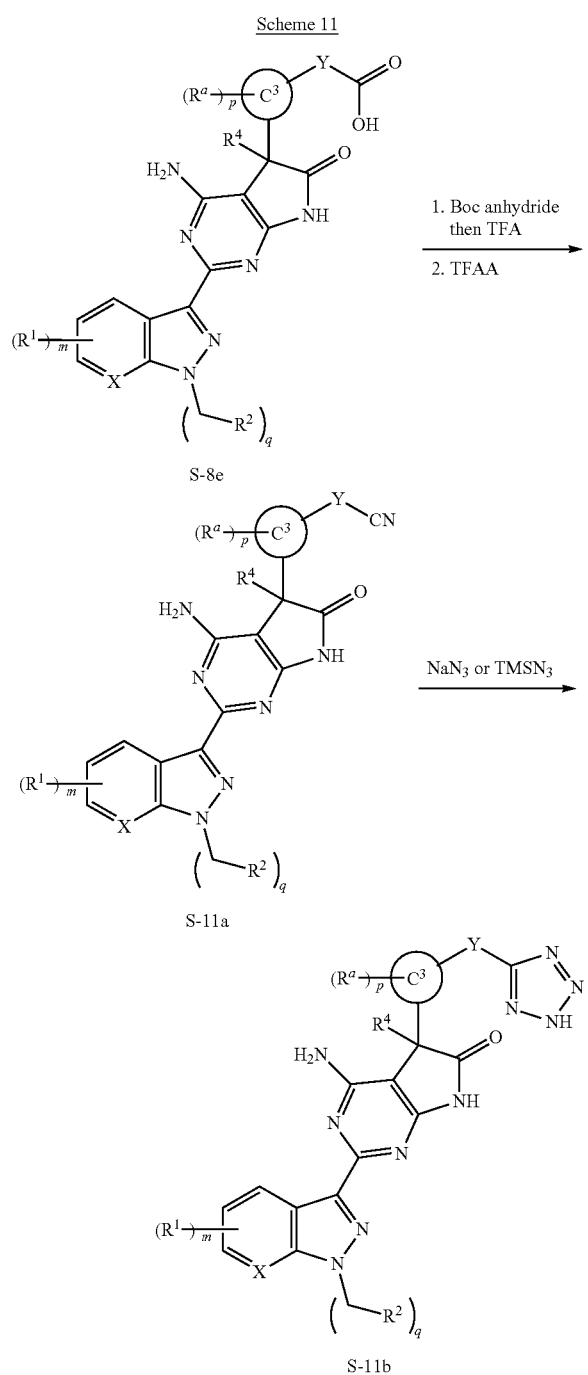

Compounds of the present invention possess an asymmetric center at the carbon bearing the $R^3$ and $R^4$ substituents which can be either R or S configuration. These enantiomeric mixtures may be separated or resolved to single enantiomers using chiral SFC chromatography. Racemic material can be resolved to enantiomerically pure compounds at the final step, or one of the earlier steps in the route as outlined in Schemes 8, 9 and 10. For example, intermediates S-1b and S-1c can undergo chiral resolution to afford enantiopure isomers that may be carried on in the coupling with amidines to enantiomerically pure compounds. Alternatively, enantiomeric resolution can be performed post formation of general intermediate S-1d. For example, chiral resolution of intermediates of the type S-8d, S-9b, or S-10a to single enantiomers may be further elaborated to enantiopure compounds or may be resolved at final compounds of type S-8e, S-9c, S-10b. Unless otherwise noted, the examples in the present invention are enantiomerically pure isomers (R or S). Biochemical assay data is listed for the more active enantiomer if only one of the enantiomers is active.

The independent synthesis of diastereomers and enantiomers or their chromatographic separations may be achieved using methods familiar to those skilled in the art and by appropriate modification of the methodology disclosed herein. Their absolute stereochemistry may be determined by X-ray crystallography of crystalline products or crystalline intermediates which are derivatized, if necessary, with a reagent containing an asymmetric center of known absolute stereochemistry, or by vibrational circular dichroism (VCD) spectroscopy.

Throughout the synthetic schemes and examples, abbreviations and acronyms may be used with the following meanings unless otherwise indicated: AIBN=2,2'-azobisisobutyronitrile; Anhydr.=Anhydrous; Aq.=aqueous; atm=atmosphere; bp, b.p.=boiling point; br s=broad singlet; Bu=butyl; t-Bu=tert-butyl; BuLi=butyllithium; t-BuOH, tert-BuOH=tert-butanol; tBuOK=potassium tert-butoxide; $CDCl_3$=deuterated chloroform; $CD_3OD$=Tetradeuteromethanol; CELITE=diatomaceous earth; $CF_3$=trifluoromethyl; cGMP=cyclic guanosine monophosphate; conc, conc.=concentrated, concentrate, concentrates; DBU=1,8-Diazabicyclo[4.3.0]undec-7-ene; DCM=dichloromethane; 1,2-DCE, DCE=1,2-dichloroethane; DETA-NO=Diethylenetriamine/nitric oxide adduct; DMA, DMAC=N,N-dimethylacetamide; DMF=N,N-dimethylformamide; DMSO=dimethylsulfoxide; dppf=1,1'-bis (diphenylphosphino)ferrocene; DTT=dithiothreitol; EAB=egg albumin; EBSS=Earle's balanced salt solution; equiv, eq.=equivalent(s); Et=ethyl; $Et_3N$=triethylamine; EtOAc=ethyl acetate; EtOH=ethanol; GTP=guanosine triphosphate; h, hr=hour; HPLC=High pressure liquid chromatography; Int.=intermediate; iPr=isopropyl; IPA, IP=inflection points; i-PrOH=Isopropanol; IT=intra-tracheal; LCMS, LC/MS=liquid chromatography-mass spectrometry; LDA=lithium diisopropylamide; LiHMDS, LHMDS=lithium bis(trimethylsilyl)amide; min, min.=minute; M=Molar; Me=methyl; MeCN, ACN=acetonitrile; MeI=methyl iodide; MeOH=methanol; mp, m.p.=melting point; mpk=milligrams per kilogram; N=Normal; $N_2$=nitrogen; NaOMe=sodium methoxide; NCS=N-chloro succinimide; NBS=N-bromo succinimide; NaHMDS=sodium bis(trimethylsilyl)amide; NMR=nuclear magnetic resonance; N.D.=not determined; NIS=N-iodo succinimide; PDA=photodiode array; $Pd_2(dba)_3$=tris(dibenzylideneacetone)dipalladium (0); Ph=phenyl; Pr=propyl; psig=pounds per square inch gauge; PTLC, prep TLC=preparative thin layer chromatography; rac=racemic; rt=retention time; RP-HPLC=reverse phase HPLC; RT=room temperature; sat., sat'd=saturated; SFC=supercritical fluid chromatography; sGC=soluble guanylate cyclase; TFA=trifluoroacetic acid; TFAA=trifluoroacetic anhydride; TLC=thin layer chromatography; THF=tetrahydrofuran; TMS=trimethylsilyl; VCD=vibrational circular dichroism; v, v/v=volume, volume to volume; w, w/w=weight, weight to weight.

Columns used in the chiral resolution of stereoisomers are set forth in the examples below as follows: AD=CHIRALPAK® AD; AD-H=CHIRALPAK® AD-H; AS=CHIRALPAK® AS; AS-H=CHIRALPAK® AS-H;

IA=CHIRALPAK® IA; IC=CHIRALPAK® IC; OD-H=CHIRALCEL® OD-H; and OJ-H=CHIRALCEL® OJ-H.

The following examples are provided to more fully illustrate the present invention, and shall not be construed as limiting the scope in any manner. Unless stated otherwise, the following conditions were employed. All operations were carried out at room or ambient temperature (RT), that is, at a temperature in the range 18-25° C. Reactions are generally done using commercially available anhydrous solvents under an inert atmosphere, either nitrogen or argon. Microwave reactions were done using a BIOTAGE Initiator™ or CEM EXPLORER® system. Evaporation of solvent was carried out using a rotary evaporator under reduced pressure (4.5-30 mmHg) with a bath temperature of up to 50° C. The course of reactions was followed by thin layer chromatography (TLC) and/or tandem high performance liquid chromatography (HPLC) followed by electron spray mass spectroscopy (MS), herein termed LCMS, and any reaction times are given for illustration only. The structure of all final compounds was assured by at least one of the following techniques: MS or proton nuclear magnetic resonance ($^1$H NMR) spectrometry, and the purity was assured by at least one of the following techniques: TLC or HPLC. $^1$H NMR spectra were recorded on either a Varian Unity or a Varian Inova instrument at 300, 400, 500 or 600 MHz using the indicated solvent. When line-listed, NMR data are in the form of delta values for major diagnostic protons, given in parts per million (ppm) relative to residual solvent peaks (multiplicity and number of hydrogens). Conventional abbreviations used for signal shape are: s. singlet; d. doublet (apparent); t. triplet (apparent); m. multiplet; br. broad; etc. MS data were recorded on a Waters Micromass or WatersZQ unit, interfaced with a Hewlett-Packard (AGILENT 1100) HPLC instrument, and operating on MASSLYNX/OpenLynx software. Electrospray ionization was used with positive (ES+) or negative ion (ES−) detection; and diode array detection. Purification of compounds by preparative reverse phase HPLC was performed on a GILSON system using a YMC-Pack Pro C18 column (150×20 mm i.d.) eluting at 20 mL/min with a water/acetonitrile (0.1% TFA) gradient (typically 5% acetonitrile to 95% acetonitrile) or using a SUNFIRE Prep C18 OBD 5 μM column (100×30 mm i.d.) eluting at 50 mL/min with a water/acetonitrile (0.1% TFA) gradient. Purification of compounds by preparative mass triggered reverse phase HPLC was performed on Waters MS directed Preparative Scale HPLC. Purification of compounds by preparative thin layer chromatography (PTLC) was conducted on 20×20 cm glass plates coated with silica gel, commercially available from Analtech; or E. Merck. Flash column chromatography was carried out on a glass silica gel column using Kieselgel 60, 0.063-0.200 mm ($SiO_2$), or on a BIOTAGE $SiO_2$ cartridge system using the BIOTAGE Horizon and BIOTAGE SP-1 systems; or a Teledyne Isco $SiO_2$ cartridge using the COMBIFLASH Rf system. Chemical symbols have their usual meanings, and the following abbreviations have also been used: h or hr (hours), min (minutes), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), μM (micromolar), nM (nanomolar), ca (circa/about).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In some of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate.

Any intermediates described below may be referred to herein by their number preceded by "I-." For illustration, the racemic parent title compound would be referred to as Intermediate 37 (I-37, or rac I-37), and the separated stereoisomers are noted as Intermediates 37A and 37B (or I-37A and I-37B). In some examples, compounds having a chiral center were derived synthetically from a single isomer intermediate; e.g., Example 13B—was made using stereoisomer I-11B. In some cases intermediates or examples contain more than one chiral center. In such cases, the separation of isomers may require more than one chiral separation. In such cases, the intermediate or example number can be followed by 2 letters (e.g. I-38AB or Ex-5BA). For these intermediates and examples, the first letter represents the A or B isomer from the first separation and the second letter represents the A or B isomer from the second separation. Absolute stereochemistry of separate stereoisomers in the Examples and Intermediates was not determined unless stated otherwise in an Example or Intermediate synthesis. An asterisk (*) may be used in a chemical structure drawing that indicates the location of a chiral center.

Intermediate 1

Methyl 3-(4-iodophenyl)-2-methylpropanoate

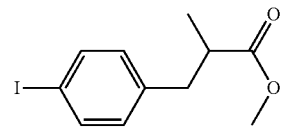

To a flask under an inert atmosphere of nitrogen, containing a solution of methyl 3-(4-iodophenyl)propanoate (2 g, 6.89 mmol) in 27 mL THF at −78° C. was slowly added a solution of potassium bis(trimethylsilyl)amide (1 M in THF, 8.3 mL, 8.3 mmol). The resulting solution was stirred 30 min at −78° C. before methyl iodide (0.560 mL, 8.96 mmol) was added. The reaction was stirred 2 h at −78° C. then quenched with a 1 M aq. solution of hydrochloric acid. The mixture was extracted with EtOAc (3×). The organic layer was washed with brine, dried over anhydr. $MgSO_4$, filtered and concentrated in vacuo to dryness. The residue was purified by silica gel chromatography using an EtOAc:hexane gradient to afford the racemic title product I-1. $^1$H NMR (500 MHz, $CDCl_3$) δ 7.66-7.60 (m, 2H), 6.94 (d, J=8.2 Hz, 2H), 3.67 (s, 3H), 2.99 (dd, J=13.5, 7.1 Hz, 1H), 2.73 (h, J=7.0 Hz, 1H), 2.64 (dd, J=13.4, 7.4 Hz, 1H), 1.18 (d, J=6.9 Hz, 3H); m/z=305 (M+1).

Intermediate 2

Methyl 3-(4-iodophenyl)-2,2-dimethylpropanoate

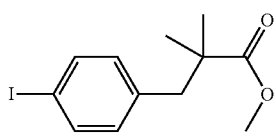

To a flask under an inert atmosphere of nitrogen, containing a solution of methyl isobutyrate (1.16 mL, 10.1 mmol) in THF (34 mL) at −78° C. was slowly added a solution of lithium diisopropylamide (1 M in THF, 11.1 mL, 11.1 mmol). The resulting solution was stirred 1 h at −78° C. before a solution of 4-iodobenzyl bromide (3 g, 10.10 mmol) in THF (2 mL) was added. The reaction was allowed to warm up to RT and stirred 2 h, then quenched by the addition of sat. aq. NH$_4$Cl. The mixture was extracted with EtOAc (3×). The organic layer was washed with brine, dried over anhydr. MgSO$_4$, filtered and concentrated in vacuo to dryness. The residue was purified by silica gel chromatography using an EtOAc:hexane gradient to afford the racemic title product I-2. $^1$H NMR (500 MHz, CDCl$_3$) δ 7.65-7.54 (m, 2H), 6.94-6.81 (m, 2H), 3.68 (s, 3H), 2.82 (s, 2H), 1.20 (s, 6H); m/z=319 (M+1).

Intermediate 3

Ethyl 3-(3-iodophenyl)-2,2-dimethylpropanoate

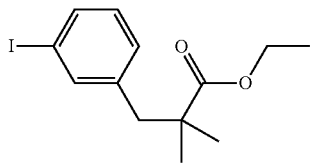 [SMILES: CCOC(=O)C(C)(C)Cc1cccc(I)c1]

The title compound I-3 was prepared using essentially the same procedures described for intermediate 2 using 3-iodobenzyl bromide and ethyl isobutyrate as starting material. m/z=333 (M+1)

Intermediate 4

Tert-butyl 3-(6-bromopyridin-3-yl)-2,2-dimethylpropanoate

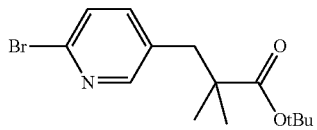 [SMILES: CC(C)(C)OC(=O)C(C)(C)Cc1ccc(Br)nc1]

The title compound I-4 was prepared using essentially the same procedures described for intermediate 2 using 2-bromo-5-(bromomethyl)pyridine and t-butyl isobutyrate as starting material. m/z=316 (M+1)

Intermediate 5

Methyl 3-(2-bromo-4-iodophenyl)propanoate

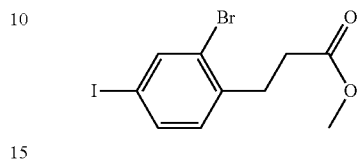

Step A—3-(2-bromo-4-nitrophenyl)propanoic acid

To a flask containing 3-(4-nitrophenyl)propanoic acid (8 g, 41.0 mmol) in water (40 mL) and concentrated sulfuric acid (40 mL) at 0° C. was slowly added N-bromosuccinimide (9.48 g, 53.3 mmol). The resulting mixture was stirred in the dark for 2 h at 40° C., then diluted with water and extracted with EtOAc (3×). The organic layer was washed with brine, dried over anhydr. Na$_2$SO$_4$, and filtered. The filtrate was concentrated in vacuo to dryness to afford the title compound.

Step B—methyl 3-(2-bromo-4-nitrophenyl)propanoate

Into a flask were placed 3-(2-bromo-4-nitrophenyl)propanoic acid (16 g, 40.9 mmol) concentrated sulfuric acid (20 mL) and MeOH (40 mL). The resulting mixture was stirred for 2 h at 80° C. then cooled to RT, diluted with water and extracted with EtOAc (3×). The organic layer was washed with brine, dried over anhydr. Na$_2$SO$_4$, and filtered. The filtrate was concentrated in vacuo and the residue was purified by silica gel column chromatography with EtOAc: petroleum ether (0-30%) to afford the title compound.

Step C—methyl 3-(4-amino-2-bromophenyl)propanoate

Into a flask were placed methyl 3-(2-bromo-4-nitrophenyl)propanoate (10.0 g, 24.3 mmol), iron (5.4 g, 97 mmol) and ammonium chloride (3.9 g, 72.9 mmol) in a mixture of ethanol (80 mL) and water (20 mL). The resulting mixture was stirred for 1 h at 90° C. The solid was filtered out, and washed with EtOAc. The organic layer was washed with brine, dried over anhydr. Na$_2$SO$_4$, and filtered. The filtrate was concentrated in vacuo and the residue was dissolved in water, the pH of the solution was adjusted to pH 1 with hydrochloric acid (1 N). The resulting solution was extracted with EtOAc (2×). The pH adjusted to 10 with sodium hydroxide (1 N). The resulting solution was extracted with EtOAc (3×) and the organic layer combined, dried over anhydr. Na$_2$SO$_4$, filtered and the filtrate was concentrated in vacuo to dryness to afford the title compound.

Step D—methyl 3-(2-bromo-4-iodophenyl)propanoate

To a flask containing methyl 3-(4-amino-2-bromophenyl) propanoate (5.0 g, 19.4 mmol), concentrated hydrochloric acid (15 mL) and water (13 mL) at 0° C. was added dropwise a solution of sodium nitrite (1.47 g, 21.3 mmol) in water (2 mL). The mixture was stirred for 1 h at 0° C. before potassium iodide (6.43 g, 38.7 mmol) was added. After an additional 5 min at 0° C. the mixture was diluted with Et₂O and washed with of aq. sat. NaHSO₄. The organic layer was dried over anhydr. MgSO₄, and filtered. The filtrate was concentrated in vacuo. The residue was purified by silica gel column chromatography with EtOAc:petroleum ether (0-30%) to afford the title compound I-5. ¹H NMR (300 MHz, CDCl₃) δ 7.85 (d, J=1.8 Hz, 1H), 7.51 (dd, J=1.8, 8.4 Hz, 1H), 6.97 (d, J=8.4 Hz, 1H), 3.65 (s, 3H), 2.98 (t, J=7.5 Hz, 2H), 2.60 (t, J=7.5 Hz, 2H).

Intermediate 6

Methyl 3-(4-iodo-2-methoxyphenyl)propanoate

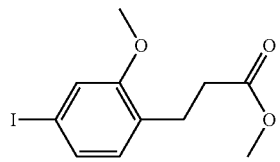

Step A—7-iodochroman-2-one

Into a flask were placed 3-(4-iodophenyl)propanoic acid (6.0 g, 21.7 mmol), trifluoroacetic acid (109 mL) and [bis(trifluoroacetoxy)iodo]benzene (14.0 g, 32.6 mmol). The mixture was cooled to 0° C. and of boron trifluoride etherate (4.1 mL, 32.6 mmol) was added dropwise. The resulting mixture was stirred for 16 h at RT. The reaction was quenched by the addition of aq. sat. NaHCO₂, extracted with EtOAc (3×). The organic layer was washed with brine, dried over anhydr. Na₂SO₄, and filtered. The filtrate was concentrated in vacuo. and the residue was purified by silica gel column chromatography with EtOAc:petroleum ether (0-30%) to afford the title compound.

Step B—3-(2-hydroxy-4-iodophenyl)propanoic acid

Into a flask containing 7-iodochroman-2-one (2.8 g, 10.2 mmol) in a THF (20 mL) water (20 mL) mixture was added LiOH (2.1 g, 51.1 mmol). The resulting mixture was stirred for 16 h at RT. The reaction was quenched by the addition of aq. solution of hydrochloric acid (2 N) extracted with EtOAc (3×). The organic layer was washed with brine, dried over anhydr. Na₂SO₄, and filtered. The filtrate was concentrated in vacuo to dryness to afford the title compound.

Step C—methyl 3-(4-iodo-2-methoxyphenyl)propanoate

Into a flask containing 3-(2-hydroxy-4-iodophenyl)propanoic acid (3.0 g, 10.3 mmol) and iodomethane (1.9 mL, 30.8 mmol) in DMF (50 mL) was added potassium carbonate (5.7 g, 41.1 mmol). The resulting mixture was stirred for 16 h at 50° C. The reaction was quenched by the addition of water extracted with EtOAc (3×). The organic layer was washed with brine, dried over anhydr. Na₂SO₄, and filtered. The filtrate was concentrated in vacuo. The residue was purified by silica gel column chromatography with EtOAc: petroleum ether (0-30%) to afford the title compound I-6. ¹H NMR (300 MHz, CDCl₃): δ 7.49 (dd, J=8.7 Hz, 2.4 Hz, 1H), 7.44 (d, J=2.4 Hz, 1H), 6.61 (d, J=8.7 Hz, 1H), 3.81 (s, 3H), 3.69 (s, 3H), 2.88 (t, J=7.5 Hz, 2H), 2.59 (t, J=7.5 Hz, 2H).

Intermediate 7

Methyl 5-bromo-2,2-dimethyl-4-oxopentanoate

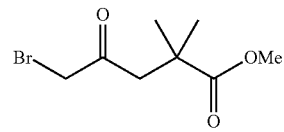

To a flask containing methyl 4-chloro-2,2-dimethylpent-4-enoate (19.0 mL, 113 mmol) in a ethanol (100 mL) water (75 mL) mixture at 0° C. was added dropwise bromine (5.95 mL, 115 mmol) and the reaction was stirred 3 h at 0° C. The reaction was diluted with water extracted with DCM (3×). The organic layers were combined washed with aq. sat. NaHCO₃ (2×) and Brine (1×), dried over anhydr. MgSO₄, and filtered. The filtrate was concentrated in vacuo to dryness to afford the title compound I-7. ¹H NMR (500 MHz, CDCl₃): δ 3.86 (s, 2H); 3.67 (s, 3H); 2.93 (s, 2H); 1.26 (s, 6H).

Intermediate 8

Trans-ethyl 2-(2-bromoacetyl)cyclopropane-1-carboxylate

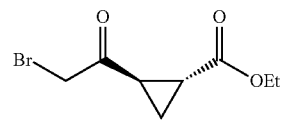 [SMILES: CCOC(=O)[C@@H]1C[C@H]1C(=O)CBr]

To a flask containing trans-ethyl 2-acetylcyclopropanecarboxylate (700 mg, 4.48 mmol) in ethanol (14 mL) at 0° C. was added dropwise bromine (0.28 mL, 5.38 mmol). The resulting mixture was stirred for 3 h at 0° C. and 16 h at RT. The reaction solution was quenched by the addition of water, extracted with DCM. The organic layers combined, washed with aq. sat. NaHCO₃ and brine, dried over anhydr. MgSO₄, and filtered. The filtrate was concentrated in vacuo to dryness to afford the title product. ¹H NMR (300 MHz, CDCl₃) δ 4.22-4.09 (m, 2H), 4.05 (s, 2H), 2.75-2.68 (m, 1H), 2.29-2.23 (m, 1H), 1.59-1.48 (m, 2H), 1.32-1.26 (m, 3H).

Intermediate 9

Methyl 1-(3-bromo-2-oxopropyl)cyclopropane-1-carboxylate

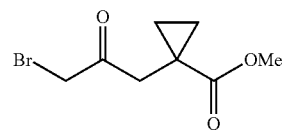 [SMILES: COC(=O)C1(CC(=O)CBr)CC1]

Step A—tert-butyl 1-(2-(bromomethyl)allyl)cyclopropane-1-carboxylate

To a flask, under an inert atmosphere of nitrogen, containing diisopropylamine (8.90 g, 88 mmol) in THF (75 mL) at −78° C. was added dropwise n-butyllithium (32.3 mL, 81 mmol, 2.5M in THF). The resulting mixture was slowly warmed to RT and stirred for 30 min at RT then cool back down to −78° C. tert-butyl cyclopropanecarboxylate (10 g, 70.3 mmol) was added dropwise and the resulting mixture was stirred for 3 h at −78° C. before 2,3-dibromoprop-1-ene (15.5 g, 77 mmol) was added dropwise. The resulting mixture was slowly warmed up to RT and stirred for 16 h at RT. The reaction was quenched by the addition of aq. sat. NH$_4$Cl, extracted with EtOAc (3×). The organic layers were combined, dried over anhydr. Na$_2$SO$_4$, and filtered. The filtrate was concentrated in vacuo. The residue was purified by silica gel column chromatography with EtOAc:petroleum ether (0-10%) to afford the title compound.

Step B—1-(3-bromo-2-oxopropyl)cyclopropane-1-carboxylic acid

To a flask containing tert-butyl 1-(2-(bromomethyl)allyl)cyclopropane-1-carboxylate (1.0 g, 3.83 mmol) in a ethanol (5 mL), and water (4 mL) mixture at 0° C. was added bromine (673 mg, 4.21 mmol). The resulting mixture was stirred for 4 h at RT then concentrated in vacuo to afford the crude title material that was used directly in step C.

Step C—methyl 1-(3-bromo-2-oxopropyl)cyclopropane-1-carboxylate

To a flask containing crude 1-(3-bromo-2-oxopropyl)cyclopropane-1-carboxylic acid (assumed 3.83 mmol) in MeOH (10 mL) was added sulfuric acid (0.5 mL, 9.38 mmol) and the resulting mixture was stirred for 2 h at reflux. The reaction mixture was cooled to RT, diluted with EtOAc washed with aq. sat. NaHCO$_3$ (2×) and brine, dried over anhydr. Na$_2$SO$_4$, and filtered. The filtrate was concentrated in vacuo. The residue was purified by silica gel column chromatography with EtOAc:petroleum ether (5-15%) to afford I-9. $^1$H NMR (400 MHz, CDCl$_3$) δ 4.00 (s, 2H), 3.66 (s, 3H), 2.86 (s, 2H), 1.45-1.35 (m, 2H), 0.93-0.84 (m, 2H).

Intermediate 10, 10A and 10B

Ethyl-2-(dicyanomethyl))-2-methylbut-3-ynoate and the S and R Isomers Thereof

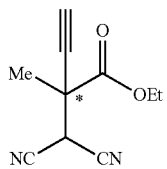

To a flask containing anhydr. LiCl (25.8 mg, 0.609 mmol) in THF (1 mL), was added a solution of ethynylmagnesium bromide (1.3 mL, 0.64 mmol, 0.5M in THF). The reaction was stirred at RT for 0.5 h. The resulting solution was then quickly added dropwise via syringe to a solution of ethyl 3,3-dicyano-2-methylprop-2-enoate (0.609 mL, 0.609 mmol, 1M solution in benzene) (prepared according to Hagiware et. al. *Synthesis* 1974, 9, 669) in THF (22.5 mL) at −10° C. The reaction was stirred for 10 min then quenched with sat. aq. NH$_4$Cl and diluted with water and EtOAc. The layers were separated and the organic layer was dried over anhydr. Na$_2$SO$_4$, and concentrated in vacuo to dryness. The residue was purified by silica gel chromatography using an EtOAc:hexanes gradient to afford the racemic title product I-10. The racemic material was resolved using chiral SFC (OJ-H column) to afford isomers I-10A (faster eluting) and I-10B (slower eluting). $^1$H NMR (500 MHz, CDCl$_3$): δ 4.34 (2H, q, J=7.2 Hz), 4.31 (1H, s), 2.66 (1H, s), 1.80 (3H, s), 1.35 (3H, t, J=7.1 Hz).

Intermediate 11, 11A and 11B

Ethyl 3,3-dicyano-2-(4-(3-methoxy-3-oxopropyl)phenyl)-2-methylpropanoate and the S and R Isomers Thereof

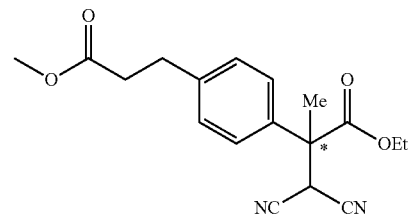 [SMILES: CCOC(=O)C(C)(c1ccc(CCC(=O)OC)cc1)C(C#N)C#N]

To a flask under an inert atmosphere of nitrogen, containing a solution of methyl 3-(4-iodophenyl)propanoate (1.3 g, 4.48 mmol) in THF (6 mL) at −40° C. was slowly added isopropylmagnesium chloride lithium chloride complex (3.9 mL, 5.18 mmol, 1.3 M in THF). The resulting solution was stirred 1 h at −30° C. then cooled −50° C. Ethyl 3,3-dicyano-2-methylprop-2-enoate (3.0 mL, 3.05 mmol, 1 M in benzene) (prepared according to Hagiware et. al. *Synthesis* 1974, 9, 669) was slowly added and the reaction was stirred for 1 h at −50° C., then quenched with sat. aq. NH$_4$Cl and diluted with water and EtOAc. The layers were separated and the organic layer was dried over anhydr. Na$_2$SO$_4$, and concentrated in vacuo to dryness. The residue was purified by silica gel chromatography using an EtOAc/petroleum ether (0%-30%) gradient to afford the racemic title product I-11. The racemic material was resolved using Chiral SFC (CHIRALPAK® AD) to afford isomers I-11A (faster eluting) and I-11B (slower eluting). $^1$H NMR (400 MHz, CDCl$_3$) δ 7.32-7.19 (m, 4H), 4.45 (s, 1H), 4.36-4.14 (m, 2H), 3.67 (s, 3H), 2.96 (t, J=7.8 Hz, 2H), 2.64 (dd, J=8.4, 7.2 Hz, 2H), 1.97 (s, 3H), 1.25 (t, J=7.1 Hz, 3H); m/z=329 (M+1).

Using a similar procedure described for the synthesis of intermediate 10 or 11, the following compounds in Table 1 were prepared using from commercial starting reagents or compounds known in the literature.

TABLE 1

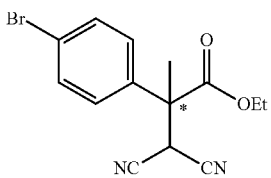 [SMILES: CCOC(=O)C(C)(c1ccc(Br)cc1)C(C#N)C#N]

| Int. | Chiral Resolution Column | R³ | m/z (M + 1) |
|---|---|---|---|
| 12 | — | 4-methoxycarbonyl-α-methylbenzyl | 343 |
| 13A 13B | IA | 4-(2-methoxy-2-oxopropan-2-yl)benzyl (gem-dimethyl) | 357 |
| 14 | — | 2-bromo-4-(methoxycarbonylmethyl)benzyl | 407 |
| 15A 15B | AS | 3-(methoxycarbonylmethyl)benzyl | 329 |
| 16 | — | 3-(2-ethoxy-2-oxopropan-2-yl gem-dimethyl)benzyl | 371 |
| 17 | — | 2-methoxy-4-(methoxycarbonylmethyl)benzyl | 357 (M − 1) |
| 18 | — | 3-(methoxycarbonyl)benzyl | ¹H NMR (400 MHz, CDCl₃) δ 8.13-8.03 (m, 2H), 7.62-7.50 (m, 2H), 4.54 (s, 1H), 4.36-4.20 (m, 2H), 3.94 (s, 3H), 2.04 (s, 3H), 1.25 (t, J = 7.1 Hz, 3H). |
| 19 | — | (5-bromopyridin-2-yl)methyl | 324 |
| 20 | — | (5-(2-tert-butoxy-2-oxopropan-2-yl)pyridin-2-yl)methyl | 400 |

Intermediate 21, 21A and 21B

Ethyl 2-(4-bromophenyl)-3,3-dicyano-2-methylpropanoate and the S and R Isomers Thereof

Step A—ethyl 2-(4-bromophenyl)propanoate

To a flask containing ethyl 2-(4-bromophenyl)acetate (20.0 g, 82.9 mmol) in THF (200 mL) at 0° C. was added dropwise a solution of lithium bis(trimethylsilyl) amide (99.6 mL, 99.6 mmol, 1M in THF). The resulting solution was stirred for 1 h at 0° C. then iodomethane (11.7 g, 82.4 mmol) was added dropwise at 0° C. The reaction mixture was allowed to warm up to RT for 2 h and quenched by the addition of sat. aq. NH₄Cl. The resulting solution was extracted with EtOAc (3×) and the organic layers were combined, dried over anhydr. Na₂SO₄ filtered and the filtrate was concentrated in vacuo to dryness. The residue was purified by silica gel chromatography using EtOAc:petroleum ether to afford the title compound.

Step B—Ethyl 2-bromo-2-(4-bromophenyl)propanoate

Into a flask were placed ethyl 2-(4-bromophenyl)propanoate (19.5 g, 75.8 mmol), 2,2'-azobisisobutyronitrile (1.25 g, 7.61 mmol) and N-bromosuccinimide (16 g, 89.9 mmol) in tetrachloromethane (100 mL). The resulting solution was stirred for 3 h at 80° C. then quenched by the addition of sat. aq. sodium thiosulfatepentahydrate. The resulting solution was extracted with EtOAc (3×) and the organic layers were combined, dried over anhydr. Na₂SO₄ filtered and the filtrate was concentrated in vacuo to dryness. The residue was purified by silica gel chromatography using EtOAc:petroleum ether to afford the title compound.

Step C—Ethyl 2-(4-bromophenyl)-3,3-dicyano-2-methylpropanoate

Into a flask containing sodium hydride (1.5 g, 62.5 mmol) in DMF (200 mL) at 0° C. was added in portions propanedinitrile (2.4 g, 36.3 mmol). The resulting solution was stirred for 30 min at 0° C. before ethyl 2-bromo-2-(4-bromophenyl) propanoate (10.0 g, 29.8 mmol) was added in portions. The resulting solution was stirred an additional 30 min at 0° C. then 16 h at RT. The reaction was quenched by the addition of brine, extracted with EtOAc (3×). The organic layers were combined, dried over anhydr. Na₂SO₄ filtered and the filtrate was concentrated in vacuo to dryness. The residue was purified by silica gel chromatography using EtOAc:petroleum ether to afford the title racemic compound I-21. The racemic material was resolved using Chiral SFC (CHIRALPAK® OJ-H) to afford isomers I-21A (faster eluting) and I-21B (slower eluting). ¹H NMR (300 MHz, CDCl$_3$) δ 7.57 (d, J=8.7 Hz, 2H), 7.25 (d, J=7.8 Hz, 2H), 4.44 (s, 1H), 4.33-4.20 (m, 2H), 1.98 (s, 3H), 1.25 (d, J=7.2 Hz, 3H); m/z=319 (M−1).

Intermediate 22

Methyl 1-(azidomethyl)cyclopropane-1-carboxylate

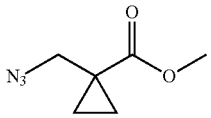

To a closed vial containing a solution of sodium azide (471 mg, 7.25 mmol) in DMSO (40 mL) at RT was added methyl 1-(bromomethyl)cyclopropanecarboxylate (1 g, 5.18 mmol). The resulting solution was stirred 48 h at 45° C. The reaction was allowed to cool down to RT and quenched by the addition of water. The mixture was extracted with Et$_2$O (2×). The organic layer was dried over anhydr. MgSO$_4$, filtered and concentrated in vacuo to dryness to afford I-22. m/z=156 (M+1).

Intermediate 23

Methyl 2-azido-2-methylpropanoate

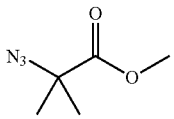

To a vial containing a solution of sodium azide (2.6 g, 40 mmol) and methyl 2-bromo-2-methylpropanoate (1.3 mL, 10 mmol) in 10 mL of a 1:1 DCM:water mixture at RT was added tetrabutylammonium hydrogen sulfate (700 mg, 2.0 mmol). The resulting solution was stirred 48 h at RT. The organic layer was washed with water (2×), dried over anhydr. MgSO$_4$, filtered and concentrated in vacuo to dryness to afford I-23. $^1$H NMR (500 MHz, CDCl$_3$) δ 3.76 (s, 3H), 1.45 (s, 6H).

Intermediate 24B

Ethyl 3,3-dicyano-2-(1-(3-methoxy-3-oxopropyl)-1H-1,2,3-triazol-4-yl)-2-methylpropanoate A flask under an inert atmosphere of nitrogen, was charged with ethyl-2-(dicyanomethyl))-2-methylbut-3-ynoate I-10B (300 mg, 1.5 mmol), bromotris(triphenylphosphine)copper(I) (144 mg, 0.16 mmol) and DMSO (7.7 mL). To this was added methyl 3-azidopropanoate (500 mg, 3.1 mmol) and the reaction was stirred at 50° C. for 18 h. The reaction mixture was diluted with EtOAc, and water. The mixture was extracted with EtOAc (3×). The organic layer was washed with brine (2×), dried over anhydr. MgSO$_4$, and filtered. The filtrate was concentrated in vacuo. The residue was purified by silica gel column chromatography with EtOAc:hexane (0-100%) to afford the title compound I-24B. $^1$H NMR (500 MHz, CDCl$_3$) δ 7.77 (s, 1H), 4.94 (s, 1H), 4.67 (t, J=6.3 Hz, 2H), 4.30 (qd, J=7.2, 1.3 Hz, 2H), 3.70 (s, 3H), 2.99 (t, J=6.3 Hz, 2H), 1.95 (s, 3H), 1.30 (t, J=7.1 Hz, 3H); m/z=320 (M+1).

Using a similar procedure to that described for the synthesis of intermediate I-24B, the following compounds in Table 2 were prepared from either commercial starting reagents or compounds known in the literature.

TABLE 2

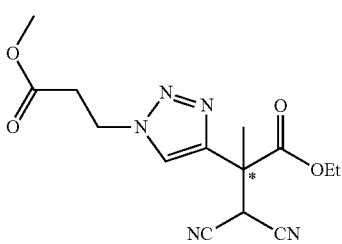 [SMILES: CCOC(=O)C(C)(c1cn(CCC(=O)OC)nn1)C(C#N)C#N]

| Int. | R$^3$ | m/z (M + 1) |
|---|---|---|
| 25B | ![structure] | 306 |
| 26B | ![structure] | 334 |
| 27B | ![structure] | 348 |
| 28B | ![structure] | 346 |

Intermediate 30

Diethyl 2-(dicyanomethyl)-2-methylmalonate

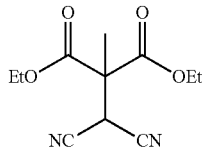 [SMILES: CCOC(=O)C(C)(C(=O)OCC)C(C#N)C#N]

Using the procedure described in WO2015/088885 intermediate 30 was prepared. $^1$H NMR (500 MHz, CDCl$_3$): δ 4.55 (1H, s), 4.28-4.39 (4H, m), 1.82 (3H, s), 1.34 (6H, t, J=7.12 Hz).

Intermediate 31

Diethyl cyclopropyl (dicyanomethyl)propanediote

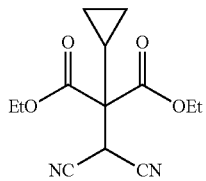 [SMILES: CCOC(=O)C(C(=O)OCC)(C(C#N)C#N)C1CC1]

Using the procedure described in WO2015/088885 intermediate 31 was prepared $^1$H NMR (500 MHz, CDCl$_3$): δ 4.41 (s, 1H); 4.38-4.26 (m, 4H); 1.52-1.45 (m, 1H); 1.33 (t, J=7.14 Hz, 6H); 0.86-0.79 (m, 2H); 0.71-0.66 (m, 2H).

Intermediate 32

Ethyl 3,3-dicyano-2-(4-(3-methoxy-2,2-dimethyl-3-oxopropyl)oxazol-2-yl)-2-methylpropanoate

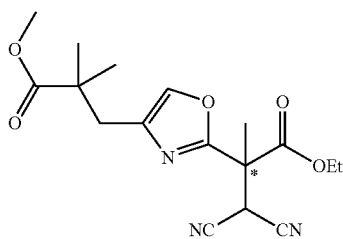 [SMILES: CCOC(=O)C(C)(c1nc(CC(C)(C)C(=O)OC)co1)C(C#N)C#N]

Step A—Ethyl 3-amino-2-methyl-3-oxopropanoate

To a flask containing ethyl 2-cyanopropanoate (20 g, 157 mmol) at 0° C. was added dropwise chlorotrimethylsilane (40.2 mL, 315 mmol) followed by the dropwise addition of water (5.7 mL, 315 mmol) maintaining the reaction temperature at 0° C. The reaction mixture was allow to warm up to RT and stirred for 4 h. The reaction mixture divided into two layers, and the supernatant was discarded. To this was added hexane and the supernatant was discarded again. The residue was then neutralised by the addition of a sat. aq. NaHCO$_3$ at 0° C. The mixture was extracted with EtOAc (3×). The organic layer was washed with brine (2×), dried over anhydr. MgSO$_4$, and filtered. The filtrate was concentrated in vacuo to dryness to afford the title compound.

Step B—Methyl 3-(2-(1-ethoxy-1-oxopropan-2-yl)oxazol-4-yl)-2,2-dimethylpropanoate To a flask containing methyl 5-bromo-2,2-dimethyl-4-oxopentanoate (8.0 g, 33.7 mmol), ethyl 3-amino-2-methyl-3-oxopropanoate (5.0 g, 34.4 mmol) in EtOAc (20 mL) was added silver trifluoromethanesulfonate (8.7 g, 33.7 mmol). The resulting mixture stirred in the dark for 2 h at 90° C., cooled to RT and filtered. The filtrate was concentrated in vacuo and the residue was applied onto a C18 column with acetonitrile/water+0.1% TFA. The residue was purified by silica gel column chromatography with EtOAc:hexane to afford the title compound.

Step C—methyl 3-(2-(2-bromo-1-ethoxy-1-oxopropan-2-yl)oxazol-4-yl)-2,2-dimethylpropanoate To a flask containing methyl 3-(2-(1-ethoxy-1-oxopropan-2-yl)oxazol-4-yl)-2,2-dimethylpropanoate (9.0 g, 31.8 mmol) in THF (300 mL) at 0° C. was added dropwise a solution of lithium bis(trimethylsilyl)amide (34.9 mL, 34.9 mmol, 1 M in THF). The resulting mixture was stirred for 30 min at 0° C. before N-bromosuccinimide (6.2 g, 34.9 mmol) was added in one portion. The resulting mixture was stirred for 30 min at 0° C. then quenched by the addition of sat. aq. NH$_4$Cl. The mixture was extracted with EtOAc (3×). The organic layer was washed with brine, dried over anhydr. Na$_2$SO$_4$, filtered and concentrated in vacuo. to dryness. The residue was purified by silica gel chromatography using an EtOAc/hexane gradient to afford the title product.

Step D—Ethyl 3,3-dicyano-2-(4-(3-methoxy-2,2-dimethyl-3-oxopropyl)oxazol-2-yl)-2-methylpropanoate In a flask containing methyl 3-(2-(2-bromo-1-ethoxy-1-oxopropan-2-yl)oxazol-4-yl)-2,2-dimethylpropanoate (6.16 g, 17.01 mmol), malononitrile (2.25 g, 34.0 mmol) in THF (200 mL) at 0° C. was added DBU (5.13 mL, 34.0 mmol). The resulting mixture was stirred for 30 min at 0° C. then quenched by the addition of sat. aq. NH$_4$Cl. The mixture was extracted with EtOAc (3×). The organic layer was washed with brine, dried over anhydr. Na$_2$SO$_4$, filtered and concentrated in vacuo to dryness. The residue was purified by silica gel chromatography using an EtOAc/hexane gradient to afford the racemic I-32. $^1$H NMR (400 MHz, CDCl$_3$) δ 7.46 (s, 1H), 4.83 (s, 1H), 4.31 (q, J=7.2 Hz, 2H), 3.70 (s, 3H), 2.80 (s, 2H), 2.02 (s, 3H), 1.29 (t, J=7.2 Hz, 3H), 1.23 (d, J=2.8 Hz, 6H); m/z=348 (M+1).

Using a similar procedure to that described for the synthesis of intermediate 32, the following compounds in Table 3 were prepared from commercial starting reagents or compounds known in the literature. The racemic material were resolved using chiral SFC (column, see table) to afford isomers A (faster eluting) and B (slower eluting).

TABLE 3

| Int. | Chiral Resolution Column | R³ | m/z (M + 1) |
|---|---|---|---|
| 33A 33B | AD | (oxazole with ethyl propanoate ester) | 334 |
| 34A 34B | AD | (oxazole with ethyl acetate) | 320 |

Intermediate 35, 35A and 35B

Ethyl 3,3-dicyano-2-(4-(3-methoxy-2,2-dimethyl-3-oxopropyl)thiazol-2-yl)-2-methylpropanoate and the S and R Isomers Thereof

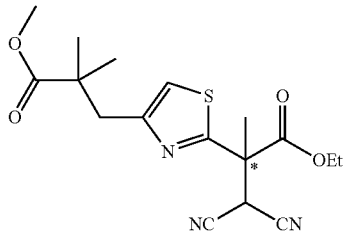 [SMILES: CCOC(=O)C(C)(c1nc(CC(C)(C)C(=O)OC)cs1)C(C#N)C#N]

Step A—methyl 3-(2-(1-ethoxy-1-oxopropan-2-yl)thiazol-4-yl)-2,2-dimethylpropanoate A flask containing ethyl 3-amino-2-methyl-3-thioxopropanoate (6.1 g, 37.8 mmol) and methyl 5-bromo-2,2-dimethyl-4-oxopentanoate (9.44 g, 37.8 mmol) in EtOH (95 mL) was stirred at 50° C. for 1.5h. The reaction was cooled to RT diluted with DCM and triethylamine (5.27 mL, 37.8 mmol) was slowly added the resulting mixture was concentrated in vacuo to dryness. The residue was purified by silica gel column chromatography with EtOAc/Hexane gradient to afford the title compound. ¹H NMR (400 MHz, DMSO-$d_6$): δ 7.18 (s, 1H); 4.17 (q, J=8.0 Hz, 1H); 4.08 (q, J=8.0 Hz, 2H); 3.05 (s, 3H); 2.88 (s, 2H), 1.45 (d, J=8.0 Hz, 3H), 1.13 (t, J=8.0 Hz, 3H), 1.08 (s, 6H). m/z=300 (M+1).

Step B—methyl 3-(2-(2-bromo-1-ethoxy-1-oxopropan-2-yl)thiazol-4-yl)-2,2-dimethylpropanoate To a flask containing methyl 3-(2-(1-ethoxy-1-oxopropan-2-yl)thiazol-4-yl)-2,2-dimethylpropanoate (10.5 g, 35.1 mmol) in toluene (175 mL) was added HCl (9.64 mL, 38.6 mmol, 4M in dioxane) dropwise, and the resulting mixture was stirred 10 min at RT. The reaction was cooled to 0° C. and KBr (4.59 g, 38.6 mmol) was added followed by the slow addition of $H_2O_2$ (3.99 mL, 45.6 mmol, 35 wt %). The reaction was stirred at 0° C. for 30 min then quenched by the addition of sodium thiosulfate (22.2 g, 140 mmol), diluted with water and extracted with EtOAc (3×). The organic layers were combined, washed with aq. sat. NaHCO₃, dried over anhydr. MgSO₄, and filtered. The filtrate was concentrated in vacuo to dryness to afford the title compound. ¹H NMR (400 MHz, DMSO-$d_6$): δ 7.41 (s, 1H); 4.20 (q, J=8.0 Hz, 2H); 3.56 (s, 3H); 2.90 (s, 2H), 2.24 (s, 3H), 1.18 (t, J=8.0 Hz, 3H), 1.08 (s, 6H). m/z=378 (M+1).

Step C—ethyl 3,3-dicyano-2-(4-(3-methoxy-2,2-dimethyl-3-oxopropyl)thiazol-2-yl)-2-methylpropanoate To a flask containing methyl 3-(2-(2-bromo-1-ethoxy-1-oxopropan-2-yl)thiazol-4-yl)-2,2-dimethylpropanoate (520 mg, 1.37 mmol) and malononitrile (182 mg, 2.75 mmol) in THF (14.5 mL) at 0° C. was added dropwise 1,8-Diazabicycloundec-7-ene (0.41 mL, 2.75 mmol). The resulting mixture was stirred for 30 min at 0° C. then quenched by the addition of aq. sat. NH₄Cl and extracted with EtOAc (3×). The organic layers were combined, washed with brine, dried over anhydr. MgSO₄, and filtered. The filtrate was concentrated in vacuo. The residue was purified by silica gel column chromatography with EtOAc/Hexane gradient to afford the title racemic compound I-35. The racemic material was resolved using chiral SFC (CHIRALPAK® IC column) to afford isomers I-35A (faster eluting) and I-35B (slower eluting). ¹H NMR (400 MHz, DMSO-$d_6$): δ 7.45 (s, 1H), 5.71 (s, 1H), 4.22 (q, J=8.0 Hz, 2H), 3.58 (s, 3H), 2.94 (m, 2H), 1.86 (s, 3H), 1.17 (t, J=8.0 Hz, 3H), 1.11 (s, 3H) 1.08 (s, 3H); m/z=364 (M+1).

Using a similar procedure to that described for the synthesis of intermediate 35, the following compound in Table 4 was prepared. The racemic material were resolved using chiral SFC (column, see table) to afford isomers A (faster eluting) and B (slower eluting).

TABLE 4

| Int. | Chiral Resolution Column | R³ | m/z (M + 1) |
|---|---|---|---|
| 36A 36B | AD-H | (thiazole with methyl propanoate chain) | 348 (M − 1) |

Intermediate 37 37A and 37B

Ethyl 4-cyano-5-ethoxy-3-methyl-2-oxo-2,3-dihydro-1H-pyrrole-3-carboxylate and the S and R Isomers Thereof

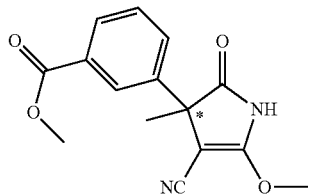 [SMILES: COC(=O)c1cccc(C2(C)C(=O)NC(OC)=C2C#N)c1]

To a flask containing a solution of I-18 (300 mg, 1.0 mmol) in 2.0 mL MeOH at RT was slowly added a solution of NaOMe (0.27 mL, 1.2 mmol, 25 wt. % in MeOH). The resulting solution was stirred 6 h at 65° C. The reaction was allowed to cool down to RT then quenched by the addition of a aq. sol 1M KH$_2$PO$_4$ and EtOAc. The mixture was extracted with EtOAc (3×). The organic layer was washed with brine, dried over anhydr. MgSO$_4$, filtered and concentrated in vacuo. to dryness. The residue was purified by silica gel chromatography using an (EtOAc:EtOH 3:1):hexane gradient to afford the racemic title product I-37. The racemic material was resolved using Chiral SFC (CHIRALPAK® AS-H) to afford isomers I-37A (faster eluting) and I-37B (slower eluting). $^1$H NMR (400 MHz, CDCl$_3$) δ 8.08 (t, J=1.8 Hz, 1H), 8.00 (dt, J=7.8, 1.4 Hz, 1H), 7.64 (ddd, J=7.9, 2.1, 1.2 Hz, 1H), 7.47 (t, J=7.8 Hz, 1H), 7.39 (s, 1H), 4.34 (s, 3H), 3.93 (s, 3H), 1.84 (s, 3H); m/z=287 (M+1).

Intermediate 38, 38AA, 38AB, 38BA and 38BB

Ethyl 4-cyano-5-ethoxy-3-methyl-2-oxo-2,3-dihydro-1H-pyrrole-3-carboxylate and the SS, SR, RS and RR Isomers Thereof

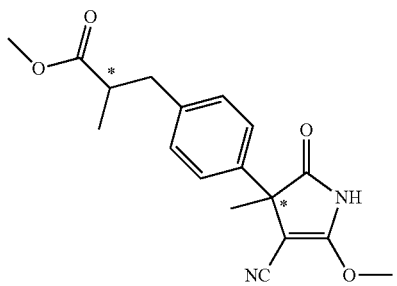

To a flask containing I-12 (683 mg, 2.0 mmol) in MeOH (4 mL) at RT was added sodium methoxide (0.55 mL, 2.4 mmol, 25 wt. % in MeOH), and the mixture was stirred at 65° C. for 2 h. The reaction was allowed to cool down to RT then quenched by the addition of a 1 M aq. solution of KH$_2$PO$_4$ and EtOAc. The mixture was extracted with EtOAc (3×). The organic layer was washed with brine, dried over anhydr. MgSO$_4$, filtered and concentrated in vacuo to dryness. The residue was purified by silica gel chromatography using an (EtOAc:EtOH 3:1):hexane gradient to afford the racemic title product I-38. The racemic material was resolved using chiral SFC (CHIRALPAK® AD-H column) to afford isomers I-38A (faster eluting) and I-38A (slower eluting). Isomer I-38A was resolved using chiral SFC (CHIRALPAK® AD-H column) to afford isomers I-38AA (faster eluting) and I-38AB (slower eluting). Isomer I-38B was resolved using chiral SFC (CHIRALPAK® AD-H column) to afford isomers I-38BA (faster eluting) and I-38BB (slower eluting).

Using a similar procedure to that described for the synthesis of intermediate I-37 or I-38, the following compounds in Table 5 were prepared

TABLE 5

![structure]

| Int. | Chiral Resolution Column | R$^3$ | R$^4$ | R$^5$ | m/z (M + 1) |
|---|---|---|---|---|---|
| 39A 39B | AS-H | ![3-substituted phenyl with ester] | Me | Et | 371 |
| 40A 40B | AS-H | ![ester with ethoxy] | Me | Et | 239 |
| 41A 41B | AS-H | ![ester with methoxy] | Me | ![cyclopropyl] | 237 |
| 42A 42B | IC | ![oxazole ester] | Me | Me | 334 |
| 43A 43B | IC | ![thiazole ester] | Me | Me | 348 (M − 1) |

Intermediate 44

Methyl 6-bromo-2,2-difluoro-5-oxohexanoate

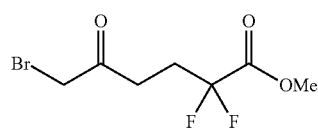 [SMILES: COC(=O)C(F)(F)CCC(=O)CBr]

To a flask containing ethyl 2,2-difluoro-5-oxohexanoate (12.0 g, 61.8 mmol) in MeOH (30 mL) at 0° C. was added dropwise bromine (9.9 g, 61.8 mmol). The resulting mixture was stirred for 16 h at RT. The reaction was quenched by the addition of aq. sat. sodium thiosulfate and extracted with EtOAc (3x). The organic layers were combined, washed with brine, dried over anhydr. Na₂SO₄, and filtered. The filtrate was concentrated in vacuo. The residue was purified by silica gel column chromatography with EtOAc:petroleum ether to afford the title compound I-44. ¹H NMR (300 MHz, CDCl₃) δ 3.88 (s, 2H), 3.23 (s, 3H), 2.99-2.83 (m, 2H), 2.71-2.51 (m, 2H).

Intermediate 45

Methyl 6-bromo-2,2-dimethyl-5-oxohexanoate

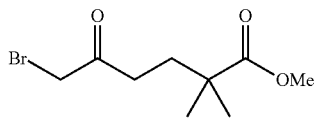

Intermediate I-45 was prepared using a similar procedure to that described for the synthesis of intermediate I-44, using methyl 2,2-dimethyl-5-oxohexanoate as starting material. ¹H NMR (300 MHz, CDCl₃) δ 3.88 (s, 2H), 3.67 (s, 3H), 2.67-2.61 (m, 2H), 1.81-1.83 (m, 2H), 1.20 (s, 6H).

Intermediate 46

Methyl 5-bromo-2,2-dimethyl-4-oxohexanoate

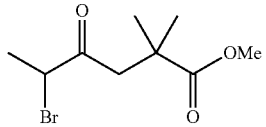

Intermediate I-46 was prepared using a similar procedure to that described for the synthesis of intermediate I-7 using methyl-4-bromo-2,2-dimethylhex-4-enoate as starting material. ¹H NMR (300 MHz, CDCl₃) δ 4.40 (q, J=5.1 Hz, 1H), 3.70 (s, 3H), 3.09 (d, J=13.2 Hz, 2H), 2.94 (d, J=13.2 Hz, 2H), 1.74 (d, J=5.1 Hz, 3H), 1.24 (s, 6H).

Intermediate 47

(R)-methyl-2-{[(9H-fluoren-9-yl)methoxy]carbonylamino}-5-bromo-4-oxopentanoate

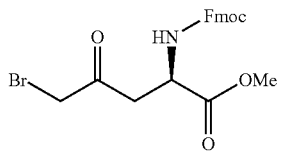

Step A—(R)-methyl-2-{[(9H-fluoren-9-yl)methoxy]carbonylamino}-4-bromopent-4-enoate To a flask containing (R)-2-({[(9H-fluoren-9-yl)methoxy]carbonyl}amino)-4-bromopent-4-enoic acid (1.9 g, 4.56 mmol) in MeOH (30 mL) at 0° C. was added sulfuryl dichloride (62 mg, 0.46 mmol) dropwise. The resulting mixture was stirred at RT for 16 h then quenched by the addition of water. The mixture was extracted with EtOAc (3x). The organic layer was washed with aq. sat. NaHCO₃ and brine, dried over anhydr. Na₂SO₄, filtered and concentrated in vacuo to afford the title product. m/z=430, 432 (M+1).

Step B—(R)-methyl-2-{[(9H-fluoren-9-yl)methoxy]carbonylamino}-5-bromo-4-oxopentanoate To a flask containing (R)-methyl 2-({[(9H-fluoren-9-yl)methoxy]carbonyl}amino)-4-bromopent-4-enoate (300 mg, 0.70 mmol) in a DMF (3 mL)-water (15 mL) mixture at 0° C. was added in portions N-bromosuccinimide (136 mg, 0.77 mmol). The resulting mixture was stirred at RT for 16 h then diluted with EtOAc (100 mL), washed with brine, dried over anhydr. Na₂SO₄, filtered and concentrated in vacuo to dryness. The residue was purified by silica gel chromatography using an EtOAc:petroleum ether gradient to afford the title product I-47 m/z=446, 448 (M+1).

Intermediates 48-52

Using a similar procedure described for the synthesis of intermediates I-10 or I-11, the following compounds in Table 6 were prepared from commercial starting reagents or compounds known in the literature. Racemic material was resolved using chiral SFC or HPLC (column, see table) to afford isomers A (faster eluting) and B (slower eluting).

TABLE 6

| Int. | Chiral Resolution Column | R³ | m/z (M + 1) |
|---|---|---|---|
| 48A 48B | AD-H | | 301 |
| 49 | — | phenyl) | 343 (M − 1) |
| 50A 50B | OJ-H | | 271 (M − 1) |
| 51A 51B | IF | pyridin-2-yl) | 344 |
| 52 | — | | 322 |

Intermediates 53-57

Using a similar procedure to that described for the synthesis of intermediate I-32, the following compounds in Table 7 were prepared from commercial starting reagents or compounds known in the literature. Racemic material was resolved using chiral SFC or HPLC (column, see table) to afford isomers A (faster eluting) and B (slower eluting).

TABLE 7

| Int. | Chiral Resolution Column | $R^3$ | m/z (M + 1) |
|---|---|---|---|
| 53A 53B | AS | [oxazole-phenyl-C(O)OEt] | 382 |
| 54 | — | [oxazole-CH2CH2-CF2-C(O)OEt] | 384 |
| 55A 55B | AS-H | [oxazole-CH2CH2-C(Me)2-C(O)OMe] | 362 |
| 56A 56B | OJ-H | [5-methyloxazole-CH2-C(Me)2-C(O)OMe] | 362 |
| 57A 57B | AD-H | [oxazole-CH2-CH(NHFmoc)-C(O)OMe] | 557 |

Intermediates 58-59

Using a similar procedure to that described for the synthesis of intermediate I-35, the following compounds in Table 8 was prepared. Racemic material was resolved using chiral SFC or HPLC (column, see table) to afford isomers A (faster eluting) and B (slower eluting).

TABLE 8

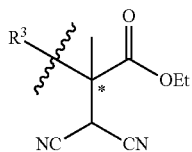

| Int. | Chiral Resolution Column | $R^3$ | m/z (M + 1) |
|---|---|---|---|
| 58A 58B | IF | [thiazole-phenyl-C(O)OEt] | 396 (M − 1) |
| 59A 59B | AD-H | [thiazole-CH2CH2-C(Me)2-C(O)OMe] | 376 (M − 1) |

Intermediates 60-61

Using a similar procedure to that described for the synthesis of intermediate I-24, the following compounds in Table 9 were prepared from either commercial starting reagents or compounds known in the literature.

TABLE 9

| Int. | $R^3$ | m/z (M + 1) |
|---|---|---|
| 60 | [triazole-CH2-C(Me)2-C(O)OEt] | 362 |
| 61 | [triazole-C(Me)2-C(O)OEt] | 348 |

Intermediate 62

Ethyl 3,3-dicyano-2-(5-(3-ethoxy-3-oxopropyl)pyridin-2-yl)-2-methylpropanoate

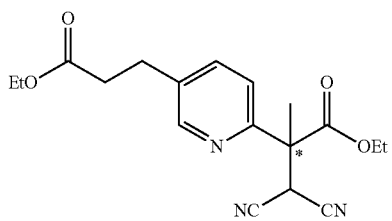 [SMILES: CCOC(=O)CCc1ccc(C(C)(C(=O)OCC)C(C#N)C#N)nc1]

To a flask under an inert atmosphere of nitrogen, containing I-19 (450 mg, 1.40 mmol) and 2nd generation XPhos precatalyst (chloro(2-dicyclohexylphosphino-2',4',6'-triisopropyl-1,1'-biphenyl)[2-(2'-amino-1,1'-biphenyl)]palladium(II), 220 mg, 0.28 mmol) in THF (16 mL) was added (3-ethoxy-3-oxopropyl)zinc(II) bromide (16.8 mL, 8.38 mmol, 0.5 M in THF). The resulting mixture was stirred for 6 h at 50° C. then quenched by the addition of aq. sat. NH$_4$Cl and extracted with EtOAc (3×). The organic layers were combined, washed with brine, dried over anhydr. MgSO$_4$, and filtered. The filtrate was concentrated in vacuo. The residue was then purified by reverse phase HPLC (ACN/water with 0.05% NH$_4$HCO$_3$ modifier) to afford the title compound I-62. $^1$H NMR (300 MHz, CDCl$_3$) δ 8.41 (d, J=2.4 Hz, 1H), 7.61 (dd, J=8.1, 2.4 Hz, 1H), 7.39 (dd, J=8.1, 0.9 Hz, 1H), 5.20 (s, 1H), 4.25-4.05 (m, 4H), 2.95 (t, J=7.5 Hz, 2H), 2.61 (t, J=7.5 Hz, 2H), 1.95 (s, 3H), 1.23-1.17 (m, 6H); m/z=342 (M−1).

Intermediate 63, 63A and 63B

Ethyl 3,3-dicyano-2-[1-(3-methoxy-2,2-dimethyl-3-oxopropyl)-1H-pyrazol-4-yl]-2-methylpropanoate and the S and R Isomers Thereof

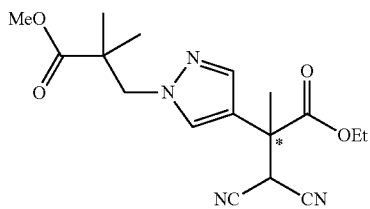 [SMILES: CCOC(=O)C(C)(c1cnn(CC(C)(C)C(=O)OC)c1)C(C#N)C#N]

Step A—Methyl 2,2-dimethyl-3-(1H-pyrazol-1-yl)propanoate

A mixture containing 1H-pyrazole (5.2 g, 77 mmol), methyl 2,2-dimethyl-3-(tosyloxy)propanoate (20 g, 69.8 mmol) and cesium carbonate (29.6 g, 91 mmol) in DMF (70 mL) was stirred in a flask at 80° C. for 48 h. The reaction was then quenched by the addition of water and extracted with EtOAc (3×). The organic layers were combined, washed with brine, dried over anhydr. NaSO$_4$, and filtered. The filtrate was concentrated in vacuo. The residue was then purified by reverse phase HPLC (ACN/water with 0.1% TFA modifier) to afford the title compound m/z=183 (M+1).

Step B—Methyl 3-[4-(2-ethoxy-2-oxoacetyl)-1H-pyrazol-1-yl]-2,2-dimethylpropanoate A mixture containing methyl 2,2-dimethyl-3-(1H-pyrazol-1-yl)propanoate (3.6 g, 19.76 mmol) and ethyl 2-chloro-2-oxoacetate (10 mL, 89 mmol) was stirred in a flask for 24 h at 100° C. The reaction mixture was then quenched by the addition of iced water. The pH was adjusted to pH 8 by the addition of NaHCO$_3$. The resulting mixture was extracted with EtOAc (3×). The organic layers were combined, washed with brine, dried over anhydr. NaSO$_4$, and filtered. The filtrate was concentrated in vacuo. The residue was then purified by reverse phase HPLC (ACN/water with 0.1% TFA modifier) to afford the title compound m/z=283 (M+1).

Step C—Ethyl 3,3-dicyano-2-[1-(3-methoxy-2,2-dimethyl-3-oxopropyl)-1H-pyrazol-4-yl]acrylate A flask containing methyl 3-[4-(2-ethoxy-2-oxoacetyl)-1H-pyrazol-1-yl]-2,2-dimethylpropanoate (1.4 g, 4.96 mmol), malononitrile (1.31 g, 19.84 mmol) and piperidine (84 mg, 0.99 mmol) in EtOH (10 mL) was stirred at RT for 16 h. The mixture was concentrated in vacuo and the residue was then purified by reverse phase HPLC (ACN/water with 0.1% TFA modifier) to afford the title compound m/z=331 (M+1).

Step D—Ethyl 3,3-dicyano-2-[1-(3-methoxy-2,2-dimethyl-3-oxopropyl)-1H-pyrazol-4-yl]-2-methylpropanoate To a flask under an inert atmosphere of nitrogen, containing ethyl 3,3-dicyano-2-[1-(3-methoxy-2,2-dimethyl-3-oxopropyl)-1H-pyrazol-4-yl]acrylate (1.4 g, 4.24 mmol) and lithium chloride (0.36 g, 8.48 mmol) in THF (40 mL) at 0° C. was added methylmagnesium bromide (8.5 mL, 8.5 mmol, 1M in THF) dropwise. The resulting mixture was stirred for 1 h at 0° C., then the reaction was quenched by the addition of aq. sat. NH$_4$Cl, extracted with EtOAc (3×). The organic layers were combined, washed with brine, dried over anhydr. NaSO$_4$, and filtered. The filtrate was concentrated in vacuo. The residue was then purified by reverse phase HPLC (ACN/water with 0.1% TFA modifier) to afford the title racemic product I-63. The racemic material was resolved using chiral SFC (CHIRALPAK® AD-H) to afford isomers I-63A (faster eluting) and I-63B (slower eluting). $^1$H NMR (400 MHz, CDCl$_3$) δ 7.50 (d, J=0.8 Hz, 1H), 7.48 (d, J=0.9 Hz, 1H), 4.41 (s, 1H), 4.34-4.28 (m, 4H), 3.73 (s, 3H), 1.91 (s, 3H), 1.32 (t, J=7.2 Hz, 3H), 1.22 (s, 3H), 1.21 (s, 3H); m/z=347 (M+1).

Intermediate 64

Ethyl 3,3-dicyano-2-[2-(3-methoxy-2,2-dimethyl-3-oxopropyl)oxazol-4-yl]-2-methylpropanoate

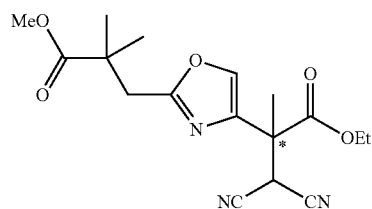 [SMILES: CCOC(=O)C(C)(c1coc(CC(C)(C)C(=O)OC)n1)C(C#N)C#N]

Step A—Methyl 4-amino-2,2-dimethyl-4-oxobutanoate

To a flask containing 4-methoxy-3,3-dimethyl-4-oxobutanoic acid (5 g, 31.2 mmol) in DCM (50 mL) at 0° C. was added oxalyl chloride (15 mL, 171 mmol) and a drop of DMF. The resulting mixture was stirred for 3 h at RT. The reaction mixture was concentrated in vacuo. The residue was dissolved in THF (20 mL), and added to a solution of ammonia hydrate (28%, 20 mL) in THF (20 mL) at 0° C. The resulting mixture was stirred for 15 min at 0° C. then concentrated in vacuo. The residue was dissolved in EtOAc, dried over anhydr. Na$_2$SO$_4$, and filtered. The filtrate was concentrated in vacuo to afford the title compound.

Step B—Methyl 3-[4-(1-ethoxy-1-oxopropan-2-yl)oxazol-2-yl]-2,2-dimethylpropanoate A flask containing methyl 4-amino-2,2-dimethyl-4-oxobutanoate (4 g, 25.1 mmol), ethyl 4-bromo-2-methyl-3-oxobutanoate (6.7 g, 30.2 mmol) and silver trifluoromethanesulfonate (6.78 g, 26.4 mmol) in EtOAc (50 mL) was stirred at 90° C. for 4 h. The reaction mixture was cooled and filtered. The filtrate was concentrated in vacuo. The residue was purified by reverse phase HPLC (ACN/water with 0.05% TFA modifier) to afford the title compound.

Step C—Methyl 3-[4-(2-bromo-1-ethoxy-1-oxopropan-2-yl)oxazol-2-yl]-2,2-dimethylpropanoate To a flask, under an inert atmosphere of nitrogen, containing methyl 3-[4-(1-ethoxy-1-oxopropan-2-yl)oxazol-2-yl]-2,2-dimethylpropanoate (1.2 g, 4.24 mmol) in THF (10 mL) at 0° C. was added dropwise lithium bis(trimethylsilyl)amide (5.08 mL, 5.08 mmol). The resulting mixture was stirred for 30 min at 0° C. then a solution of N-bromosuccinimide (0.98 g, 5.51 mmol) in THF (5 mL) was added and the mixture was stirred for 30 min at 0° C. The reaction was quenched by the addition of aq. sat. NH$_4$Cl, and extracted with EtOAc (3×). The organic layer was washed with brine, dried over anhydr. Na$_2$SO$_4$, and filtered. The filtrate was concentrated in vacuo. The residue was purified by silica gel column chromatography with EtOAc:petroleum ether to afford the title compound.

Step D—Ethyl 3,3-dicyano-2-[2-(3-methoxy-2,2-dimethyl-3-oxopropyl)oxazol-4-yl]-2-methylpropanoate To a flask, under an inert atmosphere of nitrogen, containing methyl 3-[4-(2-bromo-1-ethoxy-1-oxopropan-2-yl)oxazol-2-yl]-2,2-dimethylpropanoate (750 mg, 2.07 mmol) and malononitrile (684 mg, 10.35 mmol) in DMSO (100 mL) at 15° C. was added potassium carbonate (715 mg, 5.18 mmol) in portions. The resulting mixture was stirred for 1 h at RT. The reaction was quenched by the addition of aq. sat. NH$_4$Cl, extracted with EtOAc (3×). The organic layer was washed with brine, dried over anhydr. Na$_2$SO$_4$, and filtered. The filtrate was concentrated in vacuo. The residue was purified by silica gel column chromatography with EtOAc:petroleum ether to afford the title compound I-64. $^1$H NMR (300 MHz, CDCl$_3$) δ 7.60 (s, 1H), 4.79 (s, 1H), 4.25 (q, J=7.2 Hz, 2H), 3.66 (s, 3H), 2.99 (s, 2H), 1.83 (s, 3H), 1.28-1.22 (m, 9H); m/z=348 (M+1).

Intermediate 65, 65A and 65B

Ethyl 3,3-dicyano-2-[2-(3-methoxy-2,2-dimethyl-3-oxopropyl)thiazol-4-yl]-2-methylpropanoate and the S and R Isomers Thereof

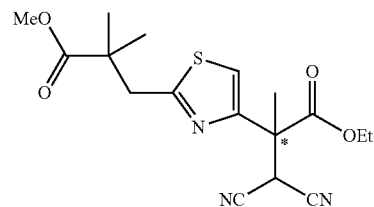 [SMILES: CCOC(=O)C(C)(c1csc(CC(C)(C)C(=O)OC)n1)C(C#N)C#N]

Step A—Methyl 4-amino-2,2-dimethyl-4-thioxobutanoate

To a flask containing methyl 4-amino-2,2-dimethyl-4-oxobutanoate (5.1 g, 32.0 mmol) in THF (200 mL) at 0° C. was added phosphorus pentasulfide (21.4 g, 96 mmol). The resulting mixture was stirred for 16 h at RT. The reaction mixture was filtered and the filtrate was concentrated in vacuo. The residue was purified by silica gel column chromatography with EtOAc:petroleum ether to afford the title compound.

Step B—Methyl 3-[4-(1-ethoxy-1-oxopropan-2-yl)thiazol-2-yl]-2,2-dimethylpropanoate A flask containing methyl 4-amino-2,2-dimethyl-4-thioxobutanoate (1.65 g, 9.42 mmol) and ethyl 4-bromo-2-methyl-3-oxobutanoate (3.50 g, 9.42 mmol) in EtOH (20 mL) was stirred at 50° C. for 30 min. The reaction mixture was concentrated in vacuo. The residue was purified by silica gel column chromatography with MeOH:DCM (0-5%). The residue was diluted with EtOAc and washed with aq. sat. NaHCO$_3$, dried over anhydr. Na$_2$SO$_4$, and filtered. The filtrate was concentrated in vacuo to afford the title compound. m/z=300 (M+1).

Step C—Methyl 3-[4-(2-bromo-1-ethoxy-1-oxopropan-2-yl)thiazol-2-yl]-2,2-dimethylpropanoate To a flask under an inert atmosphere of nitrogen, containing methyl 3-[4-(1-ethoxy-1-oxopropan-2-yl)thiazol-2-yl]-2,2-dimethylpropanoate (1.87 g, 6.25 mmol) in THF (40 mL) at 0° C. was added dropwise lithium bis(trimethylsilyl)amide (6.87 mL, 6.87 mmol, 1M in THF). The resulting mixture was stirred at 0° C. for 30 min then a solution of N-bromosuccinimide (1.223 g, 6.87 mmol) in THF (4 mL) was added. The resulting mixture was stirred at 0° C. for another 30 min, then quenched by the addition of aq. sat. NH$_4$Cl, and extracted with EtOAc (3×). The organic layer was washed with brine, dried over anhydr. Na$_2$SO$_4$, filtered and the filtrate was concentrated in vacuo. The residue was purified by reverse phase HPLC (ACN/water with 0.1% TFA modifier) to afford the title compound. m/z=378, 380 (M+1).

Step D—Ethyl 3,3-dicyano-2-[2-(3-methoxy-2,2-dimethyl-3-oxopropyl)thiazol-4-yl]-2-methylpropanoate To a flask, containing methyl 3-[4-(2-bromo-1-ethoxy-1-oxopropan-2-yl)thiazol-2-yl]-2,2-dimethylpropanoate (560 mg, 1.48 mmol) and malononitrile (489 mg, 7.40 mmol) in DMSO (20 mL) at 15° C. was added potassium carbonate (511 mg, 3.70 mmol). The resulting mixture was stirred for 1 h at RT. The reaction was quenched by the addition of aq. sat. NH$_4$Cl, and extracted with EtOAc (3×). The organic layer was washed with brine, dried over anhydr. Na$_2$SO$_4$, and filtered. The filtrate was concentrated in vacuo. The residue was purified by reverse phase HPLC (ACN/water with 0.1% TFA modifier) to afford the racemic title compound I-65. The racemic material was resolved using Chiral HPLC (CHIRALPAK® IF) to afford isomer I-65A (faster eluting) and isomer I-65B (slower eluting). $^1$H NMR (400 MHz, CDCl$_3$) δ 7.27 (s, 1H), 5.05 (s, 1H), 4.26 (q, J=7.2 Hz, 2H), 3.73 (s, 3H), 3.24 (s, 2H), 1.97 (s, 3H), 1.29-1.25 (m, 9H); m/z=364 (M+1).

Intermediate 66, 66A and 66B

Methyl 2-(1,1-dicyano-3-ethoxy-2-methyl-3-oxopropan-2-yl)benzo[d]oxazole-5-carboxylate and the S and R Isomers Thereof

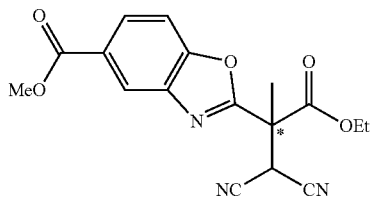 [SMILES: CCOC(=O)C(C)(c1nc2cc(C(=O)OC)ccc2o1)C(C#N)C#N]

Step A—2-(1-Ethoxy-1-oxopropan-2-yl)benzo[d]oxazole-5-carboxylate

A flask containing methyl 3-amino-4-hydroxybenzoate (5.0 g, 29.9 mmol), and diethyl 2-methylmalonate (15.6 g, 90 mmol) was stirred at 160° C. for 8 h. To this was added 4-methylbenzenesulfonic acid (1.0 g, 5.98 mmol). The resulting mixture was stirred for an additional 10 h at 160° C. then filtered. The filtrate was applied onto silica gel column chromatography with EtOAc:petroleum ether to afford the title compound m/z=278 (M+1).

Step B—Methyl 2-(2-bromo-1-ethoxy-1-oxopropan-2-yl)benzo[d]oxazole-5-carboxylate To a flask, containing methyl 2-(1-ethoxy-1-oxopropan-2-yl)benzo[d]oxazole-5-carboxylate (3 g, 10.82 mmol) in THF (100 mL) at 0° C. was added lithium bis(trimethylsilyl)amide (14.1 mL, 14.10 mmol, 1M in THF). The resulting mixture was stirred for 15 min at 0° C. then a solution of N-bromosuccinimide (2.89 g, 16.23 mmol) in THF (10 mL) was added. The resulting mixture was stirred for 30 min at 0° C. then quenched by the addition of aq. sat. NH$_4$Cl and extracted with EtOAc (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether to afford the title compound. m/z=356, 358 (M+1).

Step C—Methyl 2-(1,1-dicyano-3-ethoxy-2-methyl-3-oxopropan-2-yl)benzo[d]oxazole-5-carboxylate To a flask containing methyl 2-(2-bromo-1-ethoxy-1-oxopropan-2-yl)benzo[d]oxazole-5-carboxylate (1.5 g, 4.21 mmol) and malononitrile (1.39 g, 21.06 mmol) in DMSO (40 mL) at 15° C. was added potassium carbonate (1.46 g, 10.53 mmol) portionwise. The resulting mixture was stirred for 1 h at RT, then quenched by the addition of aq. sat. NH$_4$Cl and extracted with EtOAc (3×). The organic layers were combined, washed with brine, dried over anhydr. Na$_2$SO$_4$, and filtered. The filtrate was concentrated in vacuo. The residue was purified by reverse phase HPLC (ACN/water with 0.05% TFA modifier) to afford racemic I-66. The racemic material was resolved using Chiral HPLC (CHIRALPAK® ID) to afford isomer I-66A (faster eluting) and isomer I-66B (slower eluting)$^1$H NMR (400 MHz, CDCl$_3$) δ 8.51 (s, 1H), 8.20 (d, J=8.8 Hz, 1H), 7.64 (d, J=8.8 Hz, 1H), 4.98 (s, 1H), 4.35 (q, J=7.2 Hz, 2H), 3.99 (s, 3H), 2.17 (s, 3H), 1.31 (t, J=7.2 Hz, 3H); m/z=342 (M+1).

Intermediate 67

Methyl 2-(1,1-dicyano-3-ethoxy-2-methyl-3-oxopropan-2-yl)benzo[d]thiazole-5-carboxylate

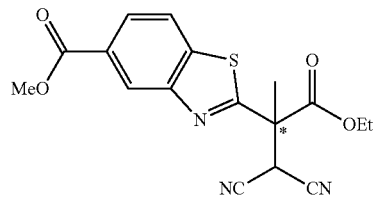 [SMILES: CCOC(=O)C(C)(c1nc2cc(C(=O)OC)ccc2s1)C(C#N)C#N]

Step A—Methyl 2-(1-ethoxy-1-oxopropan-2-yl)benzo[d]thiazole-5-carboxylate

A flask under an inert atmosphere of nitrogen, containing methyl 3-amino-4-mercaptobenzoate hydrochloride (8.4 g, 38.20 mmol) and ethyl 2-cyanopropanoate (4.9 g, 38.20 mmol) was stirred for 2 h at 120° C. The reaction was quenched by the addition of water and extracted with EtOAc (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (0-50%). The residue was purified by reverse phase HPLC (ACN/water with 0.1% TFA modifier) to afford the title compound. m/z=294 (M+1).

Step B—Methyl 2-(2-bromo-1-ethoxy-1-oxopropan-2-yl)benzo[d]thiazole-5-carboxylate To a flask under an inert atmosphere of nitrogen, containing methyl 2-(1-ethoxy-1-oxopropan-2-yl)benzo[d]thiazole-5-carboxylate (457 mg, 1.56 mmol) in THF (20 mL) at 0° C. was added dropwise a solution of lithium bis(trimethylsilyl)amide (1.56 mmol, 1.56 mL, 1 M in THF). The mixture was stirred for 15 min at 0° C. before N-bromosuccinimide (305 mg, 1.714 mmol) was added. The resulting mixture was stirred for 30 min at 0° C., then quenched by the addition of aq. sat. NH₄Cl and extracted with EtOAc (3×). The organic layers were combined, washed with brine, dried over anhydr. Na₂SO₄, and filtered. The filtrate was concentrated in vacuo. The residue was purified by silica gel column chromatography with EtOAc:petroleum ether (0-10%) to afford the title compound. m/z=372, 374 (M+1).

Step C. Methyl 2-(1,1-dicyano-3-ethoxy-2-methyl-3-oxopropan-2-yl)benzo[d]thiazole-5-carboxylate To a flask containing methyl 2-(2-bromo-1-ethoxy-1-oxopropan-2-yl)benzo[d]thiazole-5-carboxylate (269 mg, 0.72 mmol) and malononitrile (286 mg, 4.34 mmol) in DMSO (5 mL) at 15° C. was added potassium carbonate (300 mg, 2.17 mmol). The resulting mixture was stirred for 1 h at RT, then the reaction mixture was quenched by the addition of aq. sat. NH₄Cl and extracted with EtOAc (3×). The organic layers were combined, washed with brine, dried over anhydr. Na₂SO₄, and filtered. The filtrate was concentrated in vacuo. The residue was purified by reverse phase HPLC (ACN/water with 0.1% TFA modifier) to afford the title compound. ¹H NMR (400 MHz, CDCl₃) δ 8.76 (d, J=1.6 Hz 1H), 8.17 (dd, J=1.6, 8.4 Hz, 1H), 8.09 (d, J=8.4 Hz, 1H), 5.27 (s, 1H), 4.38 (q, J=7.2 Hz, 2H), 3.99 (s, 3H), 2.17 (s, 3H), 1.34 (t, J=7.2 Hz, 3H); m/z=358 (M+1).

Intermediate 68

Methyl 2-(4-{[(tert-butyldimethylsilyl)oxy]methyl}cyclohexyl)-3,3-dicyano-2-methylpropanoate

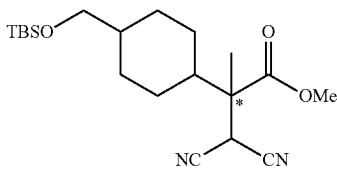 [SMILES: COC(=O)C(C)(C(C#N)C#N)C1CCC(CO[Si](C)(C)C(C)(C)C)CC1]

Step A—(4-Bromocyclohexyl)methanol

To a flask containing LiAlH₄ (5.6 g, 148 mmol) in THF (200 mL) at 0° C. was added dropwise a solution of ethyl 4-bromocyclohexane carboxylate (31.2 g, 133 mmol) in THF (50 mL). The resulting mixture was stirred at 0° C. for 1 h. The reaction mixture was slowly quenched by the addition of water (5.6 mL) at 0° C. Then to this, was added sodium hydroxide (15%, 5.6 mL) and water (16.8 mL). The resulting mixture was stirred for 15 min. To this was added anhydr. MgSO₄. The resulting mixture was stirred for 15 min, and filtered. The filtrate was concentrated in vacuo to give the title compound.

Step B—[(4-Bromocyclohexyl)methoxy](tert-butyl)dimethylsilane

To a flask containing (4-bromocyclohexyl)methanol (25.1 g, 130 mmol) and tert-butylchlorodimethylsilane (21.6 g, 143 mmol) in DMF (100 mL) at 0° C. was added portion-wise imidazole (11.5 g, 169 mmol). The resulting mixture was stirred for 3 h at RT. The reaction was then quenched by the addition of water and extracted with EtOAc (3×). The organic layers were combined, washed with brine, dried over anhydr. NaSO₄, and filtered. The filtrate was concentrated in vacuo. The residue was purified by silica gel chromatography using an EtOAc:petroleum ether gradient to afford the title compound.

Step C—Methyl 2-(4-{[(tert-butyldimethylsilyl)oxy]methyl}cyclohexyl)-2-oxoacetate To a flask under an inert atmosphere of nitrogen, containing magnesium turnings (0.79 g, 32.5 mmol), a few drops of [(4-bromocyclohexyl)methoxy](tert-butyl)dimethylsilane and iodine (0.21 g, 0.81 mmol) in diethyl ether (5 mL) was heated to reflux. A solution of [(4-bromocyclohexyl)methoxy](tert-butyl)dimethylsilane (5 g, 16.27 mmol) in diethyl ether (40 mL) was added dropwise to the reaction over approximately 1.5 h, maintaining the reaction mixture at reflux. The reaction was stirred at reflux for an additional 1 h then cooled to RT. This reaction mixture was added dropwise to a flask under an inert atmosphere of nitrogen, containing dimethyl oxalate (2.50 g, 21.15 mmol) in a diethyl ether (30 mL)-THF (50 mL) mixture at 0° C. The resulting mixture was stirred for 2 h at RT. The reaction was then quenched by the addition of aq. sat. NH₄Cl and extracted with diethyl ether (3×). The organic layers were combined, washed with brine, dried over anhydr. NaSO₄, and filtered. The filtrate was concentrated in vacuo. The residue was purified by silica gel chromatography using an EtOAc:petroleum ether gradient to afford the title compound ¹H NMR (400 MHz, CDCl₃) δ 3.92-3.88 (m, 3H), 3.48-3.41 (m, 2H), 2.10-1.80 (m, 4H), 1.70-1.25 (m, 4H), 1.10-0.95 (m, 1H), 0.95-0.90 (m, 10H), 0.07-0.05 (m, 6H).

Step D—Methyl 2-(4-{[(tert-butyldimethylsilyl)oxy]methyl}cyclohexyl)-3,3-dicyanoacrylate Into a flask were placed methyl 2-(4-{[(tert-butyldimethylsilyl)oxy]methyl}cyclohexyl)-2-oxoacetate (2.7 g, 8.59 mmol), malononitrile (1.13 g, 17.17 mmol), 3-aminopropanoic acid (0.23 g, 2.58 mmol), and water (20 mL). The resulting mixture was stirred for 15 min at RT before ethanol (20 mL) was added, and the mixture was stirred at RT for an additional 2 h. The reaction was then quenched by the addition of brine and extracted with EtOAc (3×). The organic layers were combined, washed with brine, dried over anhydr. NaSO₄, and filtered. The filtrate was concentrated in vacuo. The residue was purified by silica gel chromatography using an EtOAc:petroleum ether gradient to afford the title compound.

Step E—Methyl 2-(4-{[(tert-butyldimethylsilyl)oxy]methyl}cyclohexyl)-3,3-dicyano-2-methylpropanoate To a flask, under an inert atmosphere of nitrogen, containing methyl 2-(4-{[(tert-butyldimethylsilyl)oxy]methyl}cyclohexyl)-3,3-dicyanoacrylate (2.2 g, 6.07 mmol) and lithium chloride (0.77 g, 18.20 mmol) in THF (30 mL) at 0° C. was added methylmagnesium bromide (4.1 mL, 12.14 mmol, 3M in diethyl ether) dropwise. The resulting mixture was stirred for 1 h at 0° C., then quenched by the addition of aq. sat. NH₄Cl and extracted with EtOAc (3×). The organic layers were combined, washed with brine, dried over anhydr. NaSO₄, and filtered. The filtrate was concentrated in vacuo. The residue was purified by silica gel chromatography using an EtOAc:petroleum ether gradient to afford the title compound I-68. ¹H NMR (400 MHz, CDCl₃) δ 4.34-4.30 (m, 1H), 3.83-3.82 (brs, 3H), 3.41 (d, J=6.4 Hz, 2H), 1.90-1.65 (m, 5H), 1.57 (s, 3H), 1.40-1.35 (m, 1H), 1.15-0.80 (m, 13H), 0.06-0.04 (m, 6H); m/z=377 (M−1).

Intermediate 69, 69A and 69B

Ethyl 3,3-dicyano-2-(3-cyanophenyl)-2-methylpropanoate and the S and R Isomers Thereof

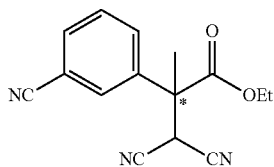 [SMILES: CCOC(=O)C(C)(c1cccc(C#N)c1)C(C#N)C#N]

Step A—Ethyl 2-bromo-2-(3-bromophenyl)propanoate

A flask, under an inert atmosphere of nitrogen, containing ethyl 2-(3-bromophenyl)propanoate (21 g, 73.5 mmol), N-bromosuccinimide (15.7 g, 88 mmol) and azodiisobutyronitrile (1.2 g, 7.35 mmol) in tetrachloromethane (300 mL) was stirred at 80° C. for 1.5 h. The reaction mixture was cooled to RT, quenched by the addition of aq. sat. sodium bisulfate, and extracted with EtOAc (3×). The organic layers were combined, washed with brine, dried over anhydr. Na₂SO₄, and filtered. The filtrate was concentrated in vacuo. The residue was purified by silica gel column chromatography with EtOAc:petroleum ether (0-30%) to afford the title compound.

Step B—Ethyl 2-(3-bromophenyl)-3,3-dicyano-2-methylpropanoate

To a flask, under an inert atmosphere of nitrogen, containing malononitrile (1.24 g, 18.8 mmol) in DMF (30 mL) at 0° C. was added in portions sodium hydride (0.56 g, 14.1 mmol, 60%). The mixture was stirred for 30 min at 0° C. before ethyl 2-bromo-2-(3-bromophenyl)propanoate (3.5 g, 9.37 mmol) was added. The resulting mixture was stirred for 1 h at 0° C., then quenched by the addition of water and extracted with EtOAc (3×). The organic layers were combined, washed with brine, dried over anhydr. Na₂SO₄, and filtered. The filtrate was concentrated in vacuo. The residue was purified by silica gel column chromatography with EtOAc:petroleum ether (0-50%) to afford the title compound. ¹H NMR (300 MHz, CDCl₃) δ 7.59-7.51 (m, 2H), 7.36-7.29 (m, 2H), 4.47 (s, 1H), 4.34-4.23 (m, 2H), 1.98 (s, 3H), 1.26 (t, J=7.2 Hz, 3H).

Step C—Ethyl 3,3-dicyano-2-(3-cyanophenyl)-2-methylpropanoate

A flask under an inert atmosphere of nitrogen, containing ethyl 2-(3-bromophenyl)-3,3-dicyano-2-methylpropanoate (2.5 g, 7.39 mmol), 1,1'-bis(diphenylphosphino)ferrocene (0.82 g, 1.479 mmol), zinc cyanide (1.13 g, 9.61 mmol), zinc (0.24 g, 3.70 mmol), tris(dibenzylideneacetone)dipalladium chloroform adduct (0.76 g, 0.739 mmol) in DMA (25 mL) was stirred for 16 h at 120° C. The mixture was cooled to RT, quenched by the addition of water and extracted with EtOAc (3×). The organic layers were combined, washed with brine, dried over anhydr. Na₂SO₄, and filtered. The filtrate was concentrated in vacuo. The residue was purified by silica gel column chromatography with EtOAc:petroleum ether (0-50%) to afford the racemic title compound I-69. The racemic material was resolved using Chiral HPLC (Chiralcel OJ-H) to afford isomer I-69A (faster eluting) and isomer I-69B (slower eluting) ¹H NMR (300 MHz, CDCl₃) δ 7.76-7.57 (m, 4H), 4.49 (s, 1H), 4.39-4.23 (m, 2H), 2.02 (s, 3H), 1.27 (t, J=7.2 Hz, 3H); m/z=266 (M 1).

Intermediate 70A

Ethyl 3,3-dicyano-2-(4-cyanophenyl)-2-methylpropanoate

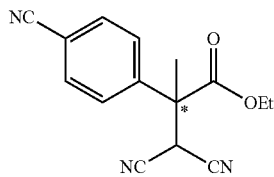 [SMILES: CCOC(=O)C(C)(c1ccc(C#N)cc1)C(C#N)C#N]

A flask under an inert atmosphere of nitrogen, containing I-21A (320 mg, 1.00 mmol), 1,1'-bis(diphenylphosphino)ferrocene (50 mg, 0.09 mmol), zinc powder (32 mg, 0.49 mmol), zinc cyanide (150 mg, 1.29 mmol) and tris(dibenzylideneacetone)dipalladium(0)-chloroform adduct (60 mg, 0.06 mmol) in DMA (10 mL) was stirred for 2 h at 120° C. The reaction was cooled to RT and quenched by the addition of water and extracted with EtOAc (3×). The organic layers were combined, washed with brine, dried over anhydr. Na₂SO₄, and filtered. The filtrate was concentrated in vacuo. The residue was purified by silica gel column chromatography with EtOAc:petroleum ether (0-20%) to afford the title compound I-70A. ¹H NMR (400 MHz, CDCl₃) δ 7.79 (d, J=8.0 Hz, 2H), 7.55 (d, J=8.4 Hz, 2H), 4.50 (s, 1H), 4.39-4.26 (m, 2H), 2.04 (s, 3H), 1.29 (t, J=7.2 Hz, 3H); m/z=266 (M−1).

Intermediate 71, 71A and 71B

Methyl 3,3-dicyano-2-(5-cyanopyridin-2-yl)-2-methylpropanoate and the S and R Isomers Thereof

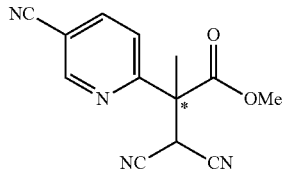 [SMILES: COC(=O)C(C)(c1ccc(C#N)cn1)C(C#N)C#N]

Step A—Ethyl 2 (5-bromopyridin-2-yl)propanoate

To a flask, containing ethyl 2-(5-bromopyridin-2-yl)acetate (4 g, 16.39 mmol) in THF (20 mL) at 0° C. was added dropwise lithium bis(trimethylsilyl)amide (18.2 mL, 18.7 mmol, 1 M in THF). The resulting solution was stirred at 0°

C. for 30 min, and iodomethane (2.3 g, 16.20 mmol) was added. The resulting solution was stirred 2 h at RT then quenched by the addition of water and extracted with EtOAc (3×). The organic layers were combined, washed with brine, dried over anhydr. $Na_2SO_4$, and filtered. The filtrate was concentrated in vacuo. The residue was purified by silica gel column chromatography with EtOAc:petroleum ether (0-10%) to afford the title compound.

Step B—Ethyl 2-(5-cyanopyridin-2-yl)propanoate

A flask, under an inert atmosphere of nitrogen, containing ethyl 2-(5-bromopyridin-2-yl)propanoate (3.8 g, 14.72 mmol), dicyanozinc (2.25 g, 19.14 mmol), zinc (0.48 g, 7.36 mmol), tris(dienzylideneacetone) dipalladium-chloroform adduct (1.52 g, 1.472 mmol) and 1,1'-ferrocenebis (diphenylphosphine) (1.63 g, 2.94 mmol) in DMA (30 mL) was stirred at 120° C. for 2 h. The mixture was cooled, diluted with a mixture DCM/MeOH (1/1) (100 mL). The solid was filtered out, and the filtrate was concentrated in vacuo. Water was added to the residue and the mixture was extracted with EtOAc (3×). The organic layers were combined, washed with brine, dried over anhydr. $Na_2SO_4$, and filtered. The filtrate was concentrated in vacuo. The residue was purified by silica gel column chromatography with MeOH:DCM (0-10%) to afford the title compound.

Step C—Ethyl 2-bromo-2-(5-cyanopyridin-2-yl)propanoate

A flask, under an inert atmosphere of nitrogen, containing ethyl 2-(5-cyanopyridin-2-yl)propanoate (2.5 g, 12.24 mmol), N-bromosuccinimide (2.83 g, 15.91 mmol) and 2,2'-azobisisobutyronitrile (0.20 g, 1.22 mmol) in carbontetrachloride (25 mL) was stirred for 4 h at 80° C. The reaction was cooled, quenched by the addition of water and extracted with DCM (3×). The organic layers were combined, washed with brine, dried over anhydr. $Na_2SO_4$, and filtered. The filtrate was concentrated in vacuo. The residue was purified by silica gel column chromatography with EtOAc:petroleum ether (0-10%) to afford the title compound.

Step D—Ethyl 3,3-dicyano-2-(5-cyanopyridin-2-yl)-2-methylpropanoate

To a flask containing sodium hydride (0.28 g, 7.06 mmol) in DMF (12 mL) at 0° C., was added dropwise a solution of malononitrile (0.47 g, 7.06 mmol) in DMF (2 mL). The mixture was stirred for 15 min at 0° C., then ethyl 2-bromo-2-(5-cyanopyridin-2-yl)propanoate (1.0 g, 3.53 mmol) was added. The reaction mixture was stirred for 2 h at 0° C. The reaction was quenched by the addition of water and extracted with EtOAc (3×). The organic layers were combined, washed with brine, dried over anhydr. $Na_2SO_4$, and filtered. The filtrate was concentrated in vacuo. The residue was purified by silica gel column chromatography with EtOAc:petroleum ether (0-10%) to afford the racemic title compound I-71. The racemic material was resolved using Chiral HPLC (CHIRALPAK® AS-H) to afford isomer I-71A (faster eluting) and isomer I-71B (slower eluting). $^1$H NMR (300 MHz, $CDCl_3$) δ 8.85 (dd, J=2.1, 0.9 Hz, 1H), 8.07 (dd, J=8.4, 2.1 Hz, 1H), 7.65 (dd, J=8.4, 0.9 Hz, 1H), 5.11 (s, 1H), 4.29-4.18 (m, 2H), 2.00 (s, 3H), 1.23 (t, J=7.2 Hz, 3H); m/z=269 (M+1).

Intermediate 72

Ethyl 3,3-dicyano-2-(6-cyanopyridin-2-yl)-2-methylpropanoate

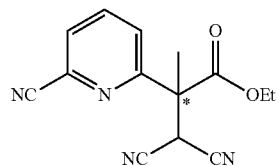 [SMILES: CCOC(=O)C(C)(c1cccc(C#N)n1)C(C#N)C#N]

A flask purged and maintained with an inert atmosphere of nitrogen, containing I-52 (197 mg, 1.68 mmol), tris(dibenzylideneacetone)dipalladium chloroform adduct (145 mg, 0.14 mmol), 1,1'-bis(diphenylphosphino)ferrocene (155 mg, 0.28 mmol) and zinc (45.7 mg, 0.698 mmol), in DMA (15 mL) was stirred for 90 min at 120° C. The reaction was cooled to RT, quenched by the addition of water and extracted with EtOAc (3×). The organic layers were combined, washed with brine, dried over anhydr. $Na_2SO_4$, and filtered. The filtrate was concentrated in vacuo. The residue was purified by silica gel column chromatography with EtOAc:petroleum ether to afford the title compound I-72. $^1$H NMR (400 MHz, $CDCl_3$) δ 8.02 (dd, J=8.0, 8.0 Hz, 1H), 7.80-7.76 (m, 2H), 5.17 (s, 1H), 4.35-4.25 (m, 2H), 2.06 (s, 3H), 1.30 (t, J=7.2 Hz, 3H); m/z=269 (M+1).

Intermediate 73

Ethyl 3,3-dicyano-2-cyclopropyl-2-[4-(3-methoxy-2, 2-dimethyl-3-oxopropyl)oxazol-2-yl]propanoate

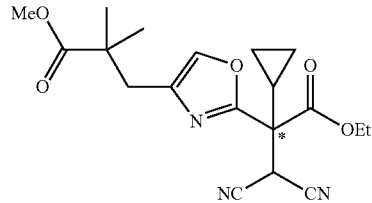 [SMILES: CCOC(=O)C(c1nc(CC(C)(C)C(=O)OC)co1)(C(C#N)C#N)C1CC1]

Step A—Ethyl 3-amino-2-cyclopropyl-3-oxopropanoate

In a flask containing ethyl 2-cyano-2-cyclopropylacetate (20 g, 131 mmol) and chlorotrimethylsilane (28.4 g, 261 mmol) was added water (4.7 mL, 261 mmol) dropwise at 0° C. The resulting mixture was stirred for 5 h at RT. The reaction mixture was divided into two layers, and the supernatant was discarded. To this was added hexane (100 mL), and the supernatant was discarded again. The aqueous layer was neutralised by the addition of aq. sat. $NHCO_3$ at 0° C. extracted with EtOAc (3×). The organic layers were combined, washed with brine, dried over anhydr. $Na_2SO_4$, and filtered. The filtrate was concentrated in vacuo. The residue was washed with hexane, and dried to afford the title compound.

Step B—Methyl 3-(2-(1-cyclopropyl-2-ethoxy-2-oxoethyl)oxazol-4-yl)-2,2-dimethyl Propanoate A flask containing ethyl 3-amino-2-cyclopropyl-3-oxopropanoate (4.7 g, 27.4 mmol), methyl 5-bromo-2, 2-dimethyl-4-oxopentanoate (5.0 g, 21.09 mmol) and silver (I) trifluoromethanesulfonate (5.96 g, 23.20 mmol) in EtOAc (10 mL) was stirred for 16 h at 80° C. The resulting mixture was filtered, and the solid was washed with EtOAc. The filtrate was concentrated in vacuo. The residue was purified by reverse phase HPLC (ACN/water with 0.1% TFA modifier) to afford the title compound.

Step C—Methyl 3-[2-(1-bromo-1-cyclopropyl-2-ethoxy-2-oxoethyl)oxazol-4-yl]-2,2-dimethylpropanoate To a flask under an inert atmosphere of nitrogen, containing methyl 3-[2-(1-cyclopropyl-2-ethoxy-2-oxoethyl)oxazol-4-yl]-2,2-dimethylpropanoate (3.4 g, 10.99 mmol) in THF (60 mL) at 0° C. was added dropwise lithium bis(trimethylsilyl)amide (13.19 mL, 13.19 mmol, 1M in THF). The resulting mixture was stirred 30 min at 0° C. before a solution of 1-bromopyrrolidine-2, 5-dione (2.93 g, 16.49 mmol) in THF (30 mL) was added at 0° C. The resulting mixture was stirred for 30 min at 0° C. then quenched by the addition of aq. sat. NH$_4$Cl and extracted with EtOAc (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (0-10%) to afford the title compound

Step D—Ethyl 3,3-dicyano-2-cyclopropyl-2-[4-(3-methoxy-2,2-dimethyl-3-oxopropyl)oxazol-2-yl]propanoate To a flask containing methyl 3-[2-(1-bromo-1-cyclopropyl-2-ethoxy-2-oxoethyl)oxazol-4-yl]-2,2-dimethylpropanoate (840 mg, 2.16 mmol) and malononitrile (858 mg, 12.98 mmol) in DMSO (5 mL) at 15° C. was added potassium carbonate (897 mg, 6.49 mmol) in portions. The resulting mixture was stirred for 1.5 h at 15° C. then quenched by the addition of aq. sat. NH$_4$Cl, extracted with EtOAc (3×). The organic layer was washed with brine, dried over anhydr. Na$_2$SO$_4$, filtered, and the filtrate was concentrated in vacuo. The residue was purified by reverse phase HPLC (ACN/water with 0.05% TFA modifier) to afford the title compound I-73. $^1$H NMR (300 MHz, CDCl$_3$) δ $^1$H NMR (300 MHz, CDCl$_3$) δ 7.44 (s, 1H), 4.67 (s, 1H), 4.33 (q, J=7.2 Hz, 2H), 3.68 (s, 3H), 2.79 (s, 2H), 1.67-1.58 (m, 1H), 1.31 (t, J=7.2 Hz, 3H), 1.22 (s, 3H), 1.21 (s, 3H), 0.85-0.77 (m, 2H), 0.66-0.57 (m, 2H); m/z=374 (M+1).

Intermediate 74, 74A and 74B

Methyl 4-(1,1-dicyano-3-methoxy-2-methyl-3-oxopropan-2-yl)picolinate and the S and R Isomers Thereof

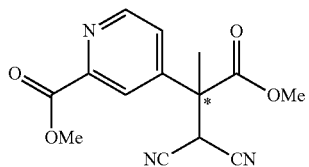 [SMILES: COC(=O)c1cc(C(C)(C(=O)OC)C(C#N)C#N)ccn1]

Step A—Methyl 4-(2-methoxy-2-oxoethyl)picolinate

To a flask, under an inert atmosphere of nitrogen, containing methyl 2-(2-bromopyridin-4-yl)acetate (2.0 g, 8.69 mmol), palladium(II) acetate (0.46 g, 2.09 mmol) and 1,1'-bis(diphenylphosphino)ferrocene (2.31 g, 4.17 mmol) in DMF (44 ml) was added N,N-diisopropylethylamine (7.59 ml, 43.5 mmol) in MeOH (31.7 ml, 782 mmol). The flask was flushed with CO and stirred 4 h under 1 atm of CO (balloon). The reaction was quenched by the addition of EtOAc and filtered. The organic layers were combined, washed with water and brine, dried over anhydr. Na$_2$SO$_4$, and filtered. The filtrate was concentrated in vacuo. The residue was purified by silica gel column chromatography with EtOAc:hexane (0-100%) to afford the title compound.

Step B—Methyl 4-(1-methoxy-1-oxopropan-2-yl)picolinate

To a flask, under an inert atmosphere of nitrogen, containing lithium bis(trimethylsilyl)amide (5.26 mL, 5.26 mmol, 1M in THF) at 0° C. was slowly added a solution of methyl 4-(2-methoxy-2-oxoethyl)picolinate (1.1 g, 5.26 mmol) in THF (10 mL), followed by methyl iodide (0.329 ml, 5.26 mmol). The resulting mixture was stirred at 0° C. for 45 min then concentrated in vacuo. The residue was purified by silica gel column chromatography with EtOAc:hexane (0-100%) to afford the title compound.

Step C—Methyl 4-(2-bromo-1-methoxy-1-oxopropan-2-yl)picolinate

To a flask containing methyl 4-(1-methoxy-1-oxopropan-2-yl)picolinate (600 mg, 2.15 mmol) in MeCN (13 mL) was added magnesium perchlorate (316 mg, 1.42 mmol). The mixture was stirred 5 min at RT before N-bromosuccinimide (928 mg, 5.16 mmol) was added. The mixture was stirred at RT for 2 days, then concentrated in vacuo. The residue was diluted in EtOAc. The organic layers were combined, washed with water, dried over anhydr. Na$_2$SO$_4$, and filtered. The filtrate was concentrated in vacuo. The residue was purified by silica gel column chromatography with EtOAc:hexane to afford the title compound.

Step D—Methyl 4-(1,1-dicyano-3-methoxy-2-methyl-3-oxopropan-2-yl)picolinate

To a flask, under an inert atmosphere of nitrogen, containing sodium hydride (53.7 mg, 1.34 mmol, 60% w) in DMF (5 mL) at 0° C. was added dropwise a solution of malononitrile (89 mg, 1.343 mmol) in DMF (5 mL), followed by a solution of methyl 4-(2-bromo-1-methoxy-1-oxopropan-2-yl)picolinate (390 mg, 1.03 mmol) in DMF (5 mL). The reaction was allowed to warm up to RT and stirred for 1 h at RT. The reaction was quenched by the addition of aq. sat. NH$_4$Cl and extracted with EtOAc (3×). The organic layers were combined, washed with brine, dried over anhydr. MgSO$_4$, and filtered. The filtrate was concentrated in vacuo. The residue was purified by silica gel column chromatography with EtOAc:hexane (0-100%) to afford the title racemic compound I-74. The racemic material was resolved using Chiral SFC (CHIRALPAK® IC) to afford isomer I-74A (faster eluting) and isomer I-74B (slower eluting). $^1$H-NMR (400 MHz, CDCl$_3$): δ2.033 (s, 3H), 3.820 (s, 3H), 4.015 (s, 3H), 4.539 (s, 1H), 7.454-7.478 (d, 1H), 8.103-8.108 (s, 1H), 8.820-8.839 (d, 1H), m/z=288 (M+1).

Intermediate 75A

Methyl 3,3-dicyano-2-cyclopropyl-2-[4-(3-ethoxy-3-oxopropyl)phenyl]propanoate

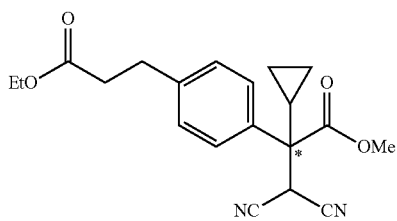 [SMILES: CCOC(=O)CCc1ccc(C(C(=O)OC)(C(C#N)C#N)C2CC2)cc1]

Step A—Methyl 2-(4-bromophenyl)-3,3-dicyano-2-cyclopropylpropanoate

To a flask, under an inert atmosphere of nitrogen containing 1,4-dibromobenzene (4.82 g, 20.43 mmol) in THF (60 mL) at −70° C. was added dropwise sec-butyllithium (17.0 mL, 22.14 mmol). The mixture was stirred for 30 min at −70° C. before a solution of methyl 3,3-dicyano-2-cyclopropylacrylate (3 g, 17.03 mmol) in THF (20 mL) was added dropwise at −70° C. The resulting mixture was stirred for 30 min at RT, then quenched by the addition of aq. sat. NH$_4$Cl and extracted with EtOAc (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (0-40%) to afford the title racemic compound. The racemic material was resolved using Chiral HPLC (CHIRALPAK® AD-H) to afford isomer A (faster eluting) and isomer B (slower eluting). $^1$H NMR (400 MHz, CDCl$_3$) δ 7.58 (d, J=8.4 Hz, 2H), 7.34 (d, J=8.4 Hz, 2H), 4.45 (s, 1H), 3.77 (s, 3H), 1.69-1.62 (m, 1H), 1.05-0.98 (m, 1H), 0.92-0.79 (m, 2H), 0.53-0.47 (m, 1H); m/z=331, 333 (M−1).

Step B methyl 3,3-dicyano-2-cyclopropyl-2-[4-(3-ethoxy-3-oxopropyl)phenyl]propanoate To a flask, under an inert atmosphere of nitrogen, containing methyl 2-(4-bromophenyl)-3,3-dicyano-2-cyclopropylpropanoate isomer A (300 mg, 0.900 mmol) and second generation Xphos precatalyst (chloro(2-dicyclohexylphosphino-2',4',6'-triisopropyl-1,1'-biphenyl)[2-(2'-amino-1,1'-biphenyl)]palladium(II), 142 mg, 0.180 mmol) in THF (10 mL) was added (3-ethoxy-3-oxopropyl)zinc(II) bromide (10.8 mL, 5.40 mmol). The resulting mixture was stirred at 50° C. for 6 h. The reaction was quenched by the addition of aq. sat. NH$_4$Cl and extracted with EtOAc (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (0-40%) to afford the title compound I-75A. $^1$H NMR (300 MHz, CDCl$_3$) δ 7.34 (d, J=8.4 Hz, 2H), 7.25 (d, J=8.4 Hz, 2H), 4.42 (s, 1H), 4.10 (q, J=7.2 Hz, 2H), 3.73 (s, 3H), 2.95 (t, J=7.8 Hz, 2H), 2.61 (t, J=7.8 Hz, 2H), 1.67-1.59 (m, 1H), 1.20 (t, J=7.2 Hz, 3H), 1.02-0.78 (m, 3H), 0.50-0.41 (m, 1H); m/z=353 (M−1).

Intermediate 76A

Methyl (E)-3-(4-(1,1-dicyano-3-ethoxy-2-methyl-3-oxopropan-2-yl)phenyl)acrylate

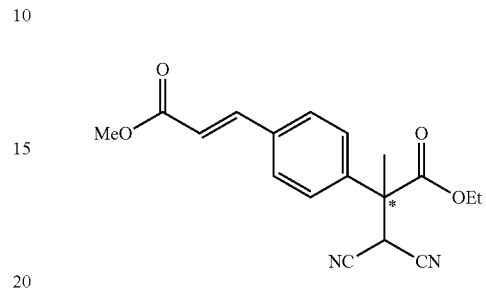

A flask, under an inert atmosphere of nitrogen, containing ethyl 2-(4-chlorophenyl)-3,3-dicyano-2-methylpropanoate (Intermediate 2A in WO 2016/081668) (500 mg, 1.80 mmol) methyl acrylate (325 µl, 3.61 mmol), tri-tert-butylphosphonium tetrafluoroborate (52.4 mg, 0.181 mmol), tris(dibenzylideneacetone)dipalladium(0) (42.2 mg, 0.045 mmol) and dicyclohexylmethylamine (464 µl, 2.168 mmol) in dioxane (9 mL) was stirred 2 h at 100° C. The reaction was cooled, quenched by the addition of water and extracted with EtOAc (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (0-10%) to afford the title compound I-76A. $^1$H NMR (400 MHz, CDCl$_3$) δ 7.67 (d, J=16.0 Hz, 1H), 7.62-7.56 (m, 2H), 7.44-7.37 (m, 2H), 6.47 (d, J=16.0 Hz, 1H), 4.48 (s, 1H), 4.35-4.18 (m, 2H), 3.82 (s, 3H), 2.00 (s, 3H), 1.26 (t, J=7.1 Hz, 3H). m/z=327 (M+1).

Intermediate 77

Ethyl 2-{4-[3-(tert-butoxy)-3-oxopropyl]-1-(4-methoxybenzyl)-1H-imidazol-2-yl}-3,3-dicyano-2-methylpropanoate

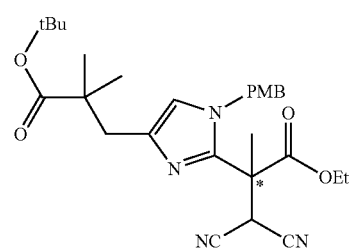

Step A—tert-Butyl 3-(1H-imidazol-4-yl)acrylate

To a flask containing 1H-imidazole-4-carbaldehyde (10 g, 104 mmol) and tert-butyl 2-(diethoxyphosphoryl)acetate (39.4 g, 156 mmol) in DMF (100 mL) at 0° C. was added in portions sodium hydride (4.99 g, 208 mmol, 60% w). The resulting mixture was stirred for 3 h at 95° C. then cooled to RT and quenched by the addition of aq. sat. NaHCO$_3$ and extracted with EtOAc (3×). The organic layers were combined, washed with water and brine, dried over anhydr. Na$_2$SO$_4$, and filtered. The filtrate was concentrated in vacuo. The residue was purified by silica gel column chromatography with EtOAc:petroleum ether (0-80%) to afford the title compound.

Step B—tert-Butyl 3-(1-(4-methoxybenzyl)-1H-imidazol-4-yl)acrylate

To a flask containing tert-butyl 3-(1H-imidazol-4-yl)acrylate (9.3 g, 43.1 mmol) and potassium carbonate (11.9 g, 86 mmol) in DMF (100 mL) at 0° C. was added dropwise 1-(chloromethyl)-4-methoxybenzene (10.1 g, 64.6 mmol). The resulting mixture was stirred for 2 h at RT then quenched by the addition of water and extracted with EtOAc (3×). The organic layers were combined, washed with water and brine, dried over anhydr. Na$_2$SO$_4$, and filtered. The filtrate was concentrated in vacuo. The residue was purified by silica gel column chromatography with EtOAc:petroleum ether (10-60%) to afford the title compound.

Step C—tert-Butyl 3-[1-(4-methoxybenzyl)-1H-imidazol-4-yl]propanoate

To a flask containing tert-butyl 3-(1-(4-methoxybenzyl)-1H-imidazol-4-yl)acrylate (10 g, 31.8 mmol) in MeOH (100 mL) was added palladium on carbon (wet, 1.5 g, 10%) at RT. The flask was evacuated and flushed three times with nitrogen, followed by flushing with hydrogen. The mixture was stirred 4 h at RT under an atmosphere of hydrogen (1.5 atm). The mixture was filtered and the residue rinsed with MeOH. The filtrate was concentrated in vacuo to afford the title compound.

Step D—tert-Butyl 3-[2-(2-ethoxy-2-oxoacetyl)-1-(4-methoxybenzyl)-1H-imidazol-4-yl]propanoate To a flask containing tert-butyl 3-[1-(4-methoxybenzyl)-1H-imidazol-4-yl]propanoate (8.5 g, 26.9 mmol) in DCM (100 mL) at −40° C. was added dropwise ethyl 2-chloro-2-oxoacetate (11.0 g, 81 mmol) followed by the dropwise addition of N-ethyl-N-isopropylpropan-2-amine (10.4 g, 81 mmol) at −40° C. The mixture was stirred for 6 h at RT then quenched by the addition of aq. sat. NaHCO$_3$ and extracted with DCM (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (10-60%) to afford the title compound.

Step E—Ethyl 2-[4-(3-tert-butoxy-3-oxopropyl)-1-(4-methoxybenzyl)-1H-imidazol-2-yl]-3,3-dicyanoacrylate To a flask containing tert-butyl 3-[2-(2-ethoxy-2-oxoacetyl)-1-(4-methoxybenzyl)-1H-imidazol-4-yl]propanoate (2.0 g, 4.80 mmol), malononitrile (1.59 g, 24.01 mmol) in chloroform (20 mL) at RT was added aluminium oxide (4.9 g, 48.0 mmol). The resulting mixture was stirred for 2 h at RT then filtered, and the residue rinsed with DCM. The filtrate was diluted with aq. sat. NH$_4$Cl and extracted with DCM (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (10-60%) to afford the title compound.

Step F—Ethyl 2-{4-[3-(tert-butoxy)-3-oxopropyl]-1-(4-methoxybenzyl)-1H-imidazol-2-yl}-3,3-dicyano-2-methylpropanoate A flask, under an inert atmosphere of nitrogen, containing ethyl 2-{4-[3-(tert-butoxy)-3-oxopropyl]-1-(4-methoxybenzyl)-1H-imidazol-2-yl}-3,3-dicyanoacrylate (550 mg, 1.18 mmol) and lithium chloride (100 mg, 2.37 mmol) in THF (10 mL) was stirred 30 min at 0° C. before methylmagnesium chloride (0.51 mL, 1.54 mmol, 3M in THF) was added dropwise at 0° C. The mixture was stirred for 2 h at 0° C., then quenched by the addition of aq. sat. NH$_4$Cl and extracted with EtOAc (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (0-50%) to afford the title compound I-77. $^1$H NMR (300 MHz, CDCl$_3$) δ 6.97 (d, J=8.7 Hz, 2H), 6.89 (d, J=8.7 Hz, 2H), 6.55 (s, 1H), 5.22 (s, 1H), 5.05 (s, 2H), 4.29-4.09 (m, 2H), 3.82 (s, 3H), 2.82 (t, J=7.2 Hz, 2H), 2.58 (t, J=7.2 Hz, 2H), 1.98 (s, 3H), 1.41 (s, 9H), 1.28 (t, J=7.2 Hz, 3H); m/z=479 (M−1).

Intermediate 78A

Ethyl 2-(4-(2-(tert-butoxy)-2-oxoethyl)phenyl)-3,3-dicyano-2-methylpropanoate

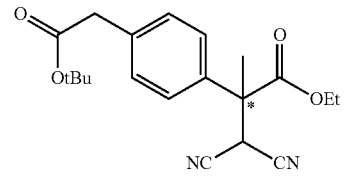 [SMILES: CCOC(=O)C(C)(c1ccc(CC(=O)OC(C)(C)C)cc1)C(C#N)C#N]

A microwave vial, under an inert atmosphere of nitrogen, containing I-21A (500 mg, 1.56 mmol), (2-(tert-butoxy)-2-oxoethyl)zinc(II) bromide (4.05 g, 15.57 mmol), tetrakis(dibenzylideneacetone)dipalladium (179 mg, 0.16 mmol) and tri-tert-butylphosphonium tetrafluoroborate (181 mg, 0.62 mmol) in THF (15 mL) was stirred for 1 h at RT and then irradiated with microwave radiation for 1 h at 120° C. The reaction was quenched by the addition of aq. sat. NH$_4$Cl and extracted with EtOAc (3×). The organic layers were combined, washed with brine, dried over anhydr. Na$_2$SO$_4$, and filtered. The filtrate was concentrated in vacuo. The residue was purified by silica gel column chromatography with EtOAc:petroleum ether (0-20%) to afford the title compound I-78A. $^1$H NMR (400 MHz, CD$_3$OD), 7.41-7.33 (m, 4H), 4.86 (s, 1H), 4.27 (q, J=7.2 Hz, 2H), 3.57 (s, 2H), 1.93 (s, 3H), 1.42 (s, 9H), 1.23 (t, J=7.2 Hz, 3H); m/z=355 (M−1).

Intermediate A1

6-chloro-1-(3,3,4,4,4-pentafluorobutyl)-1H-indazole-3-carboximidamide

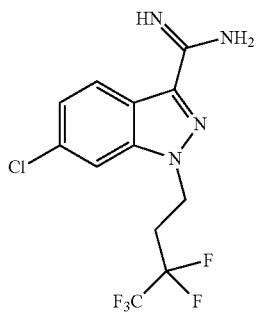 [SMILES: N=C(N)c1nn(CCC(F)(F)C(F)(F)F)c2cc(Cl)ccc12]

Step A—6-chloro-1H-indazole

Acetic anhydride (10.0 mL, 106 mmol) was added dropwise to a benzene solution (110 mL) containing 5-chloro-2-methylaniline (5.0 g, 35.3 mmol) and potassium acetate (3.8 g, 38.7 mmol) at RT. After 10 minutes the reaction mixture was heated to 80° C. tert-butyl nitrite (6.99 mL, 90%, 53.0 mmol) was added over 20 minutes. The reaction mixture was kept at 80° C. overnight, then cooled to RT and concentrated. The residue was dissolved in MeOH and stirred for 10 minutes. The solution was concentrated and to the residue was added MeOH (175 mL), THF (30 mL), water (60 mL) and LiOH monohydrate (8 g, 195 mmol). The solution was then stirred overnight at RT. The solution was then concentrated and the residue partitioned between EtOAc and 0.5 M NaOH aq. The aqueous phase was extracted with EtOAc (2×). The combined organics were washed with brine, dried over MgSO$_4$, filtered and concentrated to give the indicated product. The material was used in Step B without further purification. $^1$H NMR (400 MHz, CH$_3$CN-d$_3$): δ 11.20 (br s, 1H); 8.01 (s, 1H); 7.75-7.70 (m, 1H); 7.60 (s, 1H); 7.13 (dd, J=8.6, 1.7 Hz, 1H). m/z=153 (M+1).

Step A alternative-6-chloro-1H-indazole

A DMA (250 mL) solution containing 4-chloro-2-fluorobenzaldehyde (50 g, 315 mmol) and hydrazine monohydrate (230 mL, 4730 mmol) was stirred for 30 minutes at RT. The solution was then stirred at 100° C. for 17 hours. The reaction mixture, which was a thick white slurry, was cooled to RT. The solid was collected by filtration, washed with water and dried under vacuum to give the title product.

Step B—6-chloro-3-iodo-1H-indazole

An MeCN solution (250 mL) containing the intermediate from Step A (6.14 g, 40.2 mmol) and NIS (9.33 g, 41.4 mmol) was heated at 60° C. for 3 hours. The reaction solution was cooled to RT and concentrated to approximately 70 mL volume. The reaction was then diluted with water, the suspension was stirred for 10 minutes and then filtered. The solid was air dried on the filter to give the indicated product. The material was used in Step C without further purification. $^1$H NMR (400 MHz, CH$_3$CN-d$_3$): δ 1.52 (br s, 1H); 7.62 (d, J=1.7 Hz, 1H); 7.44 (d, J=8.6 Hz, 1H); 7.21 (dd, J=8.6, 1.7 Hz, 1H). m/z=279.0 (M+1).

Step C—6-chloro-1H-indazole-3-carbonitrile

A DMA (48 mL) solution containing the intermediate from Step B (4.0 g, 14.36 mmol), zinc powder (113 mg, 1.72 mmol), zinc cyanide (1.01 g, 8.86 mmol), 1,1'-bis(diphenylphosphino)ferrocene (318 mg, 0.58 mmol) and tris(dibenzylideneacetone)dipalladium (263 mg, 0.29 mmol) was heated at 120° C. for 45 minutes. The solution was cooled to RT and partitioned between EtOAc and 0.5M HCl aq. The organic phase was washed twice with 0.5M aq. HCl and brine. The organic phase was then dried over MgSO$_4$, filtered and concentrated. The crude material was purified by silica gel chromatography using a hexanes/EtOAc gradient to give the indicated product. $^1$H NMR (400 MHz, CH$_3$CN-d$_3$): δ 7.83 (d, J=8.7 Hz, 1H); 7.77 (d, J=1.7 Hz, 1H); 7.36 (dd, J=8.7, 1.7 Hz, 1H); m/z=178.1 (M+1).

Step D—6-chloro-1-(3,3,4,4,4-pentafluorobutyl)-1H-indazole-3-carbonitrile

An acetonitrile solution (450 mL) containing the intermediate from Step C (30 g, 169 mmol), potassium carbonate (116.6 g, 844 mmol) and 1,1,1,2,2-pentafluoro-4-iodobutane (97.2 g, 354.7 mmol) was refluxed for 36 hours. The solution was cooled to RT and partitioned between EtOAc and water. The organic phase was concentrated and the crude material was filtered through a plug of silica gel using 10% EtOAc/heptanes as the eluent. The isolated material was subsequently recrystallized from heptanes to give the indicated product. $^1$H NMR (400 MHz, CH$_3$CN-d$_3$): δ 7.87-7.80 (m, 2H); 7.40 (dd, J=8.7, 1.7 Hz, 1H); 4.77 (t, J=7.0 Hz, 2H); 2.95-2.78 (m, 2H). m/z=324.1 (M+1).

Step E—6-chloro-1-(3,3,4,4,4-pentafluorobutyl)-1H-indazole-3-carboximidamide Trimethylaluminum (23.17 mL, 46.3 mmol, 2.0 M in toluene) was added dropwise to a suspension of ammonium chloride (2.49 g, 46.5 mmol) in 69 mL toluene at 0° C. The solution was stirred at RT for 3 hours, then added to the intermediate from Step D (3.0 g, 9.27 mmol) and heated at 110° C. for 6 hours. The mixture was cooled to RT and poured to a mixture of silica gel and MeOH. After stirring for 1.5 h the suspension was filtered and the filtrate concentrated to give I-A1. $^1$H NMR (400 MHz, CH$_3$CN-d$_3$): δ 8.26 (d, J=8.7 Hz, 1H); 7.70 (d, J=1.7 Hz, 1H); 7.24 (dd, J=8.7, 1.8 Hz, 1H); 4.67 (t, J=7.1 Hz, 2H); 3.01-2.78 (m, 2H); m/z=341.1 (M+1).

Intermediate A2

1-(3,3,4,4,4-pentafluorobutyl)-1H-pyrazolo[3,4-b]pyridine-3-carboximidamide

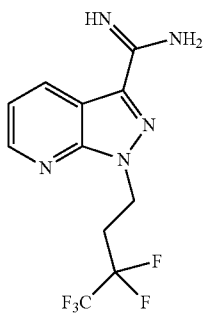 [SMILES: N=C(N)c1nn(CCC(F)(F)C(F)(F)F)c2ncccc12]

Step A—1-(3,3,4,4,4-pentafluorobutyl)-1H-pyrazolo[3,4-b]pyridine-3-carbonitrile In a flask containing 1H-pyrazolo[3,4-b]pyridine-3-carbonitrile (5 g, 34.7 mmol) in acetonitrile (75 mL) was added 1,1,1,2,2-pentafluoro-4-iodobutane (9.82 mL, 69.4 mmol) and potassium carbonate (24.0 g, 173 mmol). The reaction was stirred at 45° C. for 18 hours then cooled to RT, diluted with water and extracted with EtOAc (3×). The organic layers were combined, dried over anhydr. $Na_2SO_4$, and filtered. The filtrate was concentrated in vacuo. The residue was purified by silica gel column chromatography with EtOAc:Hex (0-100%) to afford the title compound.

Step B—1-(3,3,4,4,4-pentafluorobutyl)-1H-pyrazolo[3,4-b]pyridine-3-carboximidamide In a flask containing 1-(3,3,4,4,4-pentafluorobutyl)-1H-pyrazolo[3,4-b]pyridine-3-carbonitrile (5.1 g, 17.7 mmol) in MeOH (11 mL) at RT was added NaOMe (1.34 g, 24.7 mmol). The mixture was stirred at RT for 3 h before acetic acid (4.05 mL, 70.7 mmol) was added, followed by ammonium chloride (1.23 g, 23.0 mmol). The resulting slurry was heated to 65° C. for 4 h then cooled to RT, quenched by the addition of aq. sat. $NaHCO_3$ and extracted with EtOAc (3×). The organic layers were combined, washed with brine, dried over anhydr. $Na_2SO_4$, and filtered. The filtrate was concentrated in vacuo. The residue was purified by silica gel column chromatography with (EtOAc:MeOH 10:1):hexane gradient to afford the title compound I-A2. $^1$H NMR (400 MHz, DMSO-$d_6$) δ 9.45 (s, 3H), 8.77 (dd, J=4.5, 1.5 Hz, 1H), 8.56 (dd, J=8.3, 1.5 Hz, 1H), 7.53 (dd, J=8.3, 4.5 Hz, 1H), 4.93 (t, J=6.8 Hz, 2H), 3.06 (tt, J=19.1, 6.9 Hz, 2H); m/z=308 (M+1).

Using a similar procedure to that described in the preparation of Intermediate A1 and A2, the following compounds in Table 10 were prepared from commercial starting reagents or compounds known in the literature.

TABLE 10

| Int. | X | $R^{2s}$ | $R^{1b}$ | $R^{1a}$ | m/z (M + 1) |
|---|---|---|---|---|---|
| I-A3 | N | —CH₂CH₂CH₂CF₃ | F | H | 276 |
| I-A4 | N | —CH₂CH₂CF₂CF₃ | F | H | 326 |
| I-A5 | C(H) | —CH₂CH₂CH₂CH₃ | H | Cl | 251 |
| I-A6 | N | —CH₂CH₂CH₂CH₃ | H | H | 218 |
| I-A7 | C(H) | —CH₂CH₂OCH₃ | H | Cl | 253 |
| I-A8 | C(H) | —CH₂CH(CH₃)CH₂CF₃ | H | Cl | 305 |
| I-A9 | N | —CH₂CH(CH₃)CH₂CF₃ | H | H | 272 |
| I-A10 | N | —CH₂CH₂CH(CH₃)CF₃ | F | H | 290 |
| I-A11 | C(H) | —CH₂CH(CH₃)CH₂CH₂CH₃ | H | Cl | 265 |
| I-A12 | C(H) | —CH₂-cyclohexyl | H | Cl | 291 |

TABLE 10-continued

| Int. | X | R²ˢ | R¹ᵇ | R¹ᵃ | m/z (M + 1) |
|---|---|---|---|---|---|
| I-A13 | C(H) | n-hexyl | H | Cl | 279 |
| I-A14 | C(H) | -CH₂CH₂CH₂CF₂CF₃ | H | F | 325 |
| I-A15 | C(H) | 2-fluorobenzyl | H | Cl | 303 |
| I-A16 | N | 2-fluorobenzyl | H | H | 270 |
| I-A17 | C(H) | -CH₂CH₂CH₂C(CH₃)₃ | H | Cl | 293 |
| I-A18 | N | 2-fluorobenzyl | F | H | 288 |
| I-A19 | C(H) | (4-methylcyclohexyl)methyl | H | Cl | 305 |
| I-A20 | C(H) | (3-fluoropyridin-2-yl)methyl | H | Cl | 304 |
| I-A21 | C(H) | (tetrahydropyran-2-yl)methyl | H | Cl | 293 |
| I-A22 | C(H) | (4,4-difluorocyclohexyl)methyl | H | Cl | 327 |
| I-A23 | C(H) | 2-fluorobenzyl | H | F | 287 |
| I-A24 | C(H) | 2-fluorobenzyl | OMe | Cl | 333 |
| I-A25 | C(H) | 2-fluorobenzyl | H | Me | 283 |
| I-A26 | C(H) | adamantylmethyl | H | Cl | 343 |
| I-A27 | C(H) | 3-fluorobenzyl | H | Cl | 303 |
| I-A28 | C(H) | 4-fluorobenzyl | H | Cl | 303 |
| I-A29 | C(H) | 2,6-difluorobenzyl | H | Cl | 321 |
| I-A30 | C(H) | 2-methylbenzyl | H | Cl | 299 |
| I-A31 | C(H) | 3-methylbenzyl | H | Cl | 299 |

TABLE 10-continued

| Int. | X | R$^{2s}$ | R$^{1b}$ | R$^{1a}$ | m/z (M + 1) |
|---|---|---|---|---|---|
| I-A32 | C(H) | 4-methylbenzyl | H | Cl | 299 |
| I-A33 | C(H) | 2-fluorobenzyl | F | H | 287 |
| I-A34 | C(H) | 2-fluorobenzyl | Cl | H | 303 |

Intermediate A35

6-chloro-1-(3,3,4,4,4-pentafluorobutyl)-1H-pyrazolo[3,4-b]pyridine-3-carboximidamide

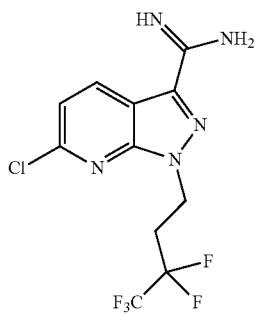

Step A—1-(3,3,4,4,4-pentafluorobutyl)-1H-pyrazolo[3,4-b]pyridine-3-carbonitrile

Using essentially the same procedures described in I-A1 steps C and D, the title compound was prepared, using 3-iodo-1H-pyrazolo[3,4-b]pyridine as starting material. m/z=291 (M+1).

Step B—3-cyano-1-(3,3,4,4,4-pentafluorobutyl)-1H-pyrazolo[3,4-b]pyridine 7-oxide In a flask containing 1-(3,3,4,4,4-pentafluorobutyl)-1H-pyrazolo[3,4-b]pyridine-3-carbonitrile (6.3 g, 21.8 mmol) and 3-chloroperbenzoic acid (22 g, 98 mmol) was added acetic acid (50 mL). The resulting mixture was stirred at 80° C. for 8 h before the mixture was cooled to RT and concentrated in vacuo to dryness. The residue was dissolved in 250 mL of a 2:1 mixture of Hexane:EtOAc and the pH was adjusted to pH 7 by addition of a sat. aq. K$_2$CO$_3$. The resulting solution was extracted with EtOAc (3×) and the organic layers were combined, washed with brine, dried over anhydr. Na$_2$SO$_4$, and filtered. The filtrate was concentrated in vacuo to dryness. The residue purified by silica gel chromatography with EtOAc:petroleum ether:NH$_3$ (2M in MeOH) (0-20%) to afford the title compound. m/z=307 (M+1).

Step C—6-chloro-1-(3,3,4,4,4-pentafluorobutyl)-1H-pyrazolo[3,4-b]pyridine-3-carbonitrile In a flask containing 3-cyano-1-(3,3,4,4,4-pentafluorobutyl)-1H-pyrazolo[3,4-b]pyridine 7-oxide (1.9 g, 1.2 mmol) was added Phosphorus (V) oxychloride (6.9 mL, 74 mmol). The resulting mixture was stirred at 80° C. for 5 h. The mixture was diluted in 250 mL of a 2:1 mixture of Hexane:EtOAc and the pH was adjusted to pH 7 by addition of a sat. aq. K$_2$CO$_3$. The resulting solution was extracted with a 2:1 mixture of hexane:EtOAc (3×). The organic layers were combined, dried over anhydr. Na$_2$SO$_4$, and filtered. The filtrate was concentrated in vacuo to dryness. The residue was purified by silica gel chromatography with EtOAc:petroleum ether to afford the title compound. m/z=325 (M+1).

Step D—6-chloro-1-(3,3,4,4,4-pentafluorobutyl)-1H-pyrazolo[3,4-b]pyridine-3-carboximidamide Trimethylaluminum (19.9 mL, 39.8 mmol, 2.0 M in toluene) was added dropwise to a suspension of ammonium chloride (2.1 g, 39.8 mmol) in 24 mL toluene at 0° C. The solution was then stirred at RT for 3 hours then added to 6-chloro-1-(3,3,4,4,4-pentafluorobutyl)-1H-pyrazolo[3,4-b]pyridine-3-carbonitrile (2.6 g, 8.0 mmol) and heated at 75° C. overnight. The reaction mixture was cooled to RT, and quenched by the addition of MeOH:DCM (1:1) and silica. After stirring for 3 hours the suspension was filtered through diatomaceous earth and the filtrate was concentrated in vacuo dryness to afford the title compound I-A35. $^1$H NMR (400 MHz, DMSO-d$_6$) δ 8.68 (d, J=8.4 Hz, 1H), 7.41 (d, J=8.4 Hz, 1H), 6.68 (br, 3H), 4.76 (t, J=7.2 Hz, 2H), 3.07-2.93 (m, 2H); m/z=342 (M+1).

Using a similar procedure to that described in the preparation of Intermediate I-A35, the following compounds in Table 7 were prepared from commercial starting reagents or compounds known in the literature.

TABLE 11

| Int. | R$^{2s}$ | m/z (M + 1) |
|---|---|---|
| I-A36 | 2-ethylbutyl | 252 |

TABLE 11-continued

| I-A37 | 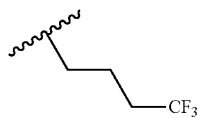 | 306 |

Intermediate A38

6-Methyl-1-(4,4,4-trifluorobutyl)-1H-pyrazolo[3,4-b]pyridine-3-carboximidamide

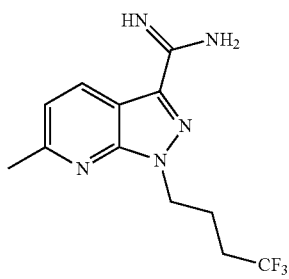 [SMILES: Cc1ccc2c(C(=N)N)nn(CCCC(F)(F)F)c2n1]

Step A—6-chloro-1-(4,4,4-trifluorobutyl)-1H-pyrazolo[3,4-b]pyridine-3-carbonitrile Using essentially the same procedures described in intermediate I-35 step A to C, the title compound was prepared. $^1$H NMR (300 MHz, CDCl$_3$) δ 8.16 (d, J=8.5 Hz, 1H), 7.38 (d, J=8.5 Hz, 1H), 4.65 (t, J=6.6 Hz, 2H), 2.38-2.09 (m, 4H); m/z=288 (M+1).

Step B—6-methyl-1-(4,4,4-trifluorobutyl)-1H-pyrazolo[3,4-b]pyridine-3-carbonitrile To a solution containing 6-chloro-1-(4,4,4-trifluorobutyl)-1H-pyrazolo[3,4-b]pyridine-3-carbonitrile (800 mg, 2.77 mmol) in THF (10 mL) was added bis(triphenylphosphine)palladium(II) dichloride (195 mg, 0.28 mmol) the resulting solution was stirred at RT for 30 min. Dimethylzinc (8.31 mL, 8.31 mmol, 1 M in THF) was added and the resulting mixture was stirred 16 hours at RT. The reaction was quenched by the addition of aq. sat. NH$_4$Cl, extracted with EtOAc (3×). The organic layer was washed with brine, dried over anhydr. Na$_2$SO$_4$, and filtered. The filtrate was concentrated in vacuo. The residue was purified by silica gel column chromatography with EtOAc:petroleum ether (0-30%) to afford the title compound. m/z=269 (M+1).

Step C—6-methyl-1-(4,4,4-trifluorobutyl)-1H-pyrazolo[3,4-b]pyridine-3-carboximidamide Trimethylaluminum (4.0 mL, 8.0 mmol, 2.0 M in toluene) was added dropwise to a suspension of ammonium chloride (570 mg, 10.6 mmol) in 10 mL toluene cooled to 0° C. The solution was then stirred at RT for 1 hours. To this solution was added 6-methyl-1-(4,4,4-trifluorobutyl)-1H-pyrazolo[3,4-b]pyridine-3-carbonitrile (270 mg, 1.00 mmol) and the resulting mixture was heated at 100° C. for 2 h. The reaction mixture was cooled to 0° C., and quenched by the addition of a MeOH:DCM (1:1) mixture. After stirring for 1 hour the suspension was filtered through diatomaceous earth and the filtrate was concentrated in vacuo dryness. The residue was diluted in EtOAc and the pH was adjusted to pH 10 by addition of 1 M NaOH (aqueous solution). The resulting solution was extracted with EtOAc (3×). The organic layer was washed with brine, dried over anhydr. Na$_2$SO$_4$, and filtered. The filtrate was concentrated in vacuo to afford the title compound I-A38. $^1$H NMR (300 MHz, DMSO-d$_6$) δ 8.50 (d, J=8.4 Hz, 1H), 7.18 (d, J=8.4 Hz, 1H), 6.48 (br, 3H), 4.52 (t, J=7.2 Hz, 2H), 2.61 (s, 3H), 2.45-2.28 (m, 2H), 2.16-2.06 (m, 2H); m/z=286 (M+1).

Intermediate A39

1-(2,3-difluoro-4-methylbenzyl)-6-methyl-1H-pyrazolo[3,4-b]pyridine-3-carboximidamide

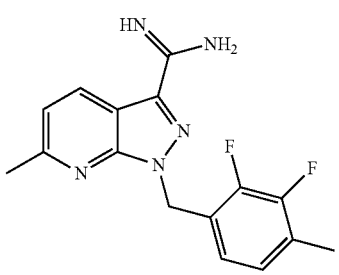

The title compound was prepared using the protocol published in WO 2015-004105-A1.

Intermediate A40

1-(2-fluorobenzyl)-1H-indazole-3-carboximidamide

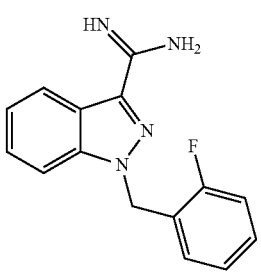 [SMILES: N=C(N)c1nn(Cc2ccccc2F)c2ccccc12]

A flask under nitrogen containing I-A15 (1.0 g, 2.95 mmol) and palladium on carbon (1.0 g, 10 w %) in MeOH (50 mL), was purged with hydrogen. The mixture was stirred at RT for 0.5 h under an atmosphere of hydrogen (~2 atm). The solid was filtered out and washed with MeOH (3×). The filtrate was concentrated in vacuo to dryness. The residue was purified by C18 column chromatography with acetonitrile:water: 0.1% trifluoroacetic acid, (20%-40%) to afford the title compound I-A40. $^1$H NMR (400 MHz, DMSO-d$_6$) δ 9.40-9.30 (br, 4H), 8.04 (d, J=8.4 Hz, 1H), 7.95 (d, J=8.4 Hz, 1H), 7.64-7.59 (m, 1H), 7.47-7.37 (m, 2H), 7.28-7.23 (m, 2H), 7.21-7.16 (m, 1H), 5.92 (s, 2H); m/z=269 (M+1).

Intermediate A41

6-Chloro-1-(cyclopentylmethyl)-1H-indazole-3-carboximidamide

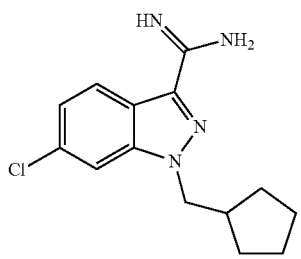 [SMILES: N=C(N)c1nn(CC2CCCC2)c2cc(Cl)ccc12]

Step A—6-Chloro-1-(cyclopentylmethyl)-1H-indazole-3-carbonitrile

To a flask containing 6-chloro-1H-indazole-3-carbonitrile (1.0 g, 5.63 mmol) and cyclopentylmethyl 4-methylbenzenesulfonate (1.9 g, 7.32 mmol) in DMF (10 mL), was added potassium phosphate (2.4 g, 11.26 mmol) and the resulting mixture was stirred for 16 h at 70° C. The reaction was cooled to RT, quenched by the addition of brine, and extracted with EtOAc (3×). The organic layer was washed with brine, dried over anhydr. $Na_2SO_4$, and filtered. The filtrate was concentrated in vacuo. The residue was purified by silica gel column chromatography with EtOAc:petroleum ether (0-10%) to afford the title compound. m/z=301 (M+1).

Step B—6-Chloro-1-(cyclopentylmethyl)-1H-indazole-3-carboximidamide

To a flask, under a inert atmosphere of nitrogen, containing 6-chloro-1-(cyclopentylmethyl)-1H-indazole-3-carbonitrile (1.0 g, 3.85 mmol) in MeOH (10 mL) was added NaOMe (0.42 g, 7.70 mmol). The solution was stirred for 2 h at RT and ammonium chloride (0.62 g, 11.55 mmol) was added. The resulting mixture was stirred for 3 h at 7° C. The mixture was cooled to RT and concentrated in vacuo to dryness. The residue was poured into water (100 mL). 2N HCl solution was added to reach pH 1~2, the resulting solution was extracted with $Et_2O$ (2×) and the aqueous layer was kept. Then the pH value of the aqueous layer was adjusted to 11~12 with NaOH (1 N). The resulting aqueous solution was extracted with EtOAc (3×), The organic layer was dried over anhydr. $Na_2SO_4$, and filtered. The filtrate was concentrated in vacuo to afford the title compound I-A41. $^1$H NMR (300 MHz, $CD_3OD$) δ 8.08 (d, J=8.7 Hz, 1H), 8.68 (d, J=1.8 Hz, 1H), 7.18 (dd, J=8.7, 1.8 Hz, 1H), 4.31 (d, J=7.5 Hz, 2H), 2.57-2.48 (m, 1H), 1.73-1.47 (m, 6H), 1.39-1.21 (m, 2H); m/z=277 (M+1).

Using a similar procedure to that described in the preparation of Intermediate A1, I-A2 and I-A41 the following compounds in Table 12 were prepared from commercial starting reagents or compounds known in the literature.

TABLE 12

| Int. | X | R2s | R1b | R1a | m/z (M + 1) |
|---|---|---|---|---|---|
| I-A42 | C(H) | 2,4-difluorobenzyl | H | Cl | 321 |
| I-A43 | C(H) | 2,3-difluorobenzyl | H | Cl | 321 |
| I-A44 | C(H) | 2,3,5,6-tetrafluorobenzyl | H | Cl | 339 |
| I-A45 | C(H) | 2-fluoro-3-methylbenzyl | H | Cl | 317 |
| I-A46 | C(H) | 2-fluoro-3-methylbenzyl | H | F | 301 |
| I-A47 | C(H) | 2-fluoro-5-methylbenzyl | H | Cl | 317 |
| I-A48 | C(H) | (tetrahydro-2H-pyran-2-yl)methyl | H | F | 277 |
| I-A49 | C(H) | 3-fluorobenzyl | H | F | 287 |
| I-A50 | C(H) | 2,3-difluorobenzyl | H | F | 305 |

TABLE 12-continued

| Int. | X | R2s | R1b | R1a | m/z (M + 1) |
|---|---|---|---|---|---|
| I-A51 | N | 3-fluorobenzyl | H | H | 270 |
| I-A52 | N | cyclohexylmethyl | H | H | 258 |
| I-A53 | C(H) | (3,3-difluorocyclobutyl)methyl | H | Cl | 299 |
| I-A54 | C(H) | cyclohexylmethyl | H | F | 275 |
| I-A55 | C(H) | (4-methylcyclohexyl)methyl | H | F | 289 |
| I-A56 | N | cyclopentylmethyl | H | H | 244 |
| I-A57 | N | (tetrahydropyran-2-yl)methyl | H | H | 260 |
| I-A58 | N | (4-methylcyclohexyl)methyl | H | H | 272 |
| I-A59 | N | 3,3-dimethylbutyl | H | H | 246 |
| I-A60 | C(H) | 3,3-dimethylbutyl | H | Cl | 279 |
| I-A61 | C(H) | (3-fluoropyridin-2-yl)methyl | H | H | 270 |
| I-A62 | C(H) | (3-fluoro-4-methylpyridin-2-yl)methyl | H | Cl | 318 |

Example 1A 3-(2-{4-Amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}oxazol-4-yl)-2,2-dimethylpropanoic acid

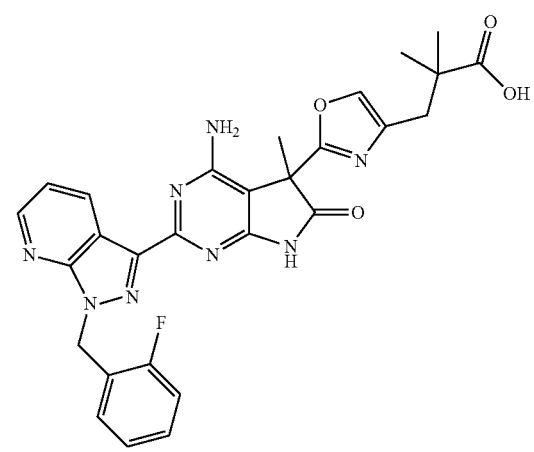 [SMILES: CC(C)(Cc1coc(C2(C)C(=O)Nc3nc(-c4nn(Cc5ccccc5F)c5ncccc45)nc(N)c32)n1)C(=O)O]

Step A—methyl 3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}oxazol-4-yl)-2,2-dimethylpropanoate Into a flask was placed I-A16 (200 mg, 0.74 mmol), I-32 (258 mg, 0.74 mmol), potassium bicarbonate (112 mg, 1.11 mmol) and t-BuOH (10 mL). The resulting mixture was stirred at 80° C. for 16 h then concentrated in vacuo to dryness. The residue was purified by silica gel chromatography using (MeOH:DCM) to afford the racemic title product. The racemic material was resolved using Chiral SFC (CHIRALPAK® AD-H) to afford isomer A (faster eluting) and isomer B (slower eluting). m/z=571 (M+1).

Step B—3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}oxazol-4-yl)-2,2-dimethylpropanoic acid To a flask containing methyl 3-(2-{4-amino-2-[1-(2-fluorobenzyl)-1H-pyrazolo[3,4-b]pyridin-3-yl]-5-methyl-6- oxo-6,7-dihydro-5H-pyrrolo[2,3-d]pyrimidin-5-yl}oxazol-4-yl)-2,2-dimethylpropanoate isomer A (160 mg, 0.280 mmol) in MeOH (5 mL) was added LiOH (67 mg, 2.80 mmol) in 1 mL of water. The resulting mixture was stirred 48 h at RT. The reaction was concentrated in vacuo to dryness. The residue was diluted with concentrated sat. Na$_2$CO$_3$ and extracted with EtOAc (3×). The pH of the aqueous phase was adjusted to pH 6 with HCl (1M) the resulting solid was collected by filtration, washed with water, and dried under vacuum to afford the title product Ex-1A. $^1$H NMR (300 MHz, CD$_3$OD) δ 9.06 (d, J=7.8 Hz, 1H), 8.61 (dd, J=4.5, 1.5 Hz, 1H), 7.63 (s, 1H), 7.40-7.27 (m, 2H), 7.16-7.06 (m, 3H), 5.91 (s, 2H), 2.86-2.72 (m, 2H), 1.92 (s, 3H), 1.23 (s, 3H), 1.19 (s, 3H); m/z=557 (M+1).

Using essentially the same procedure described in Ex-1A, the following compounds in Table 13 were prepared.

TABLE 13

| Ex. | Int. SM | Chiral Resolution Column | Structure | Name | m/z (M + 1) |
|---|---|---|---|---|---|
| 2A | I-32 | IA | 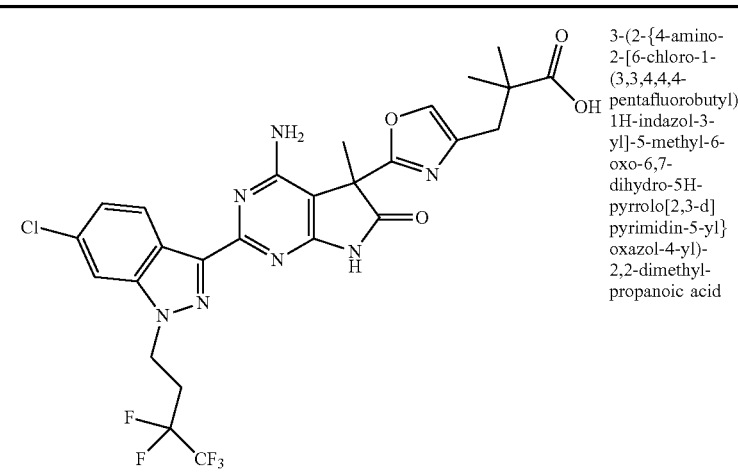 | 3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}oxazol-4-yl)-2,2-dimethyl-propanoic acid | 628 |
| 3A | I-32 | IA | 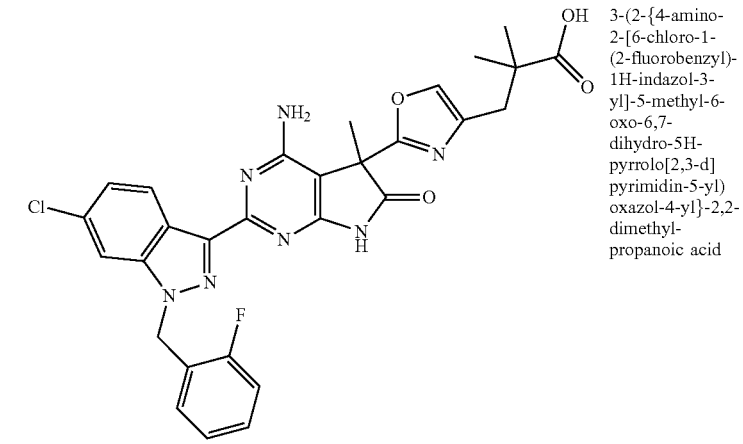 | 3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl)oxazol-4-yl}-2,2-dimethyl-propanoic acid | 590 |

TABLE 13-continued

| Ex. | Int. SM | Chiral Resolution Column | Structure | Name | m/z (M + 1) |
|---|---|---|---|---|---|
| 4B | I-14 | (R,R)WHELK-01 | 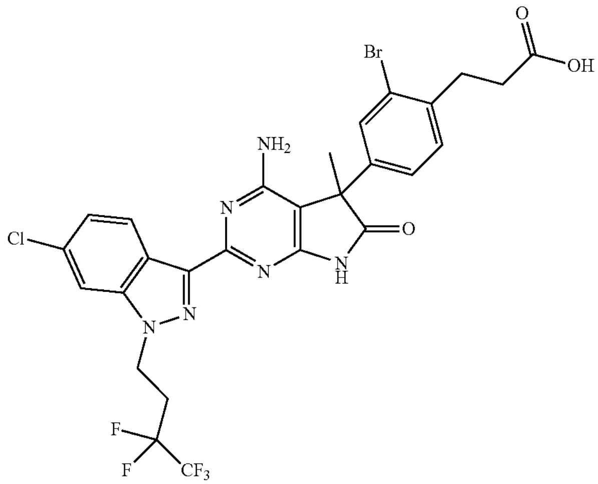 [SMILES: CC1(c2ccc(CCC(=O)O)c(Br)c2)C(=O)Nc2nc(-c3nn(CCC(F)(F)C(F)(F)F)c4cc(Cl)ccc34)nc(N)c21] | 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-bromophenyl)propanoic acid | 689 |
| 5BA | I-11B | IA | 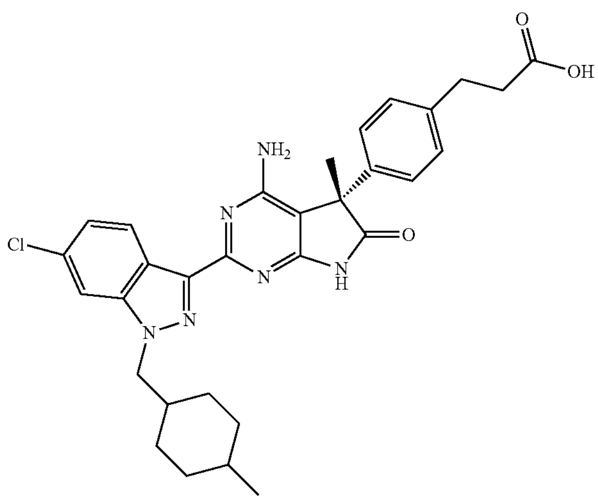 [SMILES: CC1CCC(Cn2nc(-c3nc(N)c4c(n3)NC(=O)[C@@]4(C)c3ccc(CCC(=O)O)cc3)c3ccc(Cl)cc32)CC1] | (5S)-3-{4-[4-amino-2-{6-chloro-1-[(4-methylcyclohexyl)methyl]-1H-indazol-3-yl}-5-methyl-6-oxo-6,7-dihydro-5H-pyrrolo[2,3-d]pyrimidin-5-yl]phenyl}propanoic acid | 573 |
| 5BB | I-11B | IA | 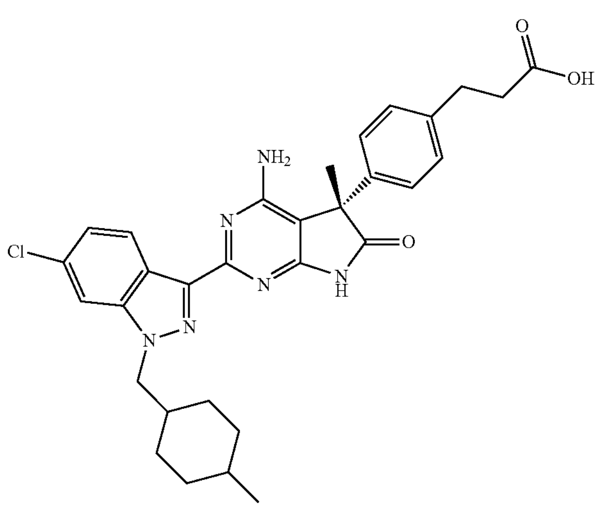 [SMILES: CC1CCC(Cn2nc(-c3nc(N)c4c(n3)NC(=O)[C@@]4(C)c3ccc(CCC(=O)O)cc3)c3ccc(Cl)cc32)CC1] | (5S)-3-{4-[4-amino-2-{6-chloro-1-[(4-methylcyclohexyl)methyl]-1H-indazol-3-yl}-5-methyl-6-oxo-6,7-dihydro-5H-pyrrolo[2,3-d]pyrimidin-5-yl]phenyl}propanoic acid | 573 |

TABLE 13-continued

| Ex. | Int. SM | Chiral Resolution Column | Structure | Name | m/z (M + 1) |
|---|---|---|---|---|---|
| 6BA | I-11B | IC | 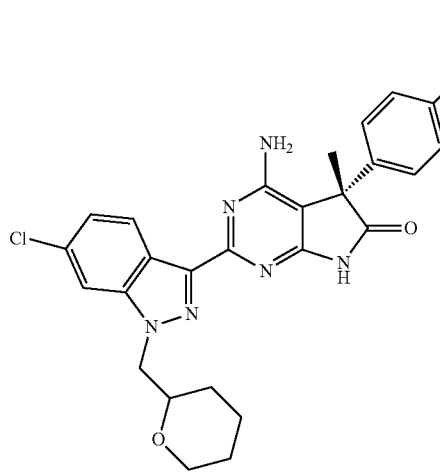 | (5S)-3-{4-[4-amino-2-{6-chloro-2-[tetrahydro-2H-pyran-2-ylmethyl]-1H-indazol-3-yl}-5-methyl-6-oxo-6,7-dihydro-5H-pyrrolo[2,3-d]pyrimidin-5-yl]phenyl}propanoic acid | 561 |
| 7A | I-11 | AD | 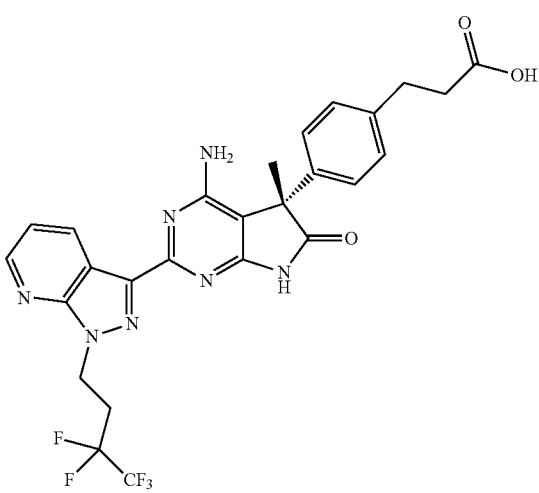 [SMILES: C[C@@]1(c2ccc(CCC(=O)O)cc2)C(=O)Nc2nc(-c3nn(CCC(F)(F)C(F)(F)F)c4ncccc34)nc(N)c21] | (S)-3-(4-{4-amino-5-methyl-6-oxo-2-[1-(3,3,4,4,4-pentafluoro-butyl)-1H-pyrazolo[3,4-b]pyridin-3-yl]-6,7-dihydro-5H-pyrrolo[2,3-d]pyrimidin-5-yl}phenyl)propanoic acid | 576 |
| 8B | I-20 | IC | 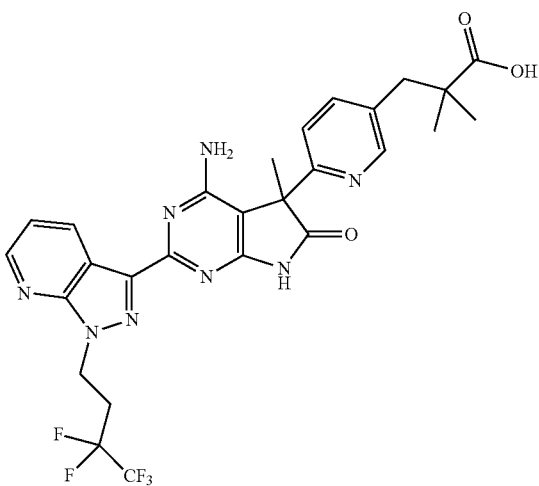 [SMILES: CC(C)(Cc1ccc(C2(C)C(=O)Nc3nc(-c4nn(CCC(F)(F)C(F)(F)F)c5ncccc45)nc(N)c32)nc1)C(=O)O] | 3-(6-{4-amino-5-methyl-6-oxo-2-[1-(3,3,4,4,4-pentafluoro-butyl)-1H-pyrazolo[3,4-b]pyridin-3-yl]-6,7-dihydro-5H-pyrrolo[2,3-d]pyrimidin-5-yl}pyridin-3-yl)-2,2-dimethyl-propanoic acid | 638 |

| | $^1$H NMR Data |
|---|---|
| 2A | $^1$H NMR (400 MHz, DMSO-$d_6$) δ 12.23 (s, 1H), 11.39 (s, 1H), 8.68 (d, J = 8.7 Hz, 1H), 8.04 (d, J = 1.7 Hz, 1H), 7.75 (s, 1H), 7.28 (dd, J = 8.7, 1.7 Hz, 1H), 6.65 (s, 2H), 4.84 (t, J = 6.9 Hz, 2H), 2.91 (tt, J = 19.4, 6.9 Hz, 2H), 2.76-2.56 (m, 2H), 1.81 (s, 3H), 1.10 (s, 3H), 1.08 (s, 3H) |

TABLE 13-continued

| Ex. | Int. SM | Chiral Resolution Column | Structure | Name | m/z (M + 1) |
|---|---|---|---|---|---|
| 3A | | | | | ¹H NMR (400 MHz, DMSO-d₆) δ 12.22 (s, 1H), 11.37 (s, 1H), 8.69 (d, J = 8.7 Hz, 1H), 8.01 (d, J = 1.7 Hz, 1H), 7.74 (s, 1H), 7.42-7.11 (m, 5H), 6.64 (s, 2H), 5.81 (s, 2H), 2.71-2.57 (m, 2H), 1.80 (s, 3H), 1.09 (d, J = 8.7 Hz, 6H) |
| 4B | | | | | ¹H NMR (300 MHz, CD₃OD) δ 8.70 (d, J = 8.7 Hz, 1H), 7.77 (s, 1H), 7.56 (d, J = 1.8 Hz, 1H), 7.41-7.21 (m, 3H), 4.83 (t, J = 7.2 Hz, 2H), 3.12-2.84 (m, 4H), 2.66-2.45 (m, 2H), 1.87 (s, 3H) |
| 5BA | | | | | ¹H NMR (300 MHz, CD₃OD) δ 8.66 (d, J = 9.0 Hz, 1H), 7.70 (s, 1H), 7.34-7.21 (m, 5H), 4.42 (d, J = 7.5 Hz, 2H), 2.91 (t, J = 7.5 Hz, 2H), 2.59 (t, J = 7.5 Hz, 2H), 2.33-2.21 (m, 1H), 1.87 (s, 3H), 1.69-1.67 (m, 1H), 1.55-1.43 (m, 8H), 1.00 (d, J = 6.9 Hz, 3H) |
| 5BB | | | | | ¹H NMR (300 MHz, CD₃OD) δ 8.66 (d, J = 8.7 Hz, 1H), 7.69 (s, 1H), 7.31-7.21 (m, 5H), 4.31 (d, J = 7.2 Hz, 2H), 2.91 (t, J = 7.5 Hz, 2H), 2.57 (t, J = 7.5 Hz, 2H), 2.09-1.95 (m, 1H), 1.87 (s, 3H), 1.72-1.69 (m, 2H), 1.61-1.57 (m, 2H), 1.43-1.29 (m, 1H), 1.21-1.09 (m, 2H), 0.96-0.88 (m, 5H) |
| 6BA | | | | | ¹H NMR (300 MHz, CD₃OD) δ 8.61 (d, J = 8.7 Hz, 1H), 7.68 (d, J = 0.9 Hz, 1H), 7.30-7.17 (m, 5H), 4.52-4.38 (m, 2H), 3.88-3.84 (m, 2H), 3.36-3.28 (m, 1H), 2.88 (t, J = 7.5 Hz, 2H), 2.55 (t, J = 7.5 Hz, 2H), 1.89-1.80 (m, 4H), 1.68-1.64 (m, 1H), 1.57-1.30 (m, 4H) |
| 7A | | | | | ¹H NMR (500 MHz, CD₃OD) δ 9.07 (dd, J = 8.1, 1.6 Hz, 1H), 8.64 (dd, J = 4.6, 1.6 Hz, 1H), 7.38 (dd, J = 8.1, 4.6 Hz, 1H), 7.35-7.21 (m, 4H), 4.98 (t, J = 7.3 Hz, 2H), 3.01 (td, J = 18.4, 9.2 Hz, 2H), 2.93 (t, J = 7.6 Hz, 2H), 2.61 (t, J = 7.6 Hz, 2H), 1.90 (s, 3H) |
| 8B | | | | | ¹H NMR (CD₃OD, 300 MHz) δ 8.60 (d, J = 9.0 Hz, 1H), 8.45 (s, 1H), 7.84 (s, 1H), 7.71 (dd, J = 8.1, 2.1 Hz, 1H), 7.49 (d, J = 8.4 Hz, 1H), 7.32 (dd, J = 8.7, 1.5 Hz, 1H), 4.88-4.83 (m, 2H), 3.09-2.87 (m, 4H), 1.93 (s, 3H), 1.20 (s, 6H) |

Example 9B 3-(4-{4-Amino-5-methyl-6-oxo-2-(1-(3,3,4,4,4-pentafluorobutyl)-2,3-dihydro-1H-pyrazolo[3,4-b]pyridin-3-yl)-6,7-dihydro-5H-pyrrolo[2,3-d]pyrimidin-5-yl}phenyl)-2,2-dimethylpropanoic acid

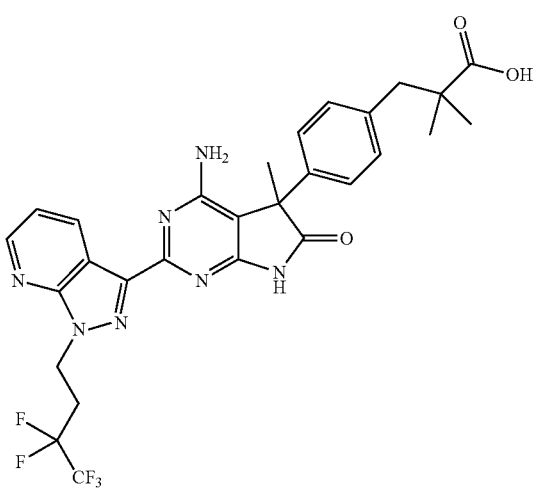 [SMILES: CC(C)(Cc1ccc(C2(C)C(=O)Nc3nc(-c4nn(CCC(F)(F)C(F)(F)F)c5ncccc45)nc(N)c32)cc1)C(=O)O]

Step A—methyl 3-(4-{4-amino-5-methyl-6-oxo-2-(1-(3,3,4,4,4-pentafluorobutyl)-2,3-dihydro-1H-pyrazolo[3,4-b]pyridin-3-yl)-6,7-dihydro-5H-pyrrolo[2,3-d]pyrimidin-5-yl}phenyl)-2,2-dimethylpropanoate Into a flask was placed I-13B (50 mg, 0.14 mmol), I-A2 (48 mg, 0.14 mmol), potassium bicarbonate (42 mg, 0.42 mmol) and t-BuOH (1.4 mL). The resulting mixture was warmed at 65° C. for 16 h. The reaction was cooled to RT and quenched by the addition of water. The resulting solution was extracted with EtOAc (3×) and the organic layers were combined, dried over anhydr. Na₂SO₄, filtered and the filtrate was concentrated in vacuo to dryness. The residue was purified by silica gel chromatography using (EtOAc:EtOH 3:1):hexane gradient to afford the title product. m/z=618.2 (M+1).

Step B—3-(4-{4-amino-5-methyl-6-oxo-2-(1-(3,3,4,4-pentafluorobutyl)-2,3-dihydro-1H-pyrazolo[3,4-b]pyridin-3-yl)-6,7-dihydro-5H-pyrrolo[2,3-d]pyrimidin-5-yl}phenyl)-2,2-dimethylpropanoic acid Into a flask was placed methyl 3-(4-{4-amino-5-methyl-6-oxo-2-(1-(3,3,4,4,4-pentafluorobutyl)-2,3-dihydro-1H-pyrazolo[3,4-b]pyridin-3-yl)-6,7-dihydro-5H-pyrrolo[2,3-d]pyrimidin-5-yl}phenyl)-2,2-dimethylpropanoate (61 mg, 0.10 mmol), LiOH (24 mg, 0.98 mmol), dioxane (2.5 mL) and water (2.5 mL). The resulting mixture was warmed at 65° C. for 16 h. The reaction was cooled to RT and quenched by the addition of acetic acid (73 μL, 1.3 mmol). The resulting solution was extracted with EtOAc (3×), the organic layers were combined, dried over anhydr. MgSO₄, filtered and the filtrate was concentrated in vacuo to dryness. The residue was purified by silica gel chromatography using (EtOAc:EtOH 3:1):hexane gradient to afford the title product Ex-9B. ¹H NMR (400 MHz, DMSO-d₆) δ 12.24 (s, 1H), 11.11 (s, 1H), 9.03 (dd, J=8.1, 1.6 Hz, 1H), 8.63 (dd, J=4.5, 1.6 Hz, 1H), 7.37 (dd, J=8.1, 4.5 Hz, 1H), 7.17 (d, J=8.4 Hz, 2H), 7.11 (d, J=8.3 Hz, 2H), 6.56 (s, 2H), 4.87 (t, J=6.8 Hz, 2H), 2.97 (tt, J=19.1, 6.8 Hz, 2H), 2.74 (s, 2H), 1.77 (s, 3H), 1.04 (s, 6H); m/z=604 (M+1)

Example 10B (S)-3-(4-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid

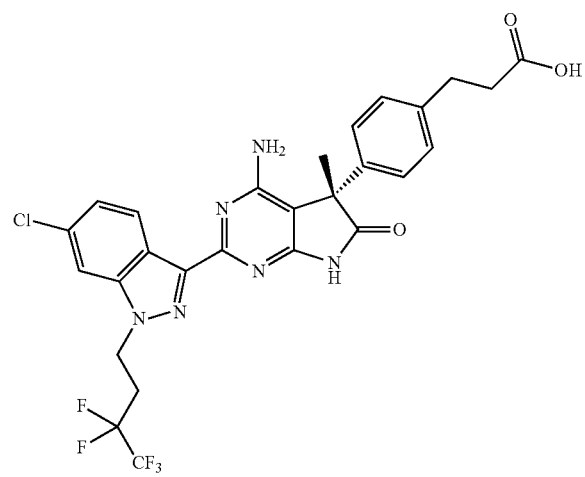 [SMILES: C[C@@]1(c2ccc(CCC(=O)O)cc2)C(=O)Nc2nc(-c3nn(CCC(F)(F)C(F)(F)F)c4cc(Cl)ccc34)nc(N)c21]

Step A—(S)-Methyl 3-(4-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoate In a flask containing I-A1 (91 mg, 0.27 mmol), I-11B (80 mg, 0.24 mmol) and potassium bicarbonate (73.2 mg, 0.73 mmol) in t-BuOH (2.4 mL) was stirred at 80° C. for 16 h. The reaction was cooled to RT, diluted with EtOAc and water, and extracted with EtOAc (3×). The organic layers were combined, washed with brine, dried over anhydr. Na$_2$SO$_4$, and filtered. The filtrate was concentrated in vacuo and the residue was purified by silica gel column chromatography with (EtOAc:EtOH 3:1):hexane (0-40%) to afford the title compound. m/z=623 (M+1).

Step B—(S)-3-(4-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid In a flask containing (S)-methyl 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoate (120 mg, 0.19 mmol) in dioxane (8.7 mL) was added LiOH (46 mg, 1.93 mmol) in water (1 mL). The reaction was stirred 2 h at 50° C. The reaction was cooled to RT, concentrated in vacuo and diluted with EtOAc. Acetic acid (132 µl, 2.31 mmol) was added and the mixture was extracted with EtOAc (3×). The organic layers were combined, washed with brine (2×), dried over anhydr. MgSO$_4$, and filtered. The filtrate was concentrated in vacuo. The residue was purified by silica gel column chromatography with (EtOAc:EtOH 3:1):hexane (0-100%) to afford the title compound Ex-10B. $^1$H NMR (400 MHz, DMSO-d$_6$) δ 12.12 (s, 1H), 11.09 (s, 1H), 8.69 (d, J=8.7 Hz, 1H), 8.03 (d, J=1.7 Hz, 1H), 7.26 (dd, J=8.7, 1.7 Hz, 1H), 7.22-7.11 (m, 4H), 6.54 (s, 2H), 4.82 (t, J=6.8 Hz, 2H), 2.90 (tt, J=19.4, 6.9 Hz, 2H), 2.77 (t, J=7.6 Hz, 2H), 2.52-2.49 (m, 2H), 1.76 (s, 3H); m/z=609 (M+1).

Example 11B 3-(3-{4-Amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid

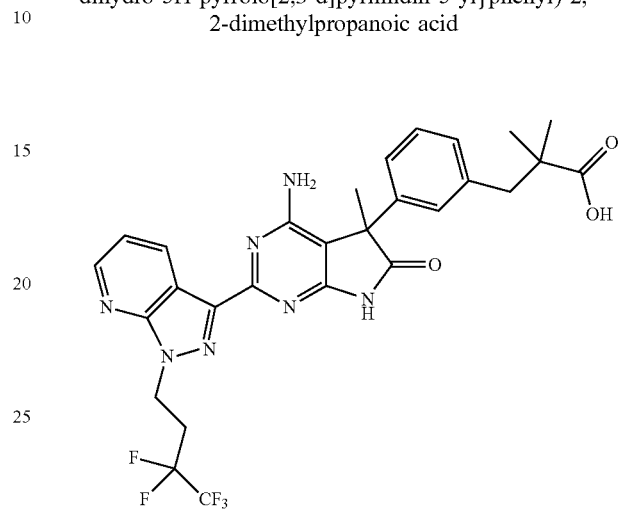

Step A—methyl 3-(3-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)-2,2-dimethyl Propanoate To a flask containing intermediate A2 (45.6 mg, 0.15 mmol) and I-39B (50 mg, 0.14 mmol) in THF (2.7 mL) was added triethylamine (56 µl, 0.40 mmol). The resulting mixture was stirred at 80° C. for 6 h then 24 h at 60° C. The reaction was cooled to RT diluted with EtOAc and water. The resulting mixture was extracted with EtOAc (3×), the organic layers were combined, washed with brine, dried over anhydr. MgSO$_4$, filtered and the filtrate was concentrated in vacuo to dryness. The residue was purified by silica gel chromatography using (EtOAc:EtOH 3:1):hexane (0-40%) to afford the title compound. m/z=632 (M+1).

Step B—3-(3-{4-amino-5-methyl-6-oxo-2-[1-(3,3,4,4-pentafluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid To a flask containing methyl 3-(3-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)-2,2-dimethyl propanoate (80 mg, 0.13 mmol) in a dioxane (5.8 mL) water (0.6 mL) mixture was added LiOH (30 mg, 1.28 mmol) the resulting mixture was stirred at 80° C. for 16 h. The reaction was cooled to RT, diluted with EtOAc and water, and quenched by the addition of acetic acid (870 µl, 1.52 mmol). The resulting solution was extracted with EtOAc (3×) and the organic layers were combined, washed with brine dried over anhydr. MgSO$_4$, filtered and the filtrate was concentrated in vacuo to dryness. The residue was purified by silica gel chromatography using (EtOAc:EtOH 3:1):hexane (10%-70%) to afford the title compound Ex-11B. ¹H NMR (500 MHz, MeOD) δ 9.03 (dd, J=8.1, 1.6 Hz, 1H), 8.60 (dd, J=4.5, 1.6 Hz, 1H), 7.35 (dd, J=8.1, 4.5 Hz, 1H), 7.30-7.18 (m, 3H), 7.18-7.11 (m, 1H), 4.95 (t, J=7.3 Hz, 2H), 3.05-2.93 (m, 2H), 2.91 (d, J=13.2 Hz, 1H), 2.79 (d, J=13.2 Hz, 1H), 1.88 (s, 3H), 1.18 (s, 3H), 1.10 (s, 3H); m/z=604 (M+1).

Using essentially the same procedure described in examples 9, 10 and 11, the following compounds in Table 14 were prepared.

TABLE 14

| Ex. | Int. SM | Structure | Name | m/z (M + 1) |
|---|---|---|---|---|
| 12B | I-24B | 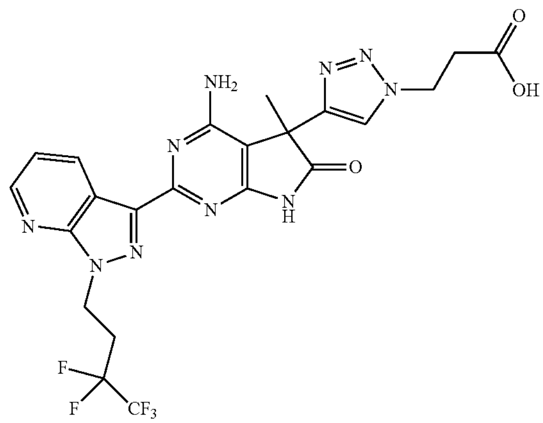 [SMILES: CC1(c2cn(CCC(=O)O)nn2)C(=O)Nc2nc(-c3nn(CCC(F)(F)C(F)(F)F)c4ncccc34)nc(N)c21] | 3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1H-1,2,3-triazol-1-yl)propanoic acid | 567 |
| 13B | I-11B | 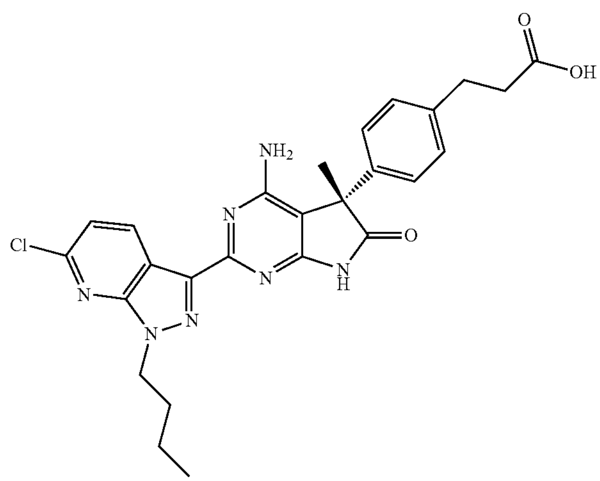 [SMILES: CCCCn1nc(-c2nc(N)c3c(n2)NC(=O)[C@@]3(C)c2ccc(CCC(=O)O)cc2)c2ccc(Cl)nc21] | (S)-3-(4-{4-amino-2-(1-butyl-6-chloro-1H-pyrazolo[3,4-b]pyridin-3-yl)-5-methyl-6-oxo-6,7-dihydro-5H-pyrrolo[2,3-d]pyrimidin-5-yl}phenyl)propanoic acid | 520 |
| 14B | I-11B | 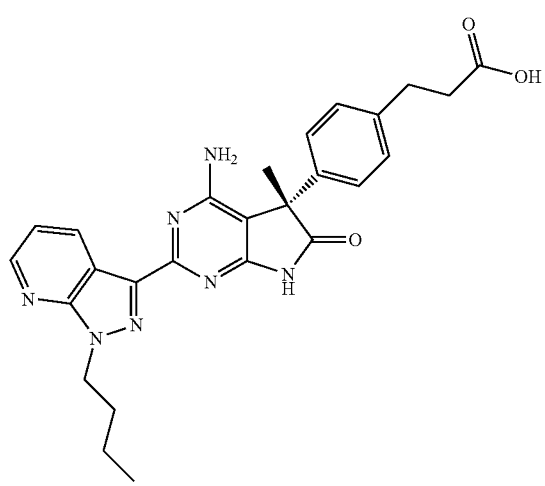 [SMILES: CCCCn1nc(-c2nc(N)c3c(n2)NC(=O)[C@@]3(C)c2ccc(CCC(=O)O)cc2)c2cccnc21] | (S)-3-(4-{4-amino-2-(1-butyl-1H-pyrazolo[3,4-b]pyridin-3-yl)-5-methyl-6-oxo-6,7-dihydro-5H-pyrrolo[2,3-d]pyrimidin-5-yl}phenyl)propanoic acid | 486 |

TABLE 14-continued

| Ex. | Int. SM | Structure | Name | m/z (M + 1) |
|---|---|---|---|---|
| 15B | I-11B | 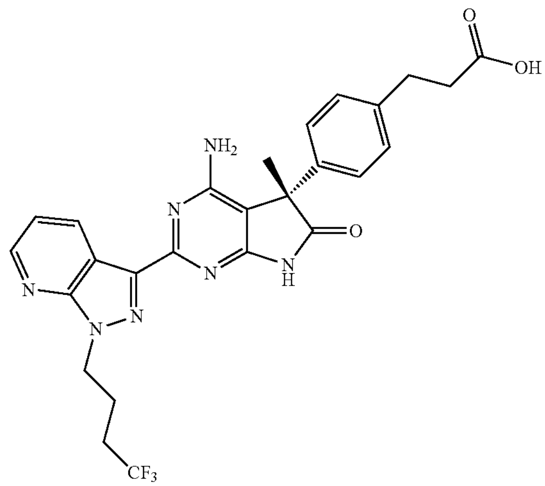 [SMILES: C[C@@]1(c2ccc(CCC(=O)O)cc2)C(=O)Nc2nc(-c3nn(CCCC(F)(F)F)c4ncccc34)nc(N)c21] | (S)-3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)propanoic acid | 540 |
| 16B | I-13B | 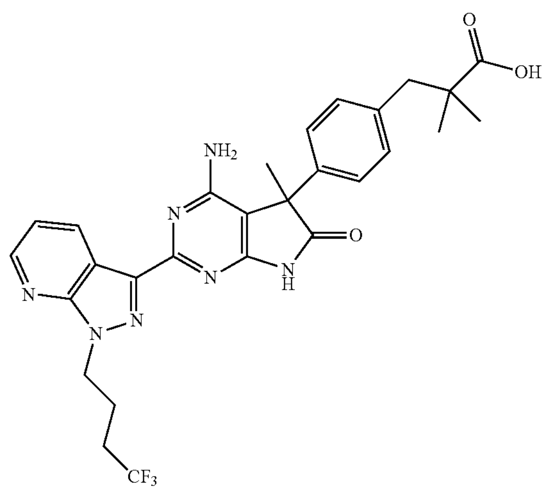 [SMILES: CC(C)(Cc1ccc(C2(C)C(=O)Nc3nc(-c4nn(CCCC(F)(F)F)c5ncccc45)nc(N)c32)cc1)C(=O)O] | 3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid | 568 |
| 17AB | I-38AB | 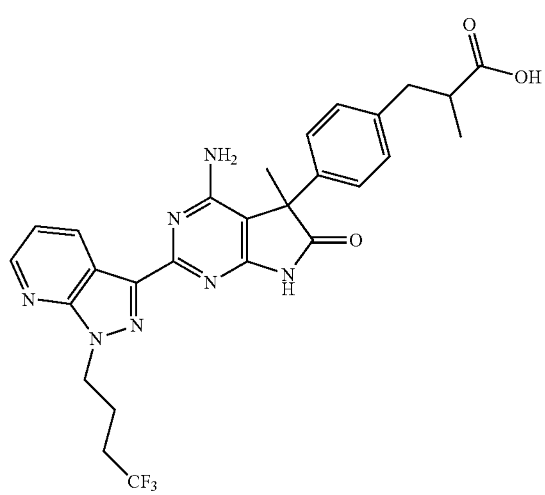 [SMILES: CC(Cc1ccc(C2(C)C(=O)Nc3nc(-c4nn(CCCC(F)(F)F)c5ncccc45)nc(N)c32)cc1)C(=O)O] | 3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2-methylpropanoic acid | 554 |

TABLE 14-continued

| Ex. | Int. SM | Structure | Name | m/z (M + 1) |
|---|---|---|---|---|
| 18B | I-11B | 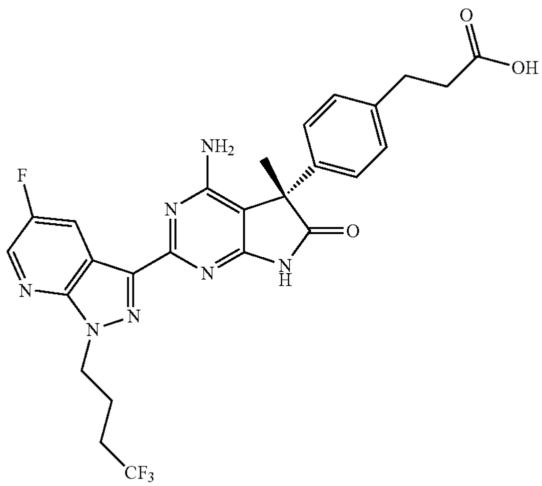 [SMILES: C[C@@]1(c2ccc(CCC(=O)O)cc2)C(=O)Nc2nc(-c3nn(CCCC(F)(F)F)c4ncc(F)cc34)nc(N)c21] | (S)-3-(4-{4-amino-2-[5-fluoro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid | 558 |
| 19B | I-11B | 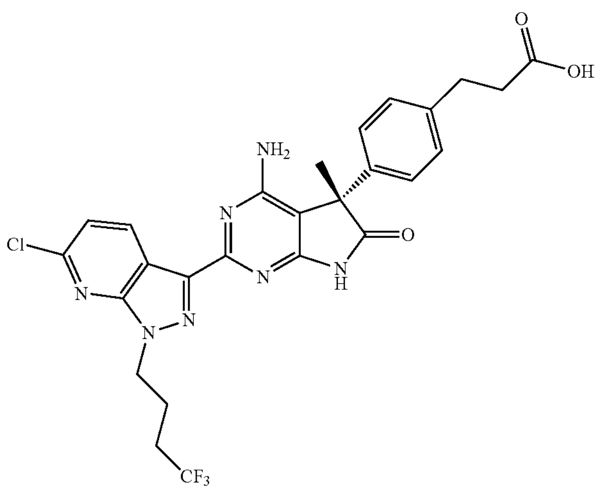 [SMILES: C[C@@]1(c2ccc(CCC(=O)O)cc2)C(=O)Nc2nc(-c3nn(CCCC(F)(F)F)c4nc(Cl)ccc34)nc(N)c21] | (S)-3-(4-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid | 574 |
| 20B | I-11B | 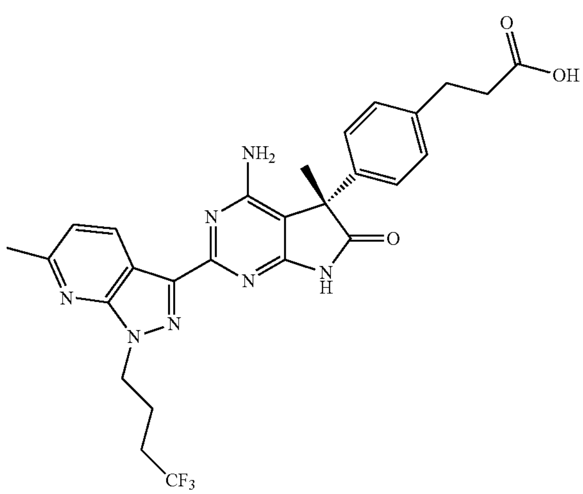 [SMILES: Cc1ccc2c(-c3nc(N)c4c(n3)NC(=O)[C@@]4(C)c3ccc(CCC(=O)O)cc3)nn(CCCC(F)(F)F)c2n1] | (S)-3-(4-{4-amino-5-methyl-2-[6-methyl-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}phenyl)propanoic acid | 554 |

TABLE 14-continued

| Ex. | Int. SM | Structure | Name | m/z (M + 1) |
|---|---|---|---|---|
| 21B | I-11B | 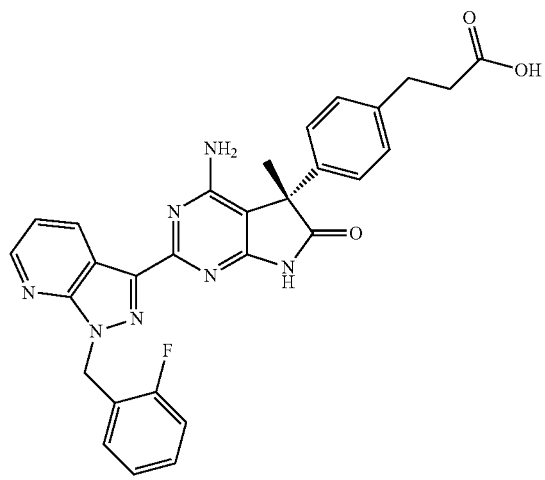 [SMILES: C[C@@]1(c2ccc(CCC(=O)O)cc2)C(=O)Nc2nc(-c3nn(Cc4ccccc4F)c4ncccc34)nc(N)c21] | (S)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid | 538 |
| 22A | I-15A | 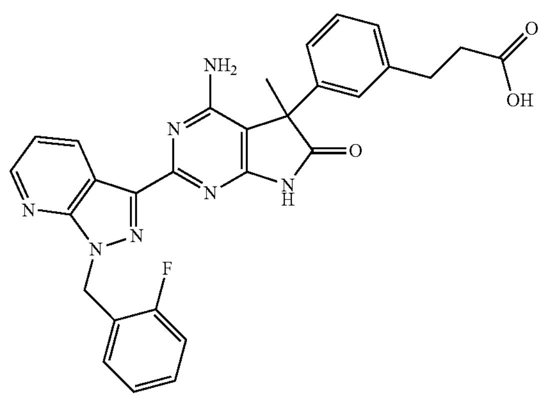 [SMILES: CC1(c2cccc(CCC(=O)O)c2)C(=O)Nc2nc(-c3nn(Cc4ccccc4F)c4ncccc34)nc(N)c21] | 3-(3-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid | 538 |
| 23B | I-11B | 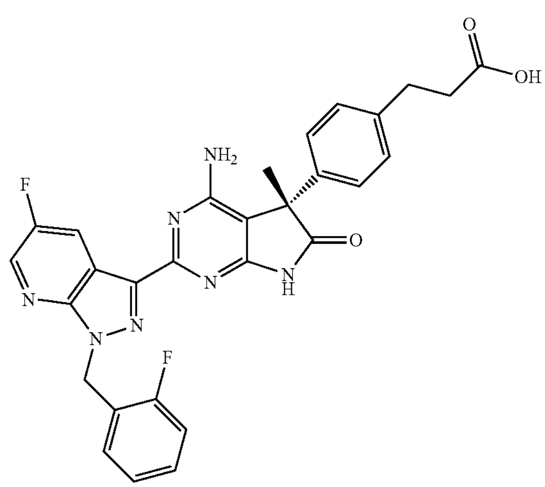 | (S)-3-(4-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid | 556 |

TABLE 14-continued

| Ex. | Int. SM | Structure | Name | m/z (M + 1) |
|---|---|---|---|---|
| 24A | I-15A | 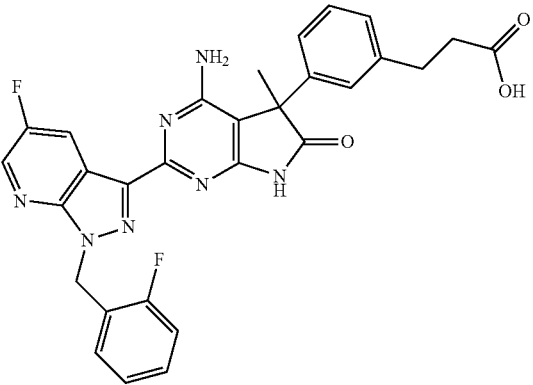 [SMILES: CC1(c2cccc(CCC(=O)O)c2)C(=O)Nc2nc(-c3nn(Cc4ccccc4F)c4ncc(F)cc34)nc(N)c21] | 3-(3-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid | 556 |
| 25B | I-11B | 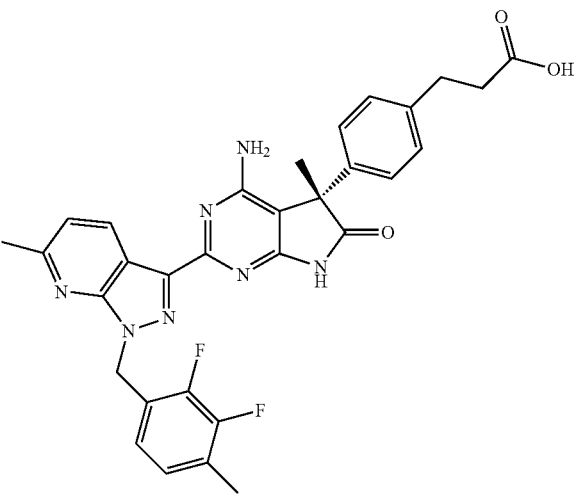 [SMILES: Cc1ccc2c(-c3nc(N)c4c(n3)NC(=O)[C@@]4(C)c3ccc(CCC(=O)O)cc3)nn(Cc3ccc(C)c(F)c3F)c2n1] | (S)-3-(4-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}phenyl)propanoic acid | 584 |
| 26B | I-37B | 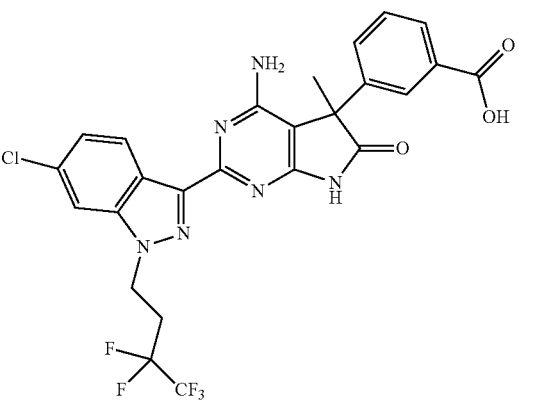 [SMILES: CC1(c2cccc(C(=O)O)c2)C(=O)Nc2nc(-c3nn(CCC(F)(F)C(F)(F)F)c4cc(Cl)ccc34)nc(N)c21] | 3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}benzoic acid | 581 |

TABLE 14-continued

| Ex. | Int. SM | Structure | Name | m/z (M + 1) |
|---|---|---|---|---|
| 27B | I-39B | 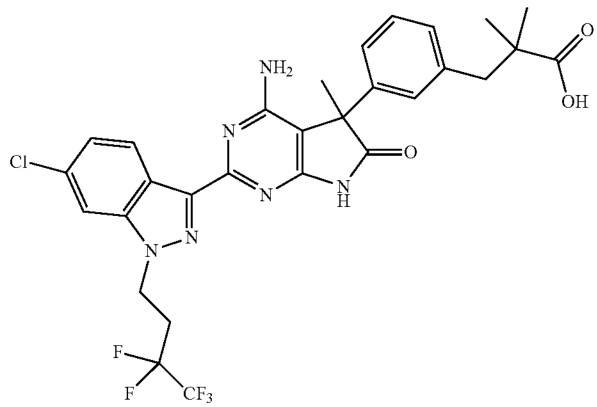 [SMILES: CC(C)(Cc1cccc(C2(C)C(=O)Nc3nc(-c4nn(CCC(F)(F)C(F)(F)F)c5cc(Cl)ccc45)nc(N)c32)c1)C(=O)O] | 3-(3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid | 638 |
| 28B | I-25B | 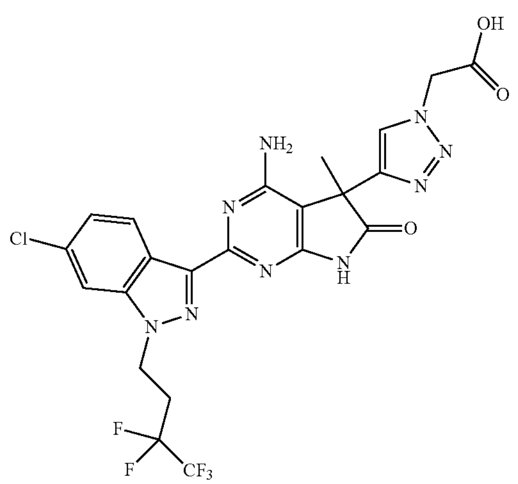 [SMILES: CC1(c2cn(CC(=O)O)nn2)C(=O)Nc2nc(-c3nn(CCC(F)(F)C(F)(F)F)c4cc(Cl)ccc34)nc(N)c21] | (4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)acetic acid | 586 |
| 29B | I-24B | 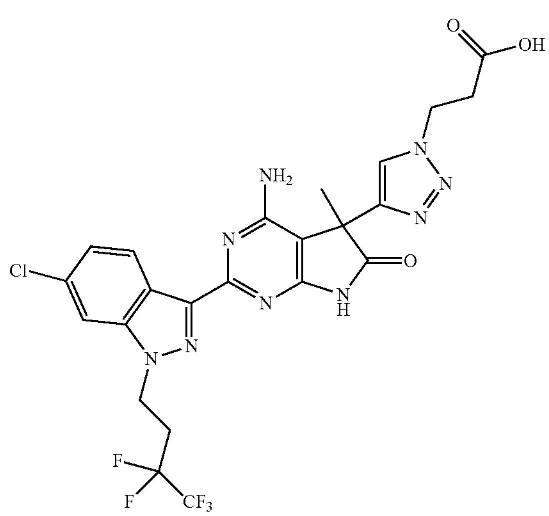 [SMILES: CC1(c2cn(CCC(=O)O)nn2)C(=O)Nc2nc(-c3nn(CCC(F)(F)C(F)(F)F)c4cc(Cl)ccc34)nc(N)c21] | 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)propanoic acid | 600 |

TABLE 14-continued

| Ex. | Int. SM | Structure | Name | m/z (M + 1) |
|---|---|---|---|---|
| 30B | I-26B | 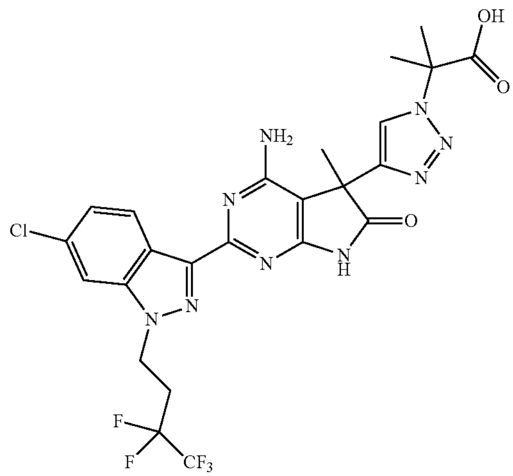 [SMILES: CC1(c2cn(C(C)(C)C(=O)O)nn2)C(=O)Nc2nc(-c3nn(CCC(F)(F)C(F)(F)F)c4cc(Cl)ccc34)nc(N)c21] | 2-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2-methylpropanoic acid | 614 |
| 31B | I-27B | 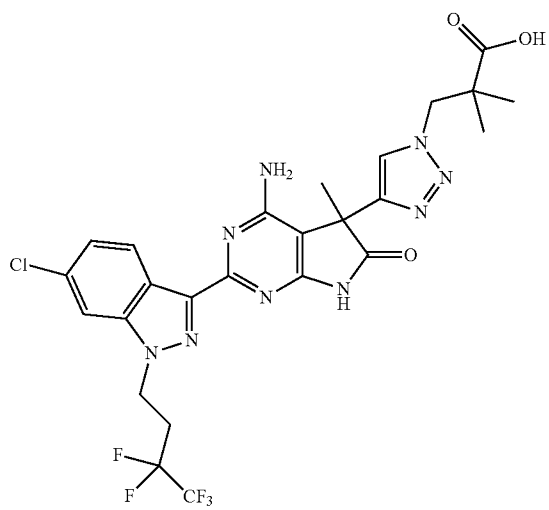 [SMILES: CC(C)(Cn1cc(C2(C)C(=O)Nc3nc(-c4nn(CCC(F)(F)C(F)(F)F)c5cc(Cl)ccc45)nc(N)c32)nn1)C(=O)O] | 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoic acid | 628 |
| 32B | I-28B | 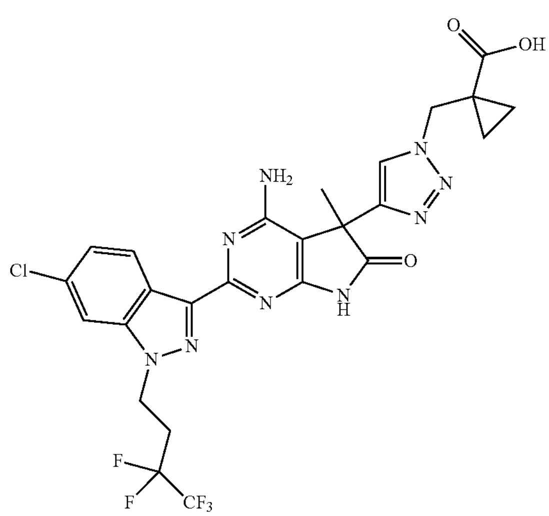 [SMILES: CC1(c2cn(CC3(C(=O)O)CC3)nn2)C(=O)Nc2nc(-c3nn(CCC(F)(F)C(F)(F)F)c4cc(Cl)ccc34)nc(N)c21] | 1-[(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)methyl]cyclopropanecarboxylic acid | 626 |

TABLE 14-continued

| Ex. | Int. SM | Structure | Name | m/z (M + 1) |
|---|---|---|---|---|
| 33B | I-13B | 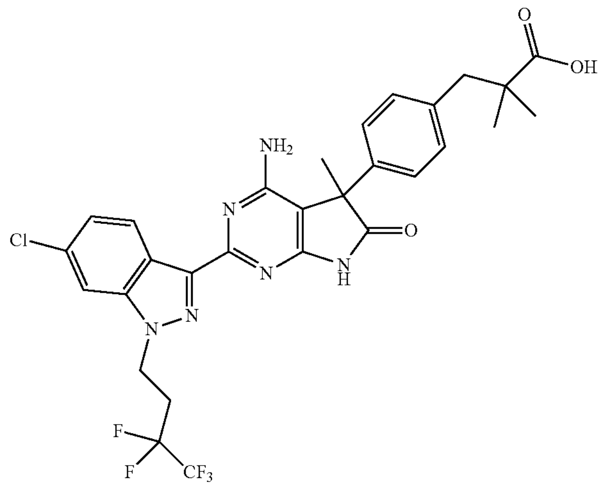 [SMILES: CC(C)(Cc1ccc(C2(C)C(=O)Nc3nc(-c4nn(CCC(F)(F)C(F)(F)F)c5cc(Cl)ccc45)nc(N)c32)cc1)C(=O)O] | 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid | 637 |
| 34AA | I-38AA | 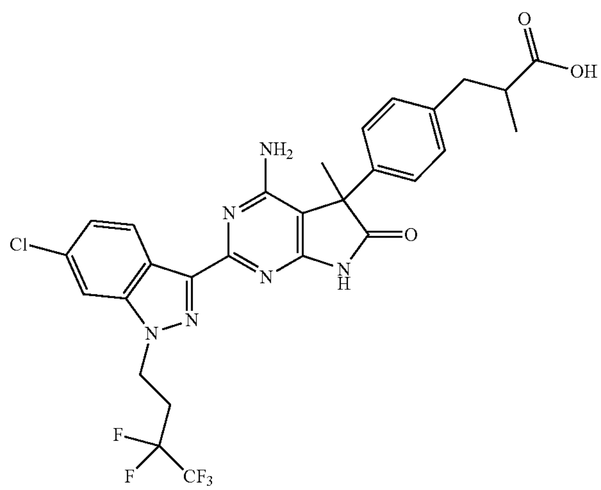 [SMILES: CC(Cc1ccc(C2(C)C(=O)Nc3nc(-c4nn(CCC(F)(F)C(F)(F)F)c5cc(Cl)ccc45)nc(N)c32)cc1)C(=O)O] | 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2-methylpropanoic acid | 623 |
| 34AB | I-38AB | 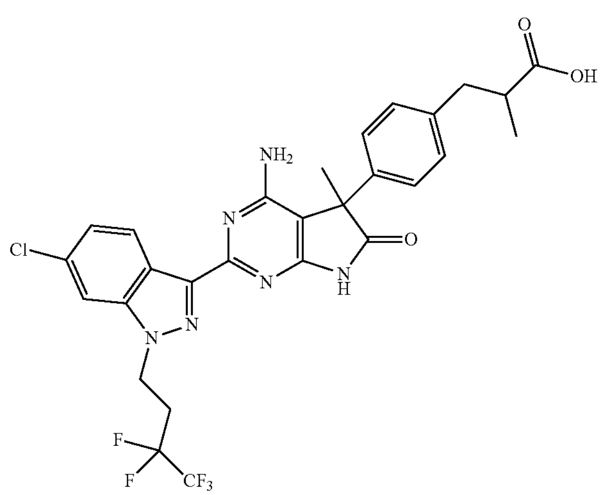 [SMILES: CC(Cc1ccc(C2(C)C(=O)Nc3nc(-c4nn(CCC(F)(F)C(F)(F)F)c5cc(Cl)ccc45)nc(N)c32)cc1)C(=O)O] | 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2-methylpropanoic acid | 623 |

TABLE 14-continued

| Ex. | Int. SM | Structure | Name | m/z (M + 1) |
|---|---|---|---|---|
| 35B | I-25B | 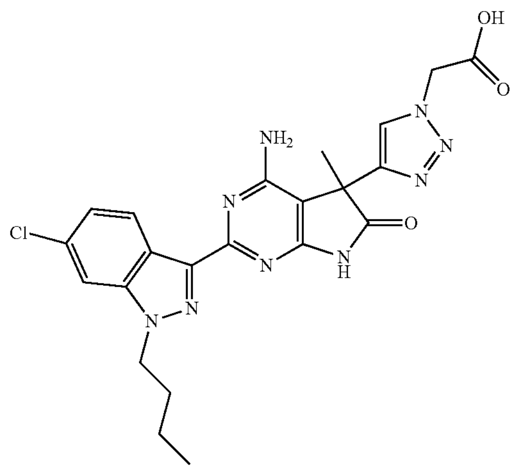 [SMILES: CCCCn1nc(-c2nc(N)c3c(n2)NC(=O)C3(C)c2cn(CC(=O)O)nn2)c2ccc(Cl)cc21] | 2-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}acetic acid | 496 |
| 36B | I-24B | 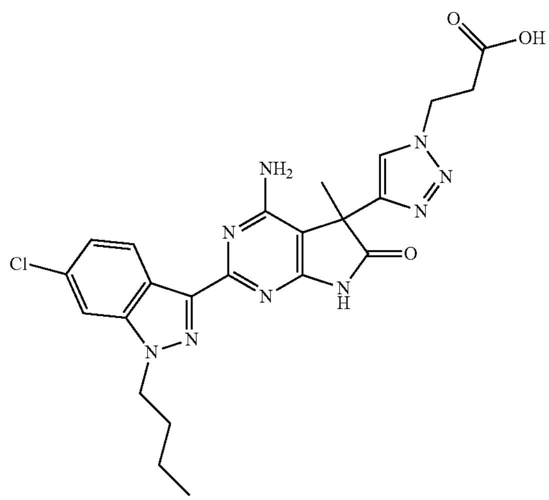 [SMILES: CCCCn1nc(-c2nc(N)c3c(n2)NC(=O)C3(C)c2cn(CCC(=O)O)nn2)c2ccc(Cl)cc21] | 3-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}propanoic acid | 510 |
| 37B | I-13B | 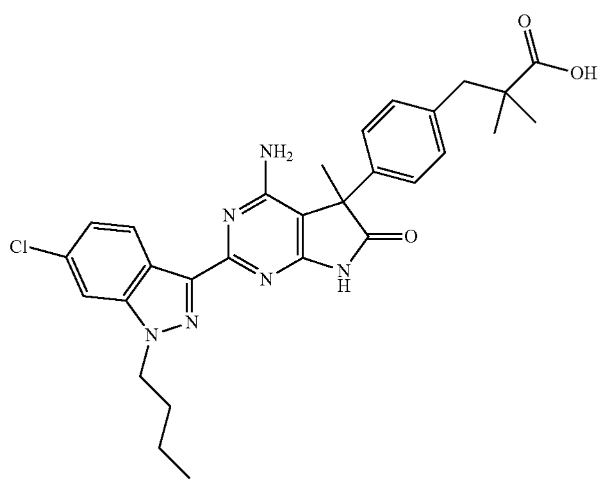 [SMILES: CCCCn1nc(-c2nc(N)c3c(n2)NC(=O)C3(C)c2ccc(CC(C)(C)C(=O)O)cc2)c2ccc(Cl)cc21] | 3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}-2,2-dimethylpropanoic acid | 547 |

TABLE 14-continued

| Ex. | Int. SM | Structure | Name | m/z (M + 1) |
|---|---|---|---|---|
| 38B | I-11B | 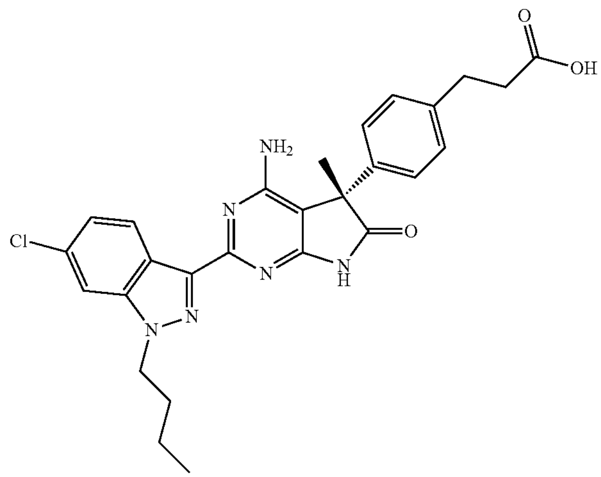 | (S)-3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}propanoic acid | 519 |
| 39B | I-39B | 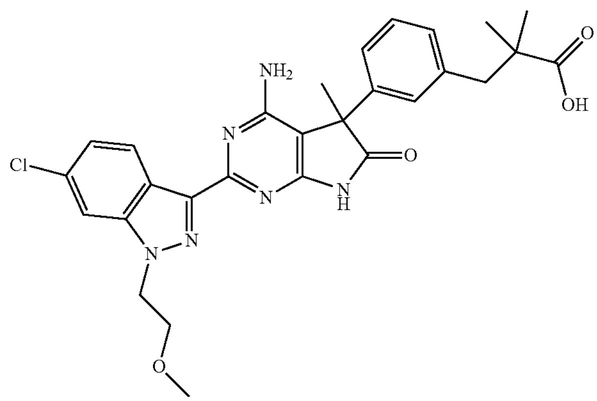 [SMILES: COCCn1nc(-c2nc(N)c3c(n2)NC(=O)C3(C)c2cccc(CC(C)(C)C(=O)O)c2)c2ccc(Cl)cc21] | 3-(3-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)-2,2-dimethylpropanoic acid | 549 |
| 40B | I-11B | 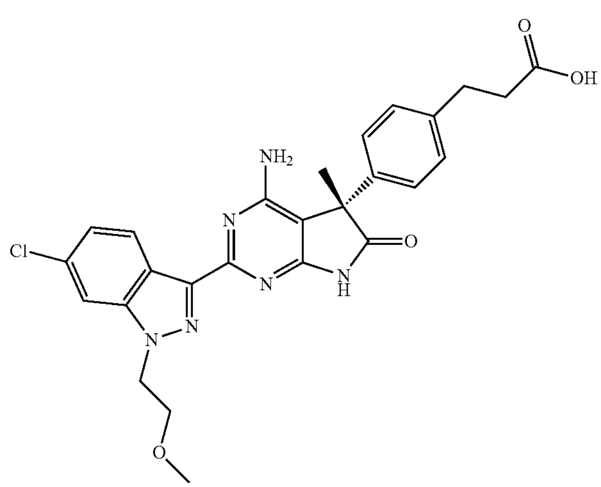 [SMILES: COCCn1nc(-c2nc(N)c3c(n2)NC(=O)[C@@]3(C)c2ccc(CCC(=O)O)cc2)c2ccc(Cl)cc21] | (S)-3-(4-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)propanoic acid | 521 |

TABLE 14-continued

| Ex. | Int. SM | Structure | Name | m/z (M + 1) |
|---|---|---|---|---|
| 41B | I-11B | 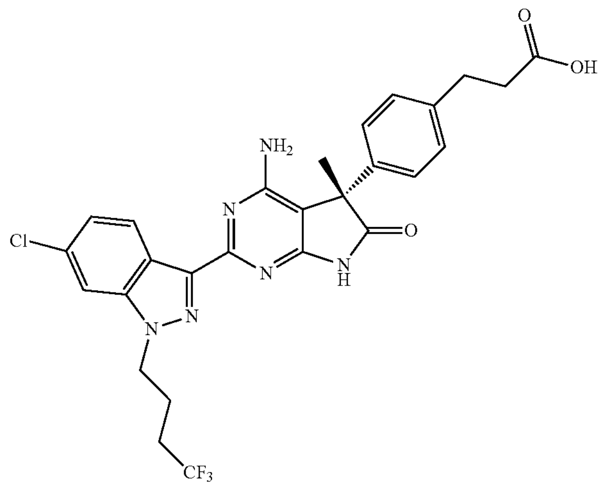 | (S)-3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)propanoic acid | 573 |
| 42B | I-13B | 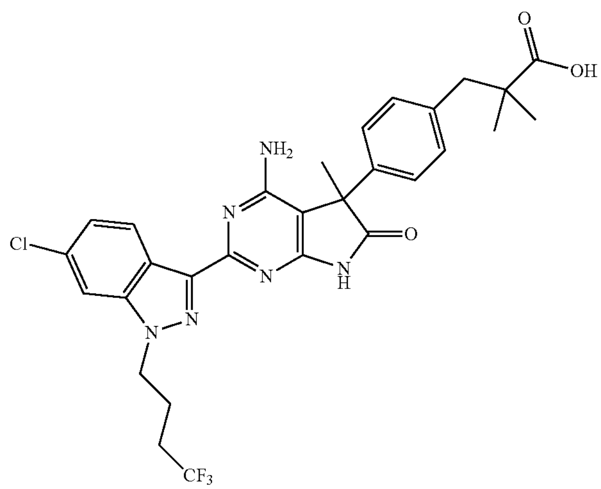 [SMILES: CC(C)(Cc1ccc(C2(C)C(=O)Nc3nc(-c4nn(CCCC(F)(F)F)c5cc(Cl)ccc45)nc(N)c32)cc1)C(=O)O] | 3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid | 601 |
| 43B | I-11B | 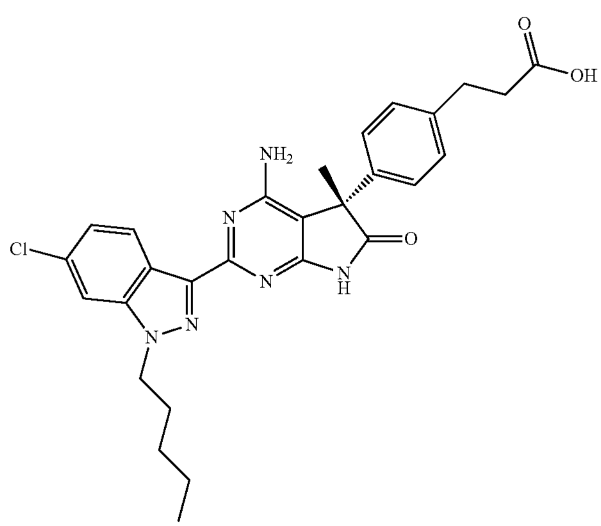 [SMILES: CCCCCn1nc(-c2nc(N)c3c(n2)NC(=O)[C@@]3(C)c2ccc(CCC(=O)O)cc2)c2ccc(Cl)cc21] | (S)-3-{4-[4-amino-2-(6-chloro-1-pentyl-1H-indazol-3-yl)-5-methyl-6-oxo-6,7-dihydro-5H-pyrrolo[2,3-d]pyrimidin-5-yl]phenyl}propanoic acid | 533 |

TABLE 14-continued

| Ex. | Int. SM | Structure | Name | m/z (M + 1) |
|---|---|---|---|---|
| 44B | I-11B | 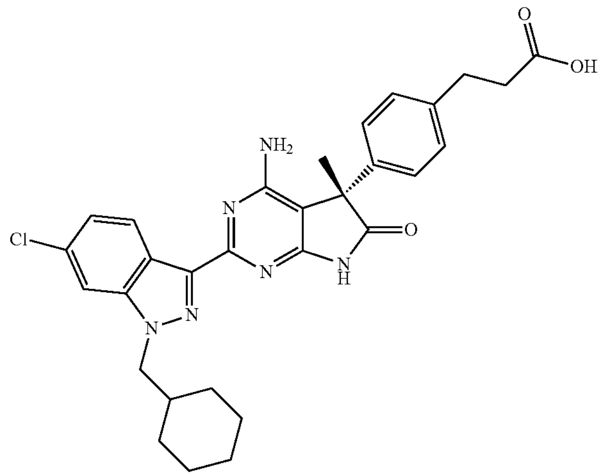 [SMILES: C[C@@]1(c2ccc(CCC(=O)O)cc2)C(=O)Nc2nc(-c3nn(CC4CCCCC4)c4cc(Cl)ccc34)nc(N)c21] | (S)-3-(4-{4-amino-2-[6-chloro-1-(cyclohexylmethyl)-1H-indazol-3-yl]-5-methyl-6-oxo-6,7-dihydro-5H-pyrrolo[2,3-d]pyrimidin-5-yl}phenyl)propanoic acid | 559 |
| 45B | I-11B | 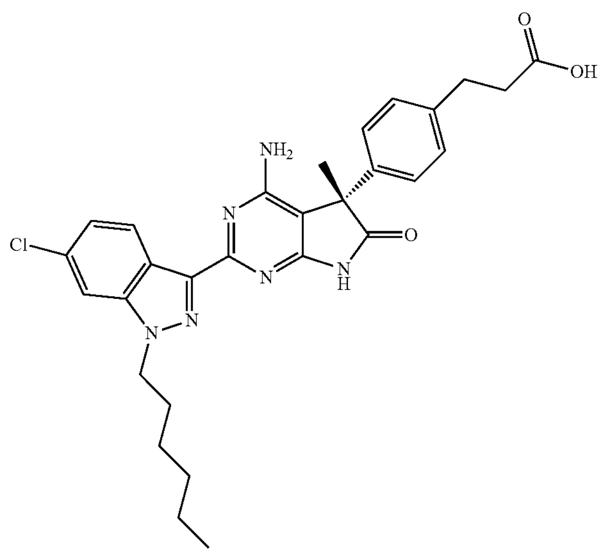 [SMILES: CCCCCCn1nc(-c2nc(N)c3c(n2)NC(=O)[C@@]3(C)c2ccc(CCC(=O)O)cc2)c2ccc(Cl)cc21] | (S)-3-{4-[4-amino-2-(6-chloro-1-hexyl-1H-indazol-3-yl)-5-methyl-6-oxo-6,7-dihydro-5H-pyrrolo[2,3-d]pyrimidin-5-yl]phenyl}propanoic acid | 547 |
| 46B | I-11B | 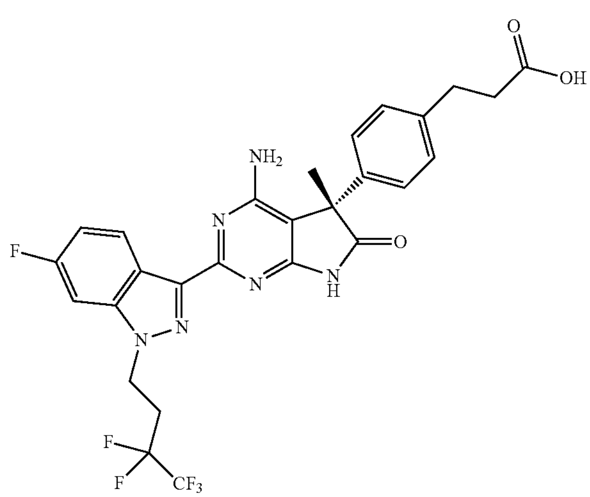 [SMILES: C[C@@]1(c2ccc(CCC(=O)O)cc2)C(=O)Nc2nc(-c3nn(CCC(F)(F)C(F)(F)F)c4cc(F)ccc34)nc(N)c21] | (S)-3-(4-{4-amino-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid | 593 |

TABLE 14-continued

| Ex. | Int. SM | Structure | Name | m/z (M + 1) |
|---|---|---|---|---|
| 47B | I-11B | 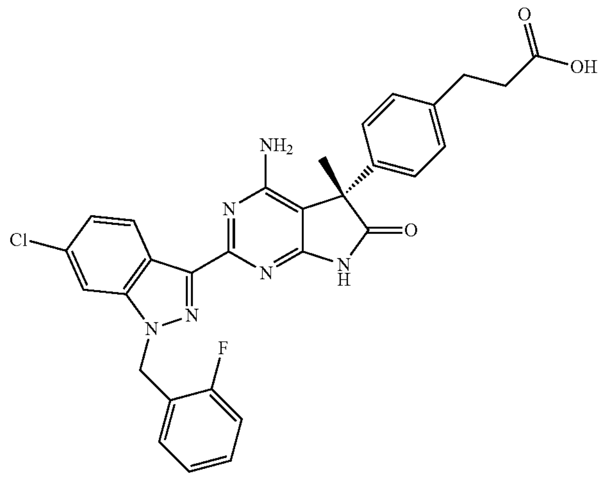 [SMILES: C[C@@]1(c2ccc(CCC(=O)O)cc2)C(=O)Nc2nc(-c3nn(Cc4ccccc4F)c4cc(Cl)ccc34)nc(N)c21] | (S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid | 571 |
| 48A | I-15A | 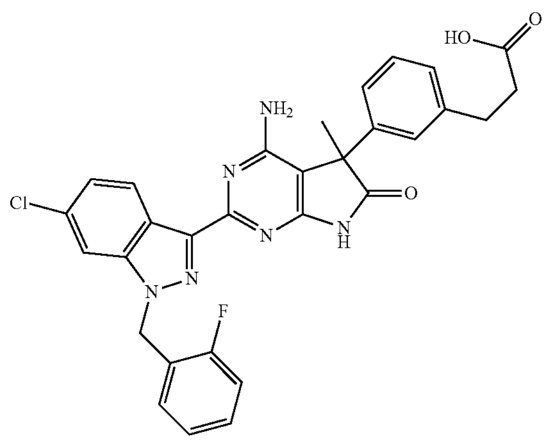 [SMILES: CC1(c2cccc(CCC(=O)O)c2)C(=O)Nc2nc(-c3nn(Cc4ccccc4F)c4cc(Cl)ccc34)nc(N)c21] | 3-(3-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}phenyl)propanoic acid | 571 |
| 49A | I-36A | 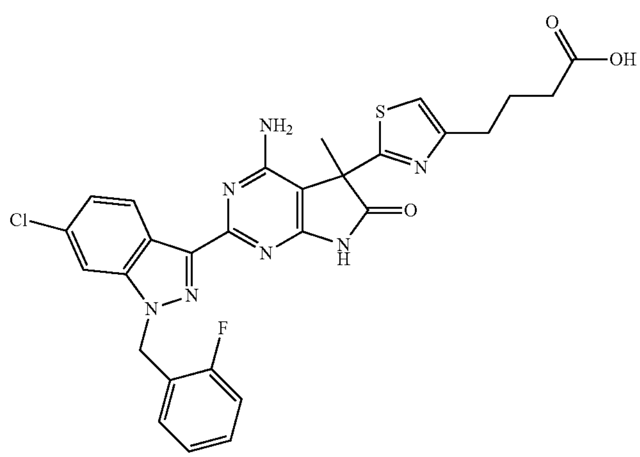 [SMILES: CC1(c2nc(CCCC(=O)O)cs2)C(=O)Nc2nc(-c3nn(Cc4ccccc4F)c4cc(Cl)ccc34)nc(N)c21] | 4-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}thiazol-4-yl)butanoic acid | 592 |

TABLE 14-continued

| Ex. | Int. SM | Structure | Name | m/z (M + 1) |
|---|---|---|---|---|
| 50A | I-33A | 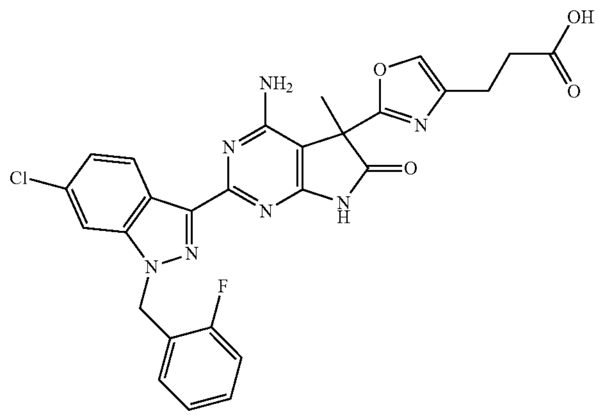 [SMILES: CC1(c2nc(CCC(=O)O)co2)C(=O)Nc2nc(-c3nn(Cc4ccccc4F)c4cc(Cl)ccc34)nc(N)c21] | 3-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}oxazol-4-yl)propanoic acid | 562 |
| 51B | I-34B | 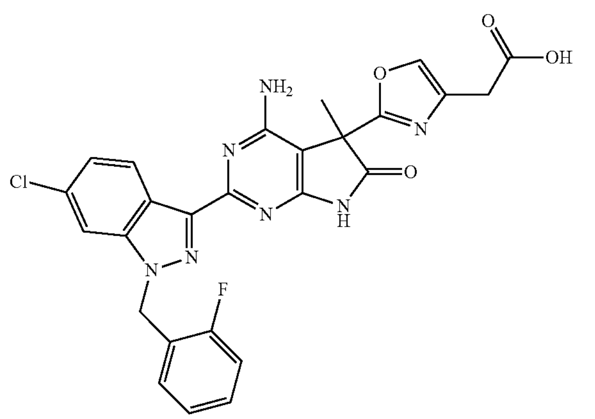 [SMILES: CC1(c2nc(CC(=O)O)co2)C(=O)Nc2nc(-c3nn(Cc4ccccc4F)c4cc(Cl)ccc34)nc(N)c21] | 2-(2-{4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl}oxazol-4-yl)acetic acid | 548 |
| 52B | I-11B | 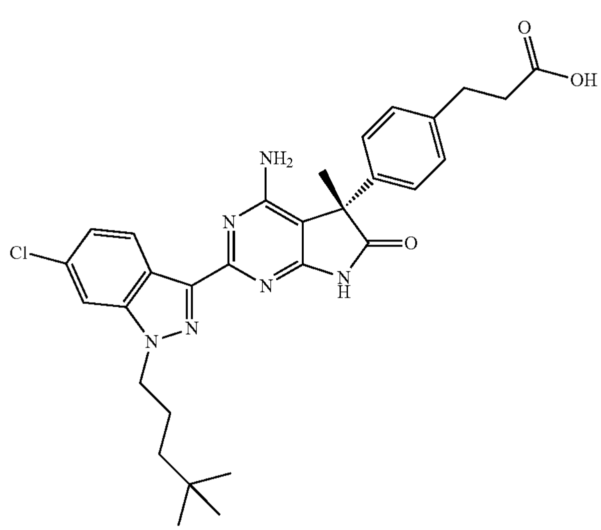 [SMILES: CC(C)(C)CCCn1nc(-c2nc(N)c3c(n2)NC(=O)[C@@]3(C)c2ccc(CCC(=O)O)cc2)c2ccc(Cl)cc21] | (S)-3-(4-{4-amino-2-[6-chloro-1-(4,4-dimethylpentyl)-1H-indazol-3-yl]-5-methyl-6-oxo-6,7-dihydro-5H-pyrrolo[2,3-d]pyrimidin-5-yl}phenyl)propanoic acid | 561 |

TABLE 14-continued
| Ex. | Int. SM | Structure | Name | m/z (M + 1) |
|---|---|---|---|---|
| 53A | I-15A | 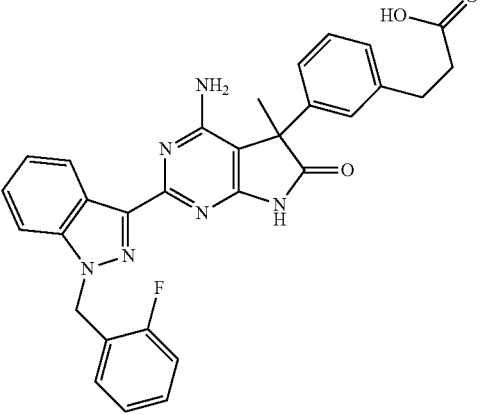 | 3-(3-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid | 537 |
| 54A | I-33A | 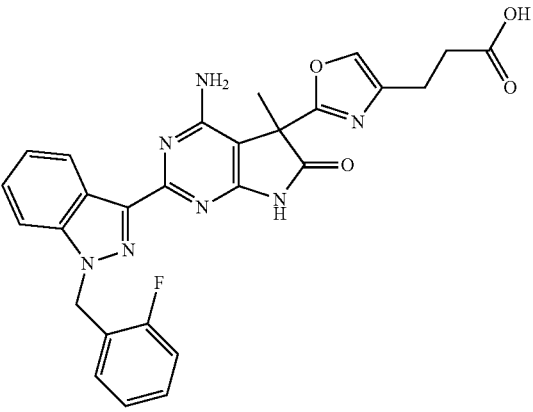 [SMILES: CC1(c2nc(CCC(=O)O)co2)C(=O)Nc2nc(-c3nn(Cc4ccccc4F)c4ccccc34)nc(N)c21] | 3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)propanoic acid | 528 |
| 55A | I-36A | 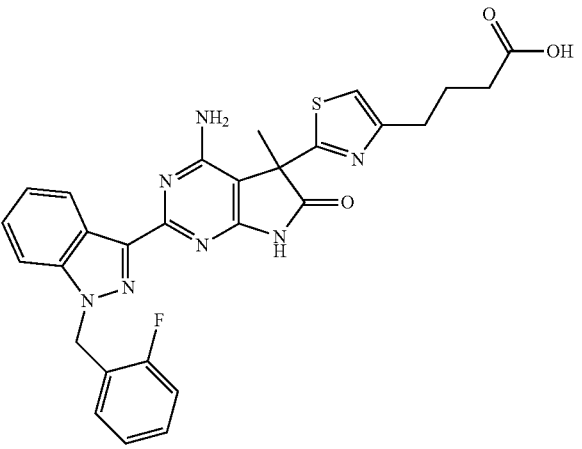 [SMILES: CC1(c2nc(CCCC(=O)O)cs2)C(=O)Nc2nc(-c3nn(Cc4ccccc4F)c4ccccc34)nc(N)c21] | 4-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)butanoic acid | 558 |

TABLE 14-continued

| Ex. | Int. SM | Structure | Name | m/z (M + 1) |
|---|---|---|---|---|
| 56A | I-42A | 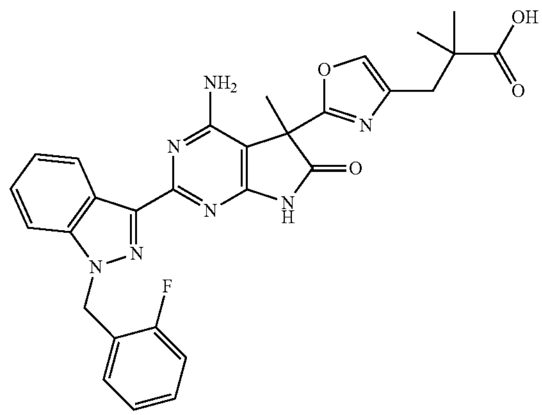 [SMILES: CC(C)(Cc1coc(C2(C)C(=O)Nc3nc(-c4nn(Cc5ccccc5F)c5ccccc45)nc(N)c32)n1)C(=O)O] | 3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid | 556 |
| 57B | I-11B | 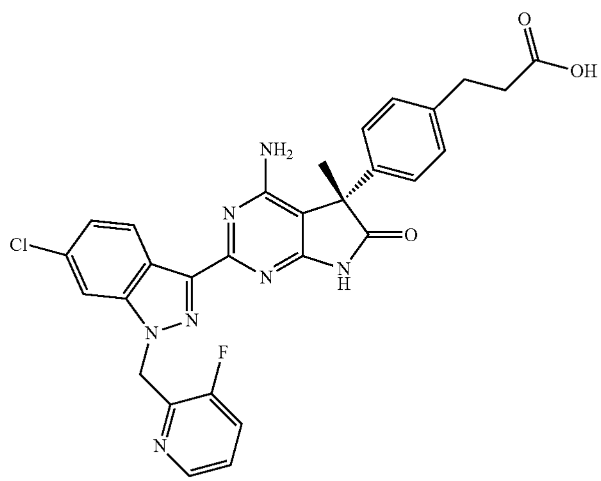 [SMILES: C[C@@]1(c2ccc(CCC(=O)O)cc2)C(=O)Nc2nc(-c3nn(Cc4ncccc4F)c4cc(Cl)ccc34)nc(N)c21] | (S)-3-(4-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]phenyl)propanoic acid | 572 |
| 58B | I-11B | 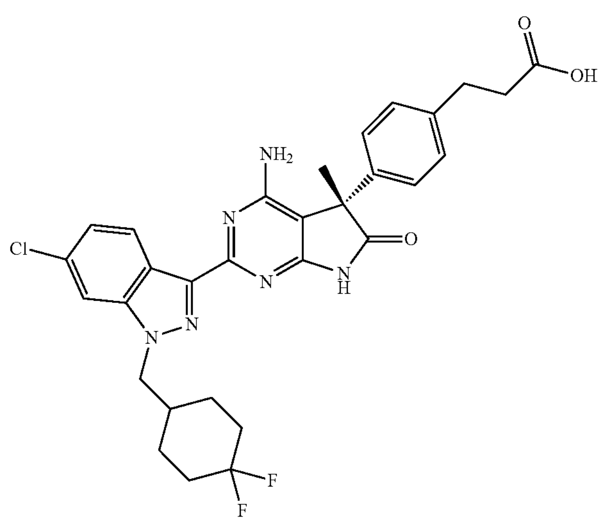 [SMILES: C[C@@]1(c2ccc(CCC(=O)O)cc2)C(=O)Nc2nc(-c3nn(CC4CCC(F)(F)CC4)c4cc(Cl)ccc34)nc(N)c21] | (S)-3-(4-[4-amino-2-{6-chloro-1-[(4,4-difluorocyclohexyl)methyl]-1H-indazol-3-yl}-5-methyl-6-oxo-6,7-dihydro-5H-pyrrolo[2,3-d]pyrimidin-5-yl]phenyl)propanoic acid | 595 |

TABLE 14-continued

| Ex. | Int. SM | Structure | Name | m/z (M + 1) |
|---|---|---|---|---|
| 59B | I-11B | 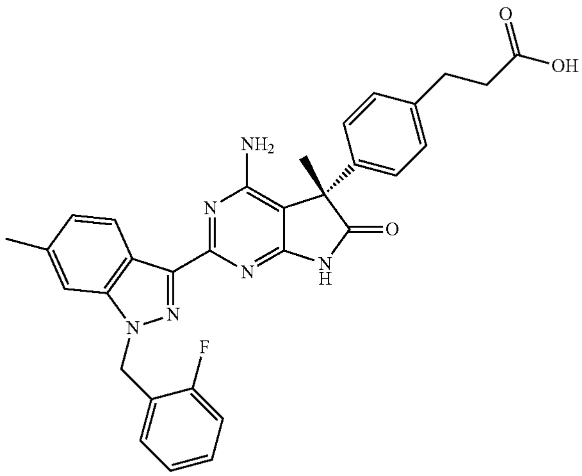 [SMILES: Cc1ccc2c(-c3nc(N)c4c(n3)NC(=O)[C@@]4(C)c3ccc(CCC(=O)O)cc3)nn(Cc3ccccc3F)c2c1] | (S)-3-(4-{4-amino-2-[1-(2-fluorobenzyl)-6-methyl-1H-indazol-3-yl]-5-methyl-6-oxo-6,7-dihydro-5H-pyrrolo[2,3-d]pyrimidin-5-yl}phenyl)propanoic acid | 551 |
| 60B | I-11B | 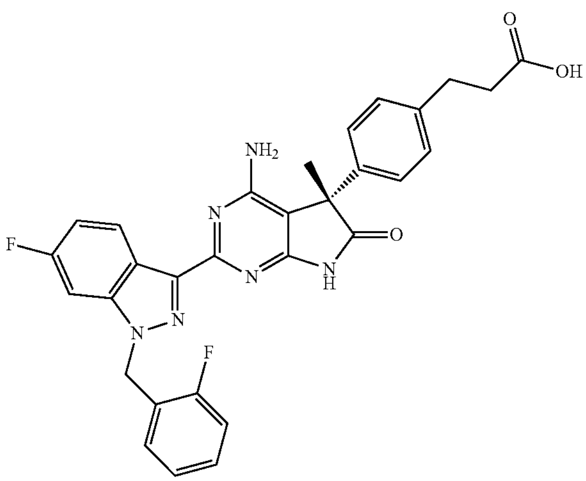 [SMILES: C[C@@]1(c2ccc(CCC(=O)O)cc2)C(=O)Nc2nc(-c3nn(Cc4ccccc4F)c4cc(F)ccc34)nc(N)c21] | (S)-3-(4-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid | 555 |
| 61A | I-15A | 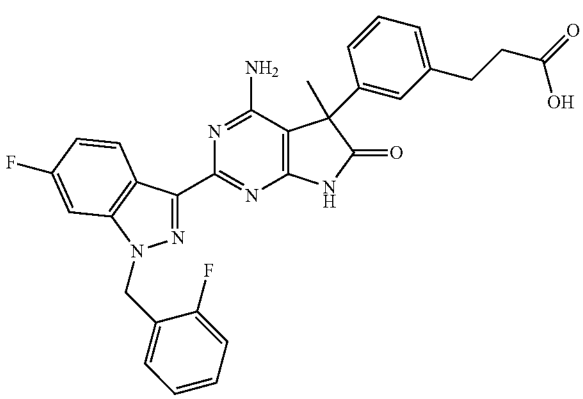 [SMILES: CC1(c2cccc(CCC(=O)O)c2)C(=O)Nc2nc(-c3nn(Cc4ccccc4F)c4cc(F)ccc34)nc(N)c21] | 3-(3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid | 555 |

TABLE 14-continued

| Ex. | Int. SM | Structure | Name | m/z (M + 1) |
|---|---|---|---|---|
| 62A | I-35A | 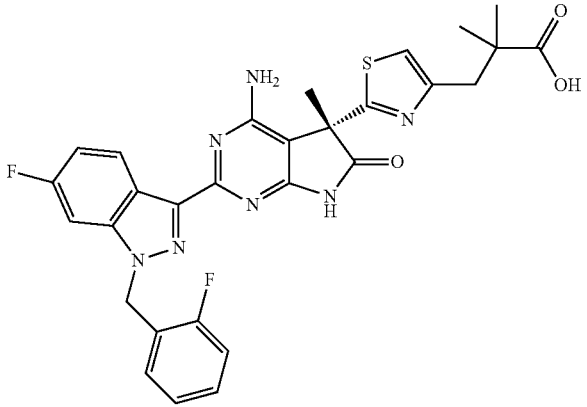 [SMILES: CC(C)(Cc1csc([C@]2(C)C(=O)Nc3nc(-c4nn(Cc5ccccc5F)c5cc(F)ccc45)nc(N)c32)n1)C(=O)O] | (S)-3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid | 590 |
| 63A | I-42A | 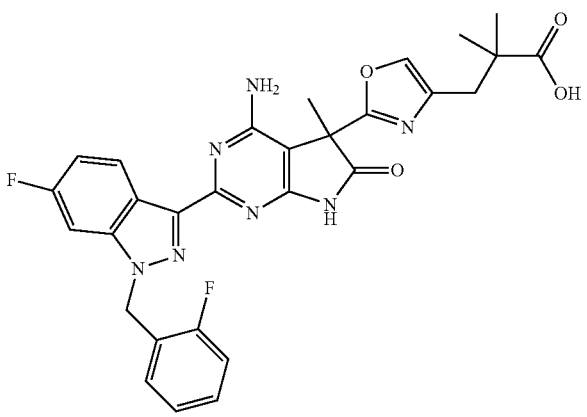 [SMILES: CC(C)(Cc1coc(C2(C)C(=O)Nc3nc(-c4nn(Cc5ccccc5F)c5cc(F)ccc45)nc(N)c32)n1)C(=O)O] | 3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid | 574 |
| 64B | I-11B | 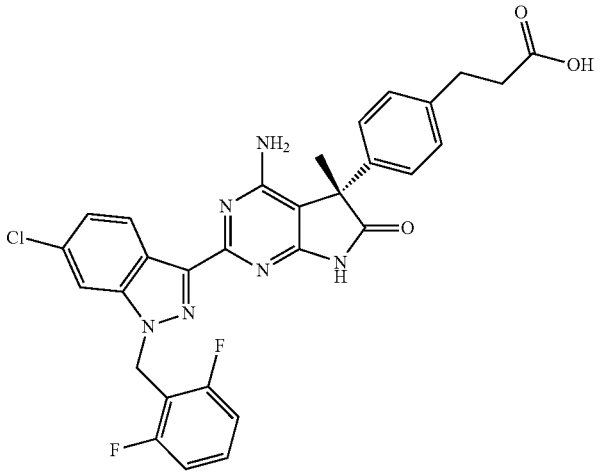 [SMILES: C[C@@]1(c2ccc(CCC(=O)O)cc2)C(=O)Nc2nc(-c3nn(Cc4c(F)cccc4F)c4cc(Cl)ccc34)nc(N)c21] | (S)-3-(4-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}phenyl)propanoic acid | 589 |

TABLE 14-continued

| Ex. | Int. SM | Structure | Name | m/z (M + 1) |
|---|---|---|---|---|
| 65B | I-11B | 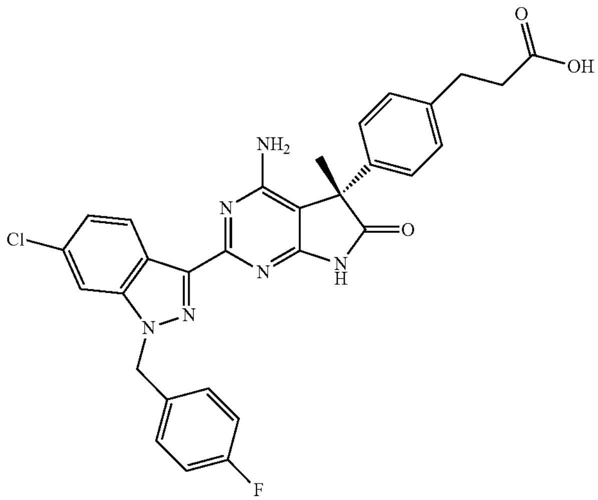 [SMILES: C[C@@]1(c2ccc(CCC(=O)O)cc2)C(=O)Nc2nc(-c3nn(Cc4ccc(F)cc4)c4cc(Cl)ccc34)nc(N)c21] | (S)-3-(4-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}phenyl)propanoic acid | 571 |
| 66B | I-11B | 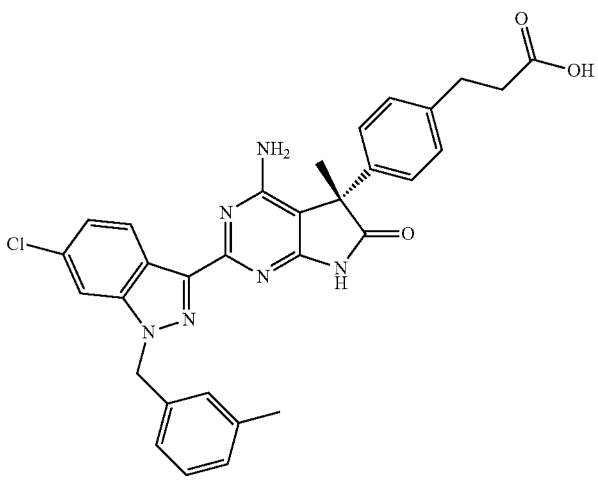 [SMILES: Cc1cccc(Cn2nc(-c3nc(N)c4c(n3)NC(=O)[C@@]4(C)c3ccc(CCC(=O)O)cc3)c3ccc(Cl)cc32)c1] | (S)-3-(4-{4-amino-2-[6-chloro-1-(3-methylbenzyl)-1H-indazol-3-yl]-5-methyl-6-oxo-6,7-dihydro-5H-pyrrolo[2,3-d]pyrimidin-5-yl}phenyl)propanoic acid | 567 |
| 67B | I-11B | 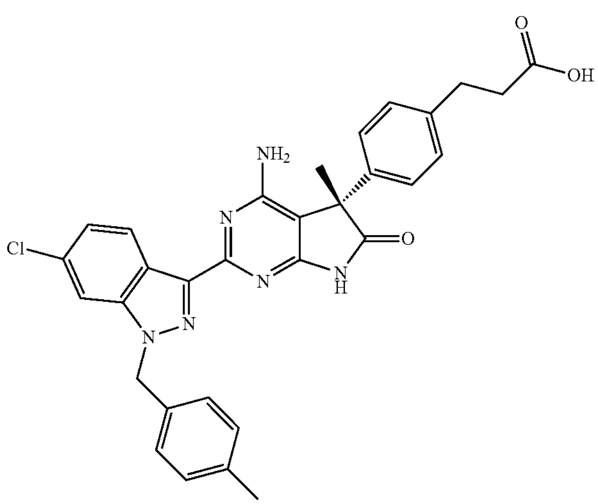 [SMILES: Cc1ccc(Cn2nc(-c3nc(N)c4c(n3)NC(=O)[C@@]4(C)c3ccc(CCC(=O)O)cc3)c3ccc(Cl)cc32)cc1] | (S)-3-(4-{4-amino-2-[6-chloro-1-(4-methylbenzyl)-1H-indazol-3-yl]-5-methyl-6-oxo-6,7-dihydro-5H-pyrrolo[2,3-d]pyrimidin-5-yl}phenyl)propanoic acid | 567 |

TABLE 14-continued

| Ex. | Int. SM | Structure | Name | m/z (M + 1) |
|---|---|---|---|---|
| 68B | I-11B | 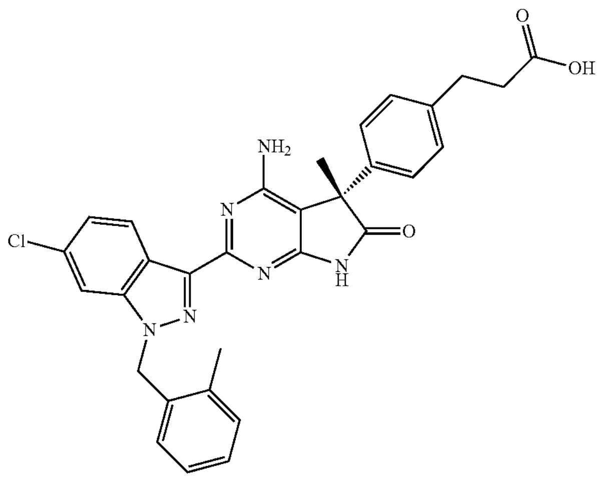 [SMILES: Cc1ccccc1Cn1nc(-c2nc(N)c3c(n2)NC(=O)[C@@]3(C)c2ccc(CCC(=O)O)cc2)c2ccc(Cl)cc21] | (S)-3-(4-{4-amino-2-[6-chloro-1-(2-methylbenzyl)-1H-indazol-3-yl]-5-methyl-6-oxo-6,7-dihydro-5H-pyrrolo[2,3-d]pyrimidin-5-yl}phenyl)propanoic acid | 567 |
| 69B | I-11B | 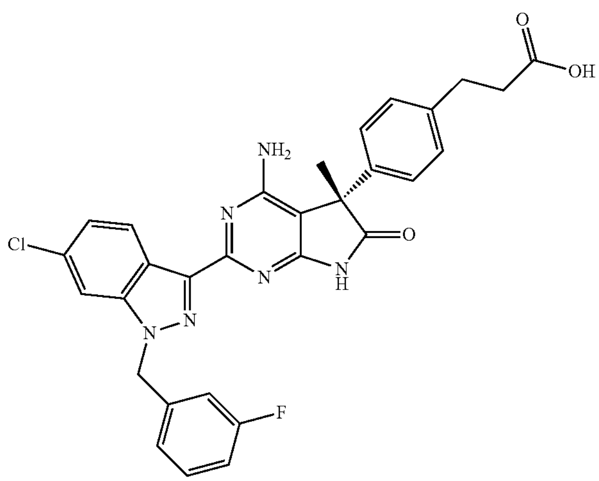 [SMILES: C[C@@]1(c2ccc(CCC(=O)O)cc2)C(=O)Nc2nc(-c3nn(Cc4cccc(F)c4)c4cc(Cl)ccc34)nc(N)c21] | (S)-3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}phenyl)propanoic acid | 571 |
| 70B | I-11B | 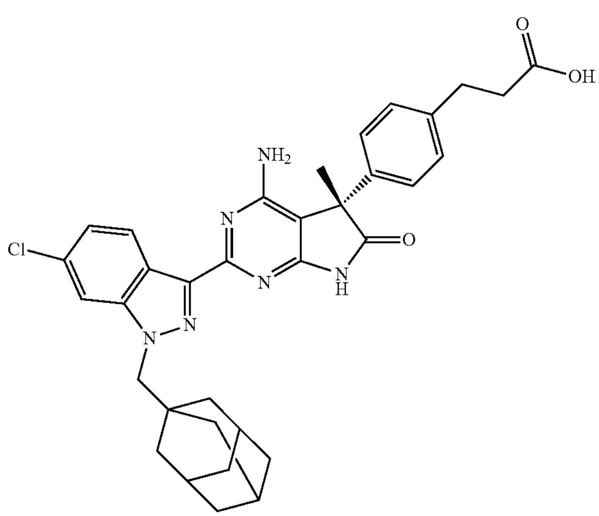 [SMILES: C[C@@]1(c2ccc(CCC(=O)O)cc2)C(=O)Nc2nc(-c3nn(CC45CC6CC(CC(C6)C4)C5)c4cc(Cl)ccc34)nc(N)c21] | (S)-3-(4-{2-[1-(adamantan-1-ylmethyl)-6-chloro-1H-indazol-3-yl]-4-amino-5-methyl-6-oxo-6,7-dihydro-5H-pyrrolo[2,3-d]pyrimidin-5-yl}phenyl)propanoic acid | 611 |

TABLE 14-continued

| Ex. | Int. SM | Structure | Name | m/z (M + 1) |
|---|---|---|---|---|
| 71B | I-11B | 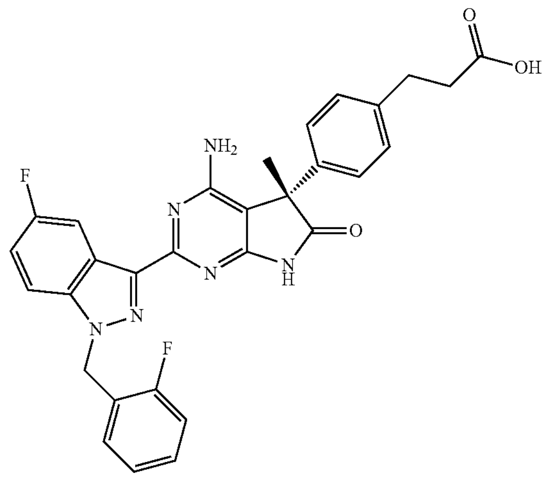 | (S)-3-(4-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid | 555 |
| 72A | I-42A | 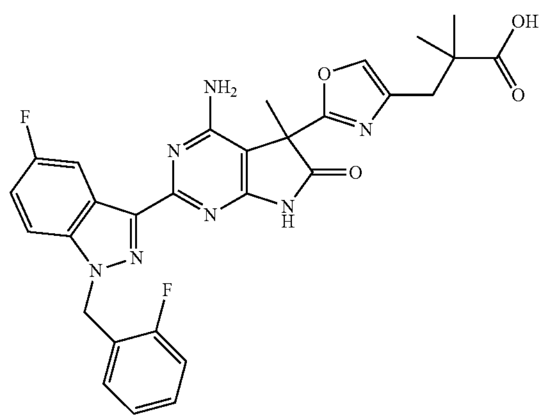 [SMILES: CC(C)(Cc1coc(C2(C)C(=O)Nc3nc(-c4nn(Cc5ccccc5F)c5ccc(F)cc45)nc(N)c32)n1)C(=O)O] | 3-(2-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid | 574 |
| 73B | I-11B | 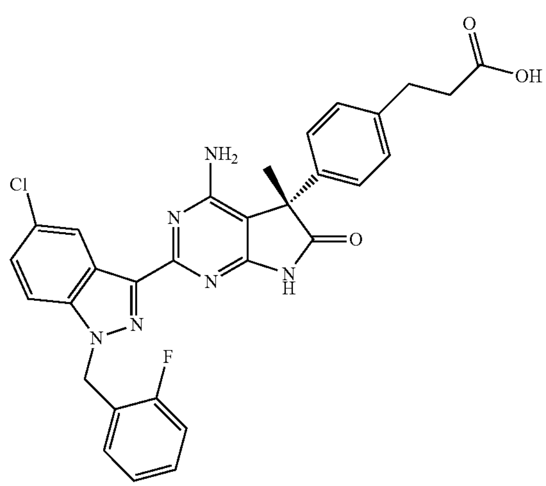 [SMILES: C[C@@]1(c2ccc(CCC(=O)O)cc2)C(=O)Nc2nc(-c3nn(Cc4ccccc4F)c4ccc(Cl)cc34)nc(N)c21] | (S)-3-(4-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid | 571 |

TABLE 14-continued

| Ex. | Int. SM | Structure | Name | m/z (M + 1) |
|---|---|---|---|---|
| 74A | I-42A | 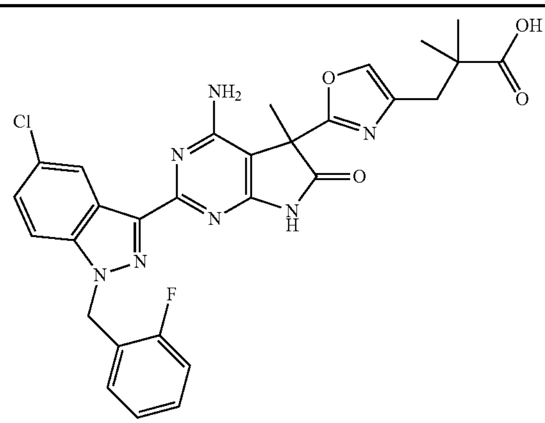 | 3-(2-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid | 590 |
| 75A | I-43A | 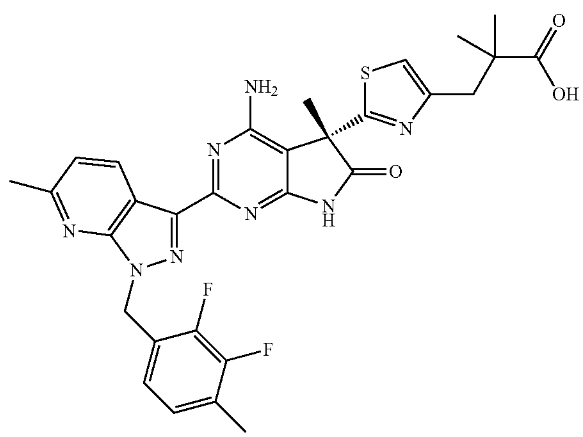 [SMILES: Cc1ccc2c(-c3nc(N)c4c(n3)NC(=O)[C@@]4(C)c3nc(CC(C)(C)C(=O)O)cs3)nn(Cc3ccc(C)c(F)c3F)c2n1] | (S)-3-(2-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}thiazol-4-yl)-2,2-dimethylpropanoic acid | 619 |

Example 76B (S)-3-(4-{4-Amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid

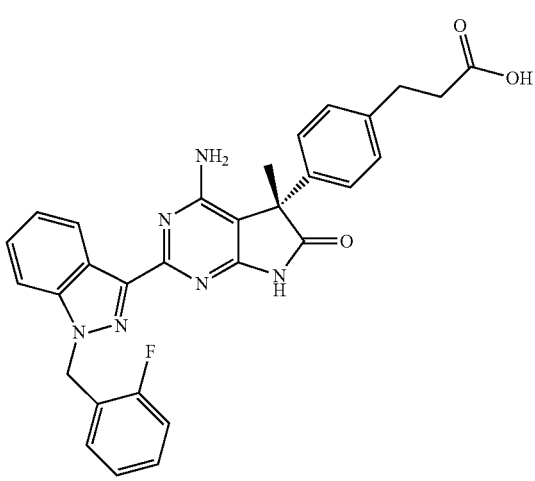 [SMILES: C[C@@]1(c2ccc(CCC(=O)O)cc2)C(=O)Nc2nc(-c3nn(Cc4ccccc4F)c4ccccc34)nc(N)c21]

Step A—(S)-methyl 3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoate The title compound was prepared using essentially the same procedures described in Example 11 Step A, using intermediate I-A15 and I-11B as starting material.

Step B—(S)-methyl 3-(4-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoate A flask under nitrogen, containing (S)-methyl 3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoate (100 mg, 0.17 mmol) and palladium on carbon (50 mg, 10 wt %) in MeOH (8 mL) was purged with hydrogen. The mixture was stirred at RT for 6 h under an atmosphere of hydrogen (~2 atm). The solid was filtered out and washed with MeOH (3×). The filtrate was concentrated in vacuo to dryness. The residue was purified by silica gel column chromatography with MeOH:DCM (0-10%) to afford the title compound. m/z=551 (M+1).

Step C—(S)-3-(4-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid To a flask containing (S)-methyl 3-(4-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoate (80 mg, 0.145 mmol) in MeOH (5 mL) was added LiOH (35 mg, 1.45 mmol) in 1 mL of water. The resulting mixture was stirred for 16 h at RT before been concentrated in vacuo. The residue was diluted with hydrochloric acid (14.5 mL, 0.1 N), the solid was collected by filtration, washed with water and dried in vacuo. The residue was then purified by reverse phase HPLC (ACN/water with 0.05% TFA modifier) to afford the title compound Ex-76B. $^1$H NMR (400 MHz, CD$_3$OD) δ 8.63 (d, J=8.0 Hz, 1H), 7.76 (d, J=8.8 Hz, 1H), 7.57 (dd, J=8.0, 7.6 Hz, 1H), 7.45-7.28 (m, 6H), 7.22-7.11 (m, 3H), 5.92 (s, 2H), 2.93 (t, J=7.2 Hz, 2H), 2.61 (t, J=7.2 Hz, 2H), 1.95 (s, 3H); m/z=537 (M+1).

Example 77B (S)-3-(2-{4-Amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid

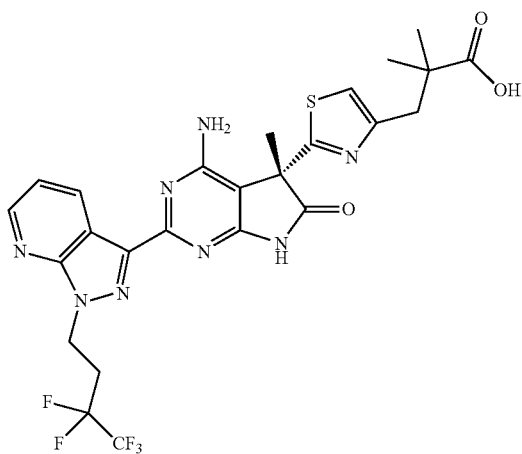 [SMILES: CC(C)(Cc1csc([C@]2(C)C(=O)Nc3nc(-c4nn(CCC(F)(F)C(F)(F)F)c5ncccc45)nc(N)c32)n1)C(=O)O]

Step A—(S)-ethyl 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxylate To a mixture of I-A2 (1.0 g, 3.2 mmol) and I-40B (1.16 g, 4.88 mmol) in THF (65 mL) at RT was added triethylamine (1.3 mL, 9.76 mmol). The resulting mixture was warmed at 65° C. for 16 h. The reaction was cooled to RT and concentrated in vacuo to dryness. The residue was purified by silica gel chromatography using MeOH:DCM (1-10%) to afford the title compound. m/z=500 (M+1).

Step B—(S)-4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxamide In a sealed tube containing (S)-ethyl 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxylate (1.5 g, 3.00 mmol) was added ammonia (30 mL, 3 N in MeOH). The resulting mixture was warmed at 40° C. for 16 h. The reaction was cooled to RT and concentrated in vacuo to dryness. The residue was purified by silica gel chromatography using MeOH:DCM (5%) to afford the title compound. m/z=471 (M+1).

Step C—(S)-4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carbothioamide Into a flask was placed (S)-4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxamide (1.1 g, 2.34 mmol) Lawesson's Reagent (1.1 g, 2.81 mmol) and toluene (67 mL). The resulting mixture was warmed at 80° C. for 16 h. The reaction was quenched by the addition of aq. sat. NaHCO$_3$, extracted with EtOAc (3×). The organic layer was washed with brine, dried over anhydr. Na$_2$SO$_4$, and filtered. The filtrate was concentrated in vacuo. The residue was purified by silica gel column chromatography with MeOH:DCM (5%) to afford the title compound. m/z=487 (M+1).

Step D—(S)-ethyl 3-(2-(4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl)thiazol-4-yl)-2,2-dimethylpropanoate In a sealed tube containing (S)-4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carbothioamide (60 mg, 0.123 mmol) and ethyl 5-bromo-2,2-dimethyl-4-oxopentanoate (48.9 mg, 0.185 mmol) in EtOH (1.2 mL) was warmed at 80° C. for 16 h. The reaction was cooled to RT and concentrated in vacuo to dryness. The residue was purified by silica gel chromatography using (EtOAc:EtOH 3:1):Hexane to afford the title compound. m/z=639 (M+1).

Step E—(S)-3-(2-{4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl}thiazol-4-yl)-2,2-dimethylpropanoic acid Into a flask was placed (S)-ethyl 3-(2-(4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl)thiazol-4-yl)-2,2-dimethylpropanoate (130 mg, 0.12 mmol), LiOH (29 mg, 1.22 mmol) dioxane (2.2 mL) and water (2.2 mL) The resulting mixture was stirred at 60° C. for 16 h. The reaction was cooled to RT, conc. in vacuo then diluted in EtOAc and water, and acetic acid (84 μl, 1.46 mmol) was added. The resulting solution was extracted with EtOAc. The organic layer was washed with brine, dried over anhydr. MgSO$_4$, and filtered. The filtrate was concentrated in vacuo. The residue was purified by silica gel column chromatography with (EtOAc:EtOH 3:1):hexane to afford the title compound Ex-77B. $^1$H NMR (400 MHz, DMSO-d$_6$) δ 12.23 (s, 1H), 11.45 (s, 1H), 9.02 (dd, J=8.1, 1.7 Hz, 1H), 8.63 (dd, J=4.5, 1.6 Hz, 1H), 7.37 (dd, J=8.1, 4.5 Hz, 1H), 7.24 (s, 1H), 6.96 (s, 2H), 4.87 (t, J=6.8 Hz, 2H), 3.06-2.85 (m, 4H), 1.80 (s, 3H), 1.08 (s, 6H); m/z=611 (M+1).

Example 78A (2-{4-Amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)acetic acid

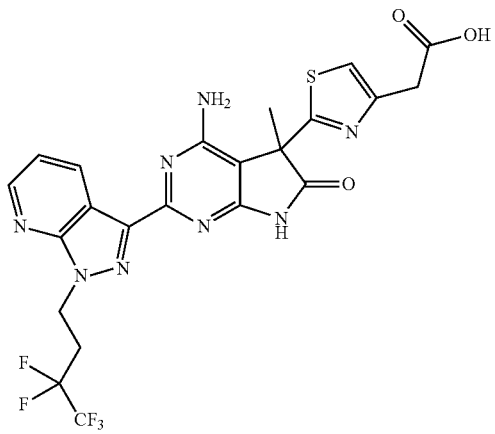 [SMILES: CC1(c2nc(CC(=O)O)cs2)C(=O)Nc2nc(-c3nn(CCC(F)(F)C(F)(F)F)c4ncccc34)nc(N)c21]

(2-{4-Amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)acetic acid was prepared using essentially the same procedures described in Example 77, using racemic I-30 as starting material to form racemic ethyl 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxylate.

Step A—ethyl 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxylate Into a flask was placed I-A2 (1.0 g, 3.2 mmol), I-30 (0.85 g, 3.6 mmol), potassium bicarbonate (390 mg, 3.9 mmol) and t-BuOH (100 mL). The resulting mixture was warmed at 70° C. for 8 h. reaction was cooled to RT and quenched by the addition of water. The resulting solution was extracted with EtOAc (3×) and the organic layers were combined, dried over anhydr. $Na_2SO_4$, filtered and the filtrate was concentrated in vacuo to dryness. The residue was purified by silica gel chromatography using MeOH:DCM (1-10%) to afford the title compound.

Racemic methyl 2-(2-{4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl}thiazol-4-yl)acetate was prepared as described in Ex-77B Step B and C using ethyl 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxylate as starting material.

Step D. Racemic methyl 2-(2-{4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl}thiazol-4-yl)acetate was resolved using Chiral SFC (CHIRALPAK® AD-H) to afford isomers A (faster eluting) and B (slower eluting). Isomer A was then hydrolysed using previously described conditions (step E in Ex-77B) to afford Ex-78A. $^1$H NMR (300 MHz, DMSO-$d_6$) δ 10.45 (br s, 1H), 11.43 (s, 1H), 9.04 (dd, J=8.1, 1.5 Hz, 1H), 8.64 (dd, J=4.5, 1.5 Hz, 1H), 7.45 (s, 1H), 7.38 (dd, J=8.1, 4.5 Hz, 1H), 6.94 (br s, 2H), 4.88 (t, J=6.6 Hz, 2H), 3.73 (s, 1H), 3.4-2.91 (m, 2H); 1.84 (s, 3H); m/z=569 (M+1).

Using essentially the same procedures to those described in examples 77B and 78A, the following compounds in Table 10 were prepared. The chirality of the compounds in Table 15 results from the use of a chiral intermediate and/or the separation of isomers performed at Step D or E.

TABLE 15

| Ex. | Int. SM/ Chiral Resolution Step/ Column | Step D Bromoketone | Structure/ m/z (M + 1) | Name |
|---|---|---|---|---|
| 79B | I-40B/ Chiral Int. | Br-CH₂-C(O)-CH₂-C(CH₃)₂-CH₂-C(O)-OEt | (structure shown) | (S)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-3-methylbutanoic acid |

TABLE 15-continued

| Ex. | Int. SM/ Chiral Resolution Step/ Column | Step D Bromoketone | Structure/ m/z (M + 1) | Name |
|---|---|---|---|---|
| 80BA | I-40B/ Step D/ AD | (±) | 595 | (5S)-2-(2-{-4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)cyclopropane-carboxylic acid |
| 81B | I-40B/ Chiral Int. | | 609 | (S)-1-[(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)methyl]cyclopropane carboxylic acid |
| 82B | I-40B/ Chiral Int. | | 583 | (S)-3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid |

TABLE 15-continued

| Ex. | Int. SM/ Chiral Resolution Step/ Column | Step D Bromoketone | Structure/ m/z (M + 1) | Name |
|---|---|---|---|---|
| 83B | I-40B/ Chiral Int. | | 583 | (S)-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-4-methyl-1,3-thiazol-5-yl)acetic acid |
| 84A | I-30/ Step E/ AD | | 629 | 3-(2-{4-amino-2-[5-fluoro-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid |
| 85A | I-30/ Step D/ IA | | 579 | 3-(2-{4-amino-2-[5-fluoro-1-(3,3,3-trifluoropropyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid |

TABLE 15-continued

| Ex. | Int. SM/ Chiral Resolution Step/ Column | Step D Bromoketone | Structure/ m/z (M + 1) | Name |
|---|---|---|---|---|
| 86A | I-30/ Step D/ IA | 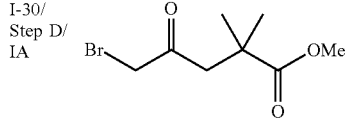 | 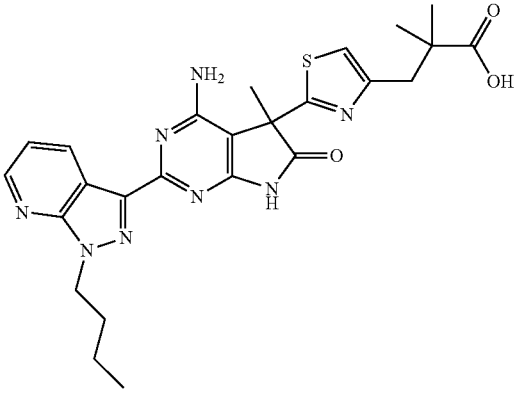 521 | 3-{2-[4-amino-2-(1-butyl-1H-pyrazolo[3,4-b]pyridin-3-yl)-5-methyl-6-oxo-6,7-dihydro-5H-pyrrolo[2,3-d]pyrimidin-5-yl]-1,3-thiazol-4-yl}-2,2-dimethylpropanoic acid |
| 87B | I-40B/ Chiral Int. | 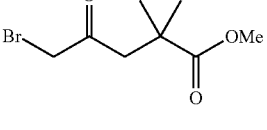 | 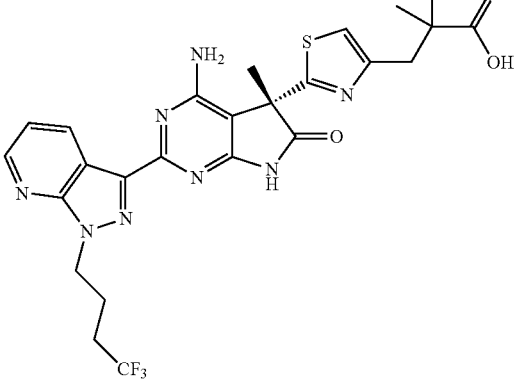 575 | (S)-3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid |
| 88B | I-40B/ Chiral Int. | 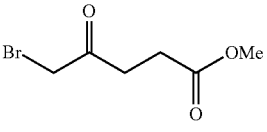 | 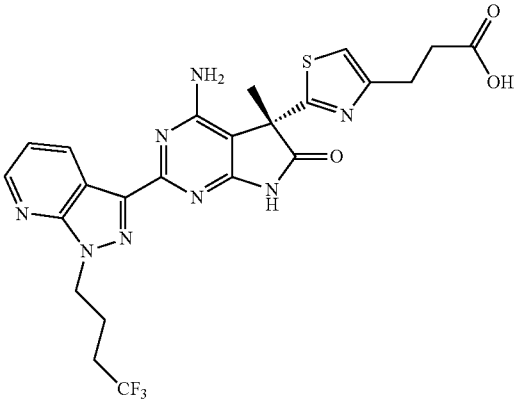 547 | (S)-3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid |

TABLE 15-continued

| Ex. | Int. SM/ Chiral Resolution Step/ Column | Step D Bromoketone | Structure/ m/z (M + 1) | Name |
|---|---|---|---|---|
| 89B | I-40B/ Chiral Int. | 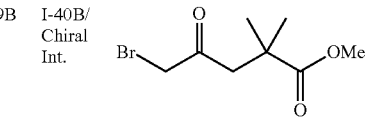 | 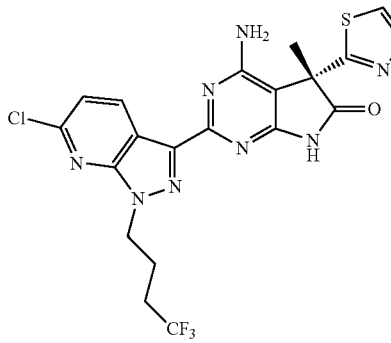<br>609 | (S)-3-(2-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid |
| 90B | I-40B/ Chiral Int. | 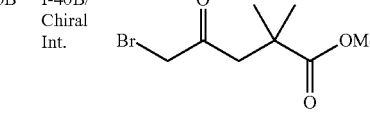 | 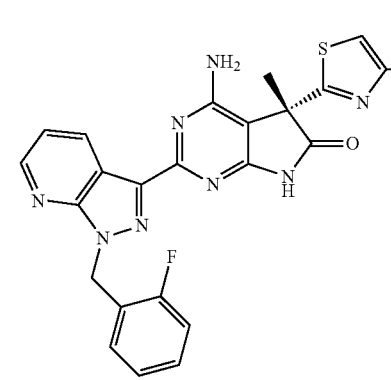<br>573 | (S)-3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid |
| 91B | I-40B/ Chiral Int. | 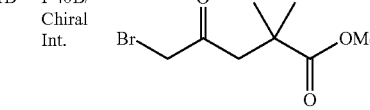 | 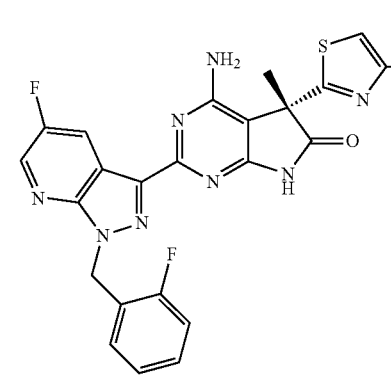<br>591 | (S)-3-(2-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid |

TABLE 15-continued

| Ex. | Int. SM/ Chiral Resolution Step/ Column | Step D Bromoketone | Structure/ m/z (M + 1) | Name |
|---|---|---|---|---|
| 92B | I-40B/ Chiral Int. | | 644 | (S)-3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid |
| 93A | I-30/ Step D/ IA | | 664 | 3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)benzoic acid |
| 94B | I-30/ Step D/ AS | | 678 | 4-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-5-methyl-1,3-thiazol-4-yl)benzoic acid |

TABLE 15-continued

| Ex. | Int. SM/ Chiral Resolution Step/ Column | Step D Bromoketone | Structure/ m/z (M + 1) | Name |
|---|---|---|---|---|
| 95B | I-40B/ Chiral Int. | Br−CH2−C(=O)−CH2−C(CH3)2−C(=O)−OMe | 606 | (S)-3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid |
| 96B | I-41B/ Chiral Int. | Br−CH2−C(=O)−CH2−C(CH3)2−C(=O)−OEt | 619 | 3-(2-{4-amino-5-cyclopropyl-2-[5-fluoro-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}thiazol-4-yl)-2,2-dimethylpropanoic acid |

187

Example 97B (S)-3-(2-{4-Amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-N-hydroxy-2,2-dimethylpropanamide

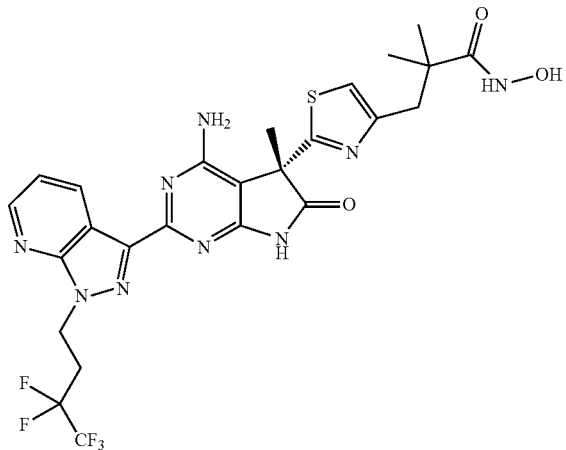 [SMILES: CC(C)(Cc1csc([C@]2(C)C(=O)Nc3nc(-c4nn(CCC(F)(F)C(F)(F)F)c5ncccc45)nc(N)c32)n1)C(=O)NO]

A flask containing example 77B (80 mg, 0.13 mmol), triethylamine (53 mg, 0.52 mmol), 1-[bis(dimethylamino)methylene]-1H-1,2,3-triazolo[4,5-b]pyridinium 3-oxid hexafluorophosphate (100 mg, 0.26 mmol) in DMF (5 mL) was stirred for 10 min at RT before hydroxylammonium chloride (18 mg, 0.26 mmol) was added. The resulting mixture was stirred for 1 h at RT then was concentrated in vacuo to dryness. The residue was purified by silica gel column chromatography with MeOH:DCM (2-4%) then by reverse phase HPLC (ACN/water with 0.05% $NH_4HCO_3$ modifier) to afford the title compound Ex-97B. $^1$H NMR (300 MHz, $CD_3OD$) δ 9.00 (dd, J=1.5, 8.1 Hz, 1H), 8.58 (dd, J=1.5, 4.5 Hz, 1H), 7.32 (dd, J=4.5, 8.1 Hz, 1H), 7.12 (s, 1H), 4.91 (t, J=7.2 Hz, 2H), 3.11-2.82 (m, 4H), 1.83 (s, 3H), 1.18 (s, 3H), 1.14 (s, 3H); m/z=626 (M+1).

Example 98A

[5-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]acetic acid

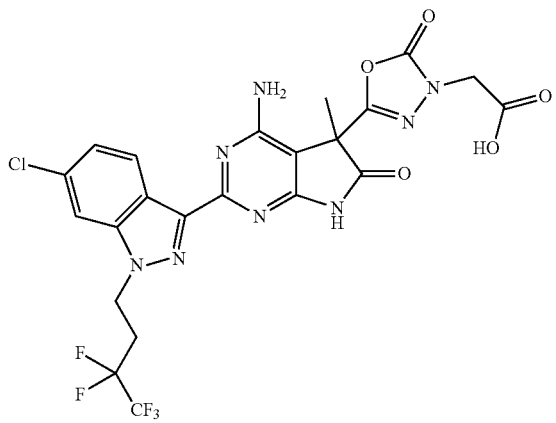 [SMILES: CC1(c2nn(CC(=O)O)c(=O)o2)C(=O)Nc2nc(-c3nn(CCC(F)(F)C(F)(F)F)c4cc(Cl)ccc34)nc(N)c21]

188

Step A—ethyl 4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidine-5-carboxylate was prepared using conditions similar to the those described for the synthesis of ethyl 4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidine-5-carboxylate, using I-A1 and I-30 as starting material.

Step B—4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidine-5-carbohydrazide A flask containing ethyl 4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidine-5-carboxylate (900 mg, 1.69 mmol) and hydrazine hydrate (863 mg, 16.89 mmol) in MeOH (10 mL) was stirred for 2 h at 70° C. The solid was collected by filtration to afford the title compound which was used in Step C without purification.

Step C—5-(4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidin-5-yl)-1,3,4-oxadiazol-2(3H)-one A flask containing 4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidine-5-carbohydrazide (400 mg, 0.77 mmol) and N,N'-carbonyldiimidazole (375 mg, 2.31 mmol) in DCM (25 mL) was stirred for 2 h at RT. The resulting mixture was concentrated in vacuo. The residue was purified by silica gel column chromatography with MeOH:DCM (2-4%) to afford the title compound.

Step D—ethyl 2-(5-(4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidin-5-yl)-2-oxo-1,3,4-oxadiazol-3(2H)-yl)acetate To a flask containing 5-(4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidin-5-yl)-1,3,4-oxadiazol-2(3H)-one (150 mg, 0.28 mmol), and potassium carbonate (19 mg, 0.14 mmol) in DMF (20 mL) at −20° C. was added ethyl 2-bromoacetate (41.5 mg, 0.25 mmol) and the mixture was stirred for 5 h at −20° C. The reaction was concentrated in vacuo to dryness. The residue was purified by silica gel chromatography using MeOH:DCM (2-10%) to afford the title racemic product. The racemic material was resolved using chiral SFC (CHIRALCEL® OD-H column) to afford isomer A (faster eluting) and isomer B (slower eluting).

Step E—[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]acetic acid To a flask containing ethyl 2-(5-(4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidin-5-yl)-2-oxo-1,3,4-oxadiazol-3(2H)-yl)acetate isomer A (25 mg, 0.04 mmol), in THF (3 mL) was added LiOH (2.9 mg, 0.12 mmol) in water (1 mL). The resulting mixture was stirred for 2 h at RT before being concentrated in vacuo. The residue was diluted with hydrochloric acid (0.1 N, 1.1 mL), the solid was collected by filtration, washed with water and dried under vacuum to afford the title product Ex-98A. $^1$H NMR (300 MHz, CD$_3$OD) δ 8.64 (d, J=8.4 Hz, 1H), 7.72 (d, J=1.2 Hz, 1H), 7.24 (dd, J=1.8, 8.7 Hz, 1H), 4.80-4.74 (m, 2H), 4.27 (s, 2H), 3.06-2.83 (m, 2H), 1.82 (s, 3H); m/z=603 (M+1).

Example 99B

2-[5-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]-2-methylpropanoic acid

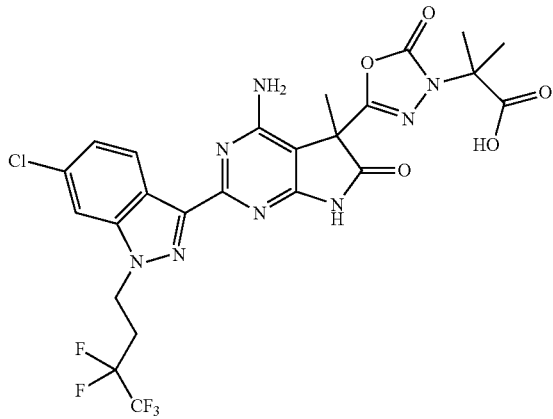 [SMILES: CC1(c2nn(C(C)(C)C(=O)O)c(=O)o2)C(=O)Nc2nc(-c3nn(CCC(F)(F)C(F)(F)F)c4cc(Cl)ccc34)nc(N)c21]

The title compound was prepared using essentially the same procedures described in Example 98A, using methyl 2-bromo-2-methylpropanoate as starting material. The racemic Ex-99 was resolved using chiral SFC (Kromasil (R,R) WHELK-01 5/100 column) to afford isomers Ex-99A (faster eluting) and Ex-99B (slower eluting) of the title compound $^1$H NMR (300 MHz, CD$_3$OD) δ 8.68 (d, J=8.7 Hz, 1H), 7.78 (d, J=1.5 Hz, 1H), 7.29 (dd, J=1.5, 8.7 Hz, 1H), 4.95-4.80 (m, 2H), 3.11-2.86 (m, 2H), 1.86 (s, 3H), 1.75 (s, 3H), 1.74 (s, 3H); m/z=631 (M+1).

Example 100B (S)-(3-(4-{4-Amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)glycine

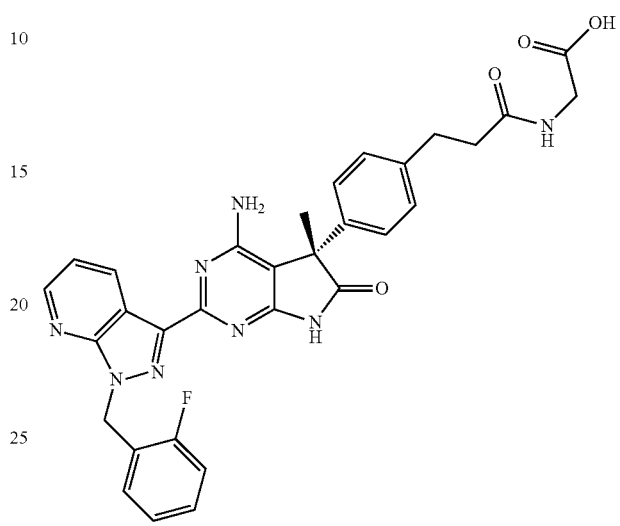

Step A—(S)-tert-butyl (3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)glycinate In a flask containing Ex-21B (20 mg, 0.037 mmol) and O-(benzotriazol-1-yl)-N,N,N',N'-tetramethyluronium tetrafluoroborate (12.19 mg, 0.04 mmol) in DMF (300 µl) at RT was added triethylamine (52 µl, 0.37 mmol). Then glycine tert-butyl ester hydrochloride (18 mg, 0.112 mmol) was added. The resulting mixture was stirred 20 min at RT. Volatiles were removed in vacuo, and then water was added and the solid was collected and dried under vacuum. The crude material was used directly in the next step.

Step B—(S)-(3-(4-{4-amino-2-(1-(2-fluorobenzyl)-1H-pyrazolo[3,4-b]pyridin-3-yl)-5-methyl-6-oxo-6,7-dihydro-5H-pyrrolo[2,3-d]pyrimidin-5-yl}phenyl)propanoyl)glycine To the crude product from step A was added trifluoroacetic acid (250 µl, 3.24 mmol) and DCM (0.7 mL) and the reaction was stirred for 2 h at RT. The reaction mixture was then concentrated in vacuo to dryness. The mixture was filtered and purified by mass triggered reverse phase HPLC (ACN/water with 0.1% TFA modifier) to afford the title compound Ex-100B as the TFA salt. $^1$H NMR (500 MHz, DMSO-d$_6$) δ 9.06 (dd, J=8.0, 1.7 Hz, 1H), 8.65 (dd, J=4.5, 1.7 Hz, 1H), 8.15 (d, J=5.9 Hz, 1H), 7.43-7.31 (m, 2H), 7.23-7.10 (m, 7H), 6.55 (s, 2H), 5.83 (s, 2H), 3.71 (d, J=5.8 Hz, 2H), 2.79 (t, J=7.9 Hz, 2H), 2.41 (t, J=8.0 Hz, 2H), 1.77 (s, 3H); m/z=595.3 (M+1).

Using a similar procedure to that described in Ex-100B, the following compounds in Table 16 were prepared using from commercial starting reagents or compounds known in the literature. Methyl esters were hydrolysed using lithium hydroxide conditions previously described.

TABLE 16

| Ex. | Step A amine | Structure | Name | m/z (M + 1) |
|---|---|---|---|---|
| 101B | 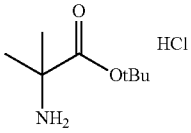 | 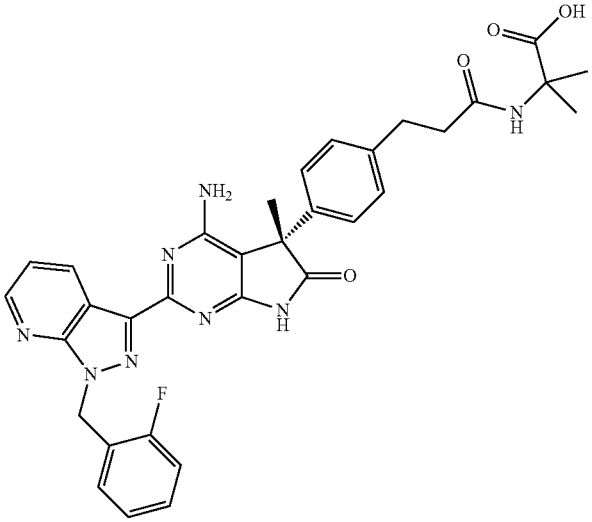 [SMILES: CC(C)(NC(=O)CCc1ccc([C@]2(C)C(=O)Nc3nc(-c4nn(Cc5ccccc5F)c5ncccc45)nc(N)c32)cc1)C(=O)O] | (S)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)-2-methylpropanoic acid | 623 |
| 102B | 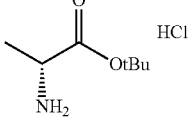 | 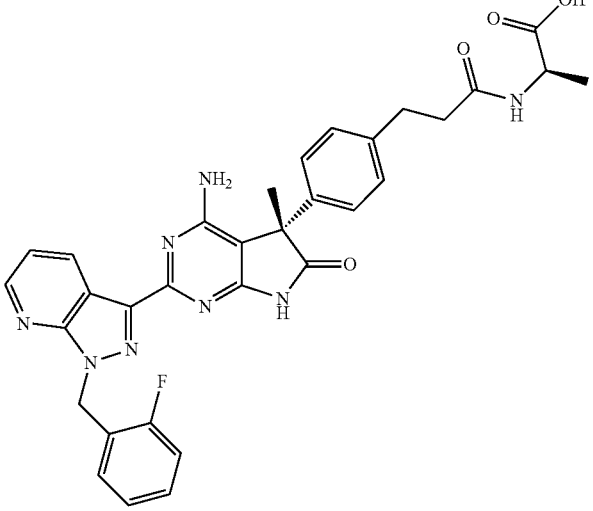 | (5S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-alanine | 609 |
| 103B | 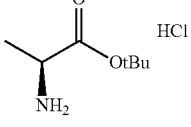 | 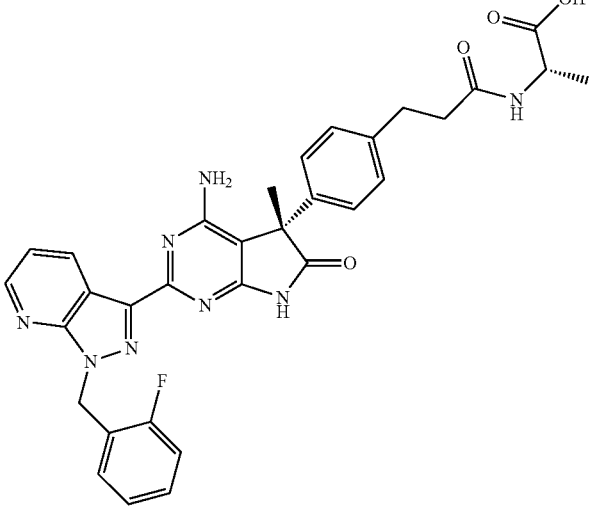 | (5S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-L-alanine | 609 |

TABLE 16-continued

| Ex. | Step A amine | Structure | Name | m/z (M + 1) |
|---|---|---|---|---|
| 104B | | 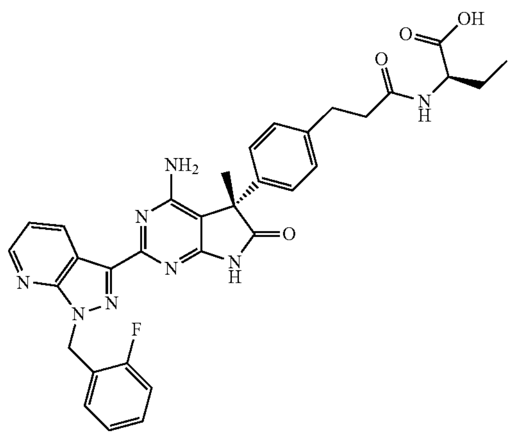 [SMILES: CC[C@@H](NC(=O)CCc1ccc([C@]2(C)C(=O)Nc3nc(-c4nn(Cc5ccccc5F)c5ncccc45)nc(N)c32)cc1)C(=O)O] | (5S,2R)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid | 623 |
| 105B | | 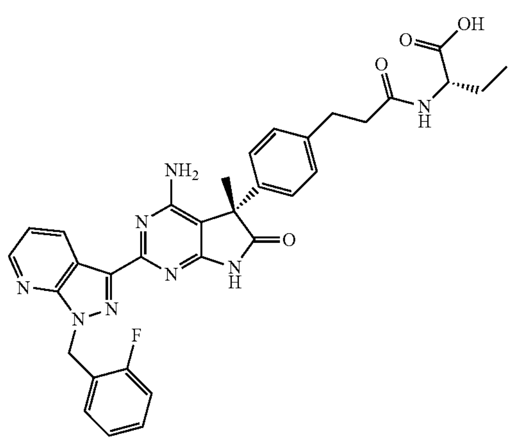 [SMILES: CC[C@H](NC(=O)CCc1ccc([C@]2(C)C(=O)Nc3nc(-c4nn(Cc5ccccc5F)c5ncccc45)nc(N)c32)cc1)C(=O)O] | (5S,2S)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid | 623 |
| 106B | | 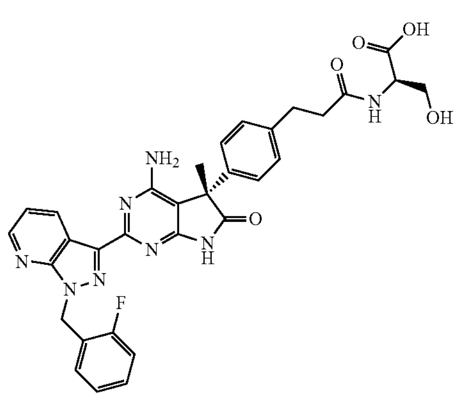 [SMILES: C[C@@]1(c2ccc(CCC(=O)N[C@H](CO)C(=O)O)cc2)C(=O)Nc2nc(-c3nn(Cc4ccccc4F)c4ncccc34)nc(N)c21] | (5S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-serine | 625 |

| Ex. | Step A amine | Structure | Name | m/z (M + 1) |
|---|---|---|---|---|
| 107B | ![amine structure] | ![structure] | (5S)-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-threonine | 639 |

Example 108B (S)—N-((2H-Tetrazol-5-yl)methyl)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamide

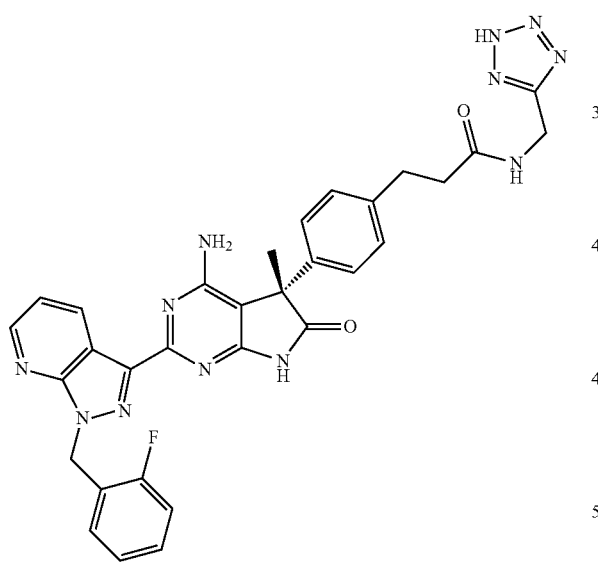

In a flask containing Ex-21B (20 mg, 0.037 mmol) and O-(benzotriazol-1-yl)-N,N,N',N'-tetramethyluronium tetrafluoroborate (29.9 mg, 0.093 mmol) in DMF (300 µl) at RT was added triethylamine (26 µl, 0.186 mmol). Then (2-trityl-2H-tetrazol-5-yl)methanamine (40 mg, 0.11 mmol) was added. The resulting mixture was stirred 20 min at RT. The reaction was concentrated in vacuo to dryness then water was added and the solid was collected and dried under vacuum. The residue was treated with HCl (1 mL, 4 M in dioxane) and the resulting mixture was stirred at 80° C. then concentrated in vacuo to dryness and the residue was purified by mass triggered reverse phase HPLC (ACN/water with 0.1% TFA modifier) to afford the title compound Ex-108B as the TFA salt. $^1$H NMR (500 MHz, DMSO-d$_6$) δ 11.10 (s, 1H), 9.06 (dd, J=8.1, 1.6 Hz, 1H), 8.65 (dd, J=4.5, 1.6 Hz, 1H), 8.58 (t, J=5.7 Hz, 1H), 7.43-7.32 (m, 2H), 7.29-7.11 (m, 7H), 6.55 (s, 2H), 5.84 (s, 2H), 4.53 (d, J=5.6 Hz, 2H), 2.81 (t, J=8.0 Hz, 2H), 2.44 (t, J=8.0 Hz, 2H), 1.78 (s, 3H); m/z=619 (M+1).

Example 109B 3-(4-{4-Amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-2H-1,2,3-triazol-2-yl)propanoic acid Step A—4-amino-5-ethynyl-5-methyl-2-(1-(3,3,4,4,4-pentafluorobutyl)-1H-pyrazolo[3,4-b]pyridin-3-yl)-5,7-dihydro-6H-pyrrolo[2,3-d]pyrimidin-6-one To a flask containing I-A2 (400 mg, 1.30 mmol) and I-10B (272 mg, 1.43 mmol) in t-BuOH (10 mL) was added potassium bicarbonate (130 mg, 1.30 mmol). The resulting mixture was stirred at 70° C. for 16 h then quenched by the addition of brine and extracted with EtOAc (3×). The combined organic layer was washed with brine, dried over anhydr. Na$_2$SO$_4$, and filtered. The filtrate was concentrated in vacuo, the residue was purified by silica gel column chromatography with MeOH:DCM to afford the title compound.

Step B—4-amino-5-methyl-2-(1-(3,3,4,4,4-pentafluorobutyl)-1H-pyrazolo[3,4-b]pyridin-3-yl)-5-(1H-1,2,3-triazol-4-yl)-5,7-dihydro-6H-pyrrolo[2,3-d]pyrimidin-6-one To a microwave vial containing 4-amino-5-ethynyl-5-methyl-2-(1-(3,3,4,4,4-pentafluorobutyl)-1H-pyrazolo[3,4-b]pyridin-3-yl)-5,7-dihydro-6H-pyrrolo[2,3-d]pyrimidin-6-one (500 mg, 1.11 mmol) and bromotris(triphenylphosphine)copper (I) (103 mg, 0.11 mmol) in DMSO (22 mL) was added azidotrimethylsilane (770 μL, 5.54 mmol). The reaction mixture was microwaved at 120° C. for 1 h. The resulting mixture was cooled to RT and diluted with EtOAc and brine. To the organic phase was added aq. ammonium hydroxide solution and the resulting mixture was stirred 16 h. The aqueous was extracted with EtOAc (3×) dried over anhydr. MgSO$_4$, filtered and the filtrate was concentrated in vacuo. The residue was purified by silica gel column chromatography with (EtOAc:EtOH 3:1):hexane gradient to afford the title compound.

Step C—Ethyl 3-(4-(4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl)-2H-1,2,3-triazol-2-yl)propanoate To a flask containing 4-amino-5-methyl-2-(1-(3,3,4,4,4-pentafluorobutyl)-1H-pyrazolo[3,4-b]pyridin-3-yl)-5-(1H-1,2,3-triazol-4-yl)-5,7-dihydro-6H-pyrrolo[2,3-d]pyrimidin-6-one (160 mg, 0.29 mmol) and K$_2$CO$_3$ (121 mg, 0.87 mmol) in DMF (2.9 mL) was added ethyl acrylate (38 μl, 0.35 mmol) The resulting mixture was stirred 2 h at RT then diluted with EtOAc and brine. The organic layer was washed with brine, dried over anhydr. MgSO$_4$, and filtered. The filtrate was concentrated in vacuo and the residue was first purified by silica gel column chromatography with (EtOAc:EtOH 3:1):hexane then by mass triggered reverse phase HPLC (ACN/water with 0.1% TFA modifier) to afford the title compound as the TFA salt.

Step D—3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-2H-1,2,3-triazol-2-yl)propanoic acid To a flask containing ethyl 3-(4-(4-amino-5-methyl-6-oxo-2-(1-(3,3,4,4,4-pentafluorobutyl)-1H-pyrazolo[3,4-b]pyridin-3-yl)-6,7-dihydro-5H-pyrrolo[2,3-d]pyrimidin-5-yl)-2H-1,2,3-triazol-2-yl)propanoate (22 mg, 0.037 mmol) in MeCN (1.8 mL) and water (1.8 mL) was added LiOH (5 mg, 0.18 mmol). The resulting mixture was stirred 30 min at RT then diluted in EtOAc and acetic acid (13 μl, 0.22 mmol). The resulting solution was extracted with EtOAc. The organic layer was washed with brine, dried over anhydr. MgSO$_4$, and filtered. The filtrate was concentrated in vacuo and purified by silica gel column chromatography with (EtOAc:EtOH 3:1):Hexane to afford the title compound Ex-109B. $^1$H NMR (400 MHz, DMSO-d$_6$) δ 11.24 (s, 1H), 9.02 (dd, J=8.1, 1.7 Hz, 1H), 8.63 (dd, J=4.5, 1.6 Hz, 1H), 7.73 (s, 1H), 7.37 (dd, J=8.1, 4.5 Hz, 1H), 6.62 (s, 2H), 4.87 (t, J=6.7 Hz, 2H), 4.49 (t, J=7.2 Hz, 2H), 2.94 (dt, J=19.1, 6.8 Hz, 3H), 2.71 (t, J=7.1 Hz, 2H), 1.75 (s, 3H). m/z=567.1 (M+1).

Example 110B (S)-3-(4-{4-Amino-2-[6-chloro-1-(2-fluorobenzyl)-5-hydroxy-1H-indazol-3-yl]-5-methyl-6-oxo-6,7-dihydro-5H-pyrrolo[2,3-d]pyrimidin-5-yl}phenyl)propanoic acid

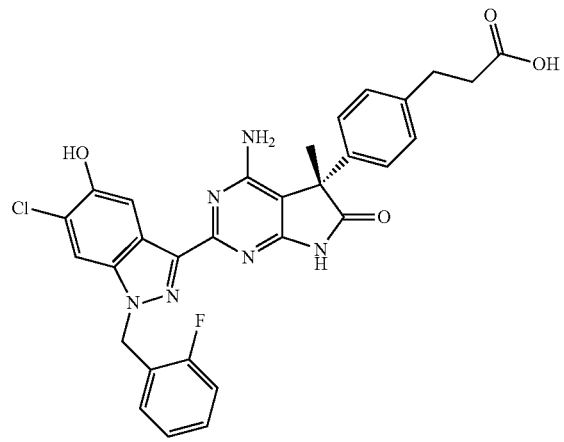 [SMILES: C[C@@]1(c2ccc(CCC(=O)O)cc2)C(=O)Nc2nc(-c3nn(Cc4ccccc4F)c4cc(Cl)c(O)cc34)nc(N)c21]

Step A—(S)-methyl 3-(4-(4-amino-2-(6-chloro-1-(2-fluorobenzyl)-5-methoxy-1H-indazol-3-yl)-5-methyl-6-oxo-6,7-dihydro-5H-pyrrolo[2,3-d]pyrimidin-5-yl)phenyl)propanoate A flask containing I-A24 (100 mg, 0.30 mmol), I-11B (99 mg, 0.30 mmol) and potassium bicarbonate (90 mg, 0.90 mmol) in t-BuOH (10 mL) was stirred for 16 h at 70° C. The reaction mixture was concentrated in vacuo to dryness. The residue was purified by silica gel column chromatography with MeOH:DCM (0-5%) to afford the title compound.

Step B—(S)-3-(4-{4-amino-2-[6-chloro-1-(2-fluorobenzyl)-5-hydroxy-1H-indazol-3-yl]-5-methyl-6-oxo-6,7-dihydro-5H-pyrrolo[2,3-d]pyrimidin-5-yl}phenyl)propanoic acid To a flask containing (S)-methyl 3-(4-(4-amino-2-(6-chloro-1-(2-fluorobenzyl)-5-methoxy-1H-indazol-3-yl)-5-methyl-6-oxo-6,7-dihydro-5H-pyrrolo[2,3-d]pyrimidin-5-yl)phenyl)propanoate (105 mg, 0.17 mmol) in DCM (10 mL) at 0° C. was added dropwise tribromoborane (1.0 mL, 10.6 mmol). The resulting mixture was stirred for 16 h at RT. The reaction was quenched by the addition of ice water and the pH value of the mixture was adjusted to pH 7-8 by the addition of NaHCO$_3$. The resulting solution was extracted with EtOAc (3×), the organic layer was washed with brine, dried over anhydr. Na$_2$SO$_4$, and filtered. The filtrate was concentrated in vacuo and the residue was purified by silica gel column chromatography with MeOH:DCM (1-6%) to afford the title compound Ex-110B, $^1$H NMR (300 MHz, CD$_3$OD): δ 8.10 (s, 1H), 7.59 (s, 1H), 7.30-7.20 (m, 5H), 7.15-7.06 (m, 3H), 5.70 (s, 2H), 2.87 (t, J=7.2 Hz, 2H), 2.56 (t, J=7.2 Hz, 2H), 1.84 (s, 3H); m/z=587 (M+1).

Example 111B (S)-3-{4-{4-amino-2-(1-butyl-6-methyl-1H-pyrazolo[3,4-b]pyridin-3-yl)-5-methyl-6-oxo-6,7-dihydro-5H-pyrrolo[2,3-d]pyrimidin-5-yl}phenyl}propanoic acid

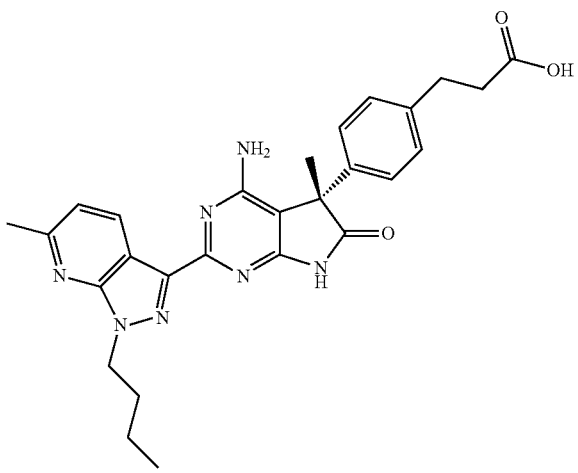 [SMILES: CCCCn1nc(-c2nc(N)c3c(n2)NC(=O)[C@@]3(C)c2ccc(CCC(=O)O)cc2)c2ccc(C)nc21]

Step A—(S)-methyl 3-(4-(4-amino-2-(1-butyl-6-chloro-1H-pyrazolo[3,4-b]pyridin-3-yl)-5-methyl-6-oxo-6,7-dihydro-5H-pyrrolo[2,3-d]pyrimidin-5-yl)phenyl)propanoate A flask containing I-A36 (50 mg, 0.20 mmol), I-11B (65 mg, 0.20 mmol) and potassium bicarbonate (60 mg, 0.60 mmol) in t-BuOH (5 mL) was stirred for 16 h at 75° C. The reaction was cooled to RT and quenched by the addition of water. The resulting solution was extracted with DCM (3×), the organic layers were combined, dried over anhydr. $Na_2SO_4$, filtered and the filtrate was concentrated in vacuo to dryness. The residue was purified by silica gel chromatography using MeOH:DCM (0-3%) to afford the title product.

Step B—(S)-methyl 3-(4-(4-amino-2-(1-butyl-6-methyl-1H-pyrazolo[3,4-b]pyridin-3-yl)-5-methyl-6-oxo-6,7-dihydro-5H-pyrrolo[2,3-d]pyrimidin-5-yl)phenyl)propanoate In a flask under inert atmosphere of nitrogen were placed (S)-methyl 3-(4-(4-amino-2-(1-butyl-6-chloro-1H-pyrazolo[3,4-b]pyridin-3-yl)-5-methyl-6-oxo-6,7-dihydro-5H-pyrrolo[2,3-d]pyrimidin-5-yl)phenyl)propanoate (140 mg, 0.26 mmol), bis(triphenylphosphine)palladium(II) chloride (28 mg, 0.039 mmol) and THF (10 mL). The resulting mixture was stirred for 30 min before dimethylzinc (1.57 mL, 1.57 mmol, 1 M in THF) was added. The mixture was stirred for 16 h at RT. The reaction was quenched by the addition of aq. sat. $NH_4Cl$, extracted with EtOAc (3×). The organic layer was washed with brine, dried over anhydr. $Na_2SO_4$, and filtered. The filtrate was concentrated in vacuo and the residue was first purified by silica gel column chromatography with MeOH:DCM (0-10%) then by reverse phase HPLC (ACN/water with 0.05% $NH_4HCO_3$ modifier) to afford the title compound.

Step C—(S)-3-{4-[4-amino-2-(1-butyl-6-methyl-1H-pyrazolo[3,4-b]pyridin-3-yl)-5-methyl-6-oxo-6,7-dihydro-5H-pyrrolo[2,3-d]pyrimidin-5-yl]phenyl}propanoic acid To a flask containing (S)-methyl 3-(4-(4-amino-2-(1-butyl-6-methyl-1H-pyrazolo[3,4-b]pyridin-3-yl)-5-methyl-6-oxo-6,7-dihydro-5H-pyrrolo[2,3-d]pyrimidin-5-yl)phenyl)propanoate (70 mg, 0.14 mmol) in THF (8 mL) was added LiOH (16 mg, 0.68 mmol) in water (0.5 mL). The resulting mixture was stirred for 16 h at RT before been concentrated in vacuo. The residue was diluted with water (2 mL) and hydrochloric acid (6.8 mL, 0.1 N) was added. The solid was collected by filtration and dried under vacuum to afford the title product Ex-111B. $^1H$ NMR (400 MHz, $CD_3OD$) δ 8.88 (d, J=8.0 Hz, 1H), 7.30-7.20 (m, 5H), 4.59 (t, J=6.8 Hz, 2H), 2.90 (t, J=7.6 Hz, 2H), 2.69 (s, 3H), 2.58 (t, J=7.6 Hz, 2H), 2.02-1.95 (m, 2H), 1.87 (s, 3H), 1.40-1.34 (m, 2H), 0.97 (t, J=7.6 Hz, 3H); m/z=500 (M+1).

Example 112B (S)-4-Amino-2-[6-chloro-1-(2-fluorobenzyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one

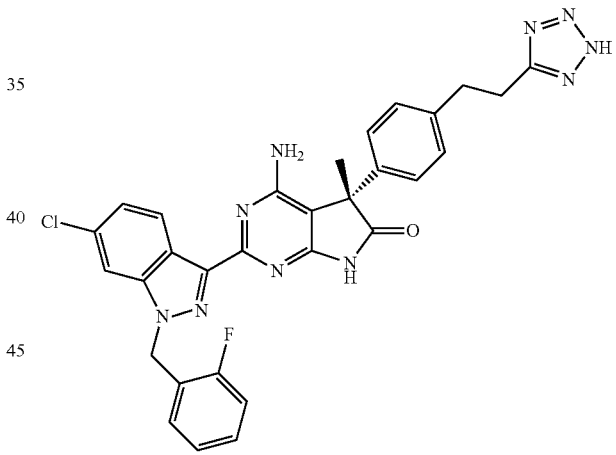

Step A—(S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanamide To a flask containing Ex-47B (1.0 g, 1.58 mmol) in DMF (10 mL) was added N,N-carbonyldiimidazole (1.28 g, 7.88 mmol). The mixture was stirred for 30 min at RT and $NH_4Cl$ (0.17 g, 3.15 mmol) was added. The resulting mixture was stirred for 16 h at RT then poured into water and extracted with EtOAc (3×). the organic layers were combined, dried over anhydr. $Na_2SO_4$, filtered and the filtrate was concentrated in vacuo to dryness. The residue was purified by silica gel chromatography using MeOH:DCM (0-5%) to afford the title compound.

Step B—(S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanenitrile To a flask containing (S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanamide (800 mg, 1.40 mmol) and pyridine (0.5 mL, 6.18 mmol) in DCM (5 mL) at 0° C. was added dropwise 2,2,2-trifluoroacetic anhydride (0.5 mL, 3.54 mmol). The mixture was stirred for 1 h at RT. The reaction was then diluted with MeOH (20 mL) and concentrated in vacuo. The residue was diluted with water, extracted with EtOAc (3×) and the organic layers were combined, dried over anhydr. $Na_2SO_4$, filtered and the filtrate was concentrated in vacuo to dryness. The residue was purified by silica gel chromatography using MeOH:DCM (0-5%) to afford the title product.

Step C—(S)-4-amino-2-[6-chloro-1-(2-fluorobenzyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one To a flask containing (S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanenitrile (170 mg, 0.31 mmol) and dibutylstannanone (15.3 mg, 0.062 mmol) in toluene (10 mL) was added azidotrimethylsilane (177 mg, 1.54 mmol). The mixture was stirred for 16 h at 100° C. then the mixture was concentrated in vacuo. The residue was first purified by silica gel column chromatography with MeOH:DCM (0-5%) then by reverse phase HPLC (ACN/water with 0.05% $NH_4HCO_3$ modifier) to afford the title compound Ex-112B. $^1$H NMR (300 MHz, $CD_3OD$) δ 8.66 (d, J=8.7 Hz, 1H), 7.63 (s, 1H), 7.35-7.05 (m, 9H), 5.76 (s, 2H), 3.16-2.96 (m, 4H), 1.83 (s, 3H); m/z=595 (M+1).

Example 113A 4-(4-{4-Amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)butanoic acid

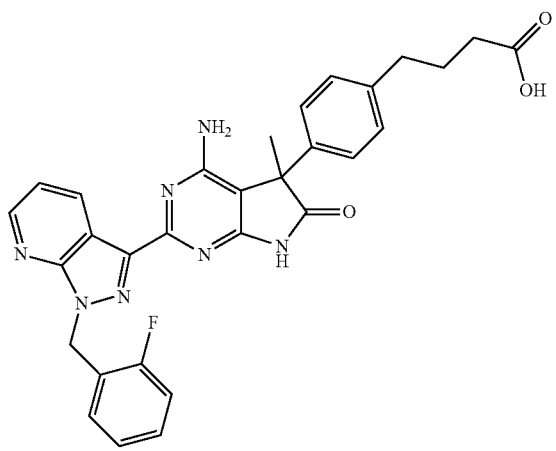 [SMILES: CC1(c2ccc(CCCC(=O)O)cc2)C(=O)Nc2nc(-c3nn(Cc4ccccc4F)c4ncccc34)nc(N)c21]

Step A—4-Amino-5-(4-bromophenyl)-2-[1-(2-fluorobenzyl)-1H-pyrazolo[3,4-b]pyridin-3-yl]-5-methyl-5,7-dihydro-6H-pyrrolo[2,3-d]pyrimidin-6-one A flask containing I-A16 (250 mg, 0.82 mmol), I-21A (263 mg, 0.82 mmol) and potassium bicarbonate (180 mg, 1.80 mmol) in t-BuOH (10 mL) was stirred at 70° C. for 16 h. The reaction mixture was concentrated in vacuo to dryness. The residue was purified by silica gel column chromatography with MeOH:DCM (0-10%) to afford the title compound. m/z=546 (M+1).

Step B—ethyl 4-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)butanoate To a flask under a inert atmosphere of nitrogen, containing 4-amino-5-(4-bromophenyl)-2-[1-(2-fluorobenzyl)-1H-pyrazolo[3,4-b]pyridin-3-yl]-5-methyl-5,7-dihydro-6H-pyrrolo[2,3-d]pyrimidin-6-one (150 mg, 0.28 mmol) and second generation Xphos precatalyst (43 mg, 0.055 mmol) in THF (0.5 mL) was added 4-ethoxy-4-oxobutylzinc bromide (3.3 mL, 1.65 mmol). The resulting mixture was stirred at 55° C. for 16 h. The reaction was quenched by the addition of aq. sat. $NH_4Cl$, extracted with EtOAc (3×). The organic layers were combined, dried over anhydr. $Na_2SO_4$, and filtered. The filtrate was concentrated in vacuo. The residue was purified by silica gel column chromatography with MeOH:DCM (0-10%) to afford the title compound.

Step C—4-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)butanoic acid To a flask containing ethyl 4-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)butanoate (100 mg, 0.17 mmol) in THF (4 mL) was added LiOH (72 mg, 1.72 mmol) in water (4 mL). The resulting mixture was stirred for 16 h at RT before been concentrated in vacuo. The residue was diluted with hydrochloric acid (0.1 N, 17.2 mL), the solid was collected by filtration, washed with water and dried under vacuum to afford the title product Ex-113A. $^1$H NMR (300 MHz, $CD_3OD$): δ 9.10 (d, J=8.1 Hz, 1H), 8.61 (dd, J=4.5 Hz, 1.2 Hz, 1H), 7.40-7.06 (m, 9H), 5.92 (s, 2H), 2.65 (t, J=7.2 Hz, 2H), 2.28 (t, J=7.2 Hz, 2H), 1.98-1.85 (m, 5H); m/z=552 (M+1).

Example 114A (4-{4-Amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)acetic acid

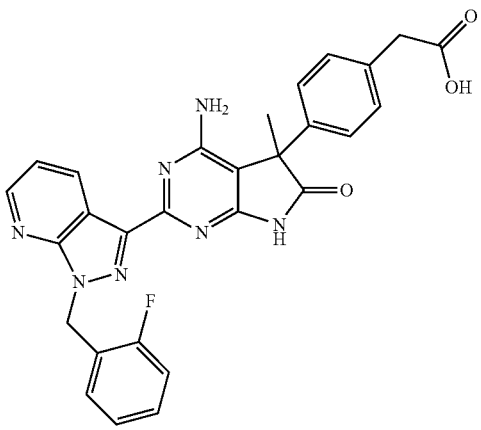 [SMILES: CC1(c2ccc(CC(=O)O)cc2)C(=O)Nc2nc(-c3nn(Cc4ccccc4F)c4ncccc34)nc(N)c21]

Step A—tert-butyl 2-(4-(4-amino-2-{1-(2-fluorobenzyl)-1H-pyrazolo[3,4-b]pyridin-3-yl}-5-methyl-6-oxo-6,7-dihydro-5H-pyrrolo[2,3-d]pyrimidin-5-yl)phenyl)acetate In a microwave vial were placed 4-amino-5-(4-bromophenyl)-2-[1-(2-fluorobenzyl)-1H-pyrazolo[3,4-b]pyridin-3-yl]-5-methyl-5,7-dihydro-6H-pyrrolo[2,3-d]pyrimidin-6-one (Ex-113A, step A, isomer A) (150 mg, 0.28 mmol), bis(dibenzylideneacetone)palladium (32 mg, 0.055 mmol), tri-tert-butylphosphonium tetrafluoroborate (32 mg, 0.11 mmol) and (2-(tert-butoxy)-2-oxoethyl)zinc(II) bromide (1.07 g, 4.13 mmol) in THF (15 mL). The reaction mixture was stirred for 1 h at RT and then microwaved for 1 h at 120° C. The reaction was quenched by the addition of aq. sat. NH$_4$Cl, extracted with EtOAc (3×). The organic layer was washed with brine, dried over anhydr. Na$_2$SO$_4$, filtered and the filtrate was concentrated in vacuo. The residue was purified by reverse phase HPLC (ACN/water with 0.05% NH$_4$HCO$_3$ modifier) to afford the title compound.

Step B—(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl) acetic acid Into a flask were placed tert-butyl 2-(4-(4-amino-2-{1-(2-fluorobenzyl)-1H-pyrazolo[3,4-b]pyridin-3-yl}-5-methyl-6-oxo-6,7-dihydro-5H-pyrrolo[2,3-d]pyrimidin-5-yl)phenyl)acetate (65 mg, 0.11 mmol), DCM (5 mL) and trifluoroacetic acid (1 mL). The resulting mixture was stirred for 16 h at RT. The reaction was concentrated in vacuo then diluted with water. The pH value was adjusted to pH 10 by addition of sodium hydroxide (1 N) and then, the pH value was adjusted to pH 6 with hydrochloric acid (1 N), the solid was collected by filtration, washed with water and dried under vacuum to afford the title product Ex-114A. $^1$H NMR (300 MHz, CD$_3$OD) δ 9.04 (dd, J=1.8 Hz, 8.4 Hz, 1H), 8.60 (dd, J=1.8 Hz, 4.5 Hz, 1H), 7.39-7.24 (m, 6H), 7.13-7.01 (m, 3H), 5.90 (s, 2H), 3.57 (s, 2H), 1.86 (s, 3H); m/z=524 (M+1).

Using essentially the same procedure described in examples 113A and 114A, the following compounds in Table 17 were prepared.

TABLE 17

| Ex | Structure | Name | m/z (M + 1) |
|---|---|---|---|
| 115A | 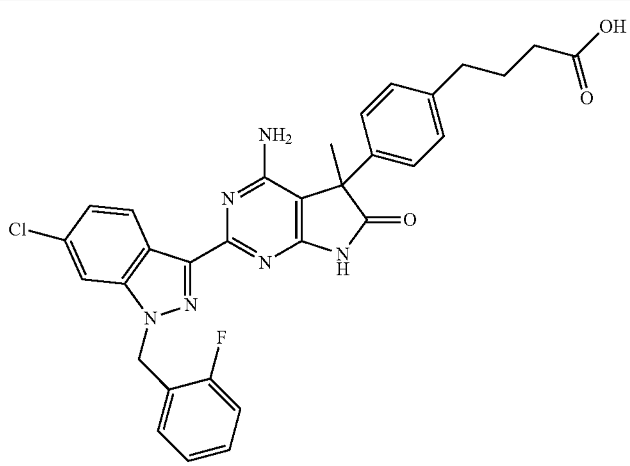 [SMILES: CC1(c2ccc(CCCC(=O)O)cc2)C(=O)Nc2nc(-c3nn(Cc4ccccc4F)c4cc(Cl)ccc34)nc(N)c21] | 4-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)butanoic acid | 585 |

TABLE 17-continued

| Ex | Structure | Name | m/z (M + 1) |
|---|---|---|---|
| 116A | 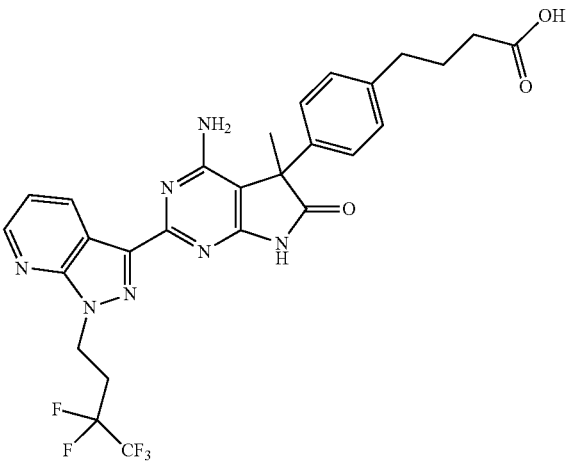 [SMILES: CC1(c2ccc(CCCC(=O)O)cc2)C(=O)Nc2nc(-c3nn(CCC(F)(F)C(F)(F)F)c4ncccc34)nc(N)c21] | 4-(4-{4-amino-5-methyl-6-oxo-2-[1-(3,3,4,4,4-pentafluorobutyl)-1H-pyrazolo[3,4-b]pyridin-3-yl)-6,7-dihydro-5H-pyrrolo[2,3-d]pyrimidin-5-yl}phenyl)butanoic acid | 590 |
| 117A | 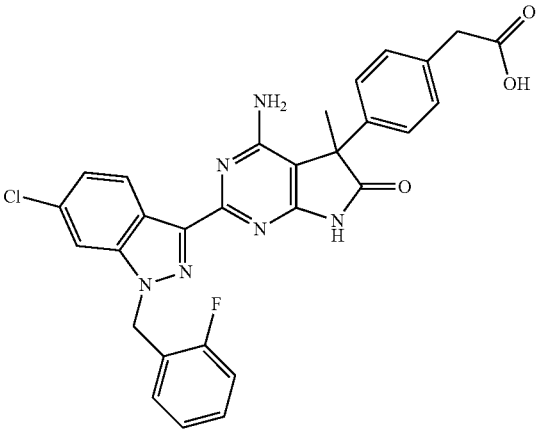 [SMILES: CC1(c2ccc(CC(=O)O)cc2)C(=O)Nc2nc(-c3nn(Cc4ccccc4F)c4cc(Cl)ccc34)nc(N)c21] | 2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)acetic acid | 557 |
| 118A | 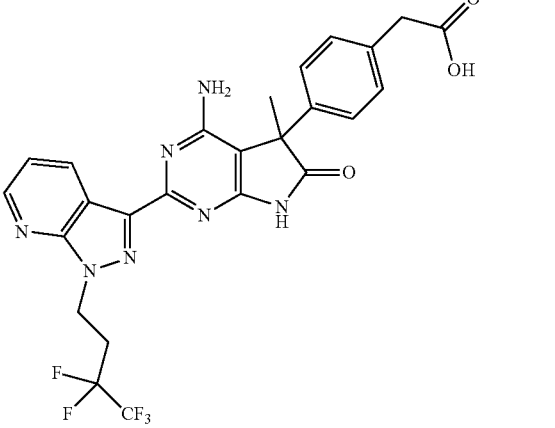 | 2-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)acetic acid | 562 |

Example 119B 3-(6-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)propanoic acid

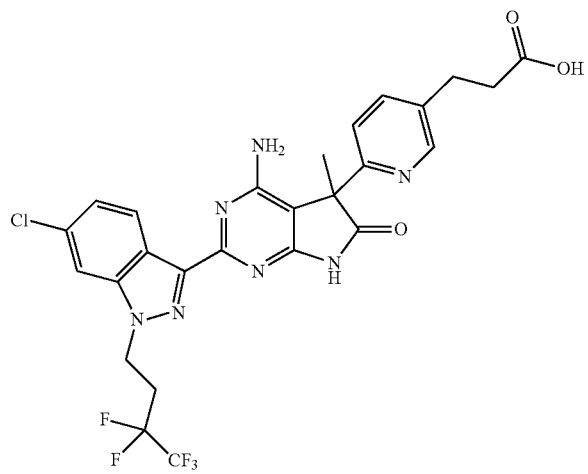 [SMILES: CC1(c2ccc(CCC(=O)O)cn2)C(=O)Nc2nc(-c3nn(CCC(F)(F)C(F)(F)F)c4cc(Cl)ccc34)nc(N)c21]

Step A—4-amino-5-(5-bromopyridin-2-yl)-2-(6-chloro-1-(3,3,4,4,4-pentafluorobutyl)-1H-indazol-3-yl)-5-methyl-5,7-dihydro-6H-pyrrolo[2,3-d]pyrimidin-6-one A flask containing I-A1 (200 mg, 0.59 mmol), I-19 (189 mg, 0.587 mmol) and potassium bicarbonate (88 mg, 0.88 mmol) in t-BuOH (10 mL) was stirred for 16 h at 75° C. The reaction mixture was concentrated in vacuo to dryness. The residue was purified by silica gel column chromatography with MeOH:DCM (0-10%) to afford the title compound.

Step B—methyl-3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)acrylate In a flask under a inert atmosphere of nitrogen were placed 4-amino-5-(5-bromopyridin-2-yl)-2-(6-chloro-1-(3,3,4,4,4-pentafluorobutyl)-1H-indazol-3-yl)-5-methyl-5,7-dihydro-6H-pyrrolo[2,3-d]pyrimidin-6-one (300 mg, 0.49 mmol), palladium (II) acetate (22 mg, 0.097 mmol), tri-tert-butylphosphine (394 mg, 0.20 mmol), triethylamine (0.14 mL, 0.97 mmol) and methyl acrylate (126 mg, 1.46 mmol) in DMF (8 mL). The resulting mixture was stirred for 16 h at 100° C. The reaction was cooled to RT and quenched by the addition of water. The resulting solution was extracted with EtOAc (3x) and the organic layers were combined, dried over anhydr. Na₂SO₄, filtered and the filtrate was concentrated in vacuo to dryness. The residue was purified by silica gel chromatography using EtOAc:petroleum ether (20%-100%) to afford the title product.

Step B—methyl 3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)propanoate A flask containing methyl-3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)acrylate (300 mg, 0.48 mmol), 4-methylbenzenesulfonhydrazide (269 mg, 1.45 mmol), sodium acetate trihydrate (328 mg, 2.41 mmol) in a mixture water (1 mL) and dimethoxyethane (10 mL) was stirred for 16 h at 80° C. The reaction was cooled to RT and quenched by the addition of water. The resulting solution was extracted with EtOAc (3x) and the organic layers were combined, dried over anhydr. Na₂SO₄, filtered and the filtrate was concentrated in vacuo to dryness. The residue was purified by silica gel chromatography using EtOAc: petroleum ether (30%-70%) then by reverse phase HPLC (ACN/water with 0.05% NH₄HCO₃ modifier) to afford the racemic title compound. The racemic material was resolved using chiral SFC (CHIRALPAK® IC column) to afford isomer A (faster eluting) and isomer B (slower eluting).

Step C—3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)propanoic acid To a flask containing methyl 3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)propanoate isomer B (70 mg, 0.11 mmol) in MeOH (2 mL) was added LiOH (13 mg, 0.56 mmol) in water (1 mL). The resulting mixture was stirred for 16 h at RT before been concentrated in vacuo. The residue was diluted with hydrochloric acid (0.1 N, 5.6 mL), the solid was collected by filtration, washed with water and dried under vacuum to afford the title product Ex-119B. ¹H NMR (300 MHz, CD₃OD) δ 8.64 (dd, J=8.7, 3.3 Hz, 1H), 8.50 (d, J=2.1 Hz, 1H), 7.73 (s, 1H), 7.70 (d, J=2.4 Hz, 1H), 7.41 (d, J=8.1 Hz, 1H), 7.25 (d, J=8.4 Hz, 1H), 4.79 (t, J=6.6 Hz, 2H), 3.01-2.84 (m, 4H), 2.64 (t, J=7.5 Hz, 2H), 1.89 (s, 3H); m/z=610 (M+1).

Example 120B 3-(4-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-cyanophenyl)propanoic acid

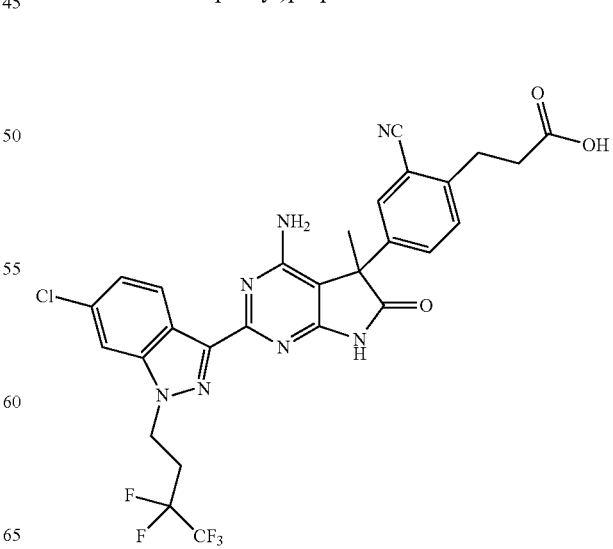

Step A—methyl 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-bromophenyl)propanoate A flask containing I-A1 (550 mg, 1.61 mmol), I-14 (657 mg, 1.61 mmol) and potassium bicarbonate (485 mg, 4.84 mmol) in t-BuOH (25 mL) was stirred for 16 h at 70° C. The reaction was cooled to RT and quenched by the addition of brine. The resulting solution was extracted with EtOAc (3×) and the organic layers were combined, dried over anhydr. $Na_2SO_4$, filtered and the filtrate was concentrated in vacuo to dryness. The residue was purified by silica gel chromatography using MeOH:DCM (0-2%) to afford the title racemic product. The racemic material was resolved using chiral SFC (Kromasil (R,R)WHELK-01 5/100 column) to afford isomer A (faster eluting) and isomer B (slower eluting). m/z=703 (M+1).

Step B—methyl 3-(4-{4-amino-2-[6-chloro-1-(3,3,4,4-pentafluorobutyl)-1H-indazol-3-yl]-5-methyl-6-oxo-6,7-dihydro-5H-pyrrolo[2,3-d]pyrimidin-5-yl}-2-cyanophenyl)propanoate A flask under an inert atmosphere of nitrogen containing methyl 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-bromophenyl)propanoate isomer B (120 mg, 0.17 mmol), zinc cyanide (26 mg, 0.22 mmol), tris(dibenzylideneacetone)dipalladium-chloroform adduct (17.7 mg, 0.017 mmol), 1,1'-bis(diphenylphosphino)ferrocene (19 mg, 0.034 mmol) and zinc (11 mg, 0.17 mmol) in DMF (10 mL) was stirred for 1 h at 120° C. The reaction was cooled to RT and quenched by the addition of brine. The resulting solution was extracted with EtOAc (3×) and the organic layers were combined, dried over anhydr. $Na_2SO_4$, filtered and the filtrate was concentrated in vacuo to dryness. The residue was purified by silica gel chromatography using MeOH:DCM (0-2%) to afford the title product.

Step C—3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-cyanophenyl)propanoic acid To a flask containing methyl 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-cyanophenyl)propanoate (58 mg, 0.090 mmol) in THF (2 mL) was added LiOH (38 mg, 0.90 mmol) in water (2 mL). The resulting mixture was stirred for 1 h at RT before been concentrated in vacuo. The residue was diluted with hydrochloric acid (0.1 N, 8.9 mL), the solid was collected by filtration, washed with water and dried under vacuum to afford the title product Ex-120B. $^1H$ NMR (300 MHz, $CD_3OD$) δ 8.64 (d, J=8.7 Hz, 1H), 7.72 (s, 1H), 7.68 (s, 1H), 7.52-7.42 (m, 2H), 7.24 (d, J=8.7 Hz, 1H), 4.82-4.76 (m, 2H), 3.10 (t, J=7.2 Hz, 2H), 3.00-2.82 (m, 2H), 2.70-2.60 (m, 2H), 1.87 (s, 3H); m/z=634 (M+1).

Example 121B 3-(4-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-methylphenyl)propanoic acid

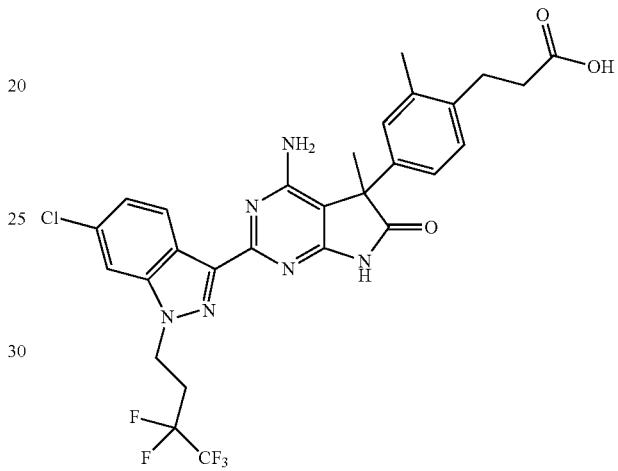

Step A—methyl 3-(4-{4-amino-2-[6-chloro-1-(3,3,4,4-pentafluorobutyl)-1H-indazol-3-yl]-5-methyl-6-oxo-6,7-dihydro-5H-pyrrolo[2,3-d]pyrimidin-5-yl}-2-methylphenyl)propanoate To a microwave tube under an inert atmosphere of nitrogen was added methyl 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-bromophenyl)propanoate isomer B (100 mg, 0.14 mmol), 1,1'-bis(di-tert-butylphosphino)ferrocene]dichloropalladium(II) (9.3 mg, 0.014 mmol) potassium carbonate (197 mg, 1.43 mmol), 2,4,6-trimethyl-1,3,5,2,4,6-trioxatriborinane (322 mg, 1.28 mmol) and dioxane (10 mL). The tube was flushed with nitrogen for 4 min then microwaved for 2 h at 70° C. The reaction was cooled to RT and quenched by the addition of brine. The resulting solution was extracted with EtOAc (3×) and the organic layers were combined, dried over anhydr. $Na_2SO_4$, filtered and the filtrate was concentrated in vacuo to dryness. The residue was purified by silica gel chromatography using MeOH:DCM (0-2%) to afford the title product.

Step B—3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-methylphenyl)propanoic acid To a flask containing methyl 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-methylphenyl)propanoate (55 mg, 0.086 mmol) in THF (2 mL) was added LiOH (36 mg, 0.86 mmol) in water (2 mL). The resulting mixture was stirred for 1 h at RT before being concentrated in vacuo. The residue was diluted with hydrochloric acid (0.1 N, 8.6 mL), the solid was collected by filtration, washed with water and dried under vacuum to afford the title product Ex-121B. $^1$H NMR (300 MHz, CD$_3$OD) δ 8.64 (d, J=8.7 Hz, 1H), 7.72 (s, 1H), 7.24 (d, J=8.7 Hz, 1H), 7.17-7.07 (m, 3H), 4.80-4.76 (m, 2H), 3.00-2.82 (m, 4H), 2.51 (t, J=7.8 Hz, 2H), 2.29 (s, 3H), 1.87 (s, 3H); m/z=623 (M+1).

Example 122B 3-(4-{4-Amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-hydroxyphenyl)propanoic acid

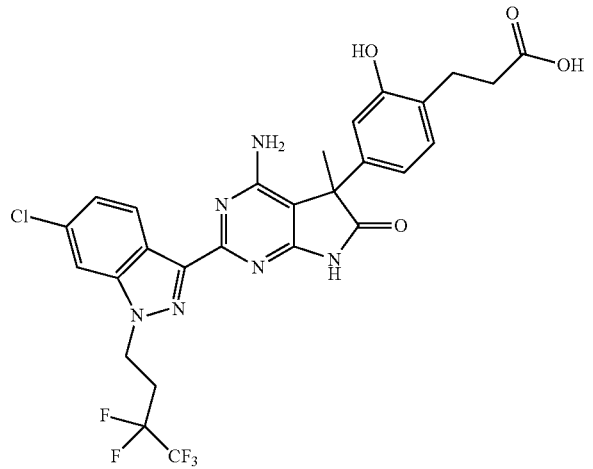 [SMILES: CC1(c2ccc(CCC(=O)O)c(C#N)c2)C(=O)Nc2nc(-c3nn(CCC(F)(F)C(F)(F)F)c4cc(Cl)ccc34)nc(N)c21]

Step A—methyl 3-(4-{4-amino-2-[6-chloro-1-(3,3,4,4-pentafluorobutyl)-1H-indazol-3-yl]-5-methyl-6-oxo-6,7-dihydro-5H-pyrrolo[2,3-d]pyrimidin-5-yl}-2-methoxyphenyl)propanoate A flask containing I-A1 (143 mg, 0.42 mmol), I-17 (150 mg, 0.42 mmol) and potassium bicarbonate (51 mg, 0.51 mmol) in t-BuOH (5 mL) was stirred for 16 h at 70° C. The reaction mixture was concentrated in vacuo to dryness. The residue was purified by silica gel column chromatography with MeOH:DCM (0-10%) to afford the racemic title compound. The racemic material was resolved using Chiral SFC (Phenomenex Lux 5u Cellulose-4) to afford isomer A (faster eluting) and isomer B (slower eluting).

Step B—4-amino-2-(6-chloro-1-(3,3,4,4,4-pentafluorobutyl)-1H-indazol-3-yl)-5-methyl-5-(2-oxochroman-7-yl)-5,7-dihydro-6H-pyrrolo[2,3-d]pyrimidin-6-one To a flask containing methyl 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-methoxyphenyl)propanoate isomer A (60 mg, 0.092 mmol) in DCM (1 mL) at 0° C. was added dropwise tribromoborane (0.2 mL, 2.11 mmol). The resulting mixture was stirred 1 h at 0° C. then 16 h at RT. The reaction was then quenched by the addition of sodium hydroxide. The pH value of the solution was adjusted to pH 6 bu the addition of hydrochloric acid (2 N). The resulting solution was extracted with EtOAc (3×) and the organic layers were combined, dried over anhydr. Na$_2$SO$_4$, filtered and the filtrate was concentrated in vacuo to dryness to afford the title product.

Step C—methyl 3-(4-{4-amino-2-[6-chloro-1-(3,3,4,4-pentafluorobutyl)-1H-indazol-3-yl]-5-methyl-6-oxo-6,7-dihydro-5H-pyrrolo[2,3-d]pyrimidin-5-yl}-2-hydroxyphenyl)propanoate A flask containing 4-amino-2-(6-chloro-1-(3,3,4,4,4-pentafluorobutyl)-1H-indazol-3-yl)-5-methyl-5-(2-oxochroman-7-yl)-5,7-dihydro-6H-pyrrolo[2,3-d]pyrimidin-6-one (60 mg, 0.099 mmol) in MeOH (4 mL) was stirred for 3 h at 110° C. The reaction mixture was concentrated in vacuo to dryness to afford the title product.

Step D—3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-hydroxyphenyl)propanoic Acid To a flask containing methyl 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-hydroxyphenyl)propanoate (60 mg, 0.094 mmol) in THF (4 mL) was added sodium hydroxide (19 mg, 0.47 mmol) in water (0.5 mL). The resulting mixture was stirred for 6 h at RT then concentrated in vacuo to dryness. The residue was diluted with water and the pH was adjusted to pH 4 with hydrochloric acid (1 N). The resulting solution was extracted with EtOAc (3×) and the organic layers were combined, dried over anhydr. Na$_2$SO$_4$, filtered and the filtrate was concentrated in vacuo to dryness. The residue was diluted with EtOAc:DCM:hexane (1:1:4) and the solid was collected by filtration and dried under vacuum to afford the title product Ex-122B. $^1$H NMR (400 MHz, CD$_3$OD): δ 8.70 (d, J=8.8 Hz, 1H), 7.78 (s, 1H), 7.29 (d, J=8.8 Hz, 1H), 7.14 (d, J=2.4 Hz, 1H), 7.04 (dd, J=8.4 Hz, 2.4 Hz, 1H), 6.78 (d, J=8.4 Hz, 1H), 4.84 (t, J=7.2 Hz, 2H), 3.03-2.86 (m, 4H), 2.60 (t, J=7.6 Hz, 2H), 1.85 (s, 3H); m/z=625 (M+1).

Examples 123A-139B

Using essentially the same procedure as described in Ex-1A, the following compounds in Table 18 were prepared.

TABLE 18

| Ex. | Int. SM | Chiral Resolution Column | Structure | Name | m/z (M + 1) |
|---|---|---|---|---|---|
| 123AA | I-35A | Lux Cellulose-4 | 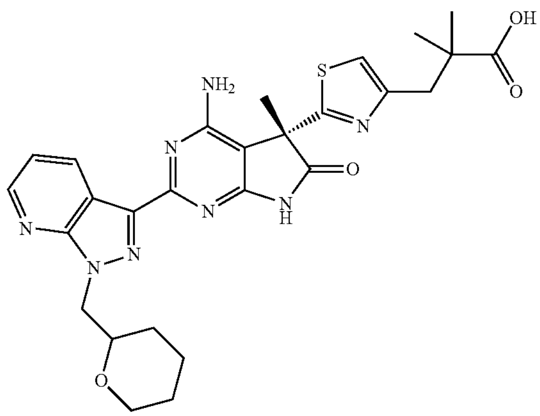 [SMILES: CC(C)(Cc1csc([C@]2(C)C(=O)Nc3nc(-c4nn(CC5CCCCO5)c5ncccc45)nc(N)c32)n1)C(=O)O] | (5S)-3-{2-[4-amino-5-methyl-6-oxo-2-{1-[tetrahydro-2H-pyran-2-ylmethyl]-1H-pyrazolo[3,4-b]pyridin-3-yl}-6,7-dihydro-5H-pyrrolo[2,3-d]pyrimidin-5-yl]-1,3-thiazol-4-yl}-2,2-dimethylpropanoic acid | 563 |
| 123AB | I-35A | Lux Cellulose-4 | 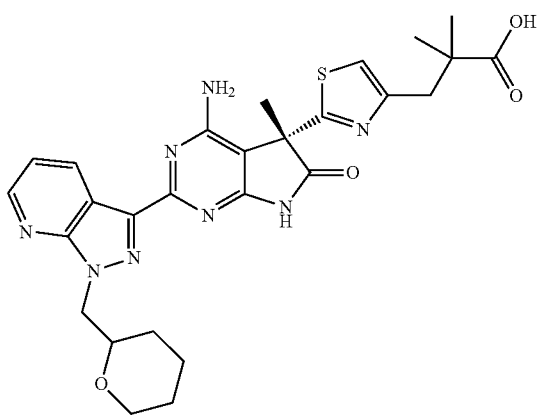 [SMILES: CC(C)(Cc1csc([C@]2(C)C(=O)Nc3nc(-c4nn(CC5CCCCO5)c5ncccc45)nc(N)c32)n1)C(=O)O] | (5S)-3-{2-[4-amino-5-methyl-6-oxo-2-{1-[tetrahydro-2H-pyran-2-ylmethyl]-1H-pyrazolo[3,4-b]pyridin-3-yl}-6,7-dihydro-5H-pyrrolo[2,3-d]pyrimidin-5-yl]-1,3-thiazol-4-yl}-2,2-dimethylpropanoic acid | 563 |
| 124AA | I-42A | IC | 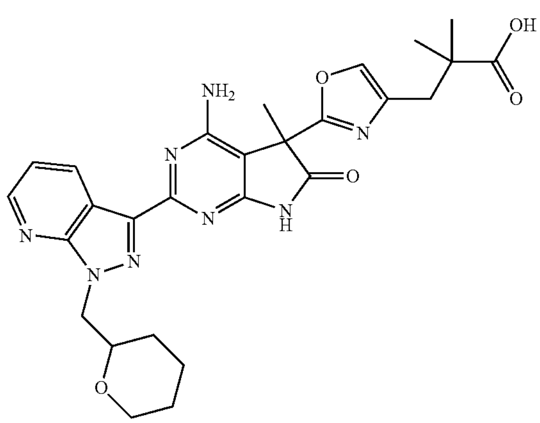 [SMILES: CC(C)(Cc1coc(C2(C)C(=O)Nc3nc(-c4nn(CC5CCCCO5)c5ncccc45)nc(N)c32)n1)C(=O)O] | 3-{2-[4-amino-5-methyl-6-oxo-2-{1-[tetrahydro-2H-pyran-2-ylmethyl]-1H-pyrazolo[3,4-b]pyridin-3-yl}-6,7-dihydro-5H-pyrrolo[2,3-d]pyrimidin-5-yl]-1,3-oxazol-4-yl}-2,2-dimethylpropanoic acid | 547 |

TABLE 18-continued

| Ex. | Int. SM | Chiral Resolution Column | Structure | Name | m/z (M + 1) |
|---|---|---|---|---|---|
| 124AB | I-42A | IC | 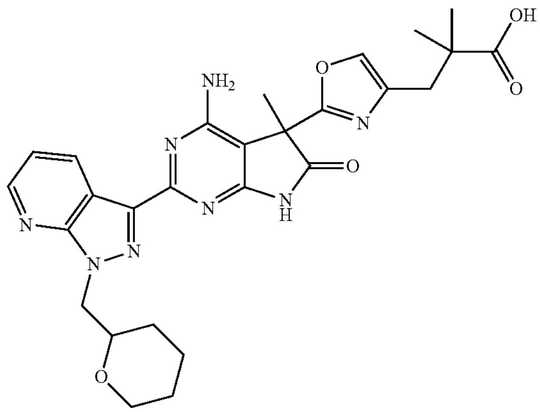 [SMILES: CC(C)(Cc1coc(C2(C)C(=O)Nc3nc(-c4nn(CC5CCCCO5)c5ncccc45)nc(N)c32)n1)C(=O)O] | 3-{2-[4-amino-5-methyl-6-oxo-2-{1-[tetrahydro-2H-pyran-2-ylmethyl]-1H-pyrazolo[3,4-b]pyridin-3-yl}-6,7-dihydro-5H-pyrrolo[2,3-d]pyrimidin-5-yl]-1,3-oxazol-4-yl}-2,2-dimethylpropanoic acid | 547 |
| 125AA | I-35A | AD-H | 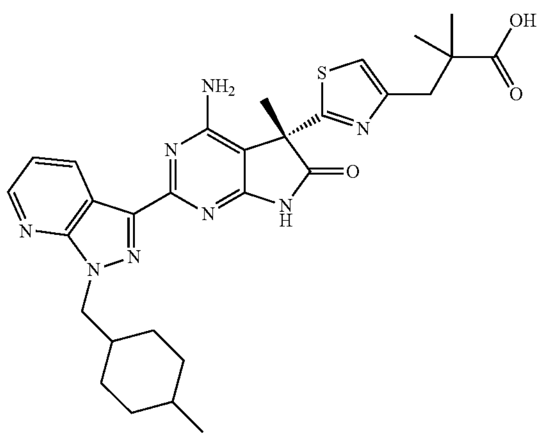 [SMILES: CC1CCC(Cn2nc(-c3nc(N)c4c(n3)NC(=O)[C@@]4(C)c3nc(CC(C)(C)C(=O)O)cs3)c3cccnc32)CC1] | (5S)-3-{2-[4-amino-5-methyl-2-{1-[4-methylcyclohexylmethyl]-1H-pyrazolo[3,4-b]pyridin-3-yl}-6-oxo-6,7-dihydro-5H-pyrrolo[2,3-d]pyrimidin-5-yl]-1,3-thiazol-4-yl}-2,2-dimethylpropanoic acid | 575 |
| 125AB | I-35A | AD-H | 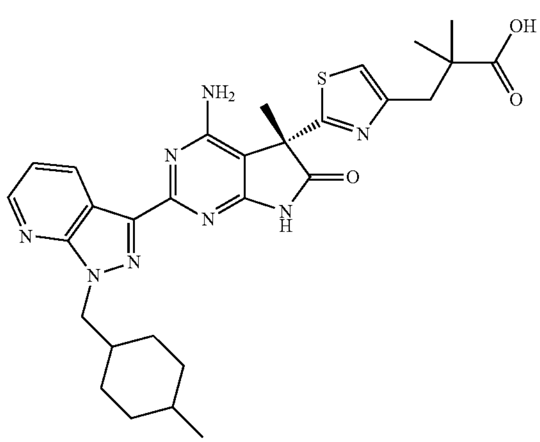 [SMILES: CC1CCC(Cn2nc(-c3nc(N)c4c(n3)NC(=O)[C@@]4(C)c3nc(CC(C)(C)C(=O)O)cs3)c3cccnc32)CC1] | (5S)-3-{2-[4-amino-5-methyl-2-{1-[4-methylcyclohexylmethyl]-1H-pyrazolo[3,4-b]pyridin-3-yl}-6-oxo-6,7-dihydro-5H-pyrrolo[2,3-d]pyrimidin-5-yl]-1,3-thiazol-4-yl}-2,2-dimethylpropanoic acid | 575 |

TABLE 18-continued

| Ex. | Int. SM | Chiral Resolution Column | Structure | Name | m/z (M + 1) |
|---|---|---|---|---|---|
| 126AA | I-42A | AD | 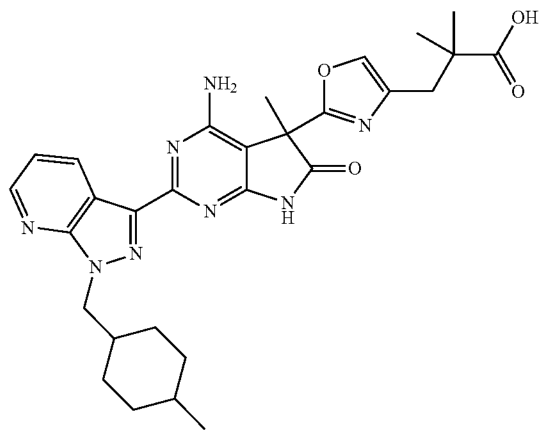 [SMILES: CC1CCC(Cn2nc(-c3nc(N)c4c(n3)NC(=O)C4(C)c3nc(CC(C)(C)C(=O)O)co3)c3cccnc32)CC1] | 3-{2-[4-amino-5-methyl-2-{1-[4-methylcyclohexylmethyl]-1H-pyrazolo[3,4-b]pyridin-3-yl}-6-oxo-6,7-dihydro-5H-pyrrolo[2,3-d]pyrimidin-5-yl]-1,3-oxazol-4-yl}-2,2-dimethylpropanoic acid | 559 |
| 126AB | I-42A | AD | 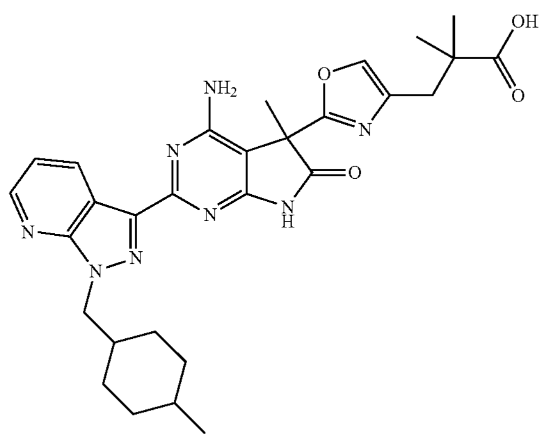 [SMILES: CC1CCC(Cn2nc(-c3nc(N)c4c(n3)NC(=O)C4(C)c3nc(CC(C)(C)C(=O)O)co3)c3cccnc32)CC1] | 3-{2-[4-amino-5-methyl-2-{1-[4-methylcyclohexylmethyl]-1H-pyrazolo[3,4-b]pyridin-3-yl}-6-oxo-6,7-dihydro-5H-pyrrolo[2,3-d]pyrimidin-5-yl]-1,3-oxazol-4-yl}-2,2-dimethylpropanoic acid | 559 |
| 127A | I-54 | IA | 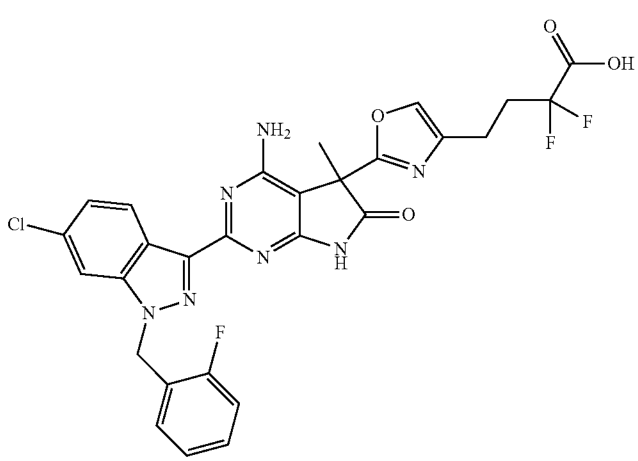 [SMILES: CC1(c2nc(CCC(F)(F)C(=O)O)co2)C(=O)Nc2nc(-c3nn(Cc4ccccc4F)c4cc(Cl)ccc34)nc(N)c21] | 4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-difluorobutanoic acid | 612 |

TABLE 18-continued

| Ex. | Int. SM | Chiral Resolution Column | Structure | Name | m/z (M + 1) |
|---|---|---|---|---|---|
| 128A | I-64 | IA | 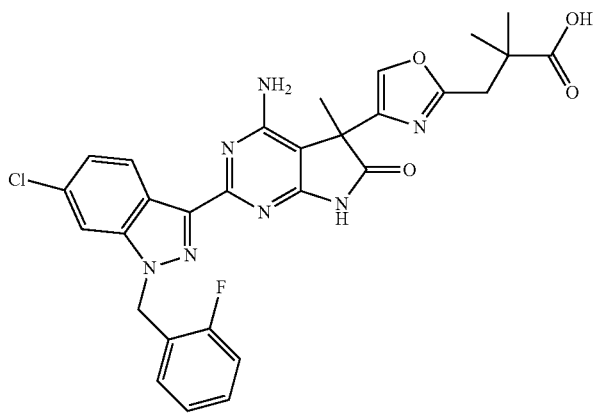 [SMILES: CC(C)(Cc1nc(C2(C)C(=O)Nc3nc(-c4nn(Cc5ccccc5F)c5cc(Cl)ccc45)nc(N)c32)co1)C(=O)O] | 3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-2-yl)-2,2-dimethylpropanoic acid | 590 |
| 129A | I-62 | Chiral Cellulose-SB | 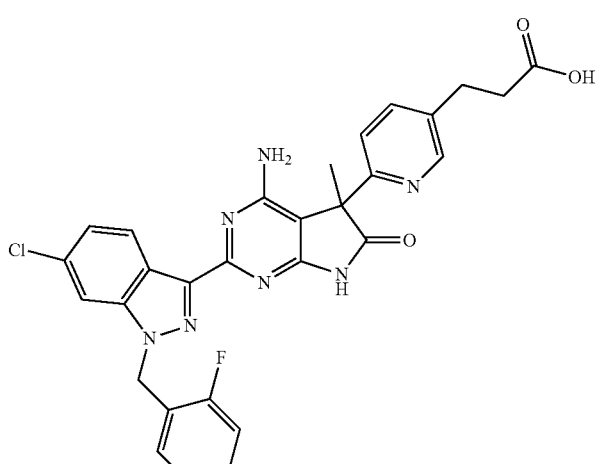 | 3-(6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridin-3-yl)propanoic acid | 572 |
| 130A | I-67 | ID | 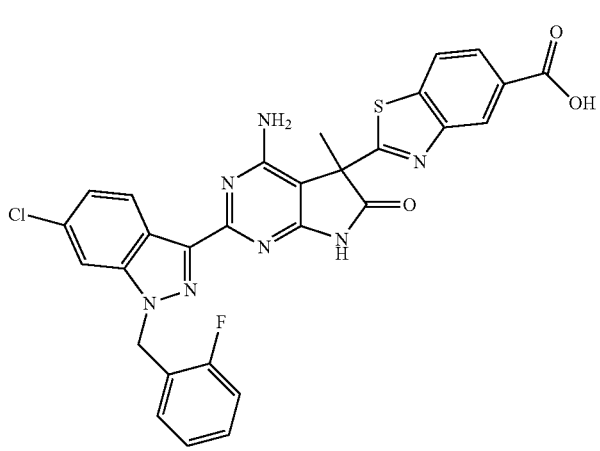 [SMILES: CC1(c2nc3cc(C(=O)O)ccc3s2)C(=O)Nc2nc(-c3nn(Cc4ccccc4F)c4cc(Cl)ccc34)nc(N)c21] | 2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-benzothiazole-5-carboxylic acid | 600 |

TABLE 18-continued

| Ex. | Int. SM | Chiral Resolution Column | Structure | Name | m/z (M + 1) |
|---|---|---|---|---|---|
| 131B | I-20 | IC | 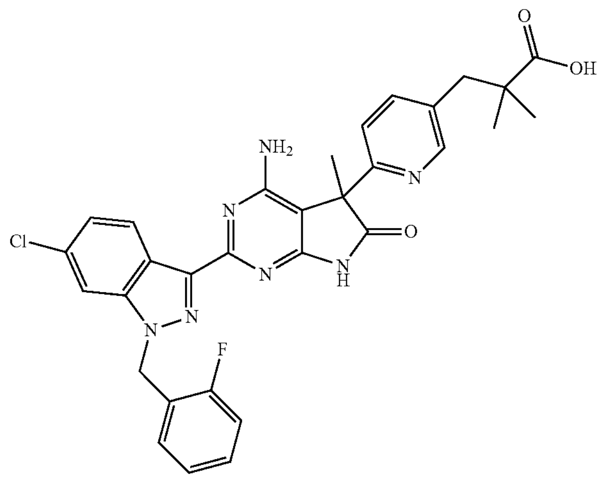 [SMILES: CC(C)(Cc1ccc(C2(C)C(=O)Nc3nc(-c4nn(Cc5ccccc5F)c5cc(Cl)ccc45)nc(N)c32)nc1)C(=O)O] | 3-(6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridin-3-yl)-2,2-dimethylpropanoic acid | 600 |
| 132AA | I-42A | Chiral Cellulose-SB | 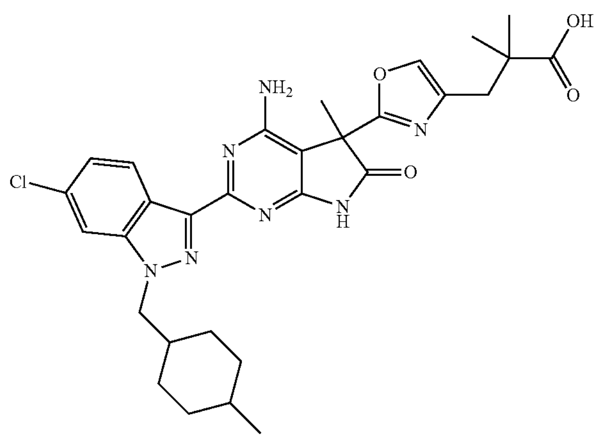 [SMILES: CC1CCC(Cn2nc(-c3nc(N)c4c(n3)NC(=O)C4(C)c3nc(CC(C)(C)C(=O)O)co3)c3ccc(Cl)cc32)CC1] | 3-{2-[4-amino-2-{6-chloro-1-[4-methylcyclohexylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid | 592 |
| 132AB | I-42A | Chiral Cellulose-SB | 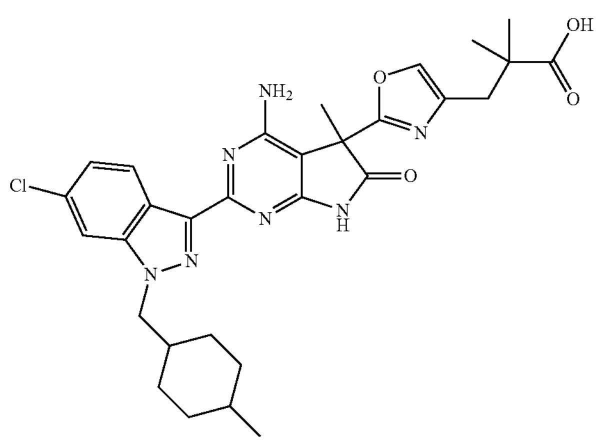 [SMILES: CC1CCC(Cn2nc(-c3nc(N)c4c(n3)NC(=O)C4(C)c3nc(CC(C)(C)C(=O)O)co3)c3ccc(Cl)cc32)CC1] | 3-{2-[4-amino-2-{6-chloro-1-[4-methylcyclohexylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid | 592 |

TABLE 18-continued

| Ex. | Int. SM | Chiral Resolution Column | Structure | Name | m/z (M + 1) |
|---|---|---|---|---|---|
| 133AA | I-35A | IC | 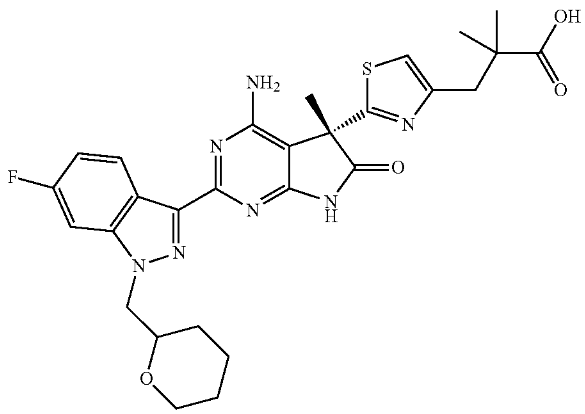 [SMILES: CC(C)(Cc1csc([C@]2(C)C(=O)Nc3nc(-c4nn(CC5CCCCO5)c5cc(F)ccc45)nc(N)c32)n1)C(=O)O] | (5S)-3-{2-[4-amino-2-{6-fluoro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]-1,3-thiazol-4-yl}-2,2-dimethylpropanoic acid | 580 |
| 133AB | I-35A | IC | 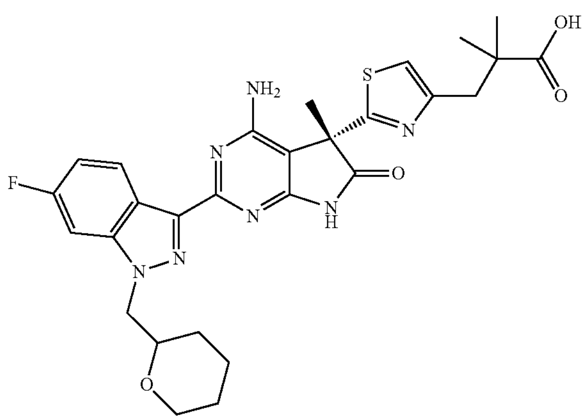 [SMILES: CC(C)(Cc1csc([C@]2(C)C(=O)Nc3nc(-c4nn(CC5CCCCO5)c5cc(F)ccc45)nc(N)c32)n1)C(=O)O] | (5S)-3-{2-[4-amino-2-{6-fluoro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]-1,3-thiazol-4-yl}-2,2-dimethylpropanoic acid | 580 |
| 134AA | I-42A | IC | 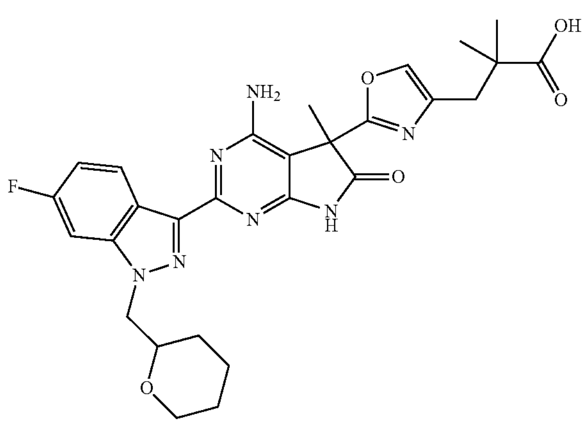 [SMILES: CC(C)(Cc1coc(C2(C)C(=O)Nc3nc(-c4nn(CC5CCCCO5)c5cc(F)ccc45)nc(N)c32)n1)C(=O)O] | 3-{2-[4-amino-2-{6-fluoro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid | 564 |

TABLE 18-continued

| Ex. | Int. SM | Chiral Resolution Column | Structure | Name | m/z (M + 1) |
|---|---|---|---|---|---|
| 134AB | I-42A | IC | 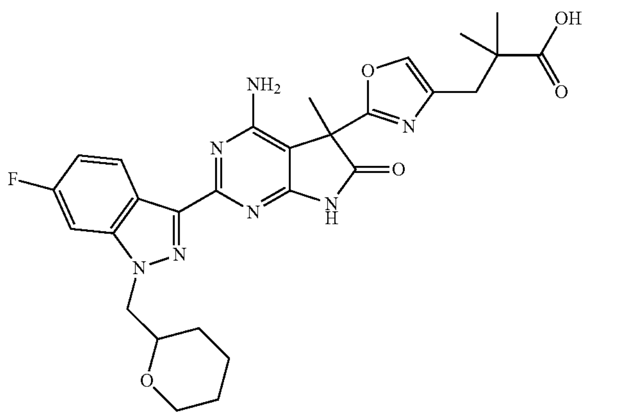 [SMILES: CC(C)(Cc1coc(C2(C)C(=O)Nc3nc(-c4nn(CC5CCCCO5)c5cc(F)ccc45)nc(N)c32)n1)C(=O)O] | 3-{2-[4-amino-2-{6-fluoro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid | 564 |
| 135A | I-54 | IA | 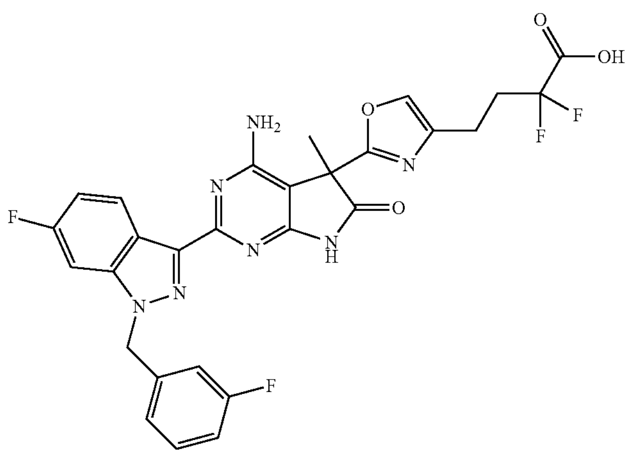 [SMILES: CC1(c2nc(CCC(F)(F)C(=O)O)co2)C(=O)Nc2nc(-c3nn(Cc4cccc(F)c4)c4cc(F)ccc34)nc(N)c21] | 4-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-difluorobutanoic acid | 596 |
| 136AA | I-35A | AD-H | 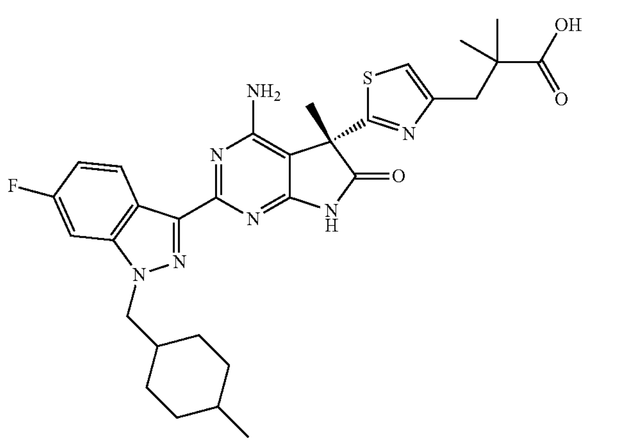 [SMILES: CC1CCC(Cn2nc(-c3nc(N)c4c(n3)NC(=O)[C@@]4(C)c3nc(CC(C)(C)C(=O)O)cs3)c3ccc(F)cc32)CC1] | (5S)-3-{2-[4-amino-2-{6-fluoro-1-[4-methylcyclohexylmethyl]-1H-indazol-3-yl}-5-methyl-6-oxo-6,7-dihydro-5H-pyrrolo[2,3-d]pyrimidin-5-yl]-1,3-thiazol-4-yl}-2,2-dimethylpropanoic acid | 592 |

TABLE 18-continued

| Ex. | Int. SM | Chiral Resolution Column | Structure | Name | m/z (M + 1) |
|---|---|---|---|---|---|
| 136AB | I-35A | AD-H | 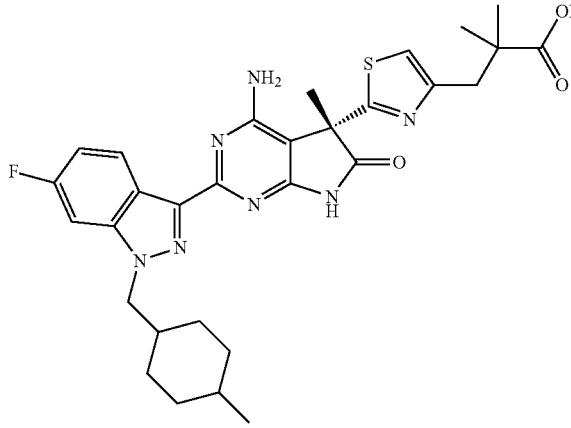 | (5S)-3-{2-[4-amino-2-{6-fluoro-1-[4-methylcyclohexylmethyl]-1H-indazol-3-yl}-5-methyl-6-oxo-6,7-dihydro-5H-pyrrolo[2,3-d]pyrimidin-5-yl]-1,3-thiazol-4-yl}-2,2-dimethylpropanoic acid | 592 |
| 137AA | I-42A | Racemic C18 | 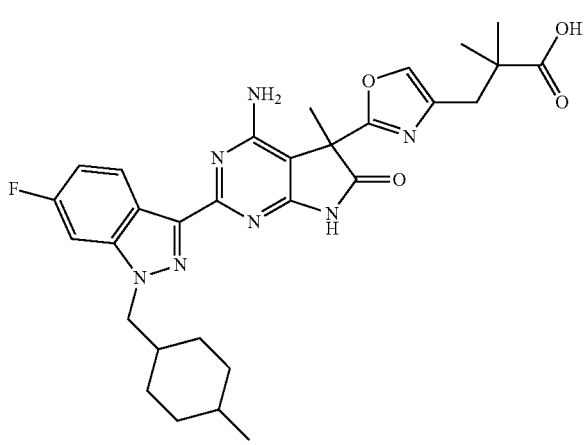 [SMILES: CC1CCC(Cn2nc(-c3nc(N)c4c(n3)NC(=O)C4(C)c3nc(CC(C)(C)C(=O)O)co3)c3ccc(F)cc32)CC1] | 3-{2-[4-amino-2-{6-fluoro-1-[4-methylcyclohexylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid | 576 |
| 137AB | I-42A | Racemic C18 | 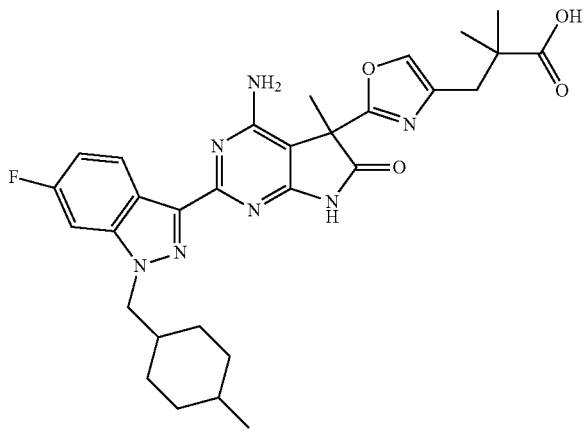 [SMILES: CC1CCC(Cn2nc(-c3nc(N)c4c(n3)NC(=O)C4(C)c3nc(CC(C)(C)C(=O)O)co3)c3ccc(F)cc32)CC1] | 3-{2-[4-amino-2-{6-fluoro-1-[4-methylcyclohexylmethyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid | 576 |

TABLE 18-continued

| Ex. | Int. SM | Chiral Resolution Column | Structure | Name | m/z (M + 1) |
|---|---|---|---|---|---|
| 138B | I-73 | (R,R)WHELK-O 1 | 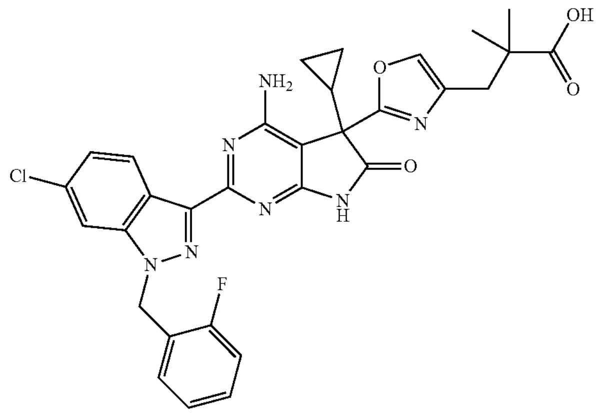 [SMILES: CC(C)(Cc1coc(C2(C3CC3)C(=O)Nc3nc(-c4nn(Cc5ccccc5F)c5cc(Cl)ccc45)nc(N)c32)n1)C(=O)O] | 3-(2-{4-amino-2-[6-chloro-1-(2-fluorobenzyl)-1H-indazol-3-yl]-5-cyclopropyl-6-oxo-6,7-dihydro-5H-pyrrolo[2,3-d]pyrimidin-5-yl}-1,3-oxazol-4-yl)-2,2-dimethylpropanoic acid | 616 |
| 139B | I-73 | (R,R)WHELK-O 1 | 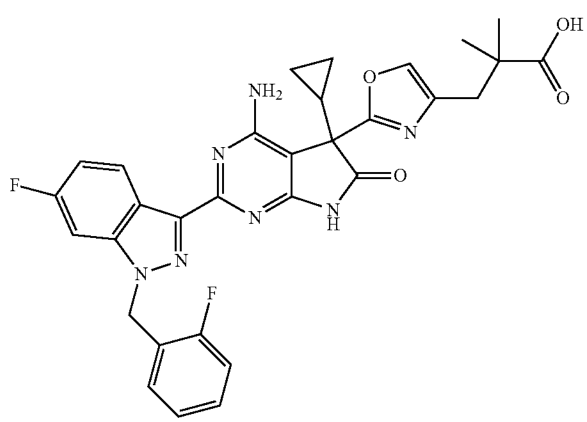 [SMILES: CC(C)(Cc1coc(C2(C3CC3)C(=O)Nc3nc(-c4nn(Cc5ccccc5F)c5cc(F)ccc45)nc(N)c32)n1)C(=O)O] | 3-(2-{4-amino-5-cyclopropyl-2-[6-fluoro-1-(2-fluorobenzyl)-1H-indazol-3-yl]-6-oxo-6,7-dihydro-5H-pyrrolo[2,3-d]pyrimidin-5-yl}-1,3-oxazol-4-yl)-2,2-dimethylpropanoic acid | 600 |

Example 140A 3-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoic acid

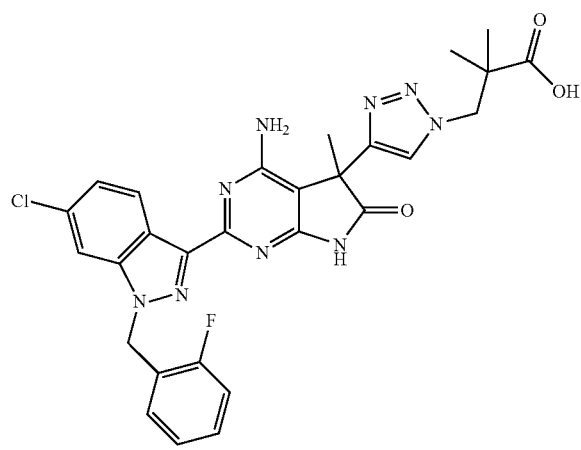 [SMILES: CC(C)(Cn1cc(C2(C)C(=O)Nc3nc(-c4nn(Cc5ccccc5F)c5cc(Cl)ccc45)nc(N)c32)nn1)C(=O)O]

Step A—Ethyl 3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoate A mixture containing I-60 (460 mg, 1.273 mmol), I-A15 (432 mg, 1.273 mmol) and potassium bicarbonate (637 mg, 6.36 mmol) in t-BuOH (10 ml) in a flask was stirred at 70° C. for 48 hours. The reaction was diluted with water and extracted with EtOAc (3×). The organic layers were combined, washed with brine, dried over anhydr. MgSO$_4$, and filtered. The filtrate was concentrated in vacuo. The residue was purified by silica gel column chromatography with (EtOAc:EtOH 3:1):hexane to afford the title compound. m/z=418 (M+1).

Step B—3-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoic Acid A flask, containing ethyl 3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoate (470 mg, 0.760 mmol) and LiOH (91 mg, 3.80 mmol) in a mixture of MeCN (5 ml) and water (5 ml) was stirred at 40° C. for 3 hours. The mixture was cooled to RT, diluted with EtOAc and aq. sat. KH$_2$PO$_4$, extracted with EtOAc, the organic layers were combined, washed with brine, dried over anhydr. MgSO$_4$, and filtered. The filtrate was concentrated in vacuo. to afford the racemic title compound Ex-140. The racemic material was resolved using chiral SFC (CHIRALPAK® AD) to afford isomer Ex-140A (faster eluting) and isomer Ex-140B (slower eluting). $^1$H NMR (400 MHz, DMSO-d$_6$) δ 12.73 (s, 1H), 11.25 (s, 1H), 8.69 (d, J=8.7 Hz, 1H), 8.01 (d, J=1.7 Hz, 1H), 7.91 (s, 1H), 7.36 (t, J=7.0 Hz, 1H), 7.29 (dd, J=8.7, 1.8 Hz, 1H), 7.27-7.20 (m, 1H), 7.19-7.10 (m, 2H), 6.73 (s, 2H), 5.81 (s, 2H), 4.48 (s, 2H), 1.24 (s, 3H), 1.07 (d, J=15.1 Hz, 6H), m/z=590 (M+1).

Example 141A 2-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-1,2,3-triazol-1-yl)-2-methylpropanoic acid

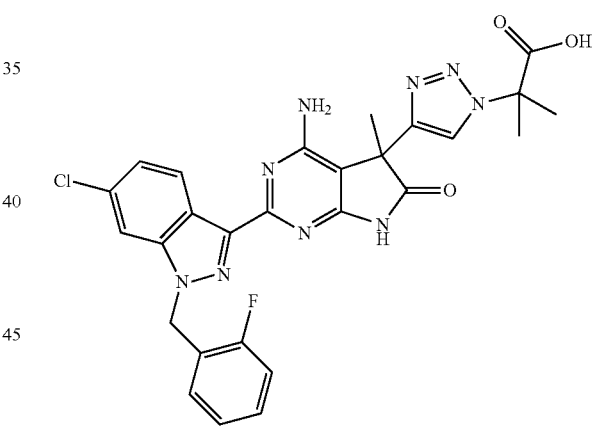

Ex-141A was prepared following essentially the same procedure described in Ex-140A, using I-61 as starting material. The racemic material was resolved using chiral SFC (CHIRALCEL® OZ) to afford isomer Ex-141A (faster eluting) and isomer Ex-141B (slower eluting).

Examples 142B-219A

Using essentially the same procedure as described in Example 9B, Ex-10B and Ex-11B, the following compounds in Table 19 were prepared.

TABLE 19

| Ex. | Int. SM | Structure | Name | m/z (M + 1) |
|---|---|---|---|---|
| 142B | I-65B | 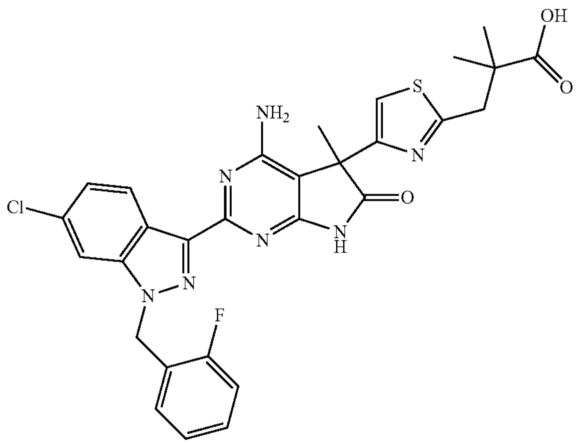 [SMILES: CC(C)(Cc1nc(C2(C)C(=O)Nc3nc(-c4nn(Cc5ccccc5F)c5cc(Cl)ccc45)nc(N)c32)cs1)C(=O)O] | 3-(4-{4-amino-2-[6-chloro-1-(2-fluoro-benzyl)-1H-indazol-3-yl]-5-methyl-6-oxo-6,7-dihydro-5H-pyrrolo[2,3-d]pyrimidin-5-yl}-1,3-thiazol-2-yl)-2,2-dimethyl-propanoic acid | 606 |
| 143B | I-74B | 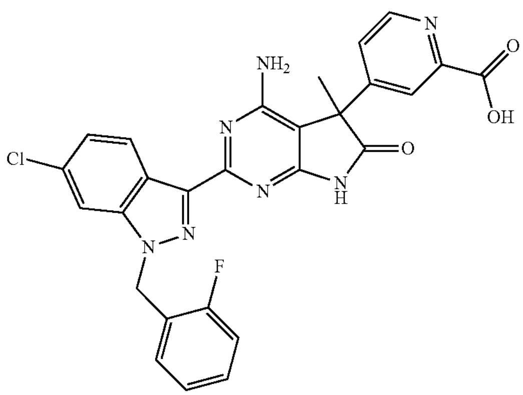 [SMILES: CC1(c2ccnc(C(=O)O)c2)C(=O)Nc2nc(-c3nn(Cc4ccccc4F)c4cc(Cl)ccc34)nc(N)c21] | 4-{4-amino-2-[6-chloro-1-(2-fluoro-benzyl)-1H-indazol-3-yl]-5-methyl-6-oxo-6,7-dihydro-5H-pyrrolo[2,3-d]pyrimidin-5-yl}pyridine-2-carboxylic acid | 544 |
| 144A | I-63A | 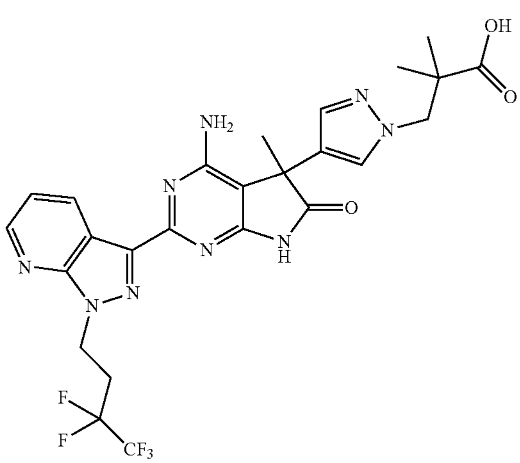 [SMILES: CC(C)(Cn1cc(C2(C)C(=O)Nc3nc(-c4nn(CCC(F)(F)C(F)(F)F)c5ncccc45)nc(N)c32)cn1)C(=O)O] | 3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1H-pyrazol-1-yl)-2,2-dimethyl-propanoic acid | 594 |

TABLE 19-continued

| Ex. | Int. SM | Structure | Name | m/z (M + 1) |
|---|---|---|---|---|
| 145A | I-63A | 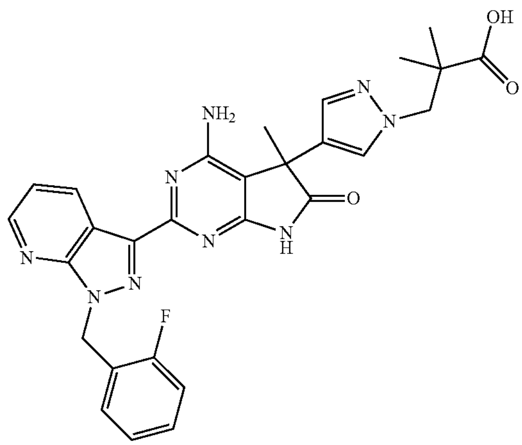 [SMILES: CC(C)(Cn1cc(C2(C)C(=O)Nc3nc(-c4nn(Cc5ccccc5F)c5ncccc45)nc(N)c32)cn1)C(=O)O] | 3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1H-pyrazol-1-yl)-2,2-dimethyl-propanoic acid | 556 |
| 146A | I-53A | 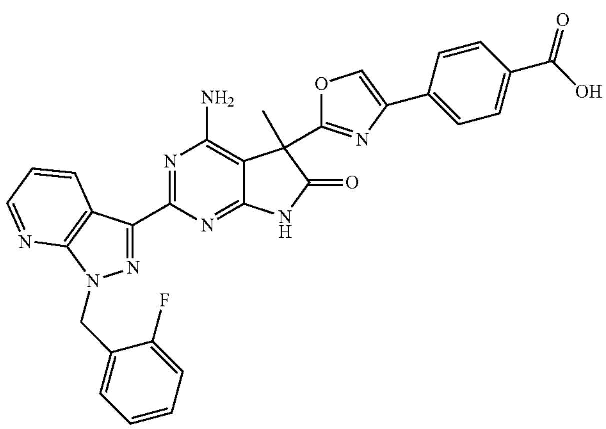 | 4-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)benzoic acid | 577 |
| 147A | I-58A | 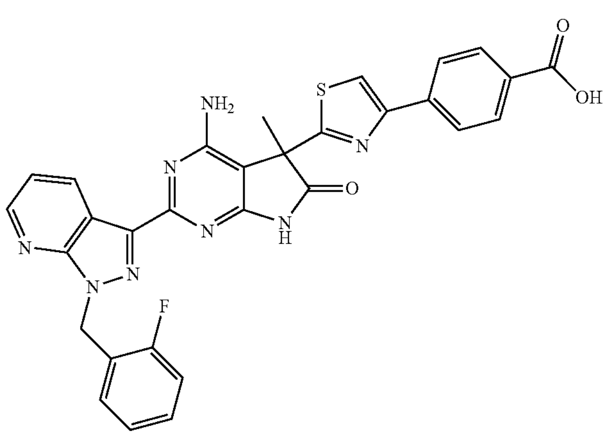 [SMILES: CC1(c2nc(-c3ccc(C(=O)O)cc3)cs2)C(=O)Nc2nc(-c3nn(Cc4ccccc4F)c4ncccc34)nc(N)c21] | 4-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)benzoic acid | 593 |

TABLE 19-continued

| Ex. | Int. SM | Structure | Name | m/z (M + 1) |
|---|---|---|---|---|
| 148A | I-75A | 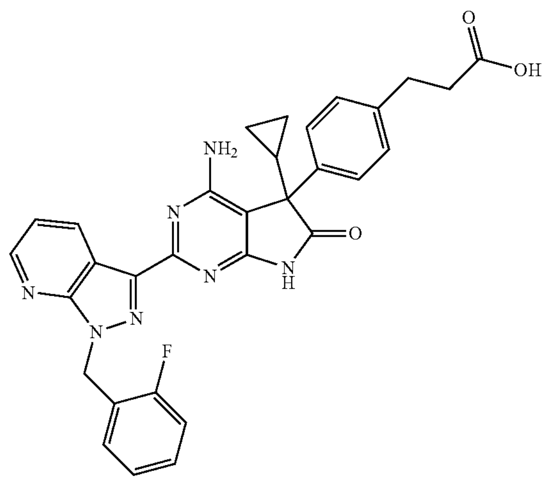 [SMILES: Nc1nc(-c2nn(Cc3ccccc3F)c3ncccc23)nc2c1C(c1ccc(CCC(=O)O)cc1)(C1CC1)C(=O)N2] | 3-(4-{4-amino-5-cyclopropyl-2-[1-(2-fluorobenzyl)-1H-pyrazolo[3,4-b]pyridin-3-yl]-6-oxo-6,7-dihydro 5H-pyrrolo[2,3-d]pyrimidin-5-yl}phenyl)propanoic acid | 564 |
| 149A | I-35A | 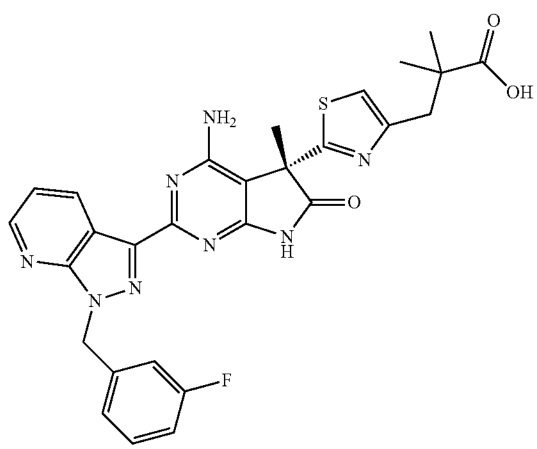 [SMILES: CC(C)(Cc1csc([C@]2(C)C(=O)Nc3nc(-c4nn(Cc5cccc(F)c5)c5ncccc45)nc(N)c32)n1)C(=O)O] | (S)-3-(2-{4-amino-2-[1-(3-fluoro-benzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 573 |
| 150A | I-42A | 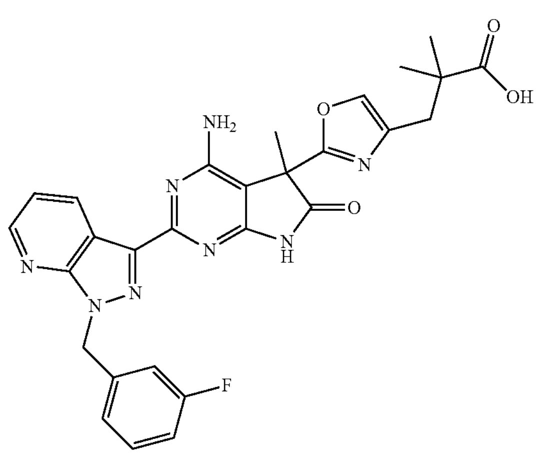 [SMILES: CC(C)(Cc1coc(C2(C)C(=O)Nc3nc(-c4nn(Cc5cccc(F)c5)c5ncccc45)nc(N)c32)n1)C(=O)O] | 3-(2-{4-amino-2-[1-(3-fluoro-benzyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 557 |

TABLE 19-continued

| Ex. | Int. SM | Structure | Name | m/z (M + 1) |
|---|---|---|---|---|
| 151A | I-35A | 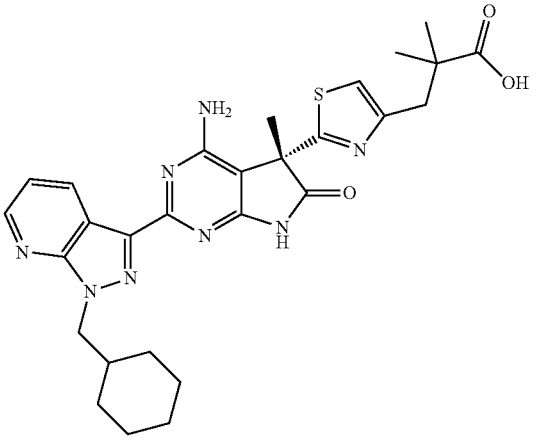 [SMILES: CC(C)(Cc1csc([C@]2(C)C(=O)Nc3nc(-c4nn(CC5CCCCC5)c5ncccc45)nc(N)c32)n1)C(=O)O] | (S)-3-(2-{4-amino-2-[1-(cyclohexyl-methyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 561 |
| 152A | I-42A | 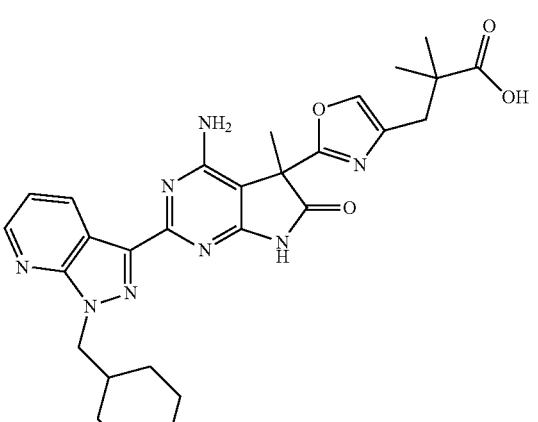 | 3-(2-{4-amino-2-[1-(cyclohexyl-methyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 545 |
| 153A | I-35A | 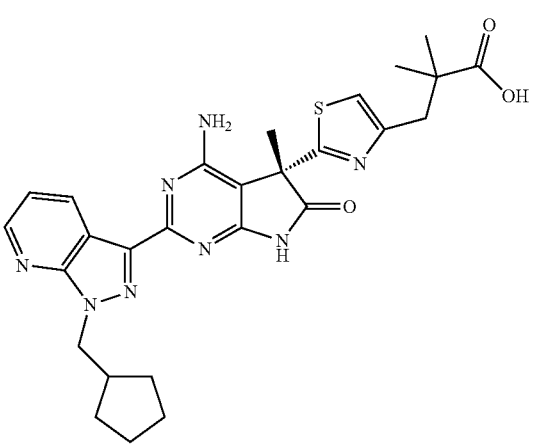 [SMILES: CC(C)(Cc1csc([C@]2(C)C(=O)Nc3nc(-c4nn(CC5CCCC5)c5ncccc45)nc(N)c32)n1)C(=O)O] | (S)-3-(2-{4-amino-2-[1-(cyclopentyl-methyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 547 |

TABLE 19-continued

| Ex. | Int. SM | Structure | Name | m/z (M + 1) |
|---|---|---|---|---|
| 154A | I-42A | 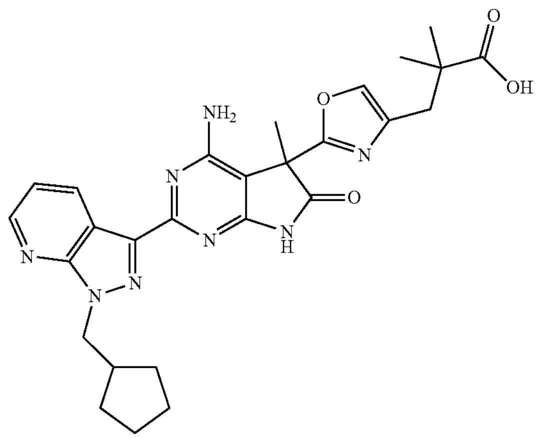 [SMILES: CC(C)(Cc1coc(C2(C)C(=O)Nc3nc(-c4nn(CC5CCCC5)c5ncccc45)nc(N)c32)n1)C(=O)O] | 3-(2-{4-amino-2-[1-(cyclopentylmethyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)-2,2-dimethylpropanoic acid | 531 |
| 155B | I-48B | 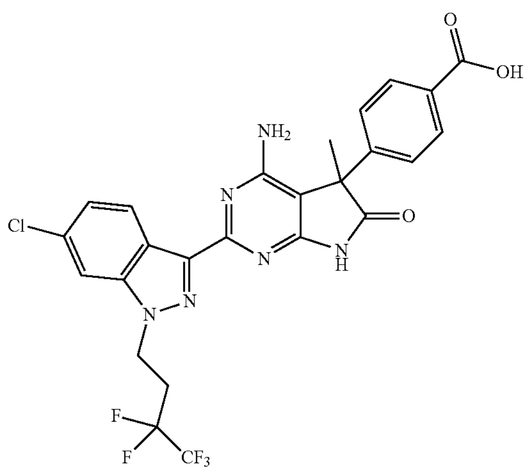 [SMILES: CC1(c2ccc(C(=O)O)cc2)C(=O)Nc2nc(-c3nn(CCC(F)(F)C(F)(F)F)c4cc(Cl)ccc34)nc(N)c21] | 4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}benzoic acid | 581 |
| 156A | I-58A | 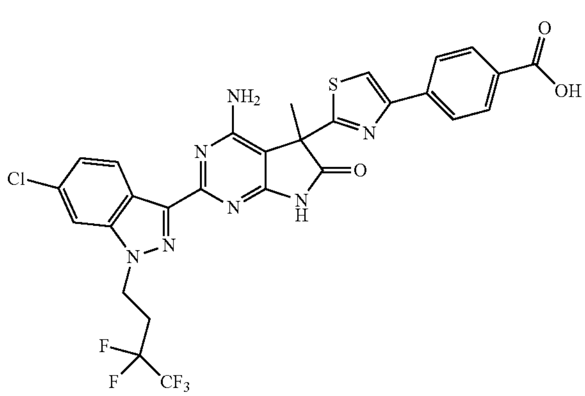 [SMILES: CC1(c2nc(-c3ccc(C(=O)O)cc3)cs2)C(=O)Nc2nc(-c3nn(CCC(F)(F)C(F)(F)F)c4cc(Cl)ccc34)nc(N)c21] | 4-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)benzoic acid | 664 |

TABLE 19-continued

| Ex. | Int. SM | Structure | Name | m/z (M + 1) |
|---|---|---|---|---|
| 157A | I-76A | 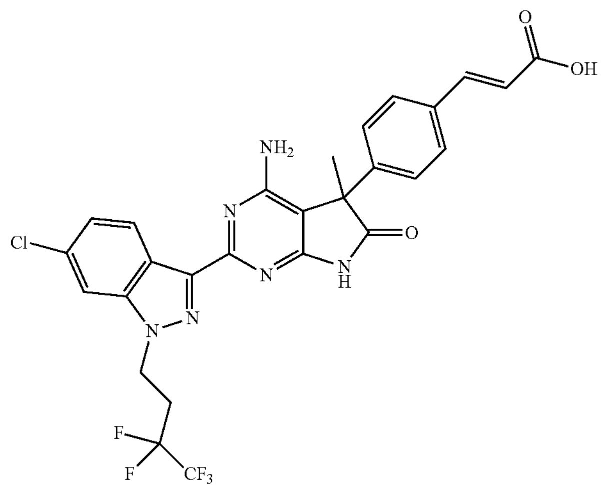 [SMILES: CC1(c2ccc(/C=C/C(=O)O)cc2)C(=O)Nc2nc(-c3nn(CCC(F)(F)C(F)(F)F)c4cc(Cl)ccc34)nc(N)c21] | (2E)-3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)prop-2-enoic acid | 607 |
| 158A | I-75A | 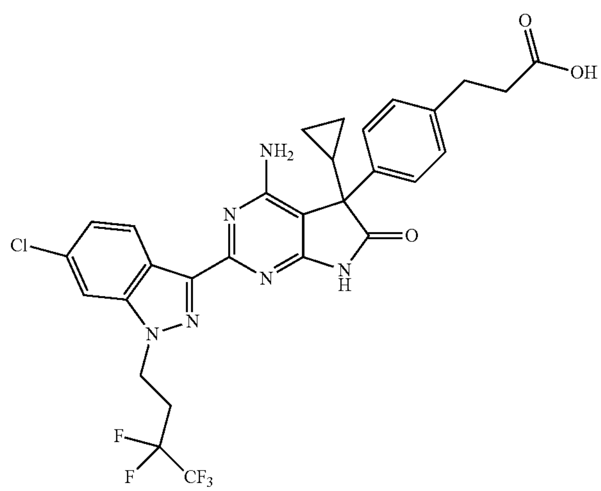 [SMILES: Nc1nc(-c2nn(CCC(F)(F)C(F)(F)F)c3cc(Cl)ccc23)nc2c1C(c1ccc(CCC(=O)O)cc1)(C1CC1)C(=O)N2] | 3-(4-{4-amino-2-[6-chloro-1-(3,3,4,4,4-pentafluorobutyl)-1H-indazol-3-yl]-5-cyclopropyl-6-oxo-6,7-dihydro-5H-pyrrolo[2,3-d]pyrimidin-5-yl}phenyl)propanoic acid | 635 |
| 159A | I-42A | 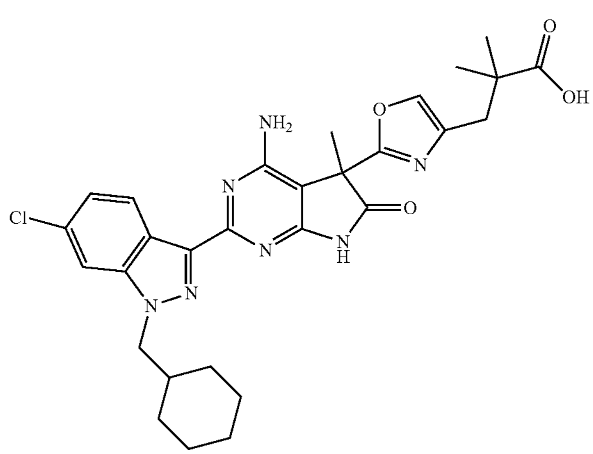 [SMILES: CC(C)(Cc1coc(C2(C)C(=O)Nc3nc(-c4nn(CC5CCCCC5)c5cc(Cl)ccc45)nc(N)c32)n1)C(=O)O] | 3-(2-{4-amino-2-[6-chloro-1-(cyclohexylmethyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid | 578 |

| Ex. | Int. SM | Structure | Name | m/z (M + 1) |
|---|---|---|---|---|
| 160B | I-11B | 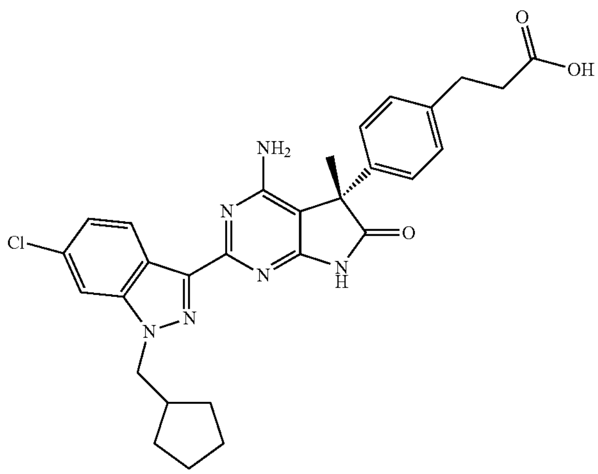 [SMILES: C[C@@]1(c2ccc(CCC(=O)O)cc2)C(=O)Nc2nc(-c3nn(CC4CCCC4)c4cc(Cl)ccc34)nc(N)c21] | (S)-3-(4-{4-amino-2-[6-chloro-1-(cyclopentylmethyl)-1H-indazol-3-yl]-5-methyl-6-oxo-6,7-dihydro-5H-pyrrolo[2,3-d]pyrimidin-5-yl}phenyl)propanoic acid | 545 |
| 161A | I-42A | 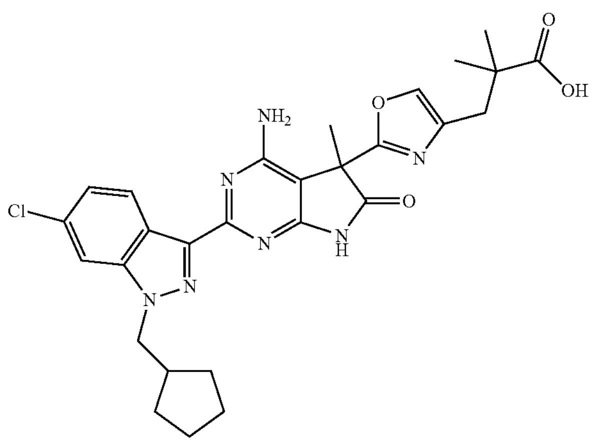 [SMILES: CC(C)(Cc1coc(C2(C)C(=O)Nc3nc(-c4nn(CC5CCCC5)c5cc(Cl)ccc45)nc(N)c32)n1)C(=O)O] | 3-(2-{4-amino-2-[6-chloro-1-(cyclopentylmethyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 564 |
| 162A | I-35A | 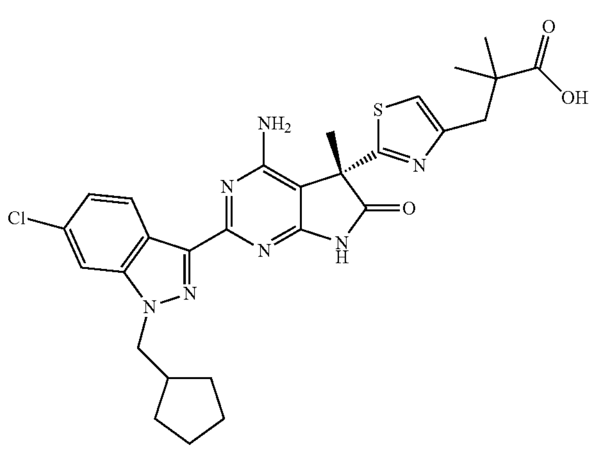 [SMILES: CC(C)(Cc1csc([C@]2(C)C(=O)Nc3nc(-c4nn(CC5CCCC5)c5cc(Cl)ccc45)nc(N)c32)n1)C(=O)O] | (S)-3-(2-{4-amino-2-[6-chloro-1-(cyclopentylmethyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 580 |

TABLE 19-continued

| Ex. | Int. SM | Structure | Name | m/z (M + 1) |
|---|---|---|---|---|
| 163B | I-11B | 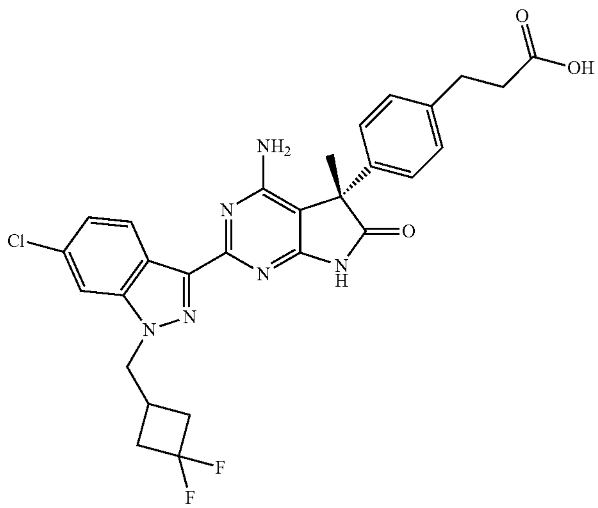 [SMILES: C[C@@]1(c2ccc(CCC(=O)O)cc2)C(=O)Nc2nc(-c3nn(CC4CC(F)(F)C4)c4cc(Cl)ccc34)nc(N)c21] | (S)-3-{4-[4-amino-2-{6-chloro-1-[(3,3-difluorocyclobutyl)methyl]-1H-indazol-3-yl}-5-methyl-6-oxo-6,7-dihydro-5H-pyrrolo[2,3-d]pyrimidin-5-yl]phenyl}propanoic acid | 567 |
| 164A | I-53A | 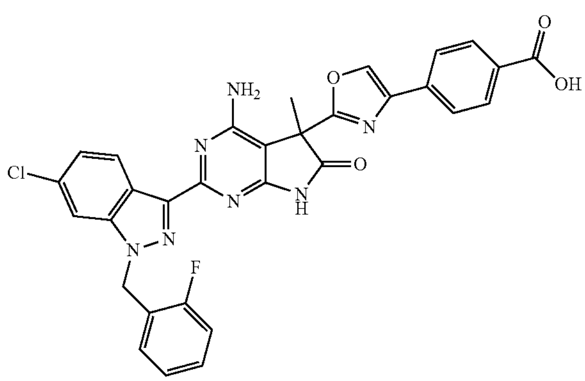 [SMILES: CC1(c2nc(-c3ccc(C(=O)O)cc3)co2)C(=O)Nc2nc(-c3nn(Cc4ccccc4F)c4cc(Cl)ccc34)nc(N)c21] | 4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)benzoic acid | 610 |
| 165A | I-58A | 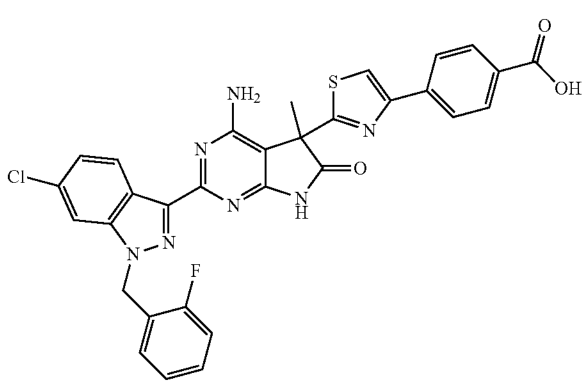 [SMILES: CC1(c2nc(-c3ccc(C(=O)O)cc3)cs2)C(=O)Nc2nc(-c3nn(Cc4ccccc4F)c4cc(Cl)ccc34)nc(N)c21] | 4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)benzoic acid | 626 |

TABLE 19-continued

| Ex. | Int. SM | Structure | Name | m/z (M + 1) |
|---|---|---|---|---|
| 166A | I-59A | 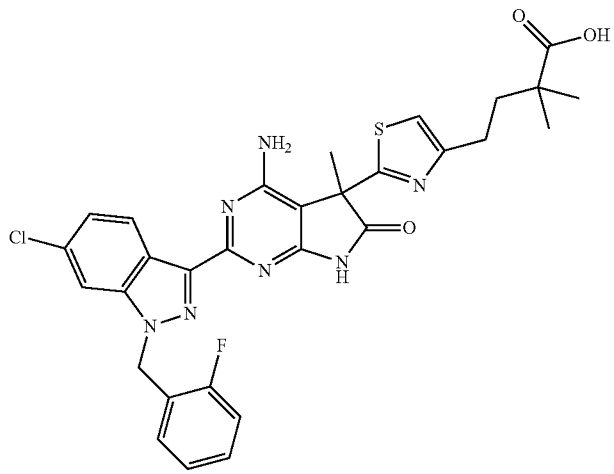 [SMILES: CC(C)(CCc1csc(C2(C)C(=O)Nc3nc(-c4nn(Cc5ccccc5F)c5cc(Cl)ccc45)nc(N)c32)n1)C(=O)O] | 4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-butanoic acid | 620 |
| 167B | I-55B | 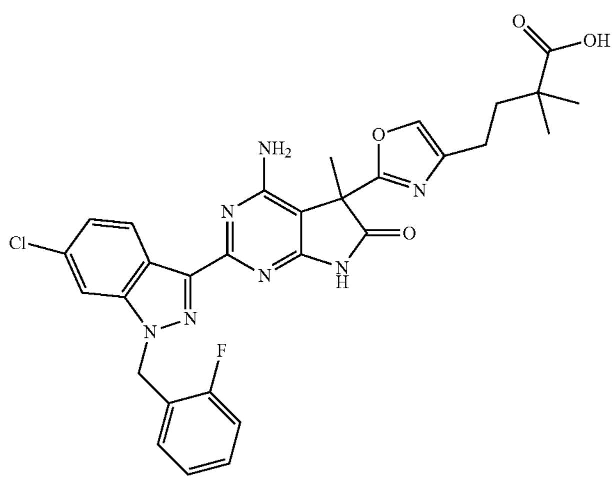 [SMILES: CC(C)(CCc1coc(C2(C)C(=O)Nc3nc(-c4nn(Cc5ccccc5F)c5cc(Cl)ccc45)nc(N)c32)n1)C(=O)O] | 4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-butanoic acid | 604 |
| 168B | I-66B | 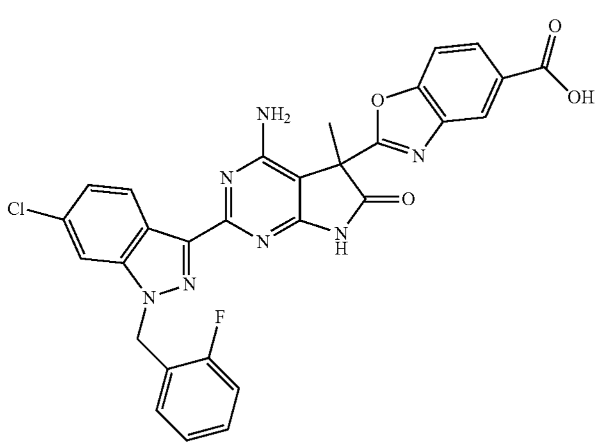 [SMILES: CC1(c2nc3cc(C(=O)O)ccc3o2)C(=O)Nc2nc(-c3nn(Cc4ccccc4F)c4cc(Cl)ccc34)nc(N)c21] | 2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-benzoxazole-5-carboxylic acid | 584 |

TABLE 19-continued

| Ex. | Int. SM | Structure | Name | m/z (M + 1) |
|---|---|---|---|---|
| 169B | I-37B | 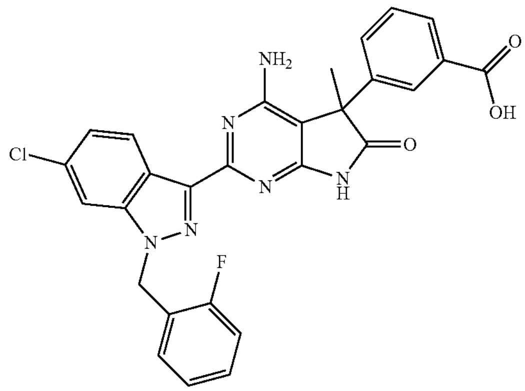 [SMILES: CC1(c2cccc(C(=O)O)c2)C(=O)Nc2nc(-c3nn(Cc4ccccc4F)c4cc(Cl)ccc34)nc(N)c21] | 3-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl} benzoic acid | 543 |
| 170B | I-56B | 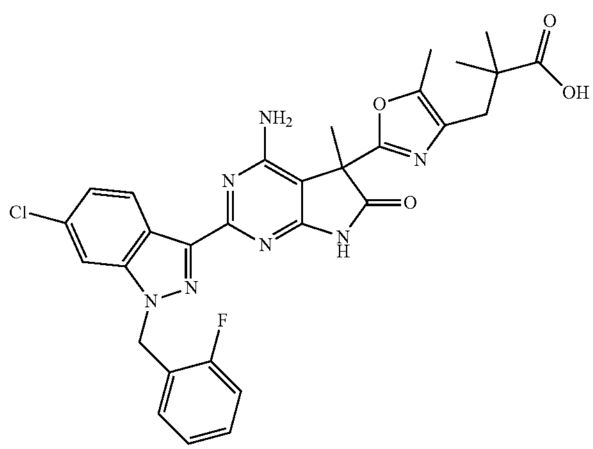 [SMILES: Cc1oc(C2(C)C(=O)Nc3nc(-c4nn(Cc5ccccc5F)c5cc(Cl)ccc45)nc(N)c32)nc1CC(C)(C)C(=O)O] | 3-(2-{4-amino-2-[6-chloro-1-(2 fluorobenzyl)-1H-indazol-3-yl]-5-methyl-6-oxo-6,7-dihydro-5H-pyrrolo[2,3-d]pyrimidin-5-yl}-5-methyl-1,3-oxazol-4-yl)-2,2-dimethylpropanoic acid | 604 |
| 171A | I-63A | 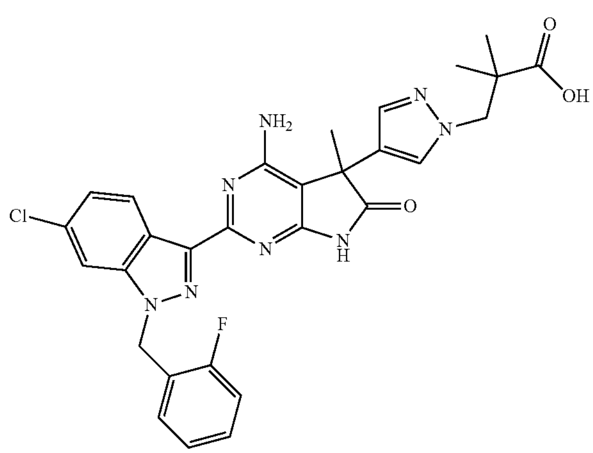 [SMILES: CC(C)(Cn1cc(C2(C)C(=O)Nc3nc(-c4nn(Cc5ccccc5F)c5cc(Cl)ccc45)nc(N)c32)cn1)C(=O)O] | 3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-pyrazol-1-yl)-2,2-dimethyl-propanoic acid | 589 |

TABLE 19-continued

| Ex. | Int. SM | Structure | Name | m/z (M + 1) |
|---|---|---|---|---|
| 172A | I-57A | 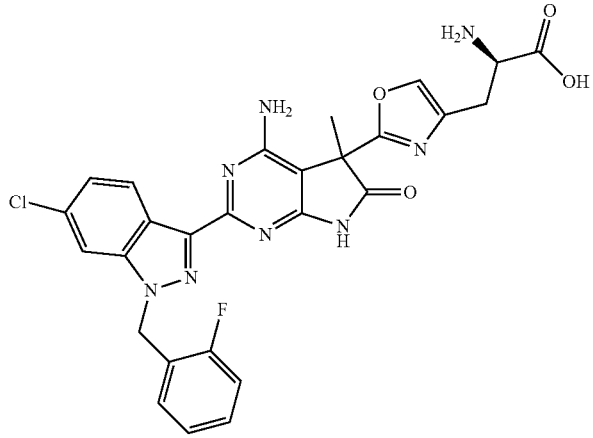 [SMILES: CC1(c2nc(C[C@@H](N)C(=O)O)co2)C(=O)Nc2nc(-c3nn(Cc4ccccc4F)c4cc(Cl)ccc34)nc(N)c21] | 3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-D-alanine | 577 |
| 173A | I-42A | 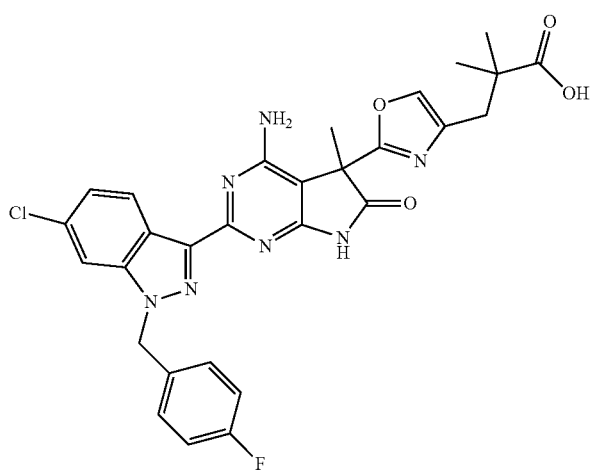 [SMILES: CC(C)(Cc1coc(C2(C)C(=O)Nc3nc(-c4nn(Cc5ccc(F)cc5)c5cc(Cl)ccc45)nc(N)c32)n1)C(=O)O] | 3-(2-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 590 |
| 174A | I-35A | 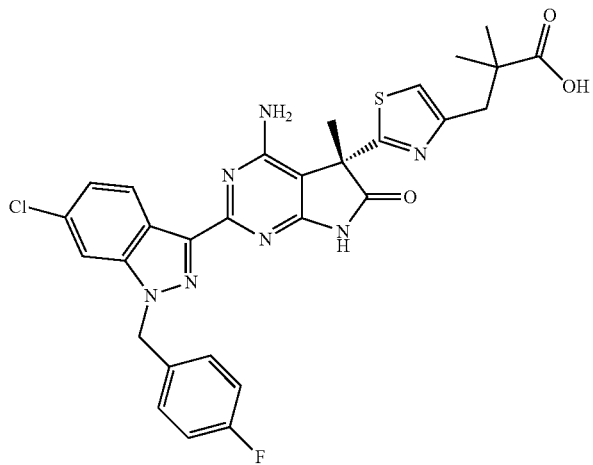 [SMILES: CC(C)(Cc1csc([C@]2(C)C(=O)Nc3nc(-c4nn(Cc5ccc(F)cc5)c5cc(Cl)ccc45)nc(N)c32)n1)C(=O)O] | (S)-3-(2-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 606 |

TABLE 19-continued

| Ex. | Int. SM | Structure | Name | m/z (M + 1) |
|---|---|---|---|---|
| 175A | I-42A | 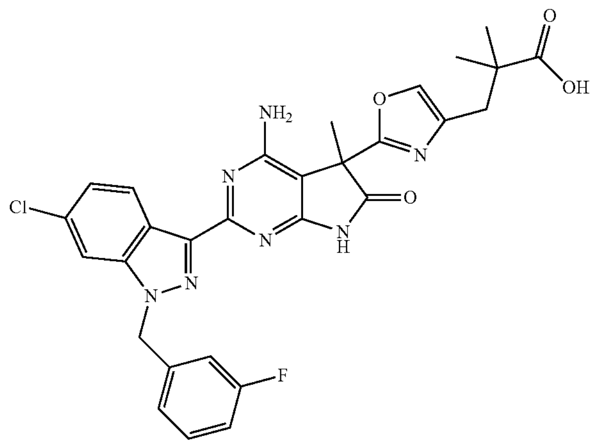 [SMILES: CC(C)(Cc1coc(C2(C)C(=O)Nc3nc(-c4nn(Cc5cccc(F)c5)c5cc(Cl)ccc45)nc(N)c32)n1)C(=O)O] | 3-(2-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 590 |
| 176B | I-56B | 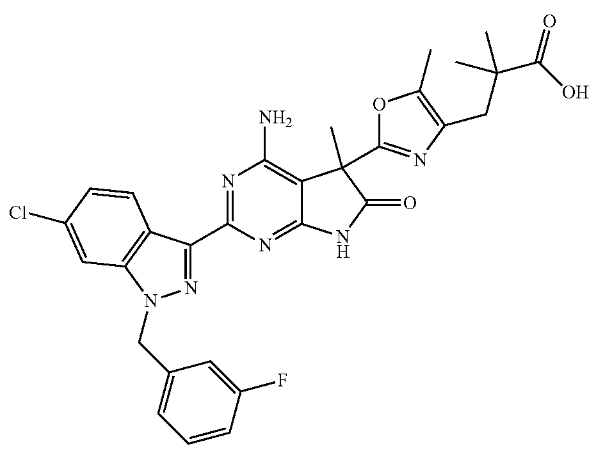 [SMILES: Cc1oc(C2(C)C(=O)Nc3nc(-c4nn(Cc5cccc(F)c5)c5cc(Cl)ccc45)nc(N)c32)nc1CC(C)(C)C(=O)O] | 3-(2-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}-5-methyl-1,3-oxazol-4-yl)-2,2-dimethyl-propanoic acid | 604 |
| 177B | I-55B | 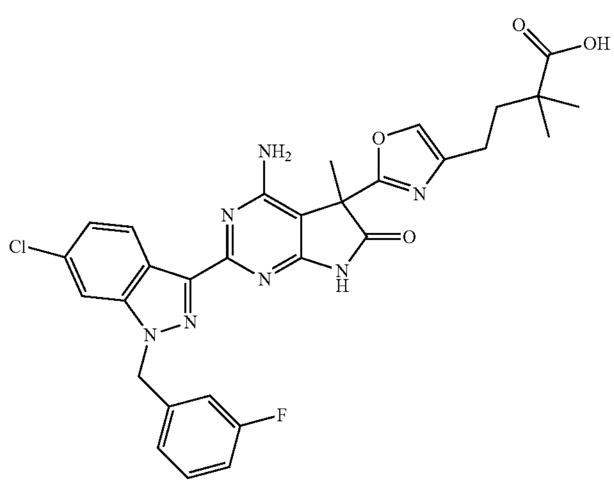 [SMILES: CC(C)(CCc1coc(C2(C)C(=O)Nc3nc(-c4nn(Cc5cccc(F)c5)c5cc(Cl)ccc45)nc(N)c32)n1)C(=O)O] | 4-(2-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-butanoic acid | 604 |

TABLE 19-continued

| Ex. | Int. SM | Structure | Name | m/z (M + 1) |
|---|---|---|---|---|
| 178A | I-42A | 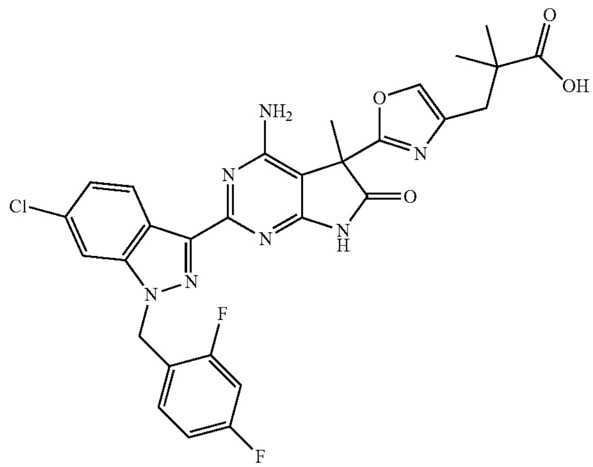 [SMILES: CC(C)(Cc1coc(C2(C)C(=O)Nc3nc(-c4nn(Cc5ccc(F)cc5F)c5cc(Cl)ccc45)nc(N)c32)n1)C(=O)O] | 3-(2-{4-amino-2-[6-chloro-1-(2,4-difluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 608 |
| 179A | I-35A | 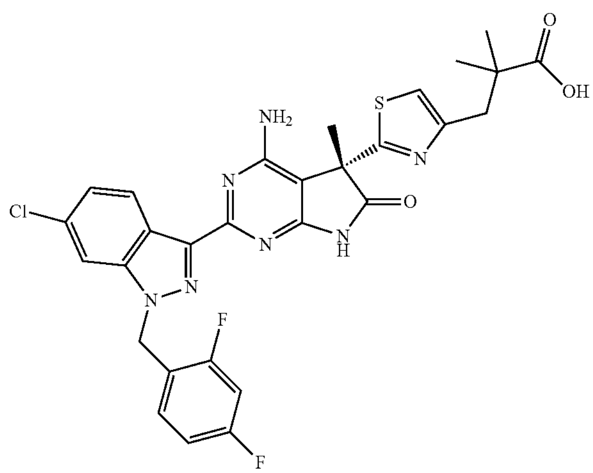 [SMILES: CC(C)(Cc1csc([C@]2(C)C(=O)Nc3nc(-c4nn(Cc5ccc(F)cc5F)c5cc(Cl)ccc45)nc(N)c32)n1)C(=O)O] | (S)-3-(2-{4-amino-2-[6-chloro-1-(2,4-difluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 624 |
| 180A | I-42A | 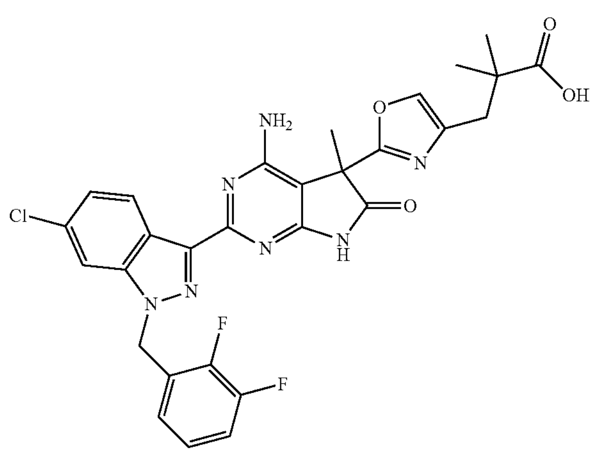 [SMILES: CC(C)(Cc1coc(C2(C)C(=O)Nc3nc(-c4nn(Cc5cccc(F)c5F)c5cc(Cl)ccc45)nc(N)c32)n1)C(=O)O] | 3-(2-{4-amino-2-[6-chloro-1-(2,3-difluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 608 |

TABLE 19-continued

| Ex. | Int. SM | Structure | Name | m/z (M + 1) |
|---|---|---|---|---|
| 181A | I-35A | 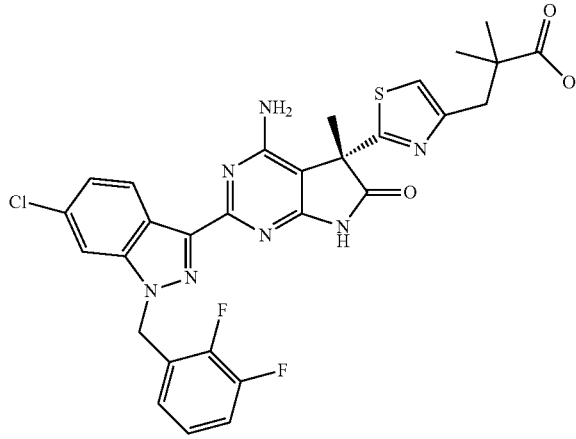 | (S)-3-(2-{4-amino-2-[6-chloro-1-(2,3-difluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 624 |
| 182A | I-42A | 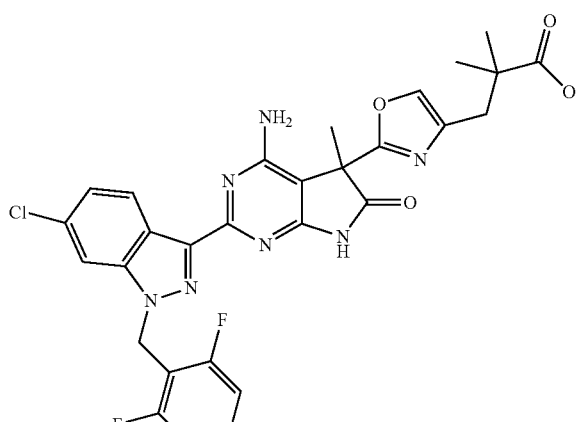 | 3-(2-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 608 |
| 183A | I-35A | 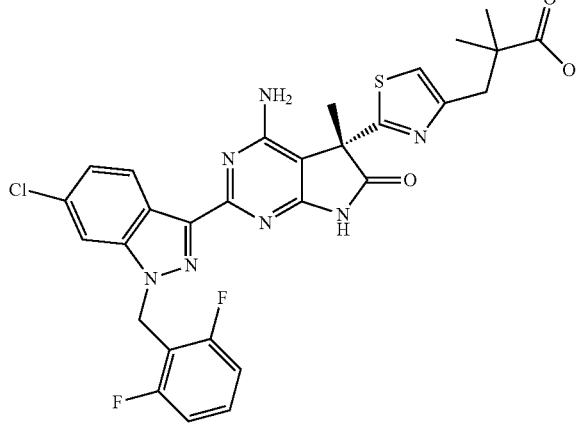 | (S)-3-(2-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 624 |

TABLE 19-continued

| Ex. | Int. SM | Structure | Name | m/z (M + 1) |
|---|---|---|---|---|
| 184A | I-42A | 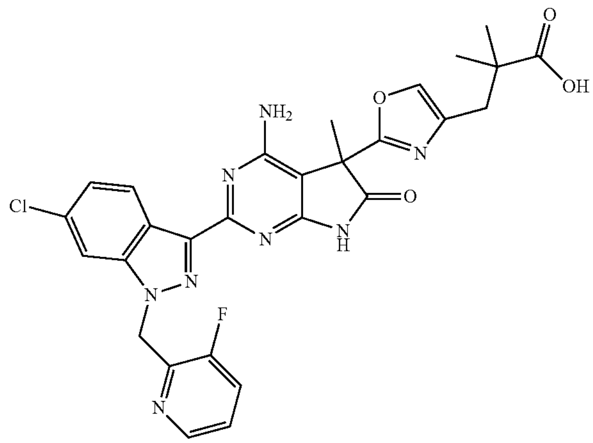 [SMILES: CC(C)(Cc1coc(C2(C)C(=O)Nc3nc(-c4nn(Cc5ncccc5F)c5cc(Cl)ccc45)nc(N)c32)n1)C(=O)O] | 3-{2-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]-1,3-oxazol-4-yl}-2,2-dimethyl-propanoic acid | 591 |
| 185A | I-35A | 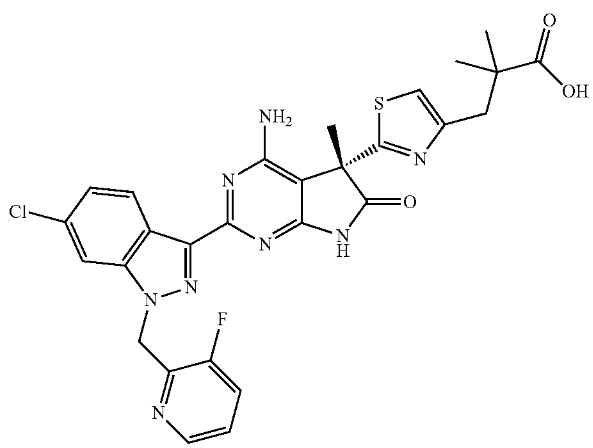 [SMILES: CC(C)(Cc1csc([C@]2(C)C(=O)Nc3nc(-c4nn(Cc5ncccc5F)c5cc(Cl)ccc45)nc(N)c32)n1)C(=O)O] | (S)-3-{2-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]-1,3-thiazol-4-yl}-2,2-dimethyl-propanoic acid | 607 |
| 186A | I-42A | 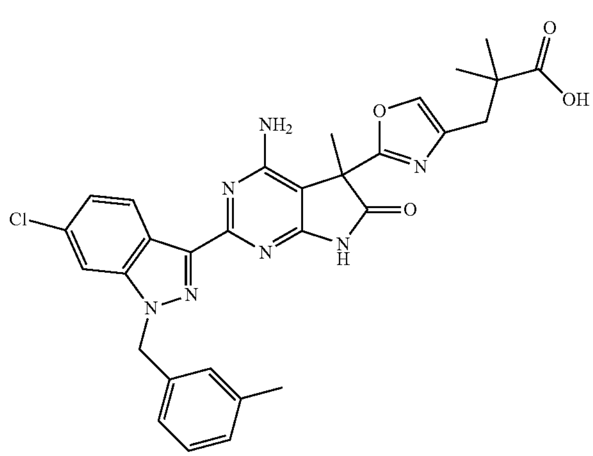 [SMILES: Cc1cccc(Cn2nc(-c3nc(N)c4c(n3)NC(=O)C4(C)c3nc(CC(C)(C)C(=O)O)co3)c3ccc(Cl)cc32)c1] | 3-(2-{4-amino-2-[6-chloro-1-(3-methylbenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 586 |

TABLE 19-continued

| Ex. | Int. SM | Structure | Name | m/z (M + 1) |
|---|---|---|---|---|
| 187A | I-42A | 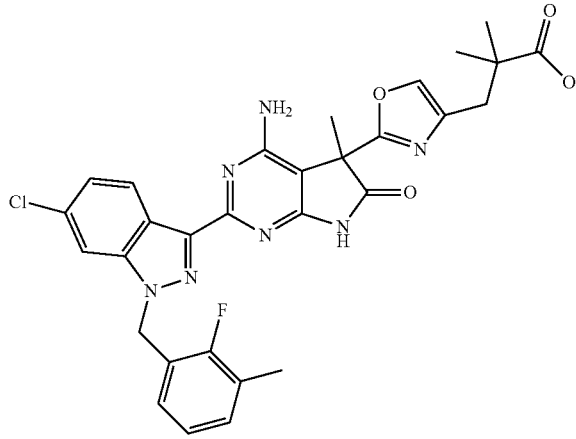 | 3-(2-{4-amino-2-[6-chloro-1-(2-fluoro-3-methyl-benzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 604 |
| 188A | I-35A | 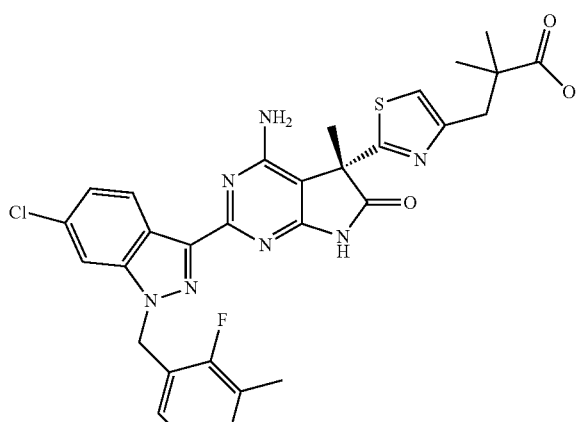 | (S)-3-(2-{4-amino-2-[6-chloro-1-(2-fluoro-3-methyl-benzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 620 |
| 189A | I-42A | 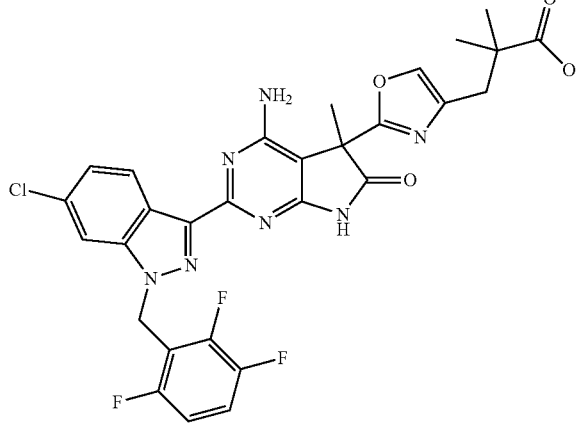 | 3-(2-{4-amino-2-[6-chloro-1-(2,3,6-trifluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 626 |

TABLE 19-continued

| Ex. | Int. SM | Structure | Name | m/z (M + 1) |
|---|---|---|---|---|
| 190A | I-35A | 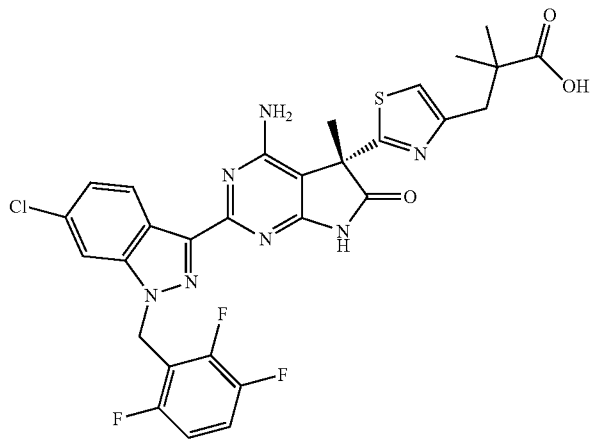 [SMILES: CC(C)(Cc1csc([C@]2(C)C(=O)Nc3nc(-c4nn(Cc5c(F)ccc(F)c5F)c5cc(Cl)ccc45)nc(N)c32)n1)C(=O)O] | (S)-3-(2-{4-amino-2-[6-chloro-1-(2,3,6-trifluoro-benzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 642 |
| 191B | I-37B | 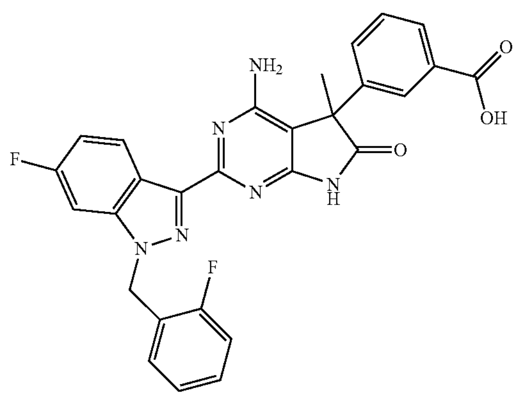 [SMILES: CC1(c2cccc(C(=O)O)c2)C(=O)Nc2nc(-c3nn(Cc4ccccc4F)c4cc(F)ccc34)nc(N)c21] | 3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}benzoic acid | 527 |
| 192A | I-63A | 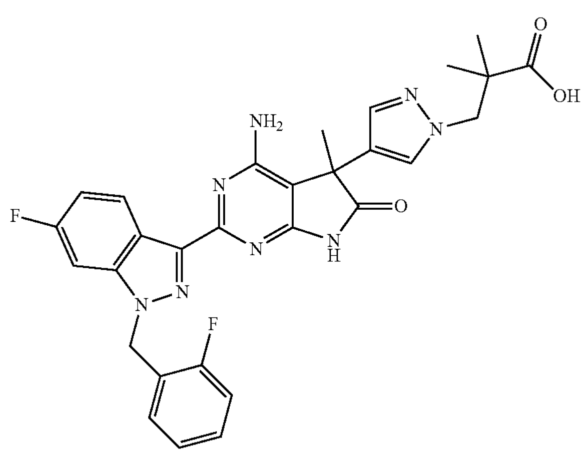 [SMILES: CC(C)(Cn1cc(C2(C)C(=O)Nc3nc(-c4nn(Cc5ccccc5F)c5cc(F)ccc45)nc(N)c32)cn1)C(=O)O] | 3-(4-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1H-pyrazol-1-yl)-2,2-dimethyl-propanoic acid | 573 |

| Ex. | Int. SM | Structure | Name | m/z (M + 1) |
|---|---|---|---|---|
| 193B | I-55B | 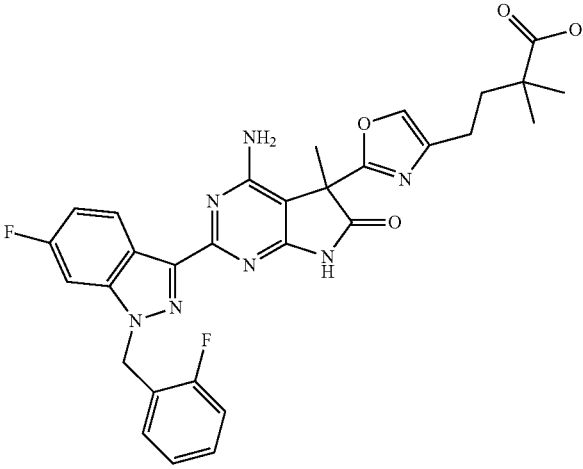 | 4-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-butanoic acid | 588 |
| 194A | I-35A | 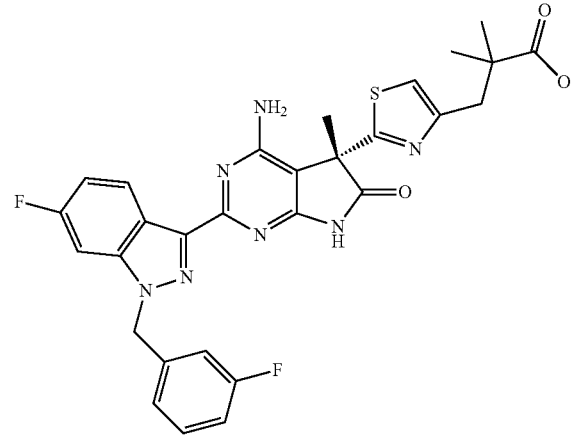 | (S)-3-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 590 |
| 195A | I-42A | 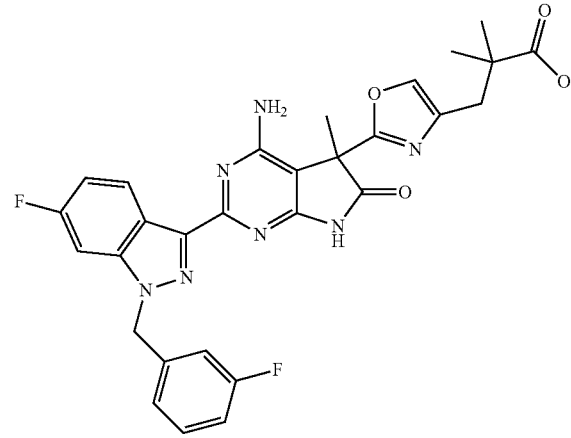 | 3-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 574 |

TABLE 19-continued

| Ex. | Int. SM | Structure | Name | m/z (M + 1) |
|---|---|---|---|---|
| 196A | I-59A | 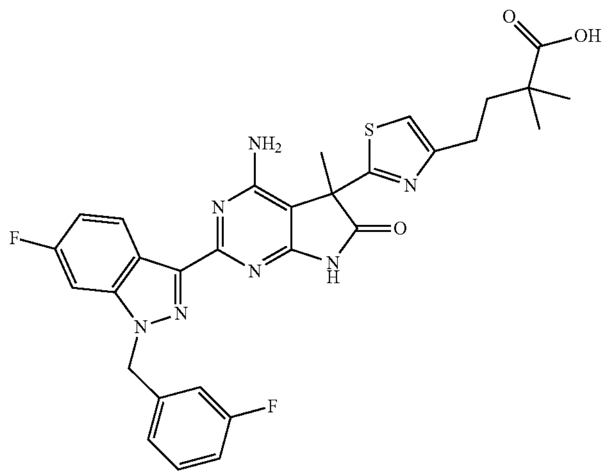 | 4-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-butanoic acid | 604 |
| 197B | I-55B | 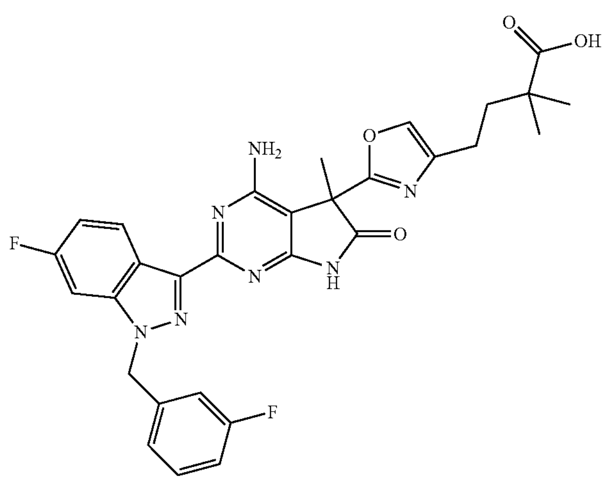 [SMILES: CC(C)(CCc1coc(C2(C)C(=O)Nc3nc(-c4nn(Cc5cccc(F)c5)c5cc(F)ccc45)nc(N)c32)n1)C(=O)O] | 4-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-butanoic acid | 588 |
| 198B | I-56B | 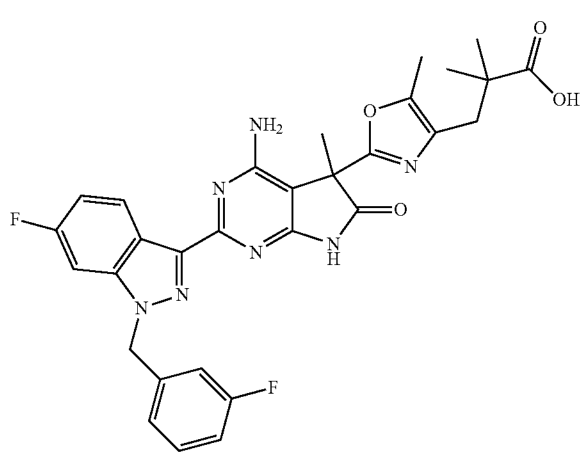 [SMILES: Cc1oc(C2(C)C(=O)Nc3nc(-c4nn(Cc5cccc(F)c5)c5cc(F)ccc45)nc(N)c32)nc1CC(C)(C)C(=O)O] | 3-(2-{4-amino-2-[6-fluoro-1-(3-fluorobenzyl)-1H-indazol-3-yl]-5-methyl-6-oxo-6,7-dihydro-5H-pyrrolo[2,3-d]pyrimidin-5-yl}-5-methyl-1,3-oxazol-4-yl)-2,2-dimethyl-propanoic acid | 588 |

TABLE 19-continued

| Ex. | Int. SM | Structure | Name | m/z (M + 1) |
|---|---|---|---|---|
| 199A | I-35A | 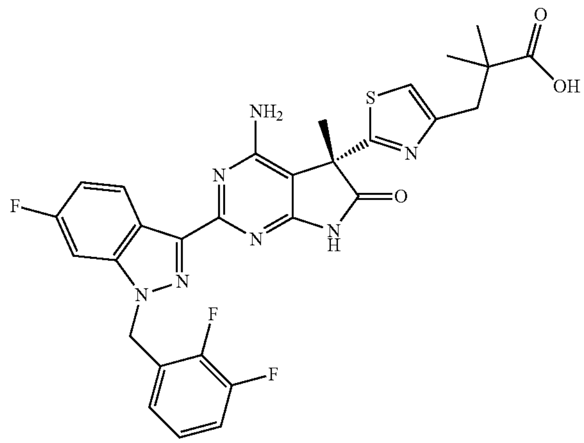 [SMILES: CC(C)(Cc1csc([C@]2(C)C(=O)Nc3nc(-c4nn(Cc5cccc(F)c5F)c5cc(F)ccc45)nc(N)c32)n1)C(=O)O] | (S)-3-(2-{4-amino-2-[1-(2,3-difluorobenzyl)-6-fluoro-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 608 |
| 200A | I-42A | 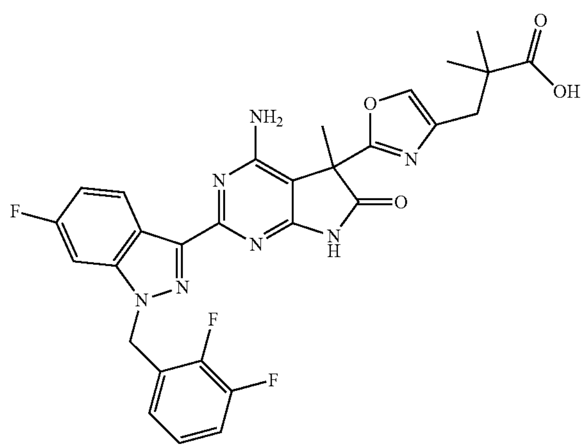 [SMILES: CC(C)(Cc1coc(C2(C)C(=O)Nc3nc(-c4nn(Cc5cccc(F)c5F)c5cc(F)ccc45)nc(N)c32)n1)C(=O)O] | 3-(2-{4-amino-2-[1-(2,3-difluorobenzyl)-6-fluoro-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 592 |
| 201A | I-35A | 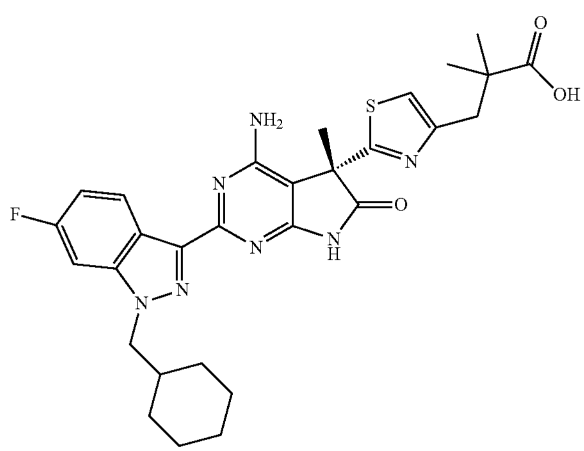 [SMILES: CC(C)(Cc1csc([C@]2(C)C(=O)Nc3nc(-c4nn(CC5CCCCC5)c5cc(F)ccc45)nc(N)c32)n1)C(=O)O] | (S)-3-(2-{4-amino-2-[1-(cyclohexyl-methyl)-6-fluoro-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 578 |

TABLE 19-continued

| Ex. | Int. SM | Structure | Name | m/z (M + 1) |
|---|---|---|---|---|
| 202A | I-42A | 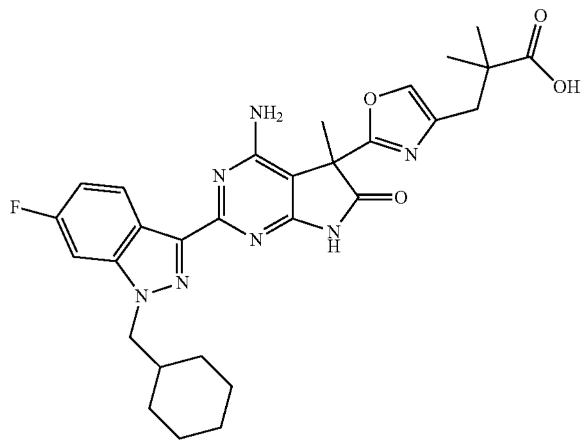 [SMILES: CC(C)(Cc1coc(C2(C)C(=O)Nc3nc(-c4nn(CC5CCCCC5)c5cc(F)ccc45)nc(N)c32)n1)C(=O)O] | 3-(2-{4-amino-2-[1-(cyclohexyl-methyl)-6-fluoro-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 562 |
| 203B | I-34B | 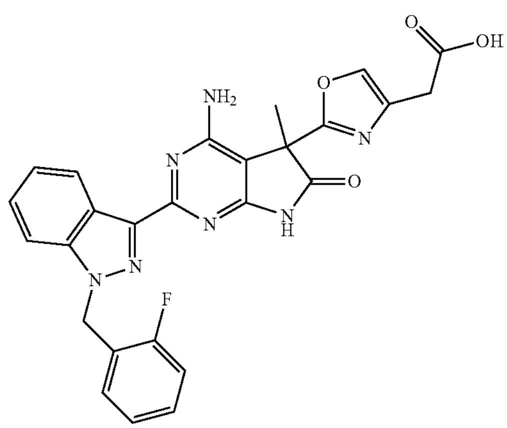 [SMILES: CC1(c2nc(CC(=O)O)co2)C(=O)Nc2nc(-c3nn(Cc4ccccc4F)c4ccccc34)nc(N)c21] | (2-{4-amino-2-[1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)acetic acid | 514 |
| 204A | I-59A | 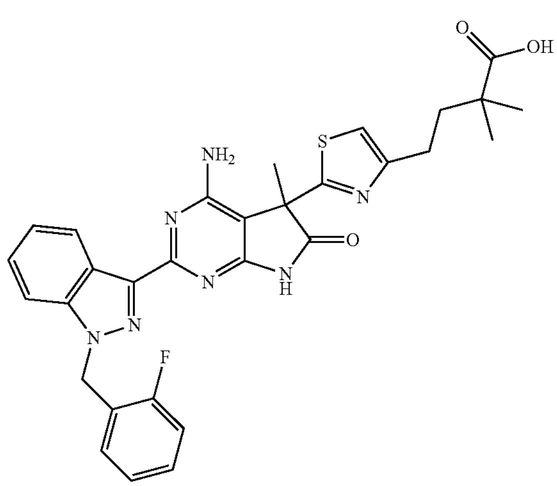 | 4-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-butanoic acid | 586 |

TABLE 19-continued

| Ex. | Int. SM | Structure | Name | m/z (M + 1) |
|---|---|---|---|---|
| 206B | I-55B | 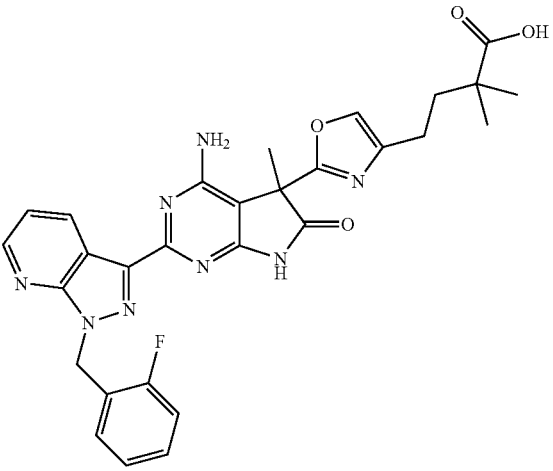 [SMILES: CC(C)(CCc1coc(C2(C)C(=O)Nc3nc(-c4nn(Cc5ccccc5F)c5ncccc45)nc(N)c32)n1)C(=O)O] | 4-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-oxazol-4-yl)-2,2-dimethyl-butanoic acid | 571 |
| 207B | I-55B | 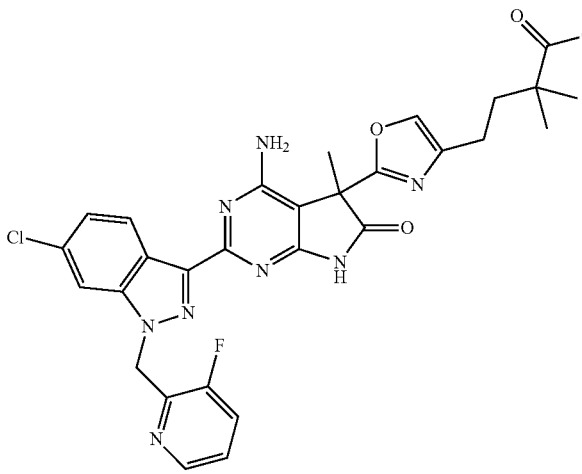 | 4-{2-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]-1,3-oxazol-4-yl}-2,2-dimethyl-butanoic acid | 605 |
| 208A | I-42A | 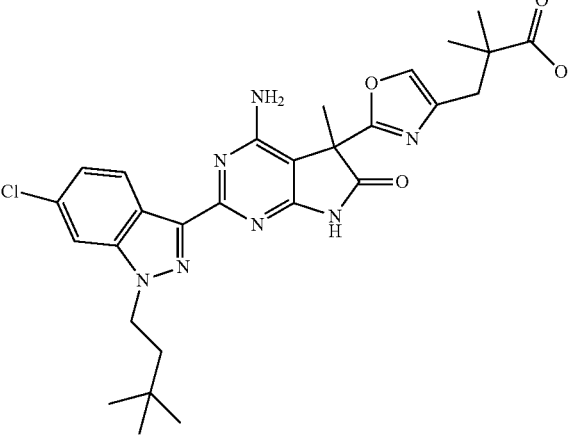 | 3-(2-{4-amino-2-[6-chloro-1-(3,3-dimethylbutyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 566 |

TABLE 19-continued

| Ex. | Int. SM | Structure | Name | m/z (M + 1) |
|---|---|---|---|---|
| 209B | I-48B | 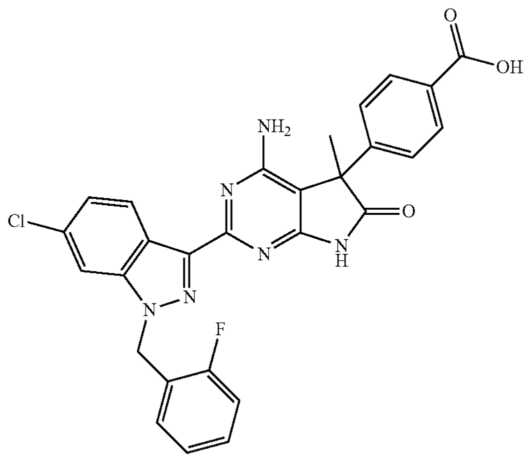 [SMILES: CC1(c2ccc(C(=O)O)cc2)C(=O)Nc2nc(-c3nn(Cc4ccccc4F)c4cc(Cl)ccc34)nc(N)c21] | 4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}benzoic acid | 543 |
| 210B | I-11B | 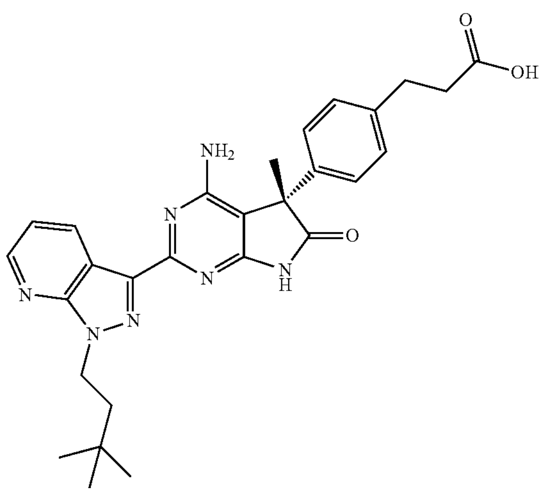 [SMILES: CC(C)(C)CCn1nc(-c2nc(N)c3c(n2)NC(=O)[C@@]3(C)c2ccc(CCC(=O)O)cc2)c2cccnc21] | (S)-3-(4-{4-amino-2-[1-(3,3-dimethylbutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid | 515 |
| 211A | I-63A | 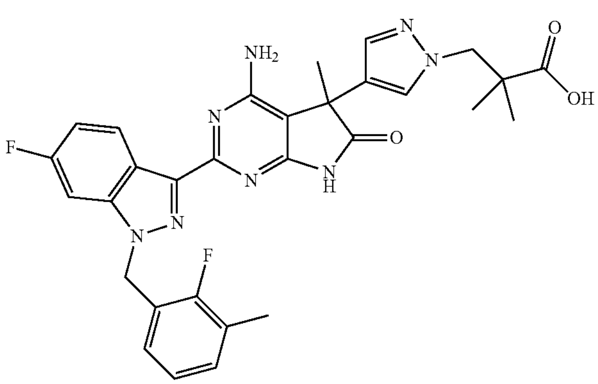 [SMILES: Cc1cccc(Cn2nc(-c3nc(N)c4c(n3)NC(=O)C4(C)c3cnn(CC(C)(C)C(=O)O)c3)c3ccc(F)cc32)c1F] | 3-(4-{4-amino-2-[6-fluoro-1-(2-fluoro-3-methyl-benzyl)-1H-indazol-3-yl]-5-methyl-6-oxo-6,7-dihydro-5H-pyrrolo[2,3-d]pyrimidin-5-yl}-1H-pyrazol-1-yl)-2,2-dimethyl-propanoic acid | 587 |

TABLE 19-continued

| Ex. | Int. SM | Structure | Name | m/z (M + 1) |
|---|---|---|---|---|
| 212A | I-42A | 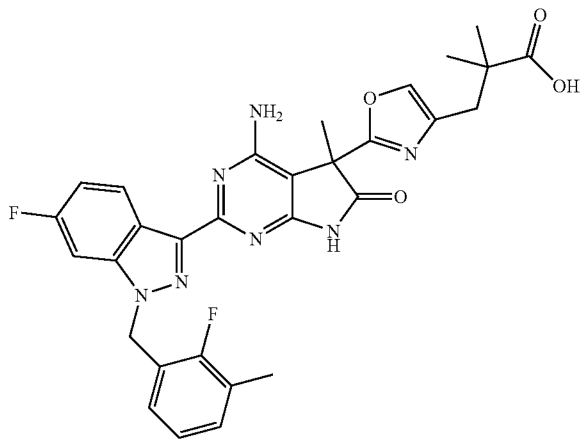 [SMILES: Cc1cccc(Cn2nc(-c3nc(N)c4c(n3)NC(=O)C4(C)c3nc(CC(C)(C)C(=O)O)co3)c3ccc(F)cc32)c1F] | 3-(2-{4-amino-2-[6-fluoro-1-(2-fluoro-3-methyl-benzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 588 |
| 213A | I-42A | 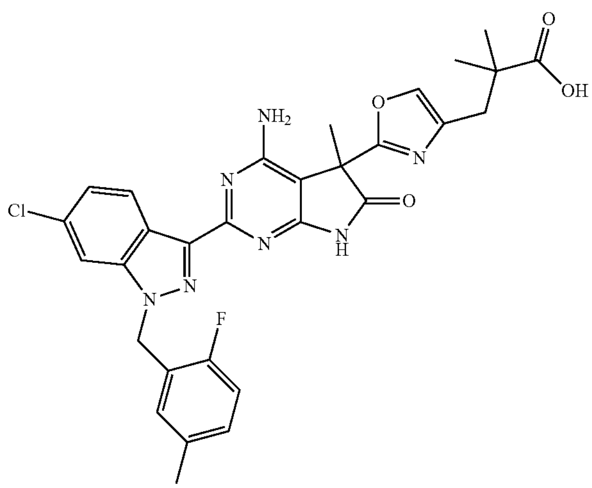 [SMILES: Cc1ccc(F)c(Cn2nc(-c3nc(N)c4c(n3)NC(=O)C4(C)c3nc(CC(C)(C)C(=O)O)co3)c3ccc(Cl)cc32)c1] | 3-(2-{4-amino-2-[6-chloro-1-(2-fluoro-5-methyl-benzyl)-1H-indazol-3-yl]-5-methyl-6-oxo-6,7-dihydro-5H-pyrrolo[2,3-d]pyrimidin-5-yl}1,3-oxazol-4-yl)-2,2-dimethyl-propanoic acid | 604 |
| 214A | I-35A | 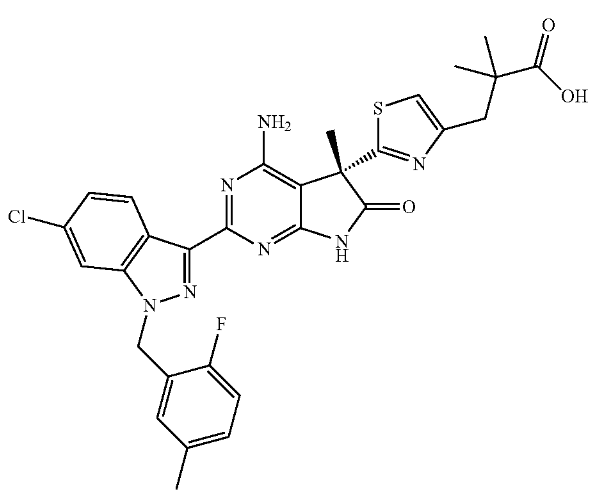 [SMILES: Cc1ccc(F)c(Cn2nc(-c3nc(N)c4c(n3)NC(=O)[C@@]4(C)c3nc(CC(C)(C)C(=O)O)cs3)c3ccc(Cl)cc32)c1] | (S)-3-(2-{4-amino-2-[6-chloro-1-(2-fluoro-5-methyl-benzyl)-1H-indazol-3-yl]-5-methyl-6-oxo-6,7-dihydro-5H-pyrrolo[2,3-d]pyrimidin-5-yl}1,3-thiazol-4-yl)-2,2-dimethyl-propanoic acid | 620 |

TABLE 19-continued

| Ex. | Int. SM | Structure | Name | m/z (M + 1) |
|---|---|---|---|---|
| 215A | I-42A | 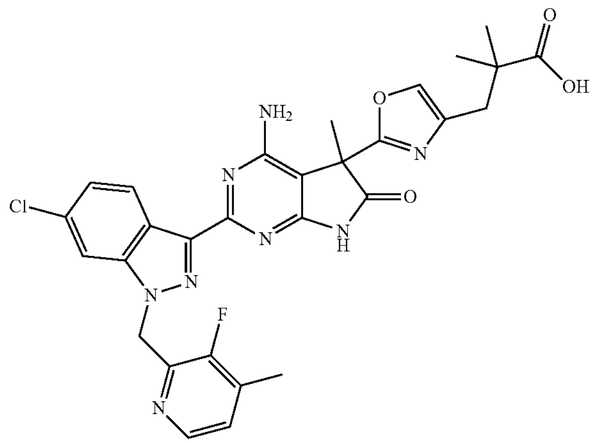 | 3-(2-{4-amino-2-[6-chloro-1-((3-fluoro-4-methyl-pyridin-2-yl)methyl)-1H-indazol-3-yl]-5-methyl-6-oxo-6,7-dihydro-5H-pyrrolo[2,3-d]pyrimidin-5-yl}1,3-oxazol-4-yl)-2,2-dimethyl-propanoic acid | 605 |
| 216A | I-35A | 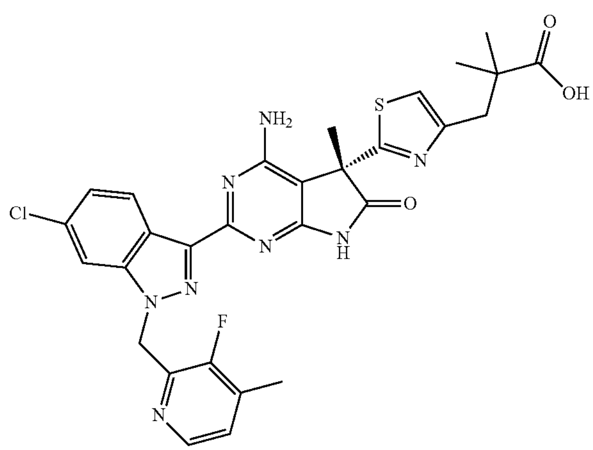 [SMILES: Cc1ccnc(Cn2nc(-c3nc(N)c4c(n3)NC(=O)[C@@]4(C)c3nc(CC(C)(C)C(=O)O)cs3)c3ccc(Cl)cc32)c1F] | (S)-3-(2-{4-amino-2-[6-chloro-1-((3-fluoro-4-methyl-pyridin-2-yl)methyl)-1H-indazol-3-yl]-5-methyl-6-oxo-6,7-dihydro-5H-pyrrolo[2,3-d]pyrimidin-5-yl}1,3-thiazol-4-yl)-2,2-dimethyl-propanoic acid | 621 |
| 217A | I-76A | 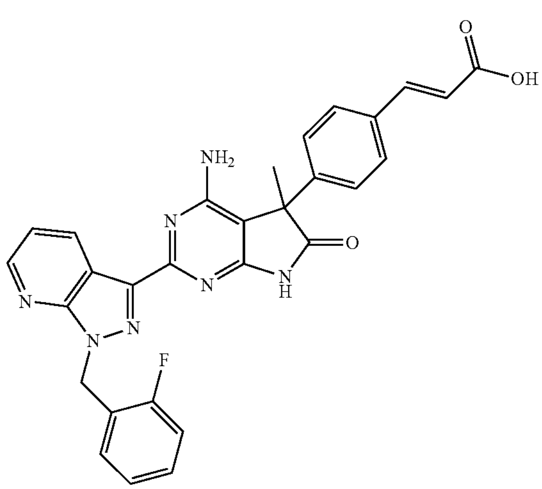 [SMILES: CC1(c2ccc(/C=C/C(=O)O)cc2)C(=O)Nc2nc(-c3nn(Cc4ccccc4F)c4ncccc34)nc(N)c21] | (2E)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)prop-2-enoic acid | 536 |

TABLE 19-continued

| Ex. | Int. SM | Structure | Name | m/z (M + 1) |
|---|---|---|---|---|
| 218A | I-76A | 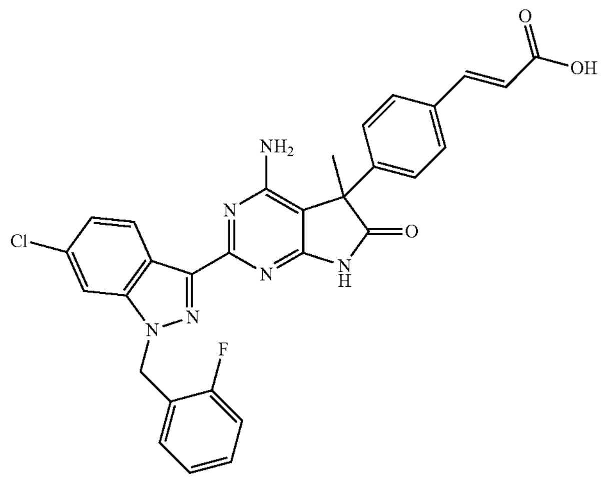 [SMILES: CC1(c2ccc(/C=C/C(=O)O)cc2)C(=O)Nc2nc(-c3nn(Cc4ccccc4F)c4cc(Cl)ccc34)nc(N)c21] | (2E)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)prop-2-enoic acid | 509 |
| 219A | I-51A | 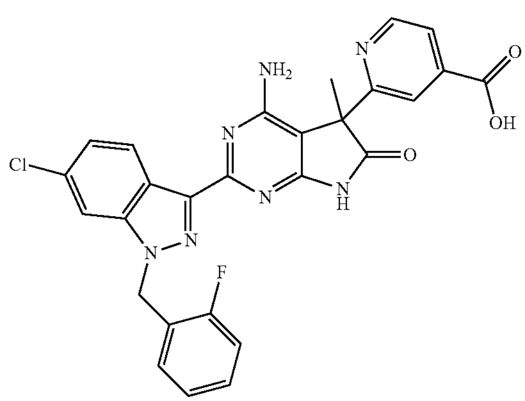 [SMILES: CC1(c2cc(C(=O)O)ccn2)C(=O)Nc2nc(-c3nn(Cc4ccccc4F)c4cc(Cl)ccc34)nc(N)c21] | 2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridine-4-carboxylic acid | 544 |

Examples 220B-233A

Using essentially the same procedure as described in Example 76B, the following compounds in Table 20 were prepared.

TABLE 20

| Ex. | Int. SM/Chiral Resolution Step/Column | Structure | Name | m/z (M + 1) |
|---|---|---|---|---|
| 220B | I-55B/- | 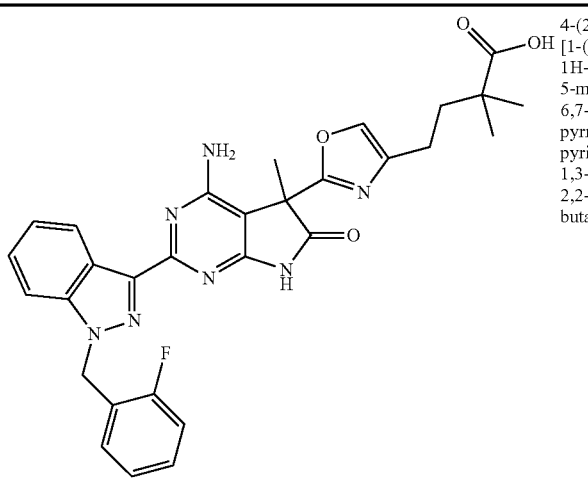 | 4-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-butanoic acid | 570 |
| 221B | I-11B/- | 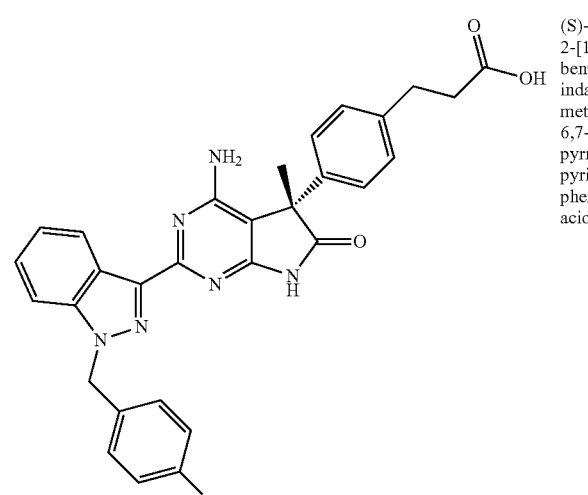 | (S)-3-(4-{4-amino-2-[1-(4-fluoro-benzyl)-1H-indazol-3-yl]-5-methyl-6-oxo-6,7-dihydro-5H-pyrrolo[2,3-d]pyrimidin-5-yl}phenyl)propanoic acid | 537 |
| 222A | I-35A/- | 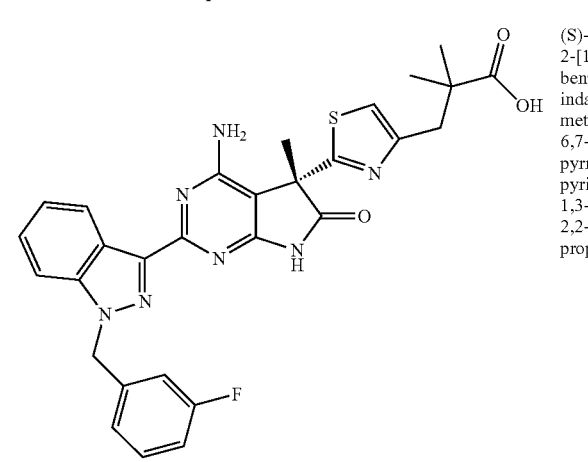 | (S)-3-(2-{4-amino-2-[1-(3-fluoro-benzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethyl-propanoic acid | 572 |

TABLE 20-continued

| Ex. | Int. SM/Chiral Resolution Step/Column | Structure | Name | m/z (M + 1) |
|---|---|---|---|---|
| 223A | I-42A/- | 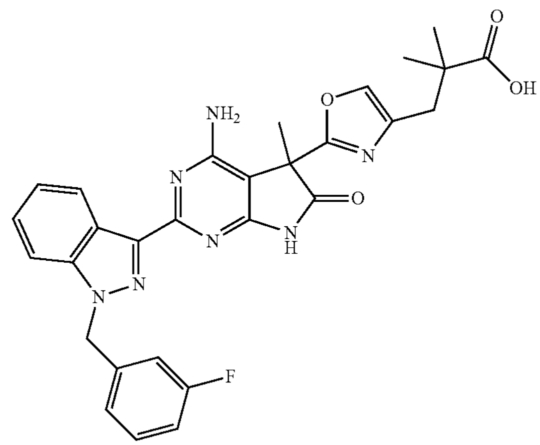 [SMILES: CC(C)(Cc1coc(C2(C)C(=O)Nc3nc(-c4nn(Cc5cccc(F)c5)c5ccccc45)nc(N)c32)n1)C(=O)O] | 3-(2-{4-amino-2-[1-(3-fluoro-benzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 556 |
| 224A | I-35A/- | 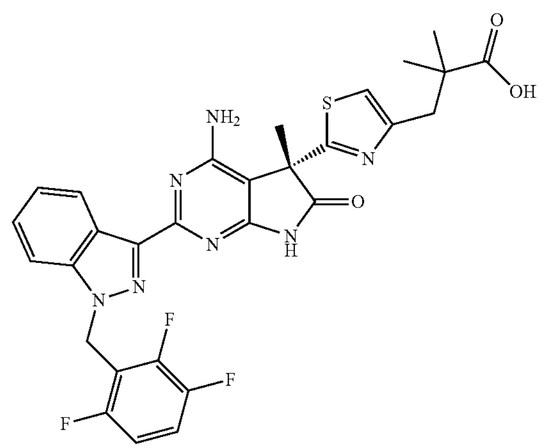 [SMILES: CC(C)(Cc1csc([C@]2(C)C(=O)Nc3nc(-c4nn(Cc5c(F)ccc(F)c5F)c5ccccc45)nc(N)c32)n1)C(=O)O] | (S)-3-(2-{4-amino-5-methyl-6-oxo-2-[1-(2,3,6-trifluorobenzyl)-1H-indazol-3-yl]-6,7-dihydro-5H-pyrrolo[2,3-d]pyrimidin-5-yl}-1,3-thiazol-4-yl)-2,2-dimethyl-propanoic acid | 608 |
| 225B | I-11B/- | 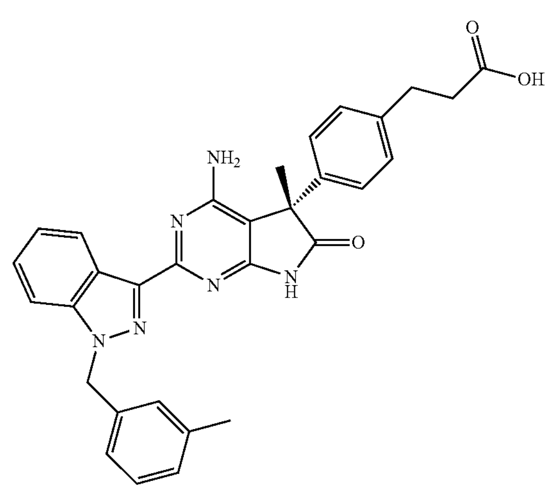 [SMILES: Cc1cccc(Cn2nc(-c3nc(N)c4c(n3)NC(=O)[C@@]4(C)c3ccc(CCC(=O)O)cc3)c3ccccc32)c1] | (S)-3-(4-{4-amino-5-methyl-2-[1-(3-methylbenzyl)-1H-indazol-3-yl]-6-oxo-6,7-dihydro-5H-pyrrolo[2,3-d]pyrimidin-5-yl}phenyl)propanoic acid | 533 |

TABLE 20-continued

| Ex. | Int. SM/Chiral Resolution Step/Column | Structure | Name | m/z (M + 1) |
|---|---|---|---|---|
| 226A | I-42A/- | 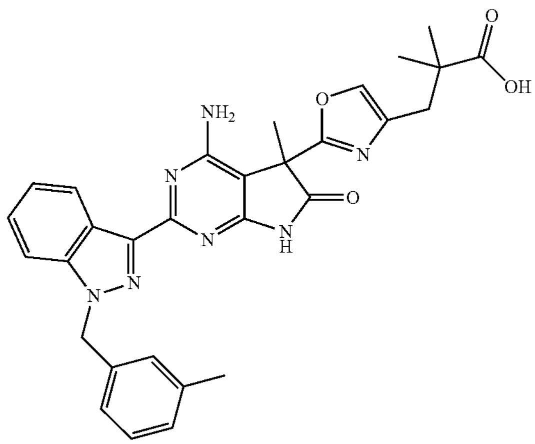 [SMILES: Cc1cccc(Cn2nc(-c3nc(N)c4c(n3)NC(=O)C4(C)c3nc(CC(C)(C)C(=O)O)co3)c3ccccc32)c1] | 3-(2-{4-amino-5-methyl-2-[1-(3-methylbenzyl)-1H-indazol-3-yl]-6-oxo-6,7-dihydro-5H-pyrrolo[2,3-d]pyrimidin-5-yl}-1,3-oxazol-4-yl)-2,2-dimethyl-propanoic acid | 552 |
| 227B | I-11B/- | 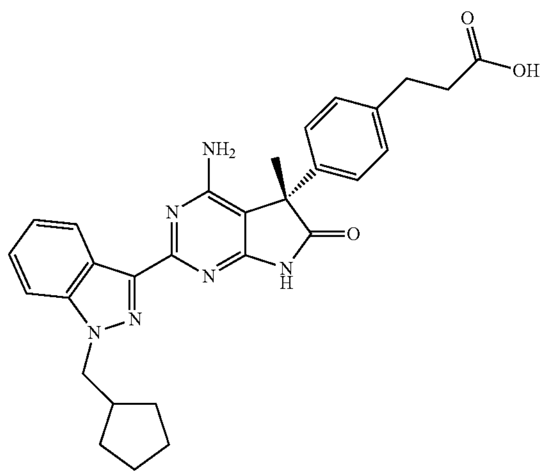 [SMILES: C[C@@]1(c2ccc(CCC(=O)O)cc2)C(=O)Nc2nc(-c3nn(CC4CCCC4)c4ccccc34)nc(N)c21] | (S)-3-(4-{4-amino-2-[1-(cyclopentyl-methyl)-1H-indazol-3-yl]-5-methyl-6-oxo-6,7-dihydro-5H-pyrrolo[2,3-d]pyrimidin-5-yl}phenyl)propanoic acid | 511 |
| 228A | I-42A/- | 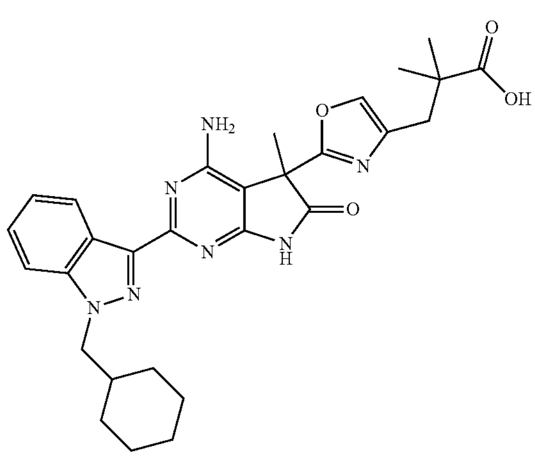 [SMILES: CC(C)(Cc1coc(C2(C)C(=O)Nc3nc(-c4nn(CC5CCCCC5)c5ccccc45)nc(N)c32)n1)C(=O)O] | 3-(2-{4-amino-2-[1-(cyclohexyl-methyl)-1H-indazol-3-yl]-5-methyl-6-oxo-6,7-dihydro-5H-pyrrolo[2,3-d]pyrimidin-5-yl}-1,3-oxazol-4-yl)-2,2-dimethyl-propanoic acid | 544 |

TABLE 20-continued

| Ex. | Int. SM/Chiral Resolution Step/Column | Structure | Name | m/z (M + 1) |
|---|---|---|---|---|
| 229AA | I-35A/Step B/IC | 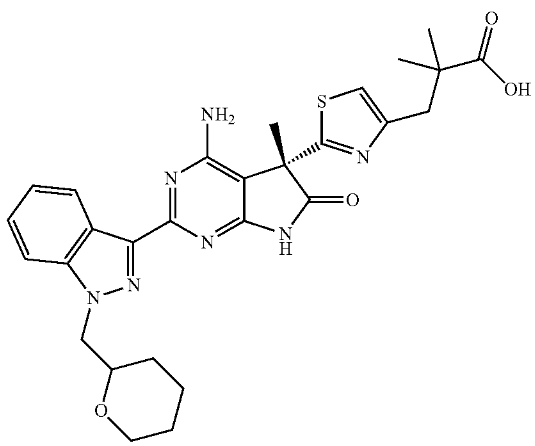 [SMILES: CC(C)(Cc1csc([C@]2(C)C(=O)Nc3nc(-c4nn(CC5CCCCO5)c5ccccc45)nc(N)c32)n1)C(=O)O] | (5S)-3-{2-[4-amino-5-methyl-6-oxo-2-{1-[tetrahydro-2H-pyran-2-ylmethyl]-1H-indazol-3-yl}-6,7-dihydro-5H-pyrrolo[2,3-d]pyrimidin-5-yl]-1,3-thiazol-4-yl}-2,2-dimethylpropanoic acid | 562 |
| 229AB | I-35A/Step B/IC | 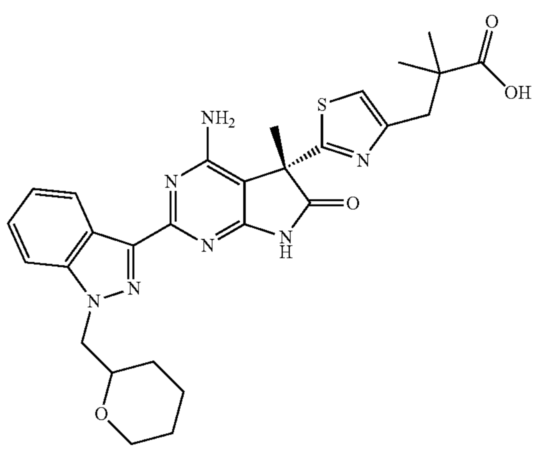 [SMILES: CC(C)(Cc1csc([C@]2(C)C(=O)Nc3nc(-c4nn(CC5CCCCO5)c5ccccc45)nc(N)c32)n1)C(=O)O] | (5S)-3-{2-[4-amino-5-methyl-6-oxo-2-{1-[tetrahydro-2H-pyran-2-yl-methyl]-1H-indazol-3-yl}-6,7-dihydro-5H-pyrrolo[2,3-d]pyrimidin-5-yl]-1,3-thiazol-4-yl}-2,2-dimethylpropanoic acid | 562 |
| 230AA | I-42A/Step B/IC | 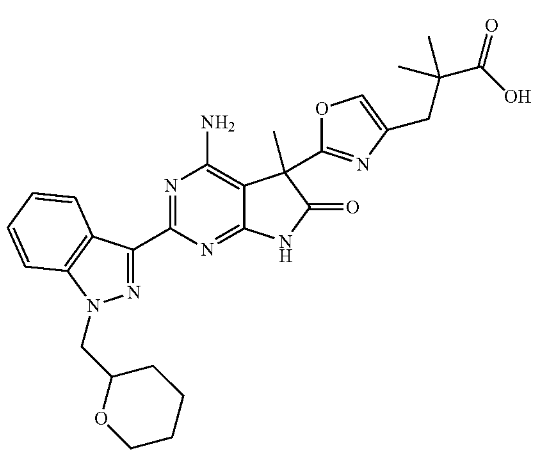 [SMILES: CC(C)(Cc1coc(C2(C)C(=O)Nc3nc(-c4nn(CC5CCCCO5)c5ccccc45)nc(N)c32)n1)C(=O)O] | 3-{2-[4-amino-5-methyl-6-oxo-2-{1-[tetrahydro-2H-pyran-2-ylmethyl]-1H-indazol-3-yl}-6,7-dihydro-5H-pyrrolo[2,3-d]pyrimidin-5-yl]-1,3-oxazol-4-yl}-2,2-dimethylpropanoic acid | 546 |

TABLE 20-continued

| Ex. | Int. SM/Chiral Resolution Step/Column | Structure | Name | m/z (M + 1) |
|---|---|---|---|---|
| 230AB | I-42A/Step B/IC | 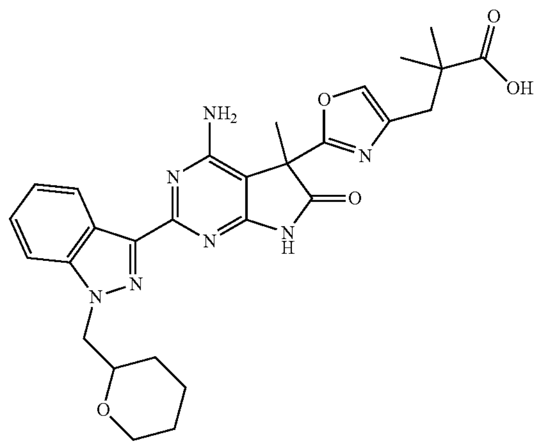 [SMILES: CC(C)(Cc1coc(C2(C)C(=O)Nc3nc(-c4nn(CC5CCCCO5)c5ccccc45)nc(N)c32)n1)C(=O)O] | 3-{2-[4-amino-5-methyl-6-oxo-2-{1-[tetrahydro-2H-pyran-2-ylmethyl]-1H-indazol-3-yl}-6,7-dihydro-5H-pyrrolo[2,3-d]pyrimidin-5-yl]-1,3-oxazol-4-yl}-2,2-dimethyl-propanoic acid | 546 |
| 231AA | I-42A/Step B/Chiral Cellulose-SB | 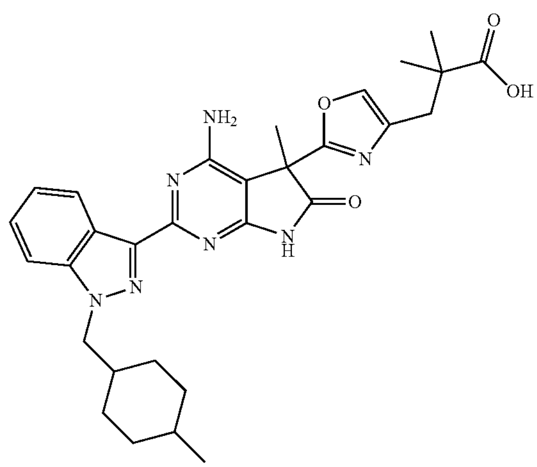 [SMILES: CC1CCC(Cn2nc(-c3nc(N)c4c(n3)NC(=O)C4(C)c3nc(CC(C)(C)C(=O)O)co3)c3ccccc32)CC1] | 3-{2-[4-amino-5-methyl-2-{1-[-4-methylcyclo-hexylmethyl]-1H-indazol-3-yl}-6-oxo-6,7-dihydro-5H-pyrrolo[2,3-d]pyrimidin-5-yl}-1,3-oxazol-4-yl}-2,2-dimethyl-propanoic acid | 558 |
| 231AB | I-42A/Step B/Chiral Cellulose-SB | 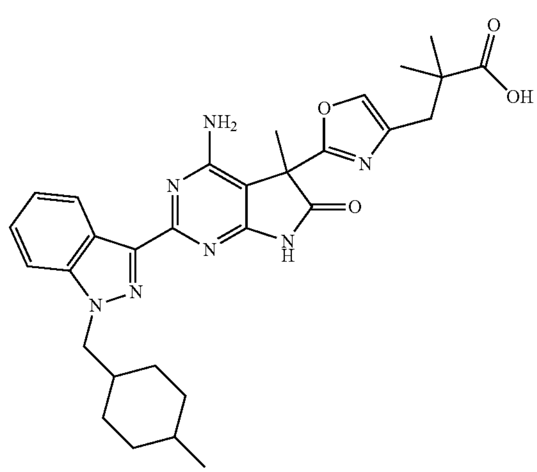 [SMILES: CC1CCC(Cn2nc(-c3nc(N)c4c(n3)NC(=O)C4(C)c3nc(CC(C)(C)C(=O)O)co3)c3ccccc32)CC1] | 3-{2-[4-amino-5-methyl-2-{1-[4-methylcyclo-hexylmethyl]-1H-indazol-3-yl}-6-oxo-6,7-dihydro-5H-pyrrolo[2,3-d]pyrimidin-5-yl}-1,3-oxazol-4-yl}-2,2-dimethyl-propanoic acid | 558 |

TABLE 20-continued

| Ex. | Int. SM/Chiral Resolution Step/Column | Structure | Name | m/z (M + 1) |
|---|---|---|---|---|
| 232B | I-11B/- | 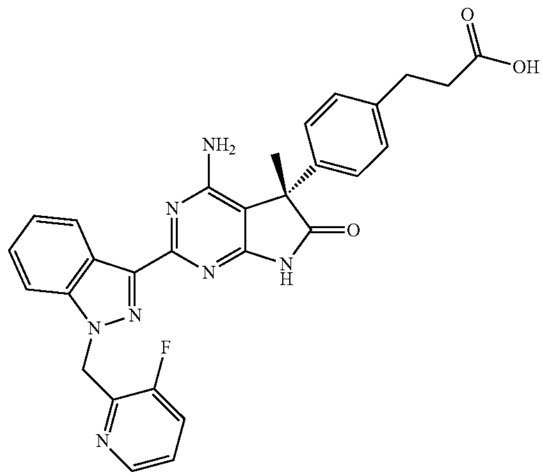 [SMILES: C[C@@]1(c2ccc(CCC(=O)O)cc2)C(=O)Nc2nc(-c3nn(Cc4ncccc4F)c4ccccc34)nc(N)c21] | (S)-3-{4-[4-amino-2-{1-[(3-fluoropyridin-2-yl)methyl]-1H-indazol-3-yl}-5-methyl-6-oxo-6,7-dihydro-5H-pyrrolo[2,3-d]pyrimidin-5-yl]phenyl}propanoic acid | 538 |
| 233A | I-42A/- | 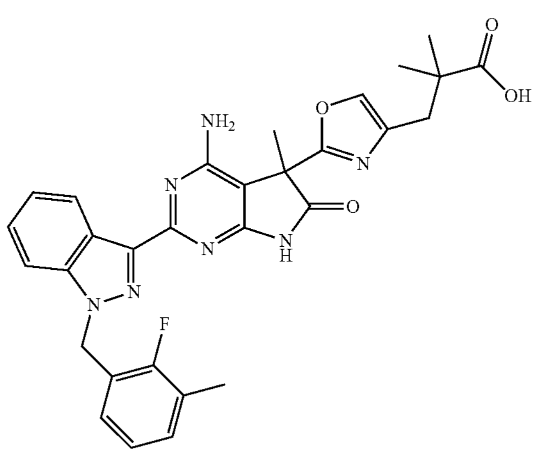 [SMILES: Cc1cccc(Cn2nc(-c3nc(N)c4c(n3)NC(=O)C4(C)c3nc(CC(C)(C)C(=O)O)co3)c3ccccc32)c1F] | 3-(2-{4-amino-2-[1-(2-fluoro-3-methylbenzyl)-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid | 570 |

Example 234B (S)-3-(2-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-D-alanine

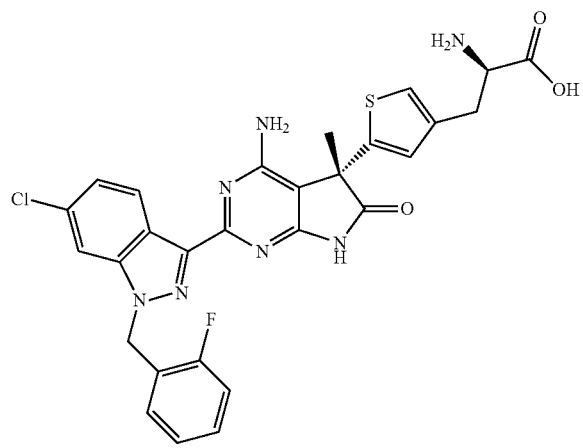 [SMILES: C[C@@]1(c2cc(C[C@@H](N)C(=O)O)cs2)C(=O)Nc2nc(-c3nn(Cc4ccccc4F)c4cc(Cl)ccc34)nc(N)c21]

Example 234B was prepared using essentially the same procedures to those described in example 77B, using I-40B as starting material and I-47 as the bromoketone. $^1$H NMR (300 MHz, CD$_3$OD): δ 8.48 (d, J=8.7 Hz, 1H), 7.89 (s, 1H), 7.48 (s, 1H), 7.43-7.28 (m, 3H), 7.17-7.11 (m, 2H), 5.89 (s, 2H), 4.38 (dd, J=7.2, 5.4 Hz, 1H), 3.51-3.32 (m, 2H), 2.00 (s, 3H); m/z=593 (M+1).

Example 235B 3-(2-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-imidazol-4-yl)propanoic acid Step A—tert-Butyl 3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1-(4-methoxybenzyl)-1H-imidazol-4-yl)propanoate A flask containing I-A15 (136 mg, 0.45 mmol), I-77 (180 mg, 0.38 mmol) and potassium bicarbonate (375 mg, 3.75 mmol) in t-BuOH (15 mL) was stirred for 16 h at 80° C. then concentrated in vacuo. The residue was purified by silica gel column chromatography with MeOH:DCM (0-10%) to afford the racemic title compound. The racemic material was resolved using Chiral HPLC (CHIRALPAK® IC) to afford isomer A (faster eluting) and isomer B (slower eluting).

Step B—3-(2-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1H-imidazol-4-yl)propanoic acid A flask containing tert-butyl 3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1-(4-methoxybenzyl)-1H-imidazol-4-yl)propanoate isomer B (70 mg, 0.095 mmol) and trifluoroacetic acid (3 mL) was stirred for 16 h at 100° C. then concentrated in vacuo. The residue was purified by reverse phase HPLC (ACN/water with 0.05% TFA modifier) to afford the title compound. $^1$H NMR (300 MHz, CD$_3$OD) δ 8.51 (d, J=8.7 Hz, 1H), 7.87 (s, 1H), 7.41-7.28 (m, 4H), 7.17-7.12 (m, 2H), 5.88 (s, 2H), 2.97 (t, J=6.9 Hz, 2H), 2.71 (t, J=6.9 Hz, 2H), 2.05 (s, 3H); m/z=561 (M+1).

Example 236A (S)-4-Amino-2-[1-(2-fluorobenzyl)-1H-indazol-3-yl]-5-methyl-5-{4-[2-methyl-2-(2H-tetrazol-5-yl)propyl]thiazol-2-yl}-5,7-dihydro-6H-pyrrolo[2,3-d]pyrimidin-6-one

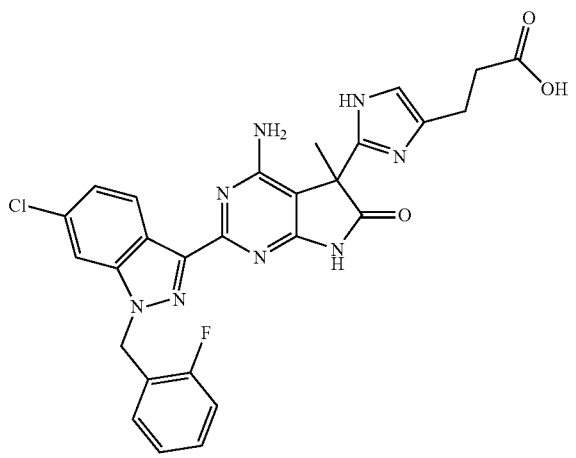 [SMILES: CC1(c2nc(CCC(=O)O)c[nH]2)C(=O)Nc2nc(-c3nn(Cc4ccccc4F)c4cc(Cl)ccc34)nc(N)c21]

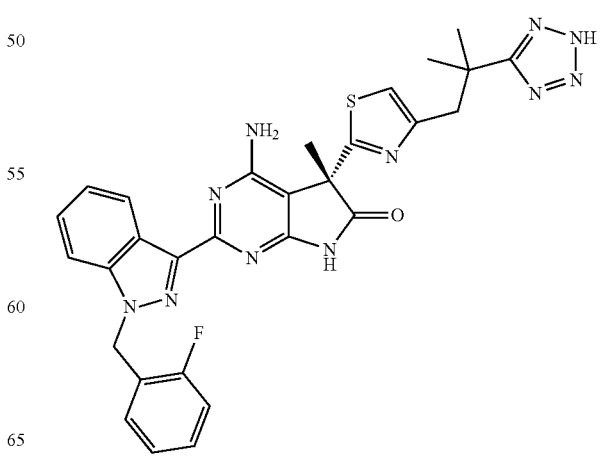

Step A—(S)-Ethyl 3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)-2,2-dimethylpropanoate A flask, containing I-A40 (130 mg, 0.49 mmol), I-35A (183 mg, 0.49 mmol) and potassium bicarbonate (97 mg, 0.97 mmol) in t-BuOH (3 mL), was stirred at 75° C. for 16 h then concentrated in vacuo to dryness. The residue was purified by silica gel chromatography using MeOH:DCM (0-5%) to afford the title product. m/z=600 (M+1)

Step B—(S)-3-(2-{4-Amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)-2,2-dimethylpropanoic acid To a flask containing (S)-ethyl 3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)-2,2-dimethylpropanoate (225 mg, 0.38 mmol) in MeOH (5 mL) and water (2.5 mL) at RT was added LiOH (180 mg, 7.50 mmol). The mixture was stirred at RT for 16 h. To the mixture was added HCl (7.5 mL, 1 N), and the solid was collected by filtration, washed with water (20 mL) and dried in an oven to afford the title compound m/z=572 (M+1).

Step C—(S)-3-(2-{4-Amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)-2,2-dimethylpropanamide To a flask containing (S)-3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)-2,2-dimethylpropanoic acid (190 mg, 0.33 mmol) and di-tert-butyl dicarbonate (160 mg, 0.731 mmol) in DCM (3 mL) at RT was added pyridine (58 mg, 0.73 mmol) and the resulting mixture was stirred at RT for 2 h. To this was added ammonium bicarbonate (79 mg, 0.99 mmol) and the mixture was stirred for 16 h at RT. The reaction was diluted with water, extracted with EtOAc (3×) and the organic layers were combined, dried over anhydr. $Na_2SO_4$, filtered and the filtrate was concentrated in vacuo to dryness. To the residue was added dichloromethane (4 mL) and TFA (2 mL). The mixture was stirred for 2 h at RT before water (10 mL) was added, and the pH of the mixture was adjusted to pH=7 with $NaHCO_3$. The resulting mixture was extracted with DCM (3×), the organic layers were combined, dried over anhydr. $Na_2SO_4$, and filtered. The filtrate was concentrated in vacuo to dryness. The residue was purified by silica gel chromatography using MeOH:DCM (0-5%) to afford the title product m/z=571 (M+1).

Step D—(S)-3-(2-{4-Amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)-2,2-dimethylpropanenitrile To a flask, containing (S)-3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)-2,2-dimethylpropanamide (180 mg, 0.32 mmol) and pyridine (0.5 mL, 6.18 mmol) in DCM (5 mL) at 0° C. was added dropwise TFAA (0.5 mL, 3.54 mmol). The mixture was stirred for 1 h at RT before MeOH (20 mL) was added and the mixture was concentrated in vacuo. The residue was diluted with water, and extracted with EtOAc (3×). The organic layers were combined, dried over anhydr. $Na_2SO_4$, and filtered. The filtrate was concentrated in vacuo to dryness. The residue was purified by silica gel chromatography using MeOH:DCM (0-5%) to afford the title product m/z=553 (M+1).

Step E—(S)-4-Amino-2-[1-(2-fluorobenzyl)-1H-indazol-3-yl]-5-methyl-5-{4-[2-methyl-2-(2H-tetrazol-5-yl)propyl]thiazol-2-yl}-5H-pyrrolo[2,3-d]pyrimidin-6(7H)-one A sealed tube containing (S)-3-(2-{4-amino-2[1-(2-fluorobenzyl)-1H-indazol-3-yl]-5-methyl-6-oxo-6,7-dihydro-5H-pyrrolo[2,3-d]pyrimidin-5-yl}thiazol-4-yl)-2,2-dimethylpropanenitrile (100 mg, 0.181 mmol), sodium azide (118 mg, 1.81 mmol) and ammonium chloride (97 mg, 1.81 mmol) in DMA (3 mL) was stirred at 120° C. for 16 h. The resulting mixture was filtered, and the filtrate was concentrated in vacuo. The residue was then purified by reverse phase HPLC (ACN/water with 0.05% $NH_4HCO_3$ modifier) to afford the title compound Ex-236A. $^1$H NMR (300 MHz, $CD_3OD$) δ 8.69 (d, J=8.4 Hz, 1H), 7.57 (d, J=8.4 Hz, 1H), 7.44 (dd, J=7.5, 7.5 Hz, 1H), 7.31-7.26 (m, 2H), 7.16-7.04 (m, 4H), 5.81 (s, 2H), 3.22 (d, J=6.6 Hz, 2H), 1.76 (s, 3H), 1.52 (s, 3H), 1.48 (s, 3H); m/z=596 (M+1).

Using essentially the same procedure as described in Ex-112B and Ex-236A, the following compounds in Table 20 were prepared.

TABLE 20

| Ex. | Int. SM/Chiral Resolution Step/Column | Structure | Name | m/z (M + 1) |
|---|---|---|---|---|
| 237B | I-11B/- | 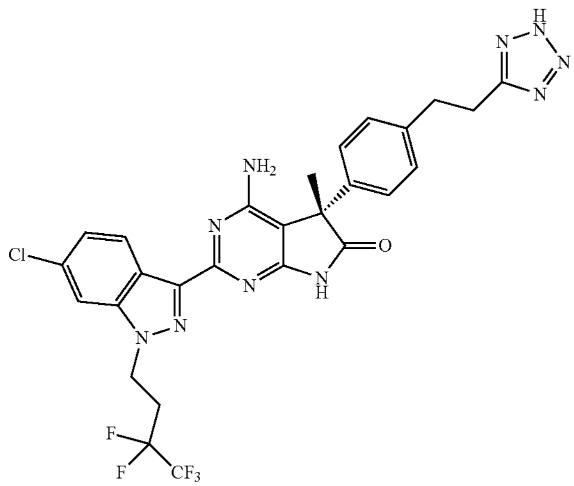 [SMILES: C[C@@]1(c2ccc(CCc3nn[nH]n3)cc2)C(=O)Nc2nc(-c3nn(CCC(F)(F)C(F)(F)F)c4cc(Cl)ccc34)nc(N)c21] | (S)-4-amino-2-[6-chloro-1-(3,3,4,4,4-pentafluorobutyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one | 633 |
| 238A | I-35A/- | 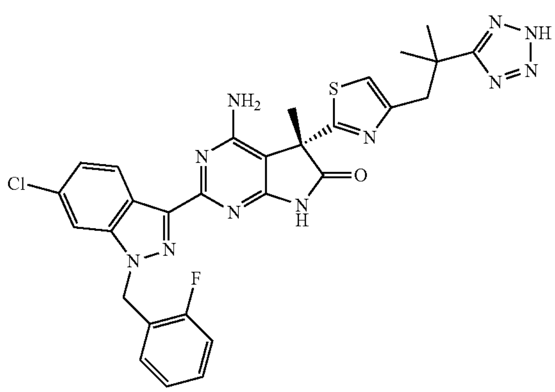 [SMILES: CC(C)(Cc1csc([C@]2(C)C(=O)Nc3nc(-c4nn(Cc5ccccc5F)c5cc(Cl)ccc45)nc(N)c32)n1)c1nn[nH]n1] | (S)-4-amino-2-[6-chloro-1-(2-fluorobenzyl)-1H-indazol-3-yl]-5-methyl-5-{4-[2-methyl-2-(2H-tetrazol-5-yl)propyl]-1,3-thiazol-2-yl}-5,7-dihydro-6H-pyrrolo[2,3-d]pyrimidin-6-one | 630 |
| 239A | I-42A/- | 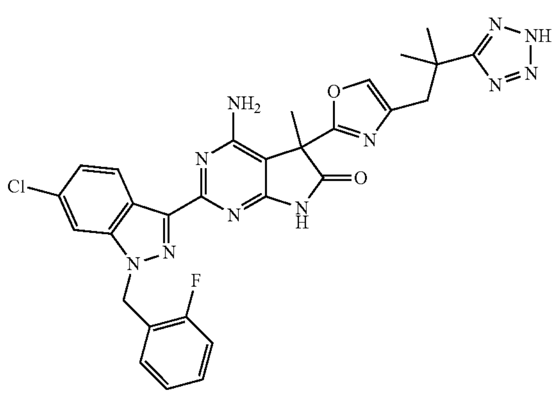 [SMILES: CC(C)(Cc1coc(C2(C)C(=O)Nc3nc(-c4nn(Cc5ccccc5F)c5cc(Cl)ccc45)nc(N)c32)n1)c1nn[nH]n1] | 4-amino-2-[6-chloro-1-(2-fluorobenzyl)-1H-indazol-3-yl]-5-methyl-5-{4-[2-methyl-2-(2H-tetrazol-5-yl)propyl]-1,3-oxazol-2-yl}-5,7-dihydro-6H-pyrrolo[2,3-d]pyrimidin-6-one | 614 |

TABLE 20-continued

| Ex. | Int. SM/Chiral Resolution Step/Column | Structure | Name | m/z (M + 1) |
|---|---|---|---|---|
| 240B | I-11B/- | 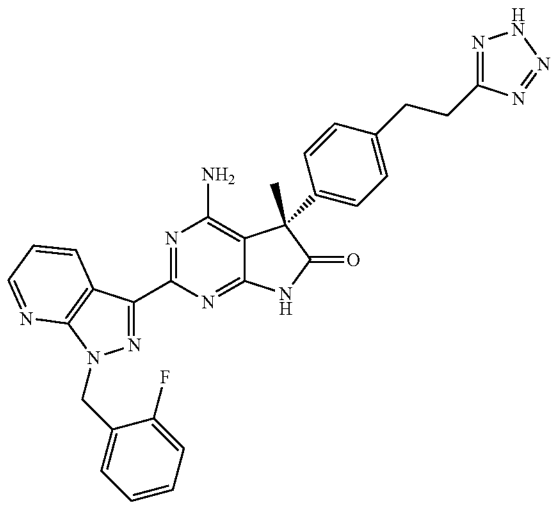 [SMILES: C[C@@]1(c2ccc(CCc3nn[nH]n3)cc2)C(=O)Nc2nc(-c3nn(Cc4ccccc4F)c4ncccc34)nc(N)c21] | (S)-4-amino-2-[1-(2-fluoro-benzyl)-1H-pyrazolo[3,4-b]pyridin-3-yl]-5-methyl-5-{4-[2-(2H-tetrazol-5-yl)ethyl]phenyl}-5,7-dihydro-6H-pyrrolo[2,3-d]pyrimidin-6-one | 562 |
| 241A | I-35A/- | 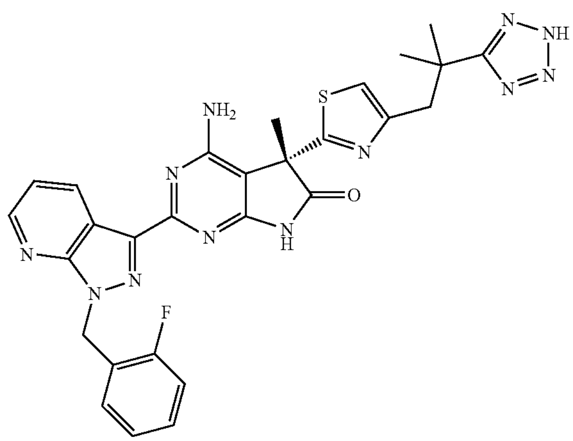 [SMILES: CC(C)(Cc1csc([C@]2(C)C(=O)Nc3nc(-c4nn(Cc5ccccc5F)c5ncccc45)nc(N)c32)n1)c1nn[nH]n1] | (S)-4-amino-2-[1-(2-fluoro-benzyl)-1H-pyrazolo[3,4-b]pyridin-3-yl]-5-methyl-5-{4-[2-methyl-2-(2H-tetrazol-5-yl)propyl]-1,3-thiazol-2-yl}-5,7-dihydro-6H-pyrrolo[2,3-d]pyrimidin-6-one | 597 |
| 242B | I-11B/- | 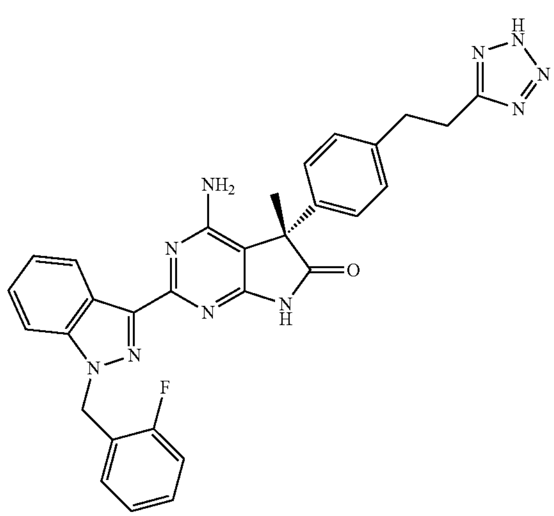 [SMILES: C[C@@]1(c2ccc(CCc3nn[nH]n3)cc2)C(=O)Nc2nc(-c3nn(Cc4ccccc4F)c4ccccc34)nc(N)c21] | (S)-4-amino-2-[1-(2-fluoro-benzyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one | 561 |

TABLE 20-continued

| Ex. | Int. SM/Chiral Resolution Step/Column | Structure | Name | m/z (M + 1) |
|---|---|---|---|---|
| 243A | I-51A/- | 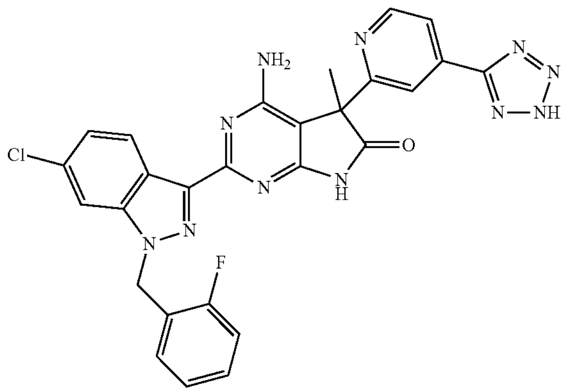 [SMILES: CC1(c2cc(-c3nn[nH]n3)ccn2)C(=O)Nc2nc(-c3nn(Cc4ccccc4F)c4cc(Cl)ccc34)nc(N)c21] | 5-[4-(2H-tetrazol-5-yl)pyridin-2-yl]-4-amino-2-[6-chloro-1-(2-fluorobenzyl)-1H-indazol-3-yl]-5-methyl-5,7-dihydro-6H-pyrrolo[2,3-d]pyrimidin-6-one | 568 |
| 244A | I-78A/- | 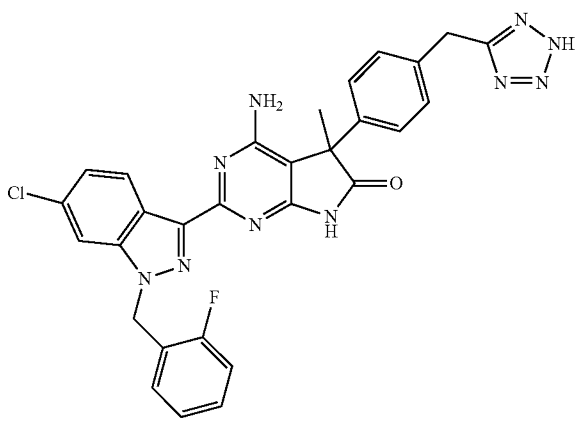 [SMILES: CC1(c2ccc(Cc3nn[nH]n3)cc2)C(=O)Nc2nc(-c3nn(Cc4ccccc4F)c4cc(Cl)ccc34)nc(N)c21] | 5-{4-[(2H-tetrazol-5-yl)methyl]phenyl}-4-amino-2-[6-chloro-2-(2-fluorobenzyl)-1H-indazol-3-yl]-5-methyl-5,7-dihydro-6H-pyrrolo[2,3-d]pyrimidin-6-one | 581 |
| 245B | I-11B/- | 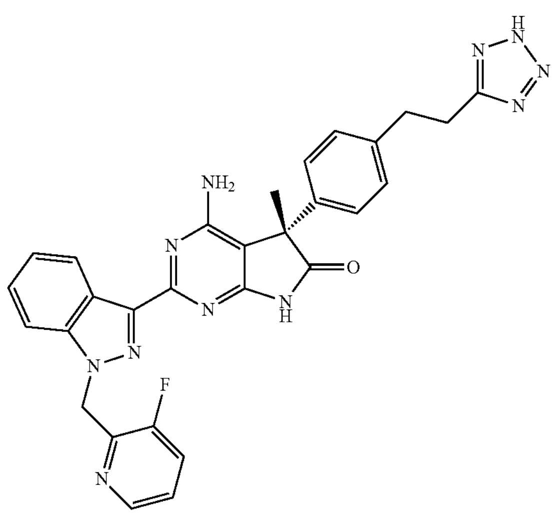 | (S)-5-{4-[2-(2H-tetrazol-5-yl)ethyl]phenyl}-4-amino-2-{1-[(3-fluoropyridin-2-yl)methyl]-1H-indazol-3-yl}-5-methyl-5,7-dihydro-6H-pyrrolo[2,3-d]pyrimidin-6-one | 562 |

TABLE 20-continued

| Ex. | Int. SM/Chiral Resolution Step/Column | Structure | Name | m/z (M + 1) |
|---|---|---|---|---|
| 246A | I-62/Step D/IA | 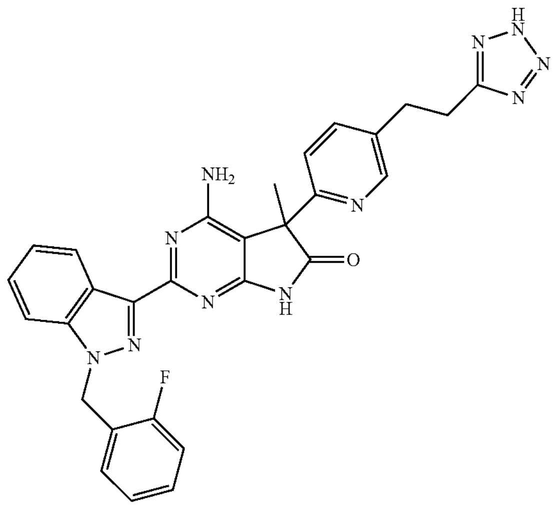 [SMILES: CC1(c2ccc(CCc3nn[nH]n3)cn2)C(=O)Nc2nc(-c3nn(Cc4ccccc4F)c4ccccc34)nc(N)c21] | 5-{5-[2-(2H-tetrazol-5-yl)ethyl]pyridin-2-yl}-4-amino-2-[1-(2-fluorobenzyl)-1H-indazol-3-yl]-5-methyl-5,7-dihydro-6H-pyrrolo[2,3-d]pyrimidin-6-one | 562 |
| 247A | I-62/Step D/IA | 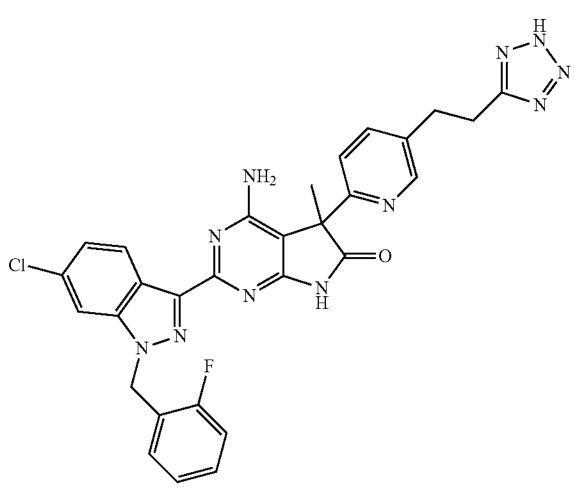 [SMILES: CC1(c2ccc(CCc3nn[nH]n3)cn2)C(=O)Nc2nc(-c3nn(Cc4ccccc4F)c4cc(Cl)ccc34)nc(N)c21] | 5-{5-[2-(2H-tetrazol-5-yl)ethyl]pyridin-2-yl}-4-amino-2-[6-chloro-1-(2-fluorobenzyl)-1H-indazol-3-yl]-5-methyl-5,7-dihydro-6H-pyrrolo[2,3-d]pyrimidin-6-one | 596 |

Example 248B

4-Amino-2-[1-(2-fluorobenzyl)-1H-indazol-3-yl]-5-methyl-5-{4-[2-methyl-2-(2H-tetrazol-5-yl)propyl]oxazol-2-yl}-5,7-dihydro-6H-pyrrolo[2,3-d]pyrimidin-6-one

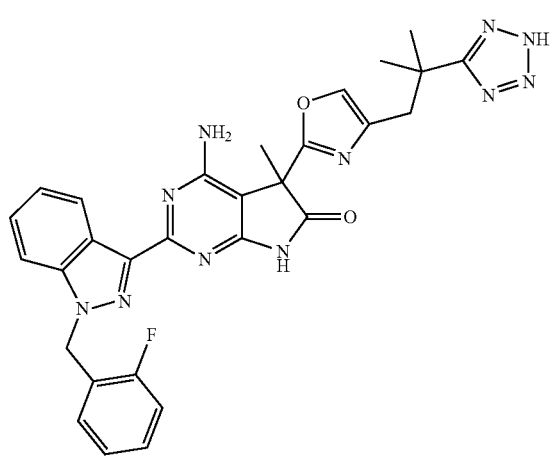 [SMILES: CC(C)(Cc1coc(C2(C)C(=O)Nc3nc(-c4nn(Cc5ccccc5F)c5ccccc45)nc(N)c32)n1)c1nn[nH]n1]

A flask containing Ex-239A (60 mg, 0.098 mmol) and palladium on carbon (80 mg, 0.068 mmol, 10 w %) in MeOH (2 mL) was evacuated and flushed (3×) with nitrogen, followed by flushing with hydrogen. The mixture was stirred for 5 h at RT under an atmosphere of hydrogen (1.5 atm). The palladium on carbon was filtered out and washed with MeOH (3×), EtOAc (3×), and DCM (3×). The combined filtrate was concentrated in vacuo. The residue was then purified by reverse phase HPLC (ACN/water with 0.05% NH$_4$HCO$_3$ modifier) to afford the title compound $^1$H NMR (300 MHz, CD$_3$OD) δ 8.68 (d, J=8.4 Hz, 1H), 7.54 (d, J=8.4 Hz, 1H), 7.41 (dd, J=7.2, 7.2 Hz, 1H), 7.32-7.23 (m, 2H), 7.14-7.00 (m, 4H), 5.78 (s, 2H), 2.91 (d, J=8.7 Hz, 2H), 1.83 (s, 3H), 1.43 (s, 3H), 1.40 (s, 3H); m/z=580 (M+1).

Example 249B

4-Amino-2-[6-fluoro-1-(2-fluorobenzyl)-1H-indazol-3-yl]-5-methyl-5-[3-(1H-tetrazol-5-yl)phenyl]-5,7-dihydro-6H-pyrrolo[2,3-d]pyrimidin-6-one

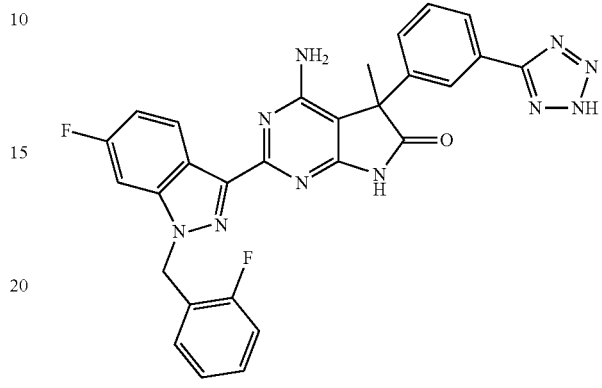

Step A—3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}benzonitrile A flask containing I-A23 (126 mg, 0.44 mmol), I-69B (98 mg, 0.37 mmol) and potassium bicarbonate (110 mg, 1.10 mmol) in t-BuOH (1.8 mL) was stirred at 80° C. for 16 h. The mixture was then concentrated in vacuo to dryness. The residue was purified by silica gel chromatography using (EtOAc:EtOH 3:1):Hexane (0-30%) to afford the title product.

Step B—4-Amino-2-[6-fluoro-1-(2-fluorobenzyl)-1H-indazol-3-yl]-5-methyl-5-[3-(1H-tetrazol-5-yl)phenyl]-5,7-dihydro-6H-pyrrolo[2,3-d]pyrimidin-6-one To a flask containing 3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}benzonitrile (120 mg, 0.24 mmol) in toluene (1 mL) was added dibutyltin oxide (6.0 mg, 0.02 mmol) and TMS azide (0.06 mL, 0.47 mmol). The resulting mixture was stirred at 130° C. for 2 days, and then concentrated in vacuo. The residue was purified by reverse phase HPLC (ACN/water with 0.05% formic acid modifier) to afford the title compound Ex-249B. $^1$H NMR (500 MHz, DMSO-d$_6$): δ 11.15 (s, 1H), 8.74 (dd, J=10 Hz, 5 Hz, 1H), 7.95-7.88 (m, 2H), 7.68 (dd, J=10 Hz, 5 Hz, 1H), 7.49-7.08 (m, 7H), 6.57 (br s, 2H), 5.77 (s, 2H), 1.83 (s, 3H); m/z=551 (M+1).

Using essentially the same procedure described in Example 249B, the following compounds in Table 21 were prepared

TABLE 21

| Ex. | Int. SM/Chiral Resolution Step/Column | Structure | Name | m/z (M + 1) |
|---|---|---|---|---|
| 250B | I-70B/- | 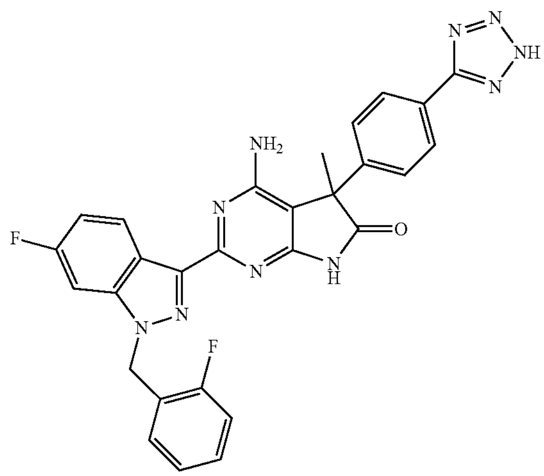 [SMILES: CC1(c2ccc(-c3nn[nH]n3)cc2)C(=O)Nc2nc(-c3nn(Cc4ccccc4F)c4cc(F)ccc34)nc(N)c21] | 4-amino-2-[6-fluoro-1-(2-fluorobenzyl)-1H-indazol-3-yl]-5-methyl-5-[4-(1H-tetrazol-5-yl)phenyl]-5,7-dihydro-6H-pyrrolo[2,3-d]pyrimidin-6-one | 551 |
| 251B | I-69/Step B/AS | 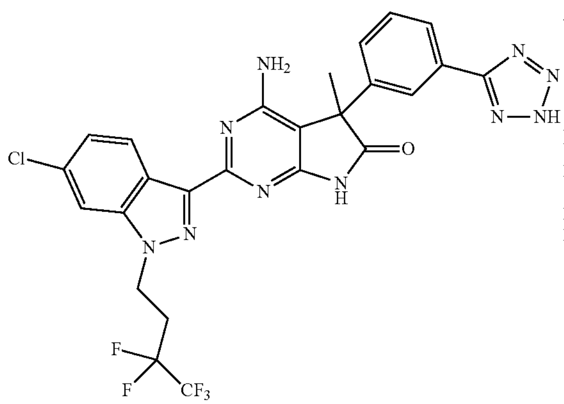 [SMILES: CC1(c2cccc(-c3nn[nH]n3)c2)C(=O)Nc2nc(-c3nn(CCC(F)(F)C(F)(F)F)c4cc(Cl)ccc34)nc(N)c21] | 4-amino-2-[6-chloro-1-(3,3,4,4,4-pentafluorobutyl)-1H-indazol-3-yl]-5-methyl-5-[3-(1H-tetrazol-5-yl)phenyl]-5,7-dihydro-6H-pyrrolo[2,3-d]pyrimidin-6-one | 605 |
| 252B | I-69/Step B/AS | 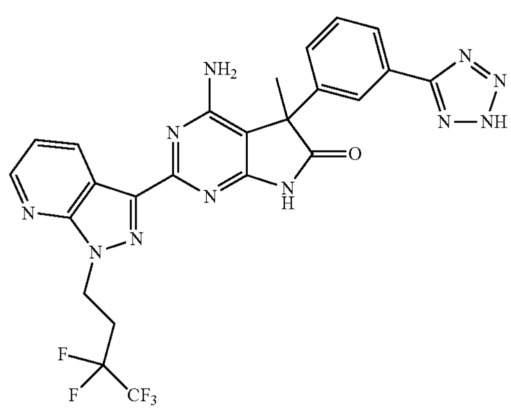 [SMILES: CC1(c2cccc(-c3nn[nH]n3)c2)C(=O)Nc2nc(-c3nn(CCC(F)(F)C(F)(F)F)c4ncccc34)nc(N)c21] | 4-amino-5-methyl-2-[1-(3,3,4,4,4-pentafluorobutyl)-1H-pyrazolo[3,4-b]pyridin-3-yl]-5-[3-(2H-tetrazol-5-yl)phenyl]-5,7-dihydro-6H-pyrrolo[2,3-d]pyrimidin-6-one | 572 |

TABLE 21-continued

| Ex. | Int. SM/Chiral Resolution Step/Column | Structure | Name | m/z (M + 1) |
|---|---|---|---|---|
| 253A | I-72/Step A/IA | 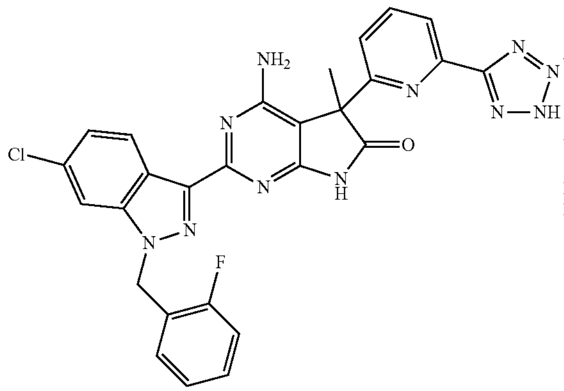 | 5-[6-(2H-tetrazol-5-yl)pyridin-2-yl]-4-amino-2-[6-chloro-1-(2-fluorobenzyl)-1H-indazol-3-yl]-5-methyl-5,7-dihydro-6H-pyrrolo[2,3-d]pyrimidin-6-one | 568 |

Example 254A

6-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyridine-3-carboxylic acid

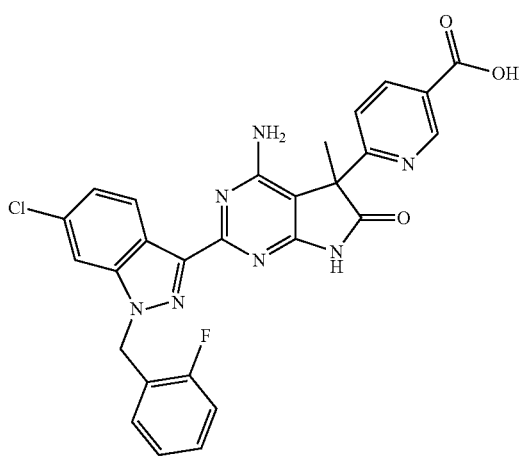 [SMILES: CC1(c2ccc(C(=O)O)cn2)C(=O)Nc2nc(-c3nn(Cc4ccccc4F)c4cc(Cl)ccc34)nc(N)c21]

Step A—6-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}nicotinonitrile A flask containing I-71A (89 mg, 0.33 mmol), I-A15 (100 mg, 0.33 mmol) and potassium bicarbonate (49 mg, 0.49 mmol) in t-BuOH (5 mL) was stirred for 16 h at 70° C., and then concentrated in vacuo. The residue was purified by silica gel column chromatography with MeOH:DCM (0-10%) to afford the title compound.

Step B—Methyl 6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}nicotinate To a flask containing 6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}nicotinonitrile (120 mg, 0.23 mmol) in MeOH (10 mL) at RT was added dropwise sulfurous dichloride (3 mL). The resulting mixture was stirred for 16 h at 80° C. then concentrated in vacuo. To the residue was added aq. sat. NaHCO$_3$ and extracted with EtOAc (3×). The organic layers were combined, washed with brine, dried over anhydr. Na$_2$SO$_4$, and filtered. The filtrate was concentrated in vacuo. The residue was purified by silica gel column chromatography with MeOH:DCM (0-10%) to afford the title compound.

Step C—6-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}nicotinic acid A flask containing methyl 6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}nicotinate (90 mg, 0.16 mmol), lithium hydroxide (1.6 mL, 1 M in water, 1.6 mmol) in MeOH (5 mL) was stirred for 16 h at RT, and then concentrated in vacuo. Water (3 mL) and hydrogen chloride (1 N, 1.6 mL) were added. The resulting solid was collected by filtration and washed with water (3×). The residue was purified by reverse phase HPLC (ACN/water with 0.05% TFA modifier) to afford the title compound Ex-254A. $^1$H NMR (300 MHz, CD$_3$OD) δ 9.11 (d, J=1.5 Hz, 1H), 8.67 (d, J=8.7 Hz, 1H), 8.28 (dd, J=8.1, 2.1 Hz, 1H), 7.64 (s, 1H), 7.49 (d, J=8.1 H, 1H), 7.37-7.29 (m, 1H), 7.25 (dd, J=8.7, 1.5 Hz, 1H), 7.18-7.07 (m, 3H), 5.77 (s, 2H), 1.92 (s, 3H); m/z=544 (M+1).

Example 255A

6-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}picolinic acid

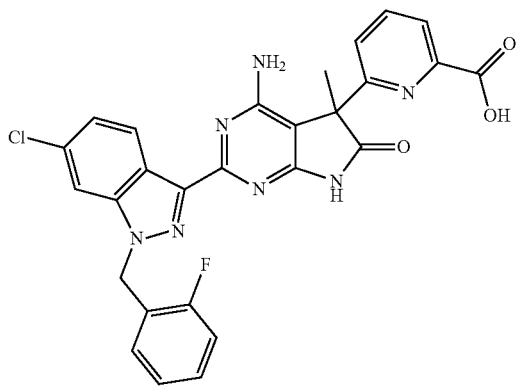 [SMILES: CC1(c2cccc(C(=O)O)n2)C(=O)Nc2nc(-c3nn(Cc4ccccc4F)c4cc(Cl)ccc34)nc(N)c21]

Step A—6-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}picolinonitrile A flask containing I-72 (430 mg, 1.60 mmol), I-A15 (510 mg, 1.68 mmol) and potassium bicarbonate (802 mg, 8.01 mmol) in t-BuOH (10 mL) was stirred at 70° C. for 16 h. The reaction mixture was concentrated in vacuo. The residue was purified by silica gel column chromatography with MeOH:DCM (0-10%) to afford the title racemic compound. The racemic material was resolved using Chiral HPLC (CHIRALPAK® IA) to afford isomer A (faster eluting) and isomer B (slower eluting).

Step B—Methyl 6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}picolinate To a flask containing 6-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}picolinonitrile isomer A (40 mg, 0.076 mmol) in MeOH (10 mL) at RT was added dropwise sulfurous dichloride (1 mL, 13.70 mmol). The resulting mixture was stirred for 16 h at 80° C., and then the mixture was concentrated in vacuo. The residue was diluted with aq. sat. NaHCO$_3$ and extracted with EtOAc (3×). The organic layers were combined, washed with brine, dried over anhydr. Na$_2$SO$_4$, and filtered. The filtrate was concentrated in vacuo. The residue was purified by silica gel column chromatography with MeOH:DCM (0-10%) to afford the title compound.

Step C—6-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}picolinic acid A flask containing methyl 6-(4-amino-2-(6-chloro-1-(2-fluorobenzyl)-1H-indazol-3-yl)-5-methyl-6-oxo-6,7-dihydro-5H-pyrrolo[2,3-d]pyrimidin-5-yl)picolinate (40 mg, 0.072 mmol) and lithium hydroxide (69 mg, 2.87 mmol) in a mixture of water (1.5 mL):THF (1.5 mL) was stirred for 16 h at RT. To this was added hydrochloric acid (28.7 mL, 0.1 N). The solid was collected by filtration, washed with water (2×5 mL), and dried in an oven to afford the title compound Ex-255A. $^1$H NMR (300 MHz, CD$_3$OD) δ 8.65 (d, J=8.7 Hz, 1H), 8.08 (d, J=7.8 Hz, 1H), 7.99 (dd, J=7.8, 7.8 Hz, 1H), 7.71 (d, J=7.8 Hz, 1H), 7.64 (s, 1H), 7.36-7.22 (m, 2H), 7.17-7.06 (m, 3H), 5.76 (s, 2H), 1.91 (s, 3H); m/z=544 (M+1).

Example 256B (S)-4-Amino-2-[6-chloro-1-(2-fluorobenzyl)-1H-indazol-3-yl]-5-methyl-5-{4-[2-(5-oxo-4,5-dihydro-1,2,4-oxadiazol-3-yl)ethyl]phenyl}-5,7-dihydro-6H-pyrrolo[2,3-d]pyrimidin-6-one

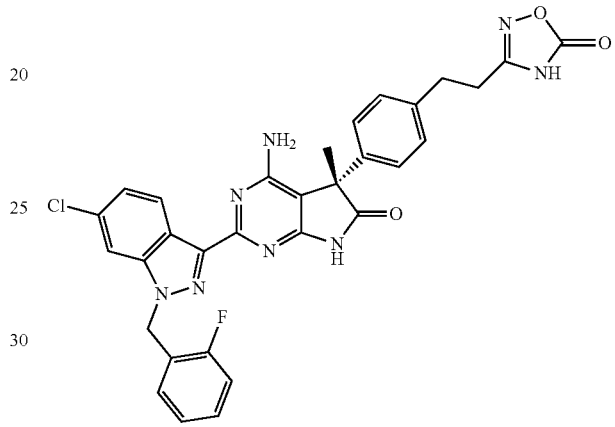

Step A—(S)-3-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanamide To a flask containing Ex-47B (1.0 g, 1.58 mmol) in DMF (10 mL) was added di(1H-imidazol-1-yl)methanone (1.28 g, 7.88 mmol). The mixture was stirred at RT for 30 min before ammonium chloride (0.17 g, 3.15 mmol) was added. The resulting mixture was stirred at RT for 16 h, then diluted with water, and extracted with EtOAc (3×). The organic layers were combined, dried over anhydr. Na$_2$SO$_4$, filtered, and the filtrate was concentrated in vacuo to dryness. The residue was purified by silica gel chromatography using MeOH:DCM (0-5%) to afford the title product, m/z=570 (M+1).

Step B—(S)-3-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanenitrile To a flask containing (S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanamide (0.8 g, 1.40 mmol) and pyridine (0.5 mL, 6.18 mmol) in DCM (5 mL) at 0° C., was added dropwise TFAA (0.5 mL, 3.54 mmol). The mixture was stirred at RT for 1 h. The mixture was diluted with MeOH and concentrated in vacuo. The residue was diluted with water, extracted with EtOAc (3×). The organic layers were combined, washed with brine, dried over anhydr. Na$_2$SO$_4$, and filtered. The filtrate was concentrated in vacuo. The residue was purified by silica gel column chromatography with MeOH:DCM (0-5%) to afford the title compound. m/z=552 (M+1).

Step C—(S)-3-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl)phenyl}-N-hydroxypropanimidamide A flask, containing (S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanenitrile (150 mg, 0.272 mmol) and aqueous hydroxylamine (7.5 mL, 0.272 mmol, 50%) in EtOH (7.5 mL) was stirred at 30° C. for 16 h. The mixture was concentrated in vacuo and the residue was lyophilized to afford the title compound m/z=585 (M+1).

Step D—(S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenethyl)-1,2,4-oxadiazol-5(4H)-one A flask containing (S)-3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)-N-hydroxypropanimidamide (120 mg, 0.21 mmol), di(1H-imidazol-1-yl)methanone (332 mg, 2.05 mmol,) in THF (12 mL) was stirred at RT for 16 h and at 50° C. for 24 h. The mixture was concentrated in vacuo, and aq. sat. NaHCO₃ was added to the residue. The mixture was extracted with EtOAc (3×). The organic layers were combined, washed with brine, dried over anhydr. Na₂SO₄, and filtered. The filtrate was concentrated in vacuo. The residue was purified by silica gel column chromatography with MeOH:DCM (0-10%) then by reverse phase HPLC (ACN/water with 0.05% TFA modifier) to afford the title compound Ex-256B. ¹H NMR (300 MHz, CD₃OD) δ 8.65 (d, J=8.7 Hz, 1H), 7.62 (s, 1H), 7.33-7.21 (m, 6H), 7.15-7.04 (m, 3H), 4.84 (s, 2H), 2.94 (t, J=7.2 Hz, 2H), 2.78 (t, J=7.2 Hz, 2H), 1.98 (s, 3H); m/z=611 (M+1).

Example 257A

[2-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)ethyl]phosphonic acid

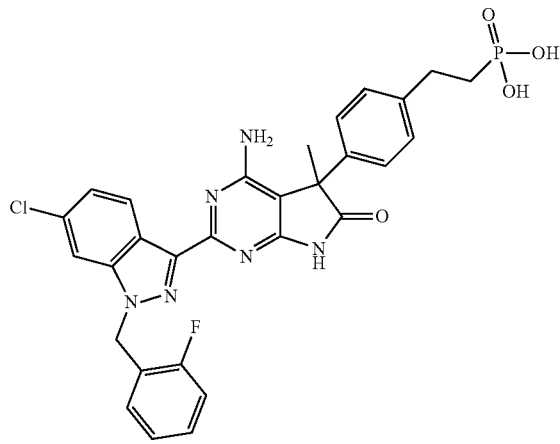 [SMILES: CC1(c2ccc(CCP(=O)(O)O)cc2)C(=O)Nc2nc(-c3nn(Cc4ccccc4F)c4cc(Cl)ccc34)nc(N)c21]

Step A—4-Amino-2-[6-chloro-1-(2-fluorobenzyl)-1H-indazol-3-yl]-5-[4-(diethoxymethyl)phenyl]-5-methyl-5H-pyrrolo[2,3-d]pyrimidin-6(7H)-one A flask containing I-A15 (200 mg, 0.66 mmol), I-49 (228 mg, 0.66 mmol) and potassium bicarbonate (79 mg, 0.79 mmol) in t-BuOH (4 mL) was stirred at 70° C. for 16 h. The reaction mixture was concentrated in vacuo to dryness to afford the title compound. m/z=601 (M+1).

Step B—4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}benzaldehyde To a flask containing 4-amino-2-[6-chloro-1-(2-fluorobenzyl)-1H-indazol-3-yl]-5-[4-(diethoxymethyl)phenyl]-5-methyl-5H-pyrrolo[2,3-d]pyrimidin-6(7H)-one (250 mg, 0.25 mmol) in DCM (10 ml) at RT was added TFA (1 mL) dropwise. The resulting mixture was stirred for 16 h at RT then concentrated in vacuo, diluted with EtOAc, washed with aq. sat. NaHCO₃, dried over anhydr. Na₂SO₄, and filtered. The filtrate was concentrated in vacuo. The residue was purified by silica gel column chromatography with MeOH:DCM (0-10%) to afford the title compound. m/z=527 (M+1).

Step C—Diethyl 4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}styrylphosphonate A flask containing 4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}benzaldehyde (120 mg, 0.228 mmol), diethyl ((triphenylphosphoranylidene)methyl) phosphonate (470 mg, 1.139 mmol), (prepared following J. Org. Chem., 1996, 61 (22), 7697) in a DMF (2 mL):toluene (10 mL) mixture was stirred at 90° C. for 16 h. The reaction was diluted with EtOAc, washed with brine, dried over anhydr. Na₂SO₄, and filtered. The filtrate was concentrated in vacuo. The residue was purified by silica gel column chromatography with MeOH:DCM (0-10%) to afford the title compound. m/z=661 (M+1).

Step D—Diethyl 4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenethylphosphonate A flask, containing diethyl 4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}styrylphosphonate (65 mg, 0.098 mmol), sodium acetate (40 mg, 0.492 mmol) and 4-methylbenzenesulfonhydrazide (55 mg, 0.295 mmol) in a 1,2-dimethoxyethane (20 mL):water (2 mL) mixture was stirred at 80° C. for 16 h. The reaction was diluted with water, extracted with EtOAc (3×). The organic layers were combined, washed with brine, dried over anhydr. Na₂SO₄, and filtered. The filtrate was concentrated in vacuo. The residue was purified by silica gel column chromatography with MeOH:DCM (0-10%) to afford racemic title product. The racemic material was resolved using Chiral HPLC (CHIRALPAK® IA) to afford isomer A (faster eluting) and isomer B (slower eluting). m/z=663 (M+1).

Step E—4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenethylphosphonic acid To a flask containing diethyl 4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenethylphosphonate isomer A (25 mg, 0.038 mmol) in DCM (20 mL) at 0° C. was added dropwise bromotrimethylsilane (2 mL). The resulting mixture was stirred for 5 days at RT. The mixture was concentrated in vacuo, and diluted with MeOH (2 mL). The resulting mixture stirred at RT for 30 min. The mixture was then concentrated in vacuo, and the residue was purified by reverse phase HPLC (ACN/water with 0.05% TFA modifier) to afford the title compound Ex-257A. $^1$H NMR (300 MHz, CD$_3$OD) δ 8.56 (d, J=8.7 Hz, 1H), 7.79 (s, 1H), 7.43-7.21 (m, 6H), 7.19-7.08 (m, 3H), 5.82 (s, 2H), 2.91-2.82 (m, 2H), 1.99-1.88 (m, 2H), 1.81 (s, 3H); m/z=607 (M+1).

Example 258B 2-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)ethanesulfonic acid

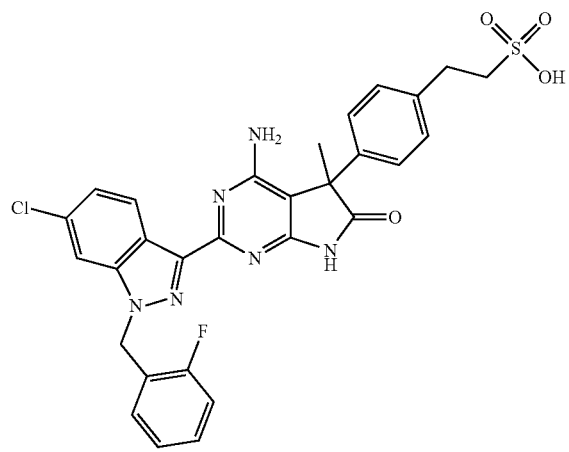 [SMILES: CC1(c2ccc(CCS(=O)(=O)O)cc2)C(=O)Nc2nc(-c3nn(Cc4ccccc4F)c4cc(Cl)ccc34)nc(N)c21]

Step A—Ethyl 2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)ethenesulfonate To a flask under an inert atmosphere of nitrogen, containing ethyl (diethoxyphosphoryl) methanesulfonate (3.46 g, 13.28 mmol) in THF (70 mL) at −78° C. was added dropwise n-butyllithium (4.3 mL, 10.63 mmol, 2.5 M in hexane). The resulting mixture was stirred for 30 min at −78° C. before 4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}benzaldehyde (700 mg, 1.33 mmol) was added, and the resulting mixture was stirred for 16 h at RT. The reaction was quenched by the addition of aq. sat. NH$_4$Cl, extracted with EtOAc (3×). The organic layers were combined, washed with brine, dried over anhydr. Na$_2$SO$_4$, and filtered. The filtrate was concentrated in vacuo. The residue was purified by silica gel column chromatography with MeOH:DCM (0-10%) to afford the title compound m/z=633 (M+1).

Step B—2-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)ethanesulfonic acid A flask, containing ethyl 2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)ethenesulfonate (750 mg, 1.19 mmol), sodium acetate (1.46 g, 17.77 mmol), 4-methylbenzenesulfonhydrazide (2.20 mg, 11.85 mmol) in a 1,2-dimethoxyethane (100 mL):water (20 mL) mixture was stirred at 80° C. for 6 h. The reaction was diluted with water, extracted with EtOAc (3×). The organic layer was washed with brine, dried over anhydr. Na$_2$SO$_4$, filtered and the filtrate was concentrated in vacuo. The residue was purified by reverse phase HPLC (ACN/water) to afford the title racemic compound Ex-258. The racemic material was resolved using chiral SFC (CHIRALPAK® IC) to afford isomer Ex-258A (faster eluting) and isomer Ex-258B (slower eluting). $^1$H NMR (300 MHz, CD$_3$OD) δ 8.71 (d, J=8.7 Hz, 1H), 7.68 (d, J=1.5 Hz, 1H), 7.41-7.30 (m, 6H), 7.27-7.10 (m, 3H), 5.81 (s, 2H), 3.13-3.00 (m, 4H), 1.89 (s, 3H); m/z=607 (M+1).

Example 259B (S)-3-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)-N-(methylsulfonyl)propanamide

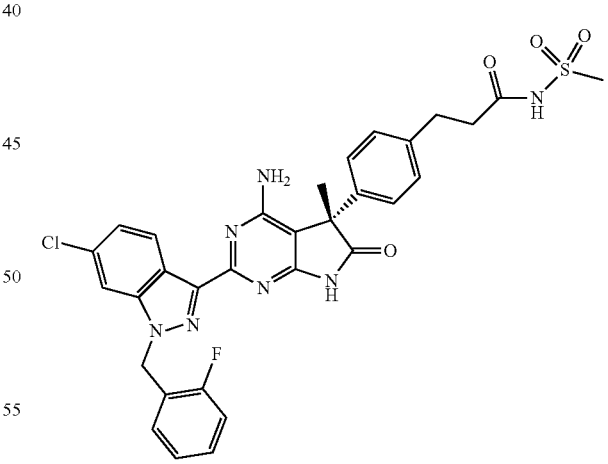

A flask containing Ex-47B (100 mg, 0.17 mmol), 4-dimethylaminopyridine (26 mg, 0.21 mmol) and N-(3-dimethylaminopropyl)-N'-ethylcarbodiimide hydrochloride (47 mg, 0.24 mmol) in DMF (16 mL) was stirred at RT for 30 min before methanesulfonamide (50 mg, 0.52 mmol) was added. The resulting mixture was stirred for 16 h at RT. The reaction was quenched by the addition of water, and extracted with EtOAc (3×). The organic layer was washed with brine, dried over anhydr. Na$_2$SO$_4$, filtered, and the filtrate was concentrated in vacuo. The residue was purified by silica gel column chromatography with MeOH:DCM (0-8%). The residue was purified by reverse phase HPLC (ACN/water with 0.05% NH$_4$HCO$_3$ modifier) to afford the title compound Ex-259B. $^1$H NMR (CD$_3$OD, 400 MHz): δ 8.71 (d, J=8.8 Hz, 1H), 7.68 (s, 1H), 7.39-7.26 (m, 6H), 7.20-7.11 (m, 3H), 5.81 (s, 2H), 3.06 (s, 3H), 2.95 (t, J=7.2 Hz, 1H), 2.59 (t, J=7.2 Hz, 2H), 1.89 (s, 3H); m/z=648 (M+1).

Example 260A (4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenoxy)acetic acid

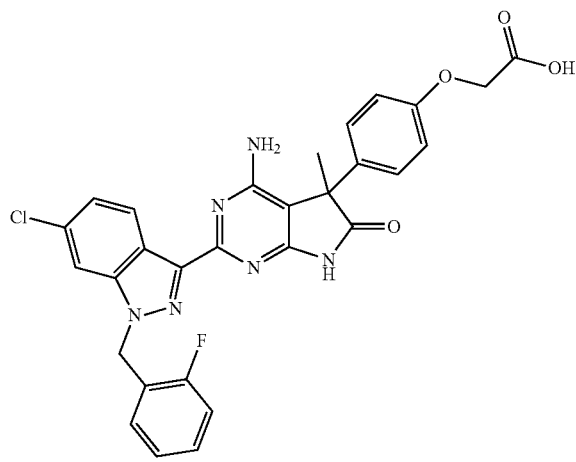 [SMILES: CC1(c2ccc(OCC(=O)O)cc2)C(=O)Nc2nc(-c3nn(Cc4ccccc4F)c4cc(Cl)ccc34)nc(N)c21]

Step A—4-Amino-2-[6-chloro-1-(2-fluorobenzyl)-1H-indazol-3-yl]-5-(4-methoxyphenyl)-5-methyl-5H-pyrrolo[2,3-d]pyrimidin-6(7H)

A flask, containing I-A15 (200 mg, 0.59 mmol), I-50A (161 mg, 0.59 mmol) and potassium bicarbonate (177 mg, 1.77 mmol) in t-BuOH (5 mL) was stirred at 75° C. for 16 h. The reaction was quenched by the addition of brine, and extracted with EtOAc (3×). The organic layers were combined, washed with brine, dried over anhydr. Na$_2$SO$_4$, and filtered. The filtrate was concentrated in vacuo. The residue was purified by silica gel column chromatography with MeOH:DCM (0-10%) to afford the title compound m/z=529 (M+1).

Step B—4-Amino-2-[6-chloro-1-(2-fluorobenzyl)-1H-indazol-3-yl]-5-(4-hydroxyphenyl)-5-methyl-5H-pyrrolo[2,3-d]pyrimidin-6(7H)-one In a flask containing 4-amino-2-[6-chloro-1-(2-fluorobenzyl)-1H-indazol-3-yl]-5-(4-methoxyphenyl)-5-methyl-5H-pyrrolo[2,3-d]pyrimidin-6(7H) (255 mg, 0.48 mmol), and tribromoborane (1 mL) in DCM (5 mL) at 0° C. The resulting mixture was stirred at RT for 16 h. The reaction was quenched by the addition of ice water. The pH of the resulting mixture was adjusted to pH 8 with NaHCO$_3$, and the resulting mixture was extracted with EtOAc (3×). The organic layers were combined, washed with brine, dried over anhydr. Na$_2$SO$_4$, and filtered. The filtrate was concentrated in vacuo. The residue was dissolved with hydrobromic acid (40%, 8 mL), and stirred for 16 h at 80° C. The reaction was poured into ice water. The pH of the resulting solution was adjusted to pH 8 with NaHCO$_3$. extracted with EtOAc (3×). The organic layers were combined, washed with brine, dried over anhydr. Na$_2$SO$_4$, and filtered. The filtrate was concentrated in vacuo. The residue was purified by silica gel column chromatography with MeOH:DCM (0-10%) to afford the title compound m/z=515 (M+1).

Step C—Ethyl 2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenoxy) acetate To a flask wrapped in aluminum foil, were placed 4-amino-2-[6-chloro-1-(2-fluorobenzyl)-1H-indazol-3-yl]-5-(4-hydroxyphenyl)-5-methyl-5H-pyrrolo[2,3-d]pyrimidin-6(7H)-one (80 mg, 0.16 mmol), silver carbonate (880 mg, 3.20 mmol), and ethyl 2-bromoacetate (7 mL) in acetonitrile (80 mL). The mixture was stirred at 80° C. for 16 h. The solid was filtered out and washed with dimethyl sulfoxide (3×). The filtrate was concentrated in vacuo. The residue was purified by reverse phase HPLC (ACN/water with 0.05% NH$_4$HCO$_3$ modifier) to afford the title compound. m/z=601 (M+1).

Step D—2-(4-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenoxy) acetic acid A flask containing ethyl 2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenoxy)acetate (55 mg, 0.09 mmol) and lithium hydroxide monohydrate (110 mg, 2.62 mmol) in a mixture of THF (4 mL):water (4 mL):MeOH (2 mL) was stirred at RT for 16 h. The resulting mixture was concentrated in vacuo. The residue was purified by reverse phase HPLC (ACN/water with 0.05% NH$_4$HCO$_3$ modifier). The fractions were combined and concentrated in vacuo. The pH of the resulting solution was adjusted to pH 4 with hydrochloric acid (1 N). The solid was collected by filtration, washed with water (2×), and dried in an oven to afford the title product Ex-260A. $^1$H NMR (400 MHz, DMSO-d$_6$): δ 13.01 (brs, 1H), 11.07 (s, 1H), 8.71 (d, J=8.7 Hz, 1H), 8.01 (d, J=1.2 Hz, 1H), 7.40-7.30 (m, 1H), 7.28 (dd, J=8.8, 1.4 Hz, 2H), 7.18-7.14 (m, 4H), 7.87 (d, J=8.8 Hz, 2H), 6.60-6.50 (br, 2H), 5.81 (s, 2H), 4.63 (s, 2H), 1.75 (s, 3H); m/z=573 (M+1).

Example 261C

3-[1-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyrrolidin-3-yl]propanoic acid

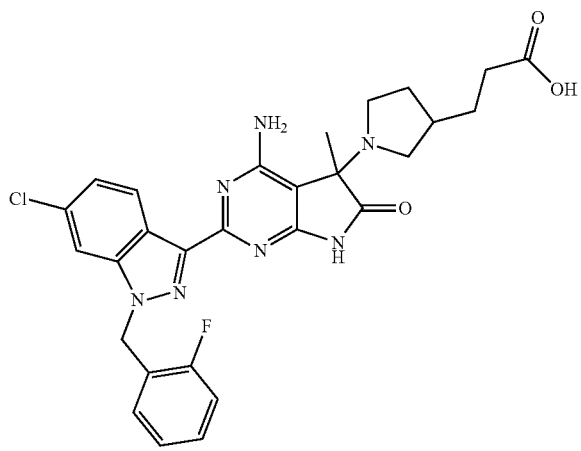 [SMILES: CC1(N2CCC(CCC(=O)O)C2)C(=O)Nc2nc(-c3nn(Cc4ccccc4F)c4cc(Cl)ccc34)nc(N)c21]

Step A—Ethyl 4-amino-2-[6-chloro-1-(2-fluorobenzyl)-1H-indazol-3-yl]-5-methyl-6-oxo-6,7-dihydro-5H-pyrrolo[2,3-d]pyrimidine-5-carboxylate A flask containing I-A15 (1 g, 2.95 mmol), I-30 (0.84 g, 3.54 mmol) and potassium bicarbonate (1.47 g, 14.74 mmol) in t-BuOH (15 mL) was stirred at 70° C. for 16 h. The resulting mixture was concentrated in vacuo. DCM and MeOH were added to the residue, and solids were removed by filtration. The filtrate was concentrated in vacuo, and the residue was re-crystallized from EtOAc:petroleum ether. m/z=495 (M+1).

Step B—4-Amino-2-[6-chloro-1-(2-fluorobenzyl)-1H-indazol-3-yl]-5-methyl-5H-pyrrolo[2,3-d]pyrimidin-6(7H)-one In a flask containing ethyl 4-amino-2-[6-chloro-1-(2-fluorobenzyl)-1H-indazol-3-yl]-5-methyl-6-oxo-6,7-dihydro-5H-pyrrolo[2,3-d]pyrimidine-5-carboxylate (1.3 g, 2.63 mmol) in EtOH (50 mL) at 0° C. was added sodium hydroxide (6.6 mL, 13.2 mmol, 2 M) dropwise. The resulting mixture was stirred for 10 min at 0° C. before the reaction was quenched by the addition of aq. sat. NH$_4$Cl and extracted with EtOAc (3×). The organic layers were combined, washed with brine, dried over anhydr. Na$_2$SO$_4$, and filtered. The filtrate was concentrated in vacuo and the residue was purified by silica gel column chromatography with EtOAc:petroleum ether to afford the title compound. m/z=423 (M+1).

Step C—Ethyl 3-(1-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyrrolidin-3-yl)propanoate To a flask containing 4-amino-2-[6-chloro-1-(2-fluorobenzyl)-1H-indazol-3-yl]-5-methyl-5H-pyrrolo[2,3-d]pyrimidin-6(7H)-one (300 mg, 0.71 mmol) in DCM (10 mL) was added bromine (227 mg, 1.42 mmol). The mixture was stirred at RT for 3 h before ethyl 3-(pyrrolidin-3-yl)propanoate (1460 mg, 8.51 mmol) was added. The resulting mixture was stirred for 2 h at RT, then quenched by the addition of water, and extracted with EtOAc (3×). The organic layers were combined, washed with brine, dried over anhydr. Na$_2$SO$_4$, and filtered. The filtrate was concentrated in vacuo. The residue was purified by silica gel column chromatography with MeOH:DCM (0-10%) to afford the racemic title compound. The racemic material was resolved using Chiral HPLC (CHIRALPAK IA) to afford 4 peaks, isomer A (faster eluting), isomer B (second eluting), isomer C (third eluting), and isomer D (slower eluting). m/z=592 (M+1).

Step D—3-(1-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyrrolidin-3-yl)propanoic acid A flask containing ethyl 3-(1-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyrrolidin-3-yl)propanoate isomer C (47 mg, 0.079 mmol), and lithium hydroxide (2 mL, 2 M in water) in THF (6 mL) was stirred for 16 h at RT. The mixture was concentrated in vacuo, water (3 mL) and hydrogen chloride (2 mL, 2 M in water) were added to the residue. Solids were collected by filtration and washed with water (3×) and dried to afford the title product Ex-261C. $^1$H NMR (400 MHz, CD$_3$OD) δ 8.64 (d, J=8.8 Hz, 1H), 7.71 (s, 1H), 7.36-7.27 (m, 2H), 7.17-7.08 (m, 3H), 5.79 (s, 2H), 3.48-3.30 (m, 1H), 3.27-2.98 (m, 3H), 2.33-2.21 (m, 3H), 2.17-2.08 (m, 1H), 1.82 (s, 3H), 1.77-1.64 (m, 2H), 1.58-1.53 (m, 1H); m/z=564 (M+1).

Example 261D

3-[1-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyrrolidin-3-yl]propanoic acid

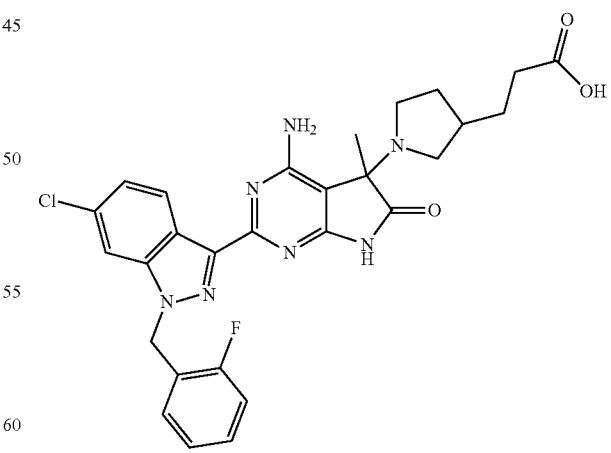

Example 261D was prepared using the same procedure as Ex-261C using ethyl 3-(1-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}pyrrolidin-3-yl)propanoate isomer D as intermediate. m/z=564 (M+1).

Example 262B 3-(1-{4-Amino-2-[6-chloro-1-(2-fluorobenzyl)-1H-indazol-3-yl]-5-methyl-6-oxo-6,7-dihydro-5H-pyrrolo[2,3-d]pyrimidin-5-yl}piperidin-4-yl)propanoic acid

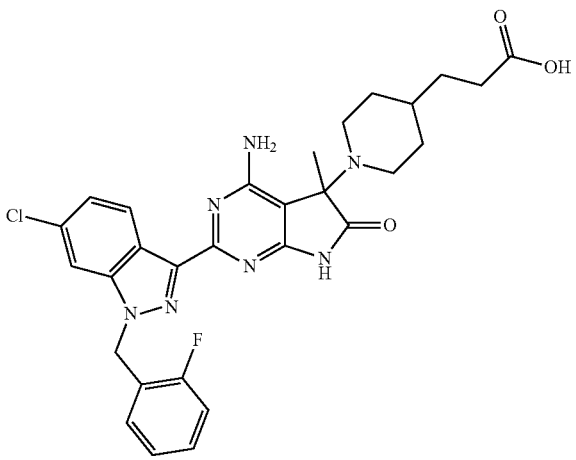 [SMILES: CC1(N2CCC(CCC(=O)O)CC2)C(=O)Nc2nc(-c3nn(Cc4ccccc4F)c4cc(Cl)ccc34)nc(N)c21]

Ex-262B was prepared using the same protocol as Ex-261C, coupling 4-amino-2-[6-chloro-1-(2-fluorobenzyl)-1H-indazol-3-yl]-5-methyl-5H-pyrrolo[2,3-d]pyrimidin-6(7H)-one with ethyl 3-(piperidin-4-yl)propanoate to afford racemic ethyl 3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}cyclohexyl)propanoate which was resolved using Chiral HPLC (CHIRALPAK IC) to afford isomer A (faster eluting), and isomer B (slower eluting). Isomer B was used to prepare Ex-262B, m/z=578 (M+1)

Example 263AA 3-(4-{4-Amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)propanoic acid

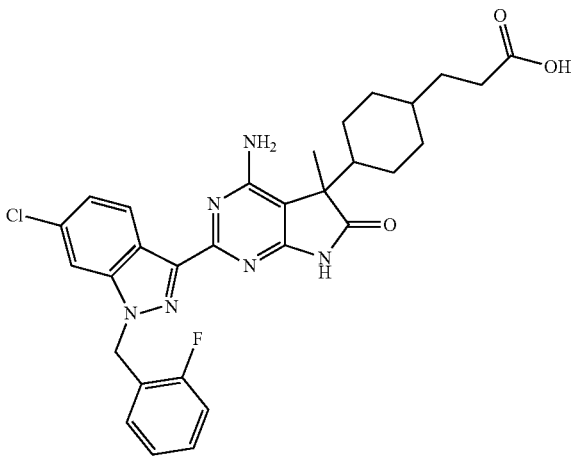

Step A—4-Amino-5-(4-{[(tert-butyldimethylsilyl)oxy]methyl}cyclohexyl)-2-[6-chloro-1-(3-fluorobenzyl)-1H-indazol-3-yl]-5-methyl-5H-pyrrolo[2,3-d]pyrimidin-6(7H)-one A flask containing I-A27 (0.8 g, 2.64 mmol), I-68 (1 g, 2.64 mmol) and potassium bicarbonate (0.4 g, 3.96 mmol) in t-BuOH (20 mL) was stirred for 16 h at 70° C. The reaction was quenched by the addition of water and extracted with EtOAc (3×). The organic layers were combined, washed with brine, dried over anhydr. $Na_2SO_4$, and filtered. The filtrate was concentrated in vacuo. The residue was purified by silica gel column chromatography with MeOH:DCM (0-10%) to afford the title compound. m/z=649 (M+1).

Step B—4-Amino-2-[6-chloro-1-(3-fluorobenzyl)-1H-indazol-3-yl]-5-[4-(hydroxymethyl)cyclohexyl]-5-methyl-5H-pyrrolo[2,3-d]pyrimidin-6(7H)-one A flask containing 4-amino-5-(4-{[(tert-butyl dimethyl silyl)oxy]methyl}cyclohexyl)-2-[6-chloro-1-(3-fluorobenzyl)-1H-indazol-3-yl]-5-methyl-5H-pyrrolo[2,3-d]pyrimidin-6(7H)-one (0.61 g, 0.940 mmol), tetra-n-butylammonium fluoride (1.3 g, 4.97 mmol) in THF (20 mL) was stirred for 16 h at RT. The reaction was quenched by the addition of brine and extracted with EtOAc (3×). The organic layers were combined, washed with brine, dried over anhydr. $Na_2SO_4$, and filtered. The filtrate was concentrated in vacuo. The residue was purified by silica gel column chromatography with EtOAc:petroleum ether (60-100%) to afford the title compound. m/z=535 (M+1).

Step C—4-(4-Amino-2-(6-chloro-1-(3-fluorobenzyl)-1H-indazol-3-yl)-5-methyl-6-oxo-6,7-dihydro-5H-pyrrolo[2,3-d]pyrimidin-5-yl)cyclohexanecarbaldehyde To a flask under a inert atmosphere of nitrogen, containing DMSO (0.14 mL, 1.97 mmol) and DCM (20 mL) at −78° C. was added dropwise oxalyl chloride (0.14 mL, 1.65 mmol) in DCM (2 mL). The resulting mixture was stirred at −78° C. for 30 min, before a solution of 4-amino-2-[6-chloro-1-(3-fluorobenzyl)-1H-indazol-3-yl]-5-[4-(hydroxymethyl)cyclohexyl]-5-methyl-5H-pyrrolo[2,3-d]pyrimidin-6(7H)-one (440 mg, 0.82 mmol) in DCM (2 mL) and DMSO (0.5 mL) was added dropwise at −78° C. The resulting mixture was stirred for 2 h at −78° C., then a solution of triethylamine (0.57 mL, 4.11 mmol) in DCM (2 mL) was added. The resulting mixture was stirred for 30 min at −78° C., then warmed to RT over 30 min. The reaction was quenched by the addition of water and extracted with DCM (3×). The organic layers were combined, washed with brine, dried over anhydr. $Na_2SO_4$, and filtered. The filtrate was concentrated in vacuo. The residue was purified by silica gel column chromatography with EtOAc:petroleum ether (60-100%) to afford the title compound. m/z=533 (M+1).

Step D—Ethyl 3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)acrylate To a flask containing ethyl 2-(diethoxyphosphoryl)acetate (1.75 g, 7.81 mmol) in $Et_2O$ (40 mL) at 0° C. was added sodium hydride (311 mg, 7.79 mmol). The resulting mixture was stirred for 15 min at RT before a solution of 4-(4-amino-2-(6-chloro-1-(3-fluorobenzyl)-1H-indazol-3-yl)-5-methyl- 6-oxo-6,7-dihydro-5H-pyrrolo[2,3-d]pyrimidin-5-yl)cyclohexanecarbaldehyde (415 mg, 0.779 mmol) in THF (6 mL) was added. The resulting mixture was stirred for 2 h at RT before it was quenched by the addition of aq. sat. NH$_4$Cl, extracted with EtOAc (3×). The organic layer was washed with brine, dried over anhydr. Na$_2$SO$_4$, and filtered. The filtrate was concentrated in vacuo. The residue was purified by reverse phase HPLC (ACN/water with 0.1% TFA modifier) to afford the title compound. m/z=603 (M+1).

Step E—Ethyl 3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)propanoate A flask containing ethyl 3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)acrylate (370 mg, 0.61 mmol), 4-methylbenzenesulfonohydrazide (472 mg, 2.53 mmol), sodium acetate (347 mg, 4.23 mmol) in diethylene glycol dimethyl ether (10 mL) and water (1 mL) was stirred at 80° C. for 16 h. The reaction was quenched by the addition of water, extracted with EtOAc (3×). The organic layer was washed with brine, dried over anhydr. Na$_2$SO$_4$, filtered, and the filtrate was concentrated in vacuo. The residue was purified by silica gel column chromatography with EtOAc: petroleum ether (0-10%). The residue was purified by reverse phase HPLC (ACN/water with 0.05% TFA modifier). to afford isomer A (faster eluting), and isomer B (slower eluting). The racemic isomer A was resolved using chiral SFC (CHIRALPAK IC) to afford isomer AA (faster eluting), isomer AB (slower eluting). m/z=605 (M+1).

Step F— 3-(4-{-4-Amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)propanoic acid A flask containing ethyl 3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)propanoate isomer AA (34 mg, 0.056 mmol), lithium hydroxide hydrate (34 mg, 0.81 mmol) in a THF (4 mL):water (3 mL) mixture was stirred at RT for 16 h. The reaction was quenched by the addition of hydrochloric acid (8.1 mL, 0.1 N) extracted with EtOAc (3×). The organic layer was washed with brine, dried over anhydr. Na$_2$SO$_4$, filtered, and the filtrate was concentrated in vacuo to afford the title compound Ex-263AA. $^1$H NMR (400 MHz, CD$_3$OD) δ 8.46 (d, J=8.4 Hz, 1H), 7.86 (s, 1H), 7.40-7.37 (m, 2H), 7.19-7.02 (m, 3H), 5.87 (s, 2H), 2.27 (t, J=6.8 Hz, 2H), 2.07-1.84 (m, 3H), 1.76-1.59 (m, 6H), 1.49-1.47 (m, 2H), 1.26-0.89 (m, 4H); m/z=577 (M+1).

Example 263BA 3-(4-{4-Amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)propanoic acid

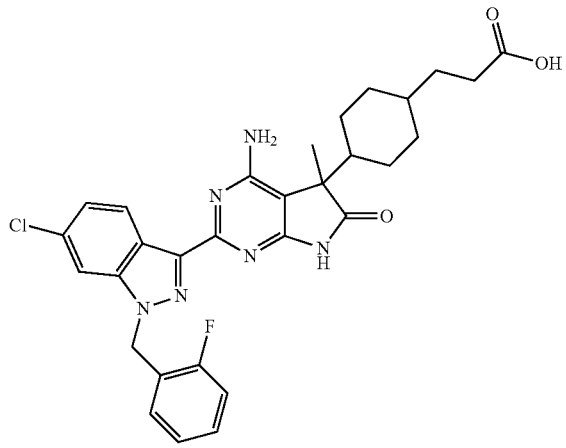 [SMILES: CC1(C2CCC(CCC(=O)O)CC2)C(=O)Nc2nc(-c3nn(Cc4ccccc4F)c4cc(Cl)ccc34)nc(N)c21]

Ethyl 3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)propanoate isomer B prepared as in Ex-263AA was resolved using chiral SFC (CHIRALPAK IB) to afford isomer BA (faster eluting) and isomer BB (slower eluting). Ethyl 3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}cyclohexyl)propanoate BA was hydrolysed to afford the title compound Ex-263BA.

Biological Assays:
Cell-Based sGC Functional Assay (Cyclic GMP Assay for sGC Activator: CASA Assay)

Soluble guanylate cyclase (sGC) is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous heme group. To determine the effect of sGC activators on enzyme activity, the CASA assay was developed to monitor the generation of cGMP in a cell line that stably expresses the heterodimeric sGC protein.

Methods:
A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 μg/mL penicillin/streptomycin, 0.5 mg/mL hygromycin and 0.25 mg/mL G418. The cells were then cryopreserved in LN2. On the day of the assay, the cells were thawed and resuspended in EBSS Assay Buffer (Sigma, E3024) supplemented with 5 mM MgCl$_2$, 10 mM HEPES (4-(2-hydroxyethyl)piperazine-1-ethanesulfonic acid) and 0.05% BSA (bovine serum albumin) (EAB) and cell density was then adjusted to 2.25×105/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 2.5%. Cells were pre-incubated in the presence and absence of 1 μM of Diethylenetriamine/nitric oxide adduct (DETA-NO; Sigma, 17018) for 30 min at 25° C. Compounds are subsequently added and incubated for 1 hr at 37° C. At the end of the incubation period, the reaction was terminated and the cells were lysed with the detection reagents from Cisbio Kits. The level of intracellular cGMP was determined using an HTRF-based assay kit (CisBio, 62GM2PEC), which detects the displacement of a fluorescence labeled cGMP from its specific antibody. The cGMP produced by test compounds was directly compared to the maximum cGMP production (this value was set to equal 100% activation.) of the published sGC-HDA compound A:

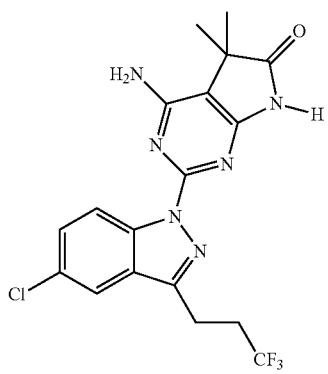 [SMILES: CC1(C)C(=O)Nc2nc(-n3nc(CCC(F)(F)F)c4cc(Cl)ccc43)nc(N)c21]

(Example 1 in WO 2010/065275, published Jun. 10, 2010). The test compounds' activity were then expressed as a percentage of compound A, the standard in every experiment. This percent activation was calculated either in the presence or absence of DETA-NO which was then plotted. Inflection points (IP) and maximum fold induction was derived using Abase analysis software for 4P fit.

Most preferred compounds had an IP of less than or equal to about 1500 nM. Data for the compounds of the Examples is provided in Table 22.

TABLE 22

| EX. | IP (nM) | % Activation |
|---|---|---|
| 1A | 409 | 120 |
| 2A | 1058 | 111 |
| 3A | 183 | 126 |
| 4B | 294 | 126 |
| 5BA | 132 | 76 |
| 5BB | 330 | 107 |
| 6A | 1263 | 85 |
| 7A | 1026 | 98 |
| 8B | 1363 | 129 |
| 9B | 1371 | 118 |
| 10B | 456 | 117 |
| 11B | 537 | 99 |
| 12B | 2877 | 81 |
| 13B | 152 | 86 |
| 14B | 525 | 90 |
| 15B | 1315 | 95 |
| 16B | 1473 | 96 |
| 17AB | 3781 | 77 |

TABLE 22-continued

| EX. | IP (nM) | % Activation |
|---|---|---|
| 18B | 2497 | 95 |
| 19B | 1042 | 89 |
| 20B | 2209 | 88 |
| 21B | 362 | 93 |
| 22A | 423 | 91 |
| 23B | 203 | 109 |
| 24A | 210 | 106 |
| 25B | 201 | 147 |
| 26B | 1922 | 102 |
| 27B | 331 | 120 |
| 28B | 2173 | 105 |
| 29B | 686 | 82 |
| 30B | 176 | 93 |
| 31B | 8333 | 130 |
| 32B | 445 | 79 |
| 33B | 804 | 100 |
| 34AA | 437 | 81 |
| 34AB | 771 | 115 |
| 35B | 2794 | 102 |
| 36B | 916 | 105 |
| 37B | 762 | 96 |
| 38B | 220 | 98 |
| 39B | 1091 | 82 |
| 40B | 2561 | 94 |
| 41B | 779 | 85 |
| 42B | 1052 | 84 |
| 43B | 142 | 105 |
| 44B | 245 | 127 |
| 45B | 210 | 95 |
| 46B | 647 | 95 |
| 47B | 218 | 88 |
| 48A | 257 | 102 |
| 49A | 119 | 91 |
| 50A | 407 | 98 |
| 51B | 485 | 116 |
| 52B | 504 | 109 |
| 53A | 124 | 102 |
| 54A | 490 | 106 |
| 55A | 432 | 105 |
| 56A | 134 | 116 |
| 57B | 1083 | 104 |
| 58B | 1130 | 65 |
| 59B | 858 | 116 |
| 60B | 167 | 128 |
| 61A | 299 | 109 |
| 62A | 141 | 148 |
| 63A | 104 | 72 |
| 64B | 302 | 101 |
| 65B | 1101 | 136 |
| 66B | 238 | 107 |
| 67B | 384 | 115 |
| 68B | 568 | 109 |
| 69B | 289 | 139 |
| 70B | 649 | 120 |
| 71B | 73 | 78 |
| 72A | 42 | 80 |
| 73B | 85 | 87 |
| 74A | 62 | 94 |
| 75A | 238 | 155 |
| 76B | 99 | 101 |
| 77B | 489 | 105 |
| 78A | 1741 | 93 |
| 79B | 843 | 124 |
| 80A | 733 | 98 |
| 81B | 504 | 110 |
| 82B | 1367 | 107 |
| 83B | 1421 | 80 |
| 84A | 130 | 113 |
| 85A | 700 | 130 |
| 86A | 247 | 102 |
| 87B | 547 | 97 |
| 88B | 1247 | 88 |
| 89B | 442 | 108 |
| 90B | 129 | 112 |
| 91B | 132 | 123 |
| 92B | 219 | 111 |
| 93A | 575 | 63 |
| 94B | 178 | 108 |

TABLE 22-continued

| EX. | IP (nM) | % Activation |
|---|---|---|
| 95B | 157 | 118 |
| 96B | 311 | 54 |
| 97B | 1146 | 122 |
| 98A | 254 | 83 |
| 99B | 186 | 110 |
| 100B | 1803 | 109 |
| 101B | 2338 | 111 |
| 102B | 573 | 100 |
| 103B | 2946 | 104 |
| 104B | 1372 | 106 |
| 105B | 2159 | 97 |
| 106B | 1499 | 70 |
| 107B | 397 | 113 |
| 108B | 842 | 122 |
| 109B | 1663 | 78 |
| 110B | 1127 | 78 |
| 111B | 9254 | 86 |
| 112B | 2516 | 130 |
| 113B | 568 | 89 |
| 114A | 1340 | 108 |
| 115A | 122 | 79 |
| 116A | 608 | 78 |
| 117A | 302 | 69 |
| 118A | 3510 | 86 |
| 119B | 839 | 103 |
| 120B | 1933 | 127 |
| 121B | 238 | 118 |
| 122B | 895 | 115 |
| 123AA | 880 | 79.0 |
| 123AB | 1957 | 95.8 |
| 124AA | 1600 | 76.5 |
| 125AB | 56 | 138.4 |
| 126AA | 74 | 89.0 |
| 126AB | 199 | 109.2 |
| 127A | 52 | 117.1 |
| 128A | 137 | 116.8 |
| 129A | 51 | 98.5 |
| 130A | 1228 | 115.7 |
| 131B | 1061 | 119.9 |
| 132AA | 125 | 108.6 |
| 132AB | 89 | 109.2 |
| 133AA | 657 | 103.8 |
| 133AB | 714 | 111.4 |
| 134AA | 807 | 103.5 |
| 135A | 254 | 92.9 |
| 136AA | 11 | 78.2 |
| 136AB | 23 | 71.4 |
| 137AA | 121 | 92.1 |
| 137AB | 38 | 98.4 |
| 138B | 375 | 114.5 |
| 139B | 3455 | 134.8 |
| 140A | 798 | 99.0 |
| 141A | 193 | 98.7 |
| 142B | 264 | 108.8 |
| 143B | 3379 | 76.1 |
| 144A | 1219 | 93.1 |
| 145A | 391 | 82.9 |
| 146A | 94 | 82.1 |
| 147A | 61 | 73.4 |
| 148A | 238 | 87.8 |
| 149A | 111 | 103.3 |
| 150A | 294 | 102.2 |
| 151A | 194 | 130.6 |
| 152A | 120 | 118.1 |
| 153A | 145 | 118.9 |
| 154A | 577 | 103.9 |
| 156A | 161 | 93.5 |
| 157A | 185 | 143.4 |
| 158A | 353 | 88.8 |
| 159A | 221 | 112.7 |
| 160B | 111 | 107.8 |
| 161A | 291 | 120.9 |
| 162A | 69 | 76.5 |
| 163B | 408 | 90.8 |
| 164A | 439 | 127.2 |
| 165A | 48 | 110.1 |
| 166A | 40 | 86.4 |
| 167B | 93 | 107.3 |
| 168B | 207 | 141.2 |
| 169B | 159 | 90.3 |
| 170B | 655 | 129.9 |
| 171A | 1218 | 135.1 |
| 172A | 1034 | 92.7 |
| 173A | 557 | 83.4 |
| 174A | 682 | 120.9 |
| 175A | 96 | 139.1 |
| 176B | 1465 | 117.9 |
| 177B | 351 | 125.7 |
| 178A | 429 | 123.8 |
| 179A | 262 | 117.8 |
| 180A | 228 | 121.4 |
| 181A | 278 | 111.9 |
| 182A | 238 | 92.0 |
| 183A | 88 | 111.3 |
| 184A | 230 | 97.7 |
| 185A | 426 | 109.5 |
| 186A | 205 | 83.3 |
| 187A | 244 | 97.1 |
| 188A | 109 | 123.7 |
| 189A | 51 | 115.6 |
| 190A | 49 | 119.6 |
| 191B | 133 | 113.7 |
| 192A | 1042 | 102.8 |
| 193B | 69 | 89.2 |
| 194A | 73 | 128.3 |
| 195A | 194 | 103.1 |
| 196A | 54 | 90.3 |
| 197B | 125 | 106.2 |
| 198B | 1071 | 134.2 |
| 199A | 66 | 108.5 |
| 200A | 220 | 120.4 |
| 201A | 39 | 91.2 |
| 202A | 212 | 122.5 |
| 203A | 330 | 122.2 |
| 204A | 47 | 97.8 |
| 206B | 549 | 113.4 |
| 207B | 1761 | 100.1 |
| 208A | 453 | 101.4 |
| 209B | 2475 | 94.4 |
| 210B | 2019 | 103.0 |
| 211A | 1176 | 96.2 |
| 212A | 119 | 134.9 |
| 213A | 839 | 94.9 |
| 214A | 320 | 116.1 |
| 215A | 3701 | 118.8 |
| 216A | 678 | 132.2 |
| 217A | 1424 | 123.6 |
| 218A | 301 | 102.8 |
| 220B | 82 | 112.8 |
| 221B | 150 | 92.1 |
| 222A | 71 | 104.7 |
| 223A | 210 | 118.8 |
| 224A | 14 | 111.3 |
| 225B | 460 | 139.8 |
| 226A | 355 | 112.5 |
| 227B | 74 | 63.5 |
| 228A | 64 | 95.0 |
| 229AA | 770 | 114.6 |
| 229AB | 179 | 72.9 |
| 230AA | 821 | 99.1 |
| 231AA | 113 | 148.2 |
| 231AB | 529 | 127.9 |
| 232B | 4154 | 89.1 |
| 233A | 204 | 141.1 |
| 234B | 265 | 135.2 |
| 235B | 626 | 86.8 |
| 236A | 478 | 109.8 |
| 237B | 5871 | 93.3 |
| 238A | 609 | 99.5 |
| 239A | 350 | 62.3 |
| 240B | 749 | 104.0 |
| 241A | 403 | 94.8 |
| 242B | 3097 | 107.3 |
| 243A | 3601 | 101.1 |
| 244A | 2726 | 93.3 |
| 246A | 7124 | 95.3 |

TABLE 22-continued

| EX. | IP (nM) | % Activation |
|---|---|---|
| 247A | 4018 | 86.9 |
| 248B | 116 | 106.1 |
| 249B | 2618 | 98.5 |
| 250B | 1704 | 102.5 |
| 252B | 2460 | 87.6 |
| 253B | 3629 | 96.7 |
| 254A | 1013 | 123.3 |
| 255A | 1481 | 108.4 |
| 256B | 2048 | 104.4 |
| 257A | 106 | 84.7 |
| 258B | 1732 | 98.2 |
| 259B | 560 | 116.2 |
| 260A | 125 | 135.6 |
| 261C | 293 | 112.9 |
| 261D | 444 | 103.8 |
| 262B | 27 | 82.4 |
| 263AA | 110 | 82.1 |

Binding Assay:

The binding potencies of sGC compounds to the human recombinant sGC enzyme were determined in a Size Exclusion Chromatography (SEC) competition binding assay using [$^3$H] Ex-77B as the radioligand.

[$^3$H] Ex-77B was prepared using a standardardized tritium exchange procedure. The parent (non-labeled) molecule was first iodinated then a Pd-catalyzed iodine to tritium exchange provided the labeled compound.

Method: The binding buffer was composed of 50 mM triethanolamine, pH 7.4, 3 mM MgCl$_2$, 0.025% BSA, 2 mM dithiothreitol (DTT), 300 μM DETA/NO and 400 μM GTP. Assays were conducted in 96-well plates in a total volume of 200 μL. Recombinant human sGC protein (40 ng) was incubated with 1.6 nM [$^3$H] Ex-77B for 24 hours at 37° C. in the presence and absence of various concentrations of sGC testing compounds delivered as DMSO solutions to give a total of 1% organic solvent content. Non-specific binding was defined by competition with 1 μM of Ex-77B. After the incubation period, the binding mixtures were loaded onto the gel-filtration plate (ThermoFischer Cat. No. 89808) pre-equilibrated with binding buffer and spun at 1000×g for 3 min at 4° C. on a Bench top centrifuge. The collected eluates in White Frame Clear Well Isoplates (Perkin Elmer Cat #6005040) received 100 μl of UltimaGold scintillation cocktail. The sealed plates were shaken vigorously and span, and counted after 6 hours with a Wallac Microbeta TriLux 1450 LSC & Luminescence Counter (Perkin Elmer). Data from competition experiments were analyzed to determine K$_i$ values using one site fit K$_i$ equation.

Most preferred compounds had an Ki of less than or equal to about 1 nM. Data for the compounds of the Examples is provided in Table 23.

TABLE 23

| EXAMPLE | Ki (pM) |
|---|---|
| 1A | 47 |
| 2A | 322 |
| 3A | 67 |
| 4B | 391 |
| 5BA | 162 |
| 5BB | 182 |
| 6A | 130 |
| 7A | 154 |
| 9B | 374 |
| 10B | 150 |
| 11B | 304 |
| 12B | 2045 |
| 13B | 112 |
| 14B | 210 |
| 15B | 455 |
| 16B | 1135 |
| 17AB | 936 |
| 18B | 920 |
| 19B | 286 |
| 20B | 4491 |
| 21B | 64 |
| 22A | 78 |
| 23B | 99 |
| 25B | 262 |
| 26B | 266 |
| 27B | 221 |
| 28B | 536 |
| 29B | 564 |
| 30B | 560 |
| 31B | 1412 |
| 32B | 1700 |
| 33B | 594 |
| 34AA | 138 |
| 34AB | 231 |
| 35B | 1119 |
| 36B | 908 |
| 37B | 484 |
| 38B | 145 |
| 39B | 3652 |
| 40B | 4379 |
| 41B | 717 |
| 42B | 951 |
| 43B | 96 |
| 44B | 123 |
| 45B | 182 |
| 46B | 216 |
| 47B | 114 |
| 52B | 413 |
| 57B | 96 |
| 58B | 493 |
| 59B | 293 |
| 60B | 102 |
| 61A | 66 |
| 62A | 22 |
| 64B | 75 |
| 66B | 495 |
| 67B | 154 |
| 68B | 3100 |
| 69B | 101 |
| 76B | 87 |
| 77B | 232 |
| 78A | 944 |
| 79B | 420 |
| 80A | 755 |
| 82B | 223 |
| 83B | 1737 |
| 84A | 166 |
| 85A | 1497 |
| 86A | 323 |
| 87B | 785 |
| 88B | 848 |
| 89B | 343 |
| 90B | 63 |
| 91B | 180 |
| 92B | 175 |
| 93A | 602 |
| 95B | 60 |
| 96B | 12150 |
| 97B | 799 |
| 98A | 395 |
| 100B | 39 |
| 101B | 26 |
| 103B | 45 |
| 105B | 42 |
| 106B | 58 |
| 108B | 56 |
| 109B | 1998 |
| 110B | 361 |
| 111B | 1113 |

TABLE 23-continued

| EXAMPLE | Ki (pM) |
|---|---|
| 112B | 66 |
| 113B | 64 |
| 114A | 92 |
| 116A | 296 |
| 118A | 166 |
| 119B | 292 |
| 120B | 410 |
| 121B | 234 |
| 122B | 326 |
| 123AA | 1231 |
| 123AB | 874 |
| 124AA | 506 |
| 124AB | 617 |
| 125AA | 783 |
| 125AB | 336 |
| 126AA | 100 |
| 126AB | 77 |
| 127A | 57 |
| 128A | 111 |
| 129A | 117 |
| 130A | 184 |
| 131B | 125 |
| 132AA | 105 |
| 132AB | 74 |
| 133AA | 513 |
| 133AB | 359 |
| 134AA | 320 |
| 134AB | 461 |
| 135A | 275 |
| 136AA | 252 |
| 136AB | 218 |
| 137AA | 128 |
| 137AB | 204 |
| 138B | 58 |
| 139B | 114 |
| 140A | 227 |
| 141A | 665 |
| 142B | 183 |
| 143B | 174 |
| 144A | 594 |
| 145A | 299 |
| 146A | 62 |
| 147A | 75 |
| 148A | 123 |
| 149A | 167 |
| 150A | 96 |
| 151A | 124 |
| 152A | 31 |
| 153A | 118 |
| 154A | 91 |
| 155B | 420 |
| 156A | 170 |
| 157A | 258 |
| 158A | 864 |
| 159A | 125 |
| 160B | 62 |
| 161A | 81 |
| 162A | 150 |
| 163B | 1852 |
| 164A | 99 |
| 165A | 81 |
| 166A | 144 |
| 167B | 70 |
| 168B | 164 |
| 169B | 104 |
| 170B | 118 |
| 171A | 94 |
| 172A | 98 |
| 173A | 252 |
| 174A | 173 |
| 175A | 151 |
| 176B | 130 |
| 177B | 118 |
| 178A | 116 |
| 179A | 144 |
| 180A | 31 |
| 181A | 94 |
| 182A | 124 |

TABLE 23-continued

| EXAMPLE | Ki (pM) |
|---|---|
| 183A | 76 |
| 184A | 92 |
| 185A | 165 |
| 186A | 120 |
| 187A | 29 |
| 188A | 100 |
| 189A | 49 |
| 190A | 31 |
| 191B | 109 |
| 192A | 116 |
| 193B | 52 |
| 194A | 41 |
| 195A | 92 |
| 196A | 468 |
| 197B | 162 |
| 198B | 107 |
| 199A | 70 |
| 200A | 52 |
| 201A | 151 |
| 202A | 186 |
| 203A | 71 |
| 204A | 269 |
| 206B | 798 |
| 207B | 95 |
| 208A | 253 |
| 209B | 1642 |
| 210B | 341 |
| 211A | 258 |
| 212A | 72 |
| 213A | 123 |
| 214A | 267 |
| 215A | 189 |
| 216A | 110 |
| 217A | 67 |
| 218A | 57 |
| 219A | 183 |
| 220B | 87 |
| 221B | 163 |
| 222A | 112 |
| 223A | 50 |
| 224A | 67 |
| 225B | 342 |
| 226A | 176 |
| 227B | 146 |
| 228A | 79 |
| 229AA | 496 |
| 229AB | 238 |
| 230AA | 185 |
| 230AB | 280 |
| 231AA | 92 |
| 231AB | 87 |
| 232B | 85 |
| 233A | 83 |
| 234B | 947 |
| 235B | 404 |
| 236A | 158 |
| 237B | 193 |
| 238A | 95 |
| 239A | 68 |
| 240B | 75 |
| 241A | 121 |
| 242B | 1111 |
| 243A | 62 |
| 244A | 63 |
| 245B | 333 |
| 246A | 220 |
| 247A | 242 |
| 248B | 48 |
| 249B | 68 |
| 250B | 108 |
| 251B | 182 |
| 252B | 292 |
| 253A | 146 |
| 254A | 199 |
| 255A | 73 |
| 256B | 74 |
| 257A | 105 |
| 258B | 80 |

TABLE 23-continued

| EXAMPLE | Ki (pM) |
| --- | --- |
| 259B | 111 |
| 260A | 58 |
| 261C | 74 |
| 261D | 187 |
| 262B | 97 |
| 263AA | 235 |
| 263BA | 127 |

Acute Efficacy in Spontaneously Hypertensive Rats (SHR)

Spontaneously hypertensive rats (SHR, male, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. On the day prior to administration of compound, a single oral dose of vehicle (10% transcutol/20% Cremophor/70% water) was administered to all animals to establish baseline control data. The blood pressure lowering efficacy of compound (PO) or vehicle was evaluated following a single oral gavage. Data were collected as hourly averages, and changes in blood pressure were calculated by subtracting control baseline data on an hourly basis. Animals were maintained on normal diet with a 12 hour light-dark cycle.

Maximum peak decreases of systolic blood pressure (SBP) in SHR at a particular P.O. dose (mpk milligrams per kilogram) for the following Example compounds are provided.

Category A=decrease in SBP in SHRs 5-25 mmHg;
Category B=decrease in SBP in SHRs 25-40 mmHg;
Category C=decrease in SBP in SHRs>40 mmHg.

TABLE 24

| EXAMPLE | Dose (P.O. mpk) | Category |
| --- | --- | --- |
| 2A | 3 | A |
| 5BA | 3 | B |
| 7A | 3 | A |
| 9B | 3 | A |
| 10B | 3 | A |
| 13B | 3 | A |
| 14B | 3 | A |
| 21B | 3 | A |
| 22A | 3 | A |
| 27B | 1 | A |
| 33B | 3 | B |
| 34AA | 3 | A |
| 34AB | 1 | A |
| 38B | 3 | A |
| 44B | 3 | C |
| 45B | 3 | B |
| 46B | 3 | A |
| 52B | 3 | A |
| 58B | 3 | A |
| 59B | 3 | A |
| 70B | 3 | A |
| 76B | 3 | B |
| 77B | 1 | C |
| 79B | 3 | A |
| 82B | 3 | A |
| 84A | 1 | C |
| 86A | 1 | A |
| 89B | 3 | B |
| 90B | 1 | B |
| 92B | 0.3 | A |
| 121B | 3 | A |

Acute Efficacy in Hypoxia-Induced Pulmonary Hypertension in Rat Following Intratracheal Administration Charles River Sprague-Dawley (CD) male rats weighing approximately 350 g were implanted with HD-S21 dual pressure telemetry transmitters (Data Sciences International (DSI)) into the pulmonary artery and femoral artery. This transmitter enables simultaneous measurement of both pulmonary and systemic hemodynamic parameters in the same animal. After a 7-10 day post-operative recovery period, animals were subjected to a normobaric hypoxic (10% oxygen) environment using a Higher Peak Mountain Air Generator (MAG-10) connected to a modified rodent cage via a fitted inlet port. Oxygen (at 10%), temperature, humidity, and $CO_2$ were controlled within normal range and animals were maintained on a 12 hour light-dark cycle with ad libitum access to food and water. After two weeks exposure to 10% $O_2$ hypoxic environment, systolic pulmonary arterial pressure readings increased from 25 mmHg to greater than 50 mmHg. Using a 48 hour baseline average, animals with readings between 50-110 mmHg (standard deviation of less than 10 mmHg) and minimal changes in systolic systemic blood pressure were enrolled for study. Animals were utilized for up to 2 studies per week for 4 weeks with a minimum of 2 days washout between doses of test agent.

Compound or vehicle was administered intra-tracheally under light isoflurane anesthesia (5% in oxygen; flow rate 2.0 L/min for 3 minutes). Once anesthetized, rats were placed on an angled intubation stand in supine position and the trachea visualized using a small laryngoscope. Animals then received either 0.5 mL/kg of vehicle or 0.5 mL/kg vehicle containing compound intra-tracheally delivered via microsprayer by use of a Penn-Century Microsprayer® needle 3" (Model IA-1B-GP) attached to a 1 mL high pressure syringe (Penn Century-Model B-SYR-PL1000) (Penn-Century, Philadelphia, Pa.). The Microsprayer® tip was inserted into the trachea up to the point at which the bend in the needle is close to the tip of the snout, which positions the tip of the Microsprayer® in front of the carina (bifurcation of trachea at the bronchi). After dose delivery the animal is placed on its back in the home cage for recovery.

Hemodynamic measurements were continuously recorded and readings consolidated to hourly moving averages. Each animal received a vehicle on Day 1 followed by vehicle or test agent on Day 2. Change from vehicle baseline was calculated by subtracting the hourly Day 1 vehicle response from the hourly Day 2 response and treatment group data was expressed as mean±SEM.

Decreases of systolic blood pressure (SBP) and systolic pulmonary arterial pressure (PAP) were measured at a particular IT dose (mpk milligrams per kilogram) for the following Example compounds. Compounds in the Table 25 achieved a minimum decrease in PAP of ≥15 mmHg for the corresponding decrease in SBP listed.

Category A=decrease in SBP 0-5 mmHg;
Category B=decrease in SBP 5-10 mmHg;
Category C=decrease in SBP>10 mmHg.

TABLE 25

| EXAMPLE | Dose (IT mpk) | Category |
|---|---|---|
| 2A | 0.03 mpk | A |
| 3A | 0.01 mpk | A |
| 7A | 0.1 mpk | B |
| 10B | 0.01 mpk | A |
| 11B | 0.03 mpk | B |
| 12B | 0.1 mpk | B |
| 21B | 0.03 mpk | A |
| 46B | 0.03 mpk | A |
| 47B | 0.03 mpk | A |
| 51B | 0.01 mpk | A |
| 63A | 0.01 mpk | A |
| 77B | 0.03 mpk | A |
| 80BA | 0.1 mpk | B |
| 81B | 0.03 mpk | B |
| 84A | 0.03 mpk | A |
| 92B | 0.03 mpk | A |
| 95B | 0.03 mpk | A |
| 112B | 0.01 mpk | A |
| 119B | 0.03 mpk | A |
| 127A | 0.03 mpk | A |
| 160B | 0.01 mpk | B |
| 163B | 0.03 mpk | C |
| 185A | 0.01 mpk | A |
| 195A | 0.01 mpk | B |
| 202A | 0.01 mpk | A |
| 220B | 0.01 mpk | B |
| 222A | 0.01 mpk | B |
| 235B | 0.01 mpk | A |
| 239A | 0.01 mpk | A |

The invention claimed is:

1. A compound of the Formula (I)

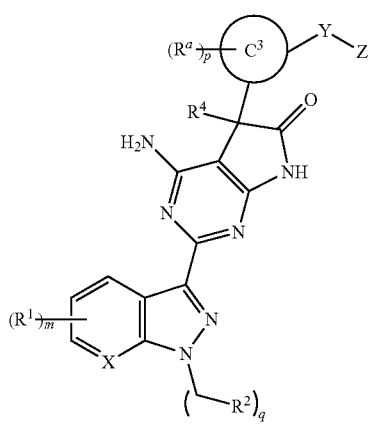

(I)

or a pharmaceutically acceptable salt thereof, wherein:
X is C(H) or N;
each $R^1$ is independently halo, hydroxy, $C_1$-$C_3$ alkyl, $C_3$-$C_6$ cycloalkyl or —O—$C_1$-$C_3$ alkyl;
$R^2$ is:
  (a.) $C_1$-$C_6$ alkyl, wherein said $C_1$-$C_6$ alkyl of $R^2$ is unsubstituted or substituted by 1 to 6 moieties independently selected from fluoro or —O—$C_1$-$C_3$ alkyl;
  (b.) ring $C^2$, wherein ring $C^2$ is:
    (i.) $C_3$-$C_{12}$ cycloalkyl;
    (ii.) phenyl;
    (iii.) a 5- or 6-membered monocyclic heteroaryl containing 1 to 2 heteroatoms selected from N, O, or S; or
    (iv.) a 5- or 6-membered monocyclic heterocyclyl containing 1 to 2 heteroatoms selected from N, O, or S;

wherein ring $C^2$ is unsubstituted or substituted by 1 to 3 moieties independently selected from halo, cyano, $C_1$-$C_3$ alkyl, —O—$C_1$-$C_3$ alkyl, or oxo;
$R^4$ is $C_1$-$C_6$ alkyl, $CF_3$, or $C_3$-$C_6$ cycloalkyl;
ring $C^3$ is:
  (a.) phenyl;
  (b.) a 5- or 6-membered monocyclic heteroaryl or a 9- to 10-membered bicyclic heteroaryl containing 1 to 3 heteroatoms selected from N, O, or S;
  (c.) a 5- or 6-membered monocyclic heterocyclyl containing 1 to 3 heteroatoms selected from N, O, or S; or
  (d.) $C_3$-$C_6$ cycloalkyl;
each $R^a$ is independently selected from halo, cyano, $C_1$-$C_3$ alkyl, —O—$C_1$-$C_3$ alkyl, oxo, or hydroxy;
Y is:
  (a.) a bond;
  (b.) a group of the formula

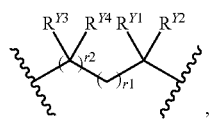

, wherein $R^{Y1}$ and $R^{Y2}$ are independently H, $C_1$-$C_3$ alkyl, hydroxy, fluoro, $C_1$-$C_3$ hydroxyalkyl, or amino; or alternatively $R^{Y1}$ and $R^{Y2}$, together with the carbon atom to which they are attached form a $C_3$-$C_6$ cycloalkyl;

$R^{Y3}$ and $R^{Y4}$ are independently H, $C_1$-$C_3$ alkyl, hydroxy, fluoro, or $C_1$-$C_3$ hydroxyalkyl; or alternatively $R^{Y3}$ and $R^{Y4}$, together with the carbon atom to which they are attached form a $C_3$-$C_6$ cycloalkyl;

(c.) a group of the formula

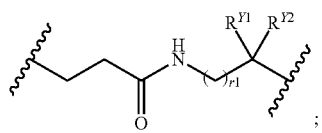

;

(d.) ring $A^H$, wherein ring $A^H$ is $C_3$-$C_6$ cycloalkyl or phenyl, wherein ring $A^H$ is unsubstituted or substituted by 1 to 3 moieties independently selected from halo or $C_1$-$C_3$ alkyl;
  (e.) a group —CH=CH—; or
  (f.) a group

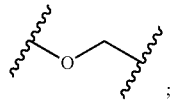 [SMILES: *CO*]

;

Z is:
(a.) —CO$_2$H; (b.) —C(O)N(H)OH;

(c.) 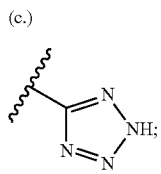

(d.) 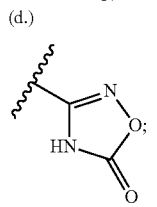

(e.) 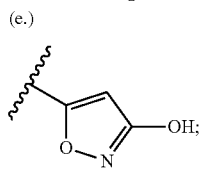

(f.) —SO$_3$H; (g.) —P(=O)(OH)$_2$; or (h.) —C(O)N(H)S(O)$_2$CH$_3$;
the subscript m is 0, 1, or 2;
the subscript p is 0, 2, or 3;
the subscript q is 0 or 1;
the subscript r1 is 0, 1, 2, 3, or 4; and
the subscript r2 is 0 or 1.

2. The compound of claim 1 or a pharmaceutically acceptable salt thereof,
wherein:
ring C$^3$ is:
(a.) phenyl;
(b.) a 5- or 6-membered monocyclic heteroaryl containing 1 to 3 heteroatoms selected from N, O, or S;
(c.) a 5- or 6-membered monocyclic heterocyclyl containing 1 to 3 heteroatoms selected from N, O, or S; or
(d.) C$_3$-C$_6$ cycloalkyl;
each R$^a$ is independently selected from halo, cyano, C$_1$-C$_3$ alkyl, —O—C$_1$-C$_3$ alkyl, or oxo;
Y is:
(a.) a bond;
(b.) a group of the formula

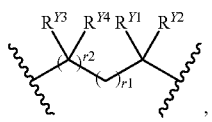, wherein R$^{Y1}$ and R$^{Y2}$ are independently H, C$_1$-C$_3$ alkyl, hydroxy, fluoro, or C$_1$-C$_3$ hydroxyalkyl; or alternatively R$^{Y1}$ and R$^{Y2}$, together with the carbon atom to which they are attached form a C$_3$-C$_6$ cycloalkyl;
R$^{Y3}$ and R$^{Y4}$ are independently H, C$_1$-C$_3$ alkyl, hydroxy, fluoro, or C$_1$-C$_3$ hydroxyalkyl; or alternatively R$^{Y3}$ and R$^{Y4}$, together with the carbon atom to which they are attached form a C$_3$-C$_6$ cycloalkyl;

(c.) a group of the formula

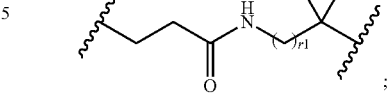;

or
(d.) ring A$^H$, wherein ring A$^H$ is C$_3$-C$_6$ cycloalkyl or phenyl, wherein ring A$^H$ is unsubstituted or substituted by 1 to 3 moieties independently selected from halo or C$_1$-C$_3$ alkyl.

3. The compound of claim 2 or a pharmaceutically acceptable salt thereof, wherein the subscript q is 1, and R$^2$ is C$_2$-C$_3$ alkyl which is unsubstituted or substituted by 1 to 5 fluoro.

4. The compound of claim 2 or a pharmaceutically acceptable salt thereof, wherein the subscript q is 1;
R$^2$ is ring C$^2$;
ring C$^2$ is phenyl, cyclohexyl, adamantyl, pyridyl, or tetrahydropyranyl;
wherein ring C$^2$ is unsubstituted or independently substituted by 1 to 3 fluoro or methyl.

5. The compound of claim 1 or a pharmaceutically acceptable salt thereof, wherein ring C$^3$ is phenyl, thiazolyl, oxazolyl, oxadiazolyl, triazolyl, or pyridyl.

6. The compound of claim 1 or a pharmaceutically acceptable salt thereof; wherein Y is the group of the formula

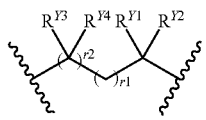.

7. The compound of claim 1 or a pharmaceutically acceptable salt thereof, wherein Y is the group of the formula

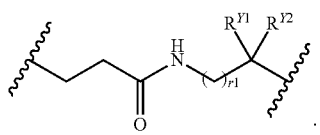.

8. The compound of claim 6 or a pharmaceutically acceptable salt thereof, wherein
the subscript r1 is 1;
the subscript r2 is 0; and
R$^{Y1}$ and R$^{Y2}$ are independently H or C$_1$-C$_3$ alkyl.

9. The compound of claim 1 or a pharmaceutically acceptable salt thereof, wherein Z is (a.) —CO$_2$H; (b.) —C(O)N(H)OH;

(c.) 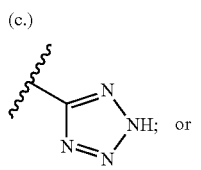 or

-continued (d.) 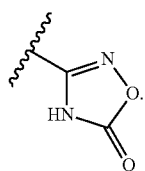

10. The compound of claim 9 or a pharmaceutically acceptable salt thereof, wherein Z is
—CO$_2$H.

11. The compound of claim 1, wherein X is C(H).

12. The compound of claim 1, wherein X is N.

13. The compound of claim 1, wherein R$^4$ is methyl or cyclopropyl.

14. The compound of claim 2 or a pharmaceutically acceptable salt thereof, wherein the compound of Formula (I) has the Formula (IA)

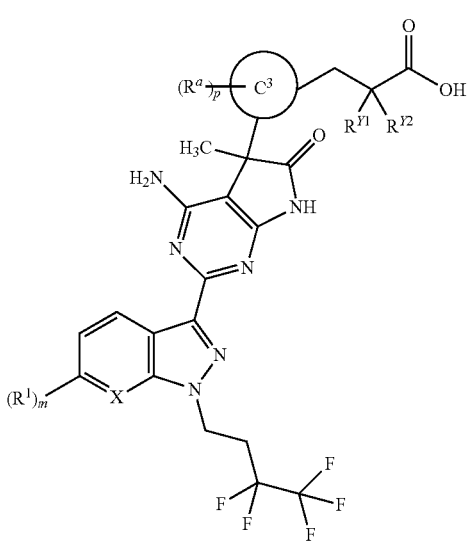

IA wherein
X is C(H) or N;
R$^1$ is methyl or halo;
C$^3$ is phenyl or thiazolyl;
R$^a$ is methyl, cyano, or halo;
R$^{Y1}$ and R$^{Y2}$ are independently H or methyl;
the subscript m is 0 or 1; and
the subscript p is 0 or 1.

15. The compound of claim 2 or a pharmaceutically acceptable salt thereof, wherein the compound of Formula (I) has the Formula (IB)

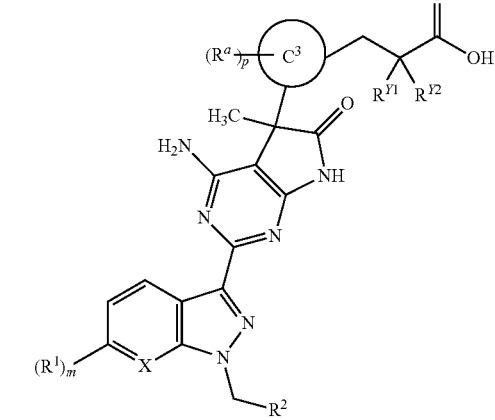

IB wherein
X is C(H) or N;
R$^1$ is methyl or halo;
R$^2$ is ring C$^2$, wherein ring C$^2$ is:
(i.) C$_3$-C$_{12}$ cycloalkyl;
(ii.) phenyl;
(iii.) a 5- or 6-membered monocyclic heteroaryl containing 1 to 2 heteroatoms selected from N, O, or S; or
(iv.) a 5- or 6-membered monocyclic heterocyclyl containing 1 to 2 heteroatoms selected from N, O, or S;
wherein ring C$^2$ is unsubstituted or substituted by 1 to 3 moieties independently selected from halo, cyano, C$_1$-C$_3$ alkyl, —O—C$_1$-C$_3$ alkyl, or oxo
C$^3$ is phenyl, thiazolyl, or oxazolyl;
R$^a$ is methyl, cyano, or halo;
R$^{Y1}$ and R$^{Y2}$ are independently H or methyl;
the subscript m is 0 or 1; and
the subscript p is 0 or 1.

16. The compound of claim 1 or a pharmaceutically acceptable salt thereof, wherein the compound of Formula (I) has the Formula (IA)

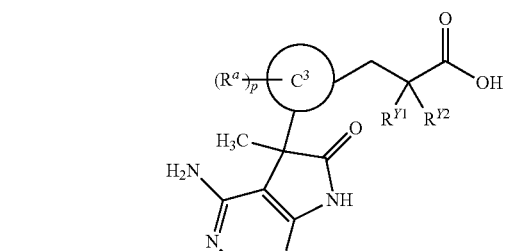

IA

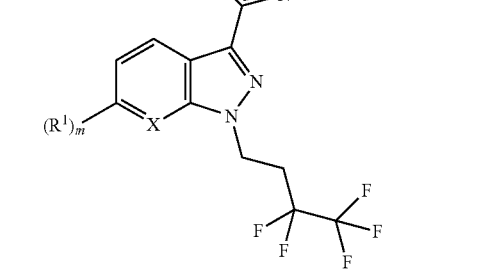

wherein
X is C(H) or N;
R¹ is halo;
C³ is phenyl, thiazolyl, oxazolyl, or benzothiazolyl;
R$^a$ is methyl, cyano, or halo;
R$^{Y1}$ and R$^{Y2}$ are independently H, methyl, or amino;
the subscript m is 0 or 1; and
the subscript p is 0 or 1.

17. The compound of claim 1 or a pharmaceutically acceptable salt thereof, wherein the compound is:

3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}oxazol-4-yl)-2,2-dimethylpropanoic acid;

3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl)oxazol-4-yl}-2,2-dimethylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-bromophenyl)propanoic acid;

3-{4-[4-amino-2-{6-chloro-1-[(4-methylcyclohexyl)methyl]-1H-indazol-3-yl}-5-methyl-6-oxo-6,7-dihydro-5H-pyrrolo[2,3-d]pyrimidin-5-yl]phenyl}propanoic acid;

3-{4-[4-amino-2-{6-chloro-1-[tetrahydro-2H-pyran-2-ylmethyl]-1H-indazol-3-yl}-5-methyl-6-oxo-6,7-dihydro-5H-pyrrolo[2,3-d]pyrimidin-5-yl]phenyl}propanoic acid;

3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)propanoic acid;

3-(6-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}pyridin-3-yl)-2,2-dimethylpropanoic acid;

3-(4-{4-amino-5-methyl-6-oxo-2-(1-(3,3,4,4,4-pentafluorobutyl)-2,3-dihydro-1H-pyrazolo[3,4-b]pyridin-3-yl)-6,7-dihydro-5H-pyrrolo[2,3-d]pyrimidin-5-yl}phenyl)-2,2-dimethylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid;

3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl)}-1H-1,2,3-triazol-1-yl)propanoic acid;

3-(4-{4-amino-2-(1-butyl-6-chloro-1H-pyrazolo[3,4-b]pyridin-3-yl)-5-methyl-6-oxo-6,7-dihydro-5H-pyrrolo[2,3-d]pyrimidin-5-yl}phenyl)propanoic acid;

3-(4-{4-amino-2-(1-butyl-1H-pyrazolo[3,4-b]pyridin-3-yl)-5-methyl-6-oxo-6,7-dihydro-5H-pyrrolo[2,3-d]pyrimidin-5-yl}phenyl)propanoic acid;

3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)propanoic acid;

3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2,2-dimethylpropanoic acid;

3-(4-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}phenyl)-2-methylpropanoic acid;

3-(4-{4-amino-2-[5-fluoro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-5-methyl-2-[6-methyl-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}phenyl)propanoic acid;

3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(3-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3(3-{4-amino-2-[5-fluoro-1H-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-(4-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}phenyl)propanoic acid;

3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}benzoic acid;

3-(3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)acetic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)propanoic acid;

2-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2-methylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)-2,2-dimethylpropanoic acid;

1-[(4-{4-amino-2-[6-chloro-1H-(3,3,4,4,4-pentafluorobutyl)-1H-indazol-3-yl]-5-methyl-6-oxo-6,7-dihydro-5H-pyrrolo[2,3-d]pyrimidin-5-yl}-1H-1,2,3-triazol-1-yl)methyl]cyclopropanecarboxylic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2-methylpropanoic acid;

2-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}acetic acid;

3-{4-[4-amino-2-(1-butyl-6-chloro-1H-indazol-3-yl)-5-methyl-6-oxo-6,7-dihydro-5H-pyrrolo[2,3-d]pyrimidin-5-yl]-1H-1,2,3-triazol-1-yl}propanoic acid;

3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}-2,2-dimethylpropanoic acid;

3-{4-[4-amino-2-(1-butyl-6-chloro-1H-indazol-3-yl)-5-methyl-6-oxo-6,7-dihydro-5H-pyrrolo[2,3-d]pyrimidin-5-yl]phenyl}propanoic acid;

3-(3-{4-amino-2-[6-chloro-1H-(2-methoxyethyl)-1H-indazol-3-yl]-5-methyl-6-oxo-6,7-dihydro-5H-pyrrolo[2,3-d]pyrimidin-5-yl}phenyl)-2,2-dimethylpropanoic acid;

3-(4-{4-amino-2-[6-chloro-1-(2-methoxyethyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4,4,4-trifluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

3-{4-[4-amino-2-(6-chloro-1-pentyl-1H-indazol-3-yl)-5-methyl-6-oxo-6,7-dihydro-5H-pyrrolo[2,3-d]pyrimidin-5-yl]phenyl}propanoic acid;

3-(4-{4-amino-2-[6-chloro-1-(cyclohexylmethyl)-1H-indazol-3-yl]-5-methyl-6-oxo-6,7-dihydro-5H-pyrrolo[2,3-d]pyrimidin-5-yl}phenyl)propanoic acid;

3-{4-[4-amino-2-(6-chloro-1H-hexyl-1H-indazol-3-yl)-5-methyl-6-oxo-6,7-dihydro-5H-pyrrolo[2,3-d]pyrimidin-5-yl]phenyl}propanoic acid;

3-(4-{4-amino-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

4-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}thiazol-4-yl)butanoic acid;

3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}oxazol-4-yl)propanoic acid;

2-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}oxazol-4-yl)acetic acid;

3-(4-{4-amino-2-[6-chloro-1-(4,4-dimethylpentyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)propanoic acid;

4-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}thiazol-4-yl)butanoic acid, 3-(2-{4-amino-2-[1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(4-[4-amino-2-{6-chloro-1-[(3-fluoropyridin-2-yl)methyl]1H-indazol-3-yl}-5-methyl-6-oxo-6,7-dihydro-5H-pyrrolo[2,3-d]pyrimidin-5-yl]phenyl)propanoic acid;

3-(4-[4-amino-2-{6-chloro-1-[(4,4-difluorocyclohexyl)methyl]-1H-indazol-3-yl}-5-methyl-6-oxo-6,7-dihydro-5H-pyrrolo[2,3-d]pyrimidin-5-yl]phenyl)propanoic acid;

3-(4-{4-amino-2-[1-(2-fluorobenzyl)-6-methyl-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(4-{4-amino-2-[6-chloro-1-(2,6-difluorobenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4-fluorobenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(3-methylbenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(4-methylbenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(2-methylbenzyl)-1H-indazol-3-yl]-5-methyl-6-oxo-6,7-dihydro-5H-pyrrolo[2,3-d]pyrimidin-5-yl}phenyl)propanoic acid;

3-(4-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}phenyl)propanoic acid;

3-(4-{2-[1-(adamantan-1-ylmethyl)-6-chloro-1H-indazol-3-yl]-4-amino-5-methyl-6-oxo-6,7-dihydro-5H-pyrrolo[2,3-d]pyrimidin-5-yl}phenyl) propanoic acid;

3-(4-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[5-fluoro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(4-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-2-[5-chloro-1-(2-fluorobenzyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(2-{4-amino-2-[1-(2,3-difluoro-4-methylbenzyl)-6-methyl-1H-pyrazolo[3,4-b]pyridin-3-yl]-5-methyl-6-oxo-6,7-dihydro-5H-pyrrolo[2,3-d]pyrimidin-5-yl}thiazol-4-yl)-2,2-dimethylpropanoic acid;

3-(4-{4-amino-2-[1-(2-fluorobenzyl)-1H-indazol-3-yl]-5-methyl-6-oxo-6,7-dihydro-5H-pyrrolo[2,3-d]pyrimidin-5-yl}phenyl)propanoic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid;

(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)acetic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-3-methylbutanoic acid;

2-(2-{-4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)cyclopropanecarboxylic acid;

1-[(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)methyl]cyclopropanecarboxylic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid;

(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-4-methyl-1,3-thiazol-5-yl)acetic acid;

3-(2-{4-amino-2-[5-fluoro-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[5-fluoro-1-(3,3,3-trifluoropropyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-{2-[4-amino-2-(1-butyl-1H-pyrazolo[3,4-b]pyridin-3-yl)-5-methyl-6-oxo-6,7-dihydro-5H-pyrrolo[2,3-d]pyrimidin-5-yl]-1,3-thiazol-4-yl}-2,2-dimethylpropanoic acid;

3-(2-(4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl)-1,3-thiazol-4-yl)-2,2-dimethylpropanoic acid;

3-(2-{4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidin-5-yl}-1,3-thiazol-4-yl)propanoic acid;

3-(2-{4-amino-2-[6-chloro-1-(4,4,4-trifluorobutyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[5-fluoro-1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-1,3-thiazol-4-yl)benzoic acid;

4-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-5-methyl-1,3-thiazol-4-yl)benzoic acid;

3-(2-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-5-cyclopropyl-2-[5-fluoro-1-(4,4,4-trifluorobutyl)-1H-pyrazolo[3,4-b]pyridin-3-yl]-6-oxo-6,7-dihydro-5H-pyrrolo[2,3-d]pyrimidin-5-yl}thiazol-4-yl)-2,2-dimethylpropanoic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-N-hydroxy-2,2-dimethylpropanamide;

[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]acetic acid;

2-[5-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-oxo-1,3,4-oxadiazol-3(2H)-yl]-2-methylpropanoic acid, (3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)glycine;

2-(3-(4-{4-amino-2-[1-(2-fluorobenzyl)-1H-pyrazol o[3,4-b]pyridin-3-yl]-5-methyl-6-oxo-6,7-dihydro-5H-pyrrolo[2,3-d]pyrimidin-5-yl}phenyl)propanamido)-2-methylpropanoic acid;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-alanine;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-L-alanine; (2R)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid;

(2S)-2-(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamido)butanoic acid;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-serine;

(3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanoyl)-D-threonine;

N-((2H-tetrazol-5-yl)methyl)-3-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)propanamide;

3-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-2H-1,2,3-triazol-2-yl)propanoic acid;

3(4-{4-amino-2-[6-chloro-1-(2-fluorobenzyl)-5-hydroxy-1H-indazol-3-yl]-5-methyl-6-oxo-6,7-dihydro-5H-pyrrolo[2,3-d]pyrimidin-5-yl}phenyl)propanoic acid;

3-{4-[4-amino-2-(1-butyl-6-methyl-1H-pyrazolo[3,4-b]pyridin-3-yl)-5-methyl-6-oxo-6,7-dihydro-5H-pyrrolo[2,3-d]pyrimidin-5-yl]phenyl}propanoic acid;

4-amino-2-[6-chloro-1-(2-fluorobenzyl)-1H-indazol-3-yl]-5-methyl-5-{4-[2-(2H-tetrazol-5-yl)ethyl]phenyl}-5,7-dihydro-6H-pyrrolo[2,3-d]pyrimidin-6-one;

4-(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)butanoic acid;

(4-{4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidin-5-yl}phenyl)acetic acid;

4-(4-{4-amino-2-[6-chloro-1(2-fluorobenzyl)-1H-indazol-3-yl]-5-methyl-6-oxo-6,7-dihydro-5H-pyrrolo[2,3-d]pyrimidin-5-yl}phenyl)butanoic acid;

4-(4-{4-amino-5-methyl-6-oxo-2-[1-(3,3,4,4,4-pentafluorobutyl)-1H-pyrazolo[3,4-b]pyridin-3-yl)-6,7-dihydro-5H-pyrrolo[2,3-d]pyrimidin-5-yl}phenyl)butanoic acid;

2-(4-{4-amino-2-[6-chloro-1-(2-fluorobenzyl)-1H-indazol-3-yl]-5-methyl-6-oxo-6,7-dihydro-5H-pyrrolo[2,3-d]pyrimidin-5-yl}phenyl)acetic acid;

2-(4-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}phenyl)acetic acid;

3-(6-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}pyridin-3-yl)propanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-cyanophenyl)propanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-methylphenyl)propanoic acid; or 3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-2-hydroxyphenyl)propanoic acid.

18. A pharmaceutical composition comprising the compound of claim 1 or a pharmaceutically acceptable salt thereof, and a pharmaceutically acceptable carrier.

19. The pharmaceutical composition of claim 18, further comprising one or more additional active agents is selected from an angiotensin converting enzyme inhibitor, an angiotensin II receptor antagonist, a neutral endopeptidase inhibitor, an aldosterone antagonist, a renin inhibitor, an endothelin receptor antagonist, an aldosterone synthase inhibitor, a phosphodiesterase-5 inhibitor, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent or a metabolic altering agent.

20. The compound of claim 1 or a pharmaceutically acceptable salt thereof, wherein the compound is:
3-(2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}oxazol-4-yl)-2,2-dimethylpropanoic acid;

3-(4-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)propanoic acid;

3-(3-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}phenyl)-2,2-dimethylpropanoic acid;

3-(2-{4-amino-2-[6-fluoro-1-(2-fluorobenzyl)-1H-indazol-3-yl]-5-methyl-6-oxo-6,7-dihydro-5H-pyrrolo[2,3-d]pyrimidin-5-yl}-1,3-thiazol-4-yl)-2,2-dimethylpropanoic acid;

3-(2-{4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}-1,3-thiazol-4-yl)-2,2-dimethylpropanoic acid;

3-{2-[4-amino-2-{6-chloro-1-[(3-fluoropyridin-2-yl)methyl]-1H-indazol-3-yl}-5-methyl-6-oxo-6,7-dihydro-5H-pyrrolo[2,3-d]pyrimidin-5-yl]-1,3-oxazol-4-yl}-2,2-dimethylpropanoic acid;

3-(2-{4-amino-2-[6-chloro-1-(3-fluorobenzyl)-1H-indazol-3-yl]-5-methyl-6-oxo-6,7-dihydro-5H-pyrrolo[2,3-d]pyrimidin-5-yl}-5-methyl-1,3-oxazol-4-yl)-2,2-dimethylpropanoic acid;

3-(2-{4-amino-2-[1-(2,3-difluorobenzyl)-6-fluoro-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid; or 3-(2-{4-amino-2-[1-(cyclohexylmethyl)-6-fluoro-1H-indazol-3-yl]-5-methyl-6-oxo-6,7-dihydro-5H-pyrrolo[2,3-d]pyrimidin-5-yl}-1,3-oxazol-4-yl)-2,2-dimethylpropanoic acid.

21. A compound which is

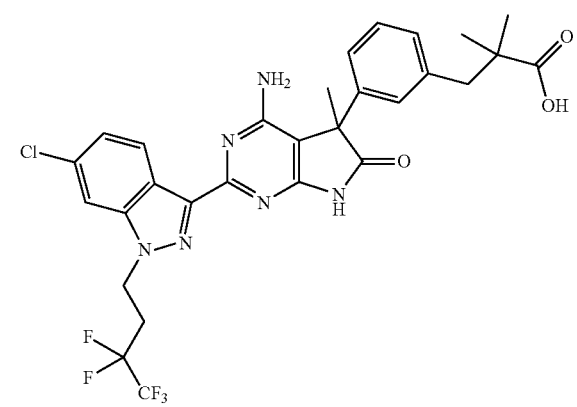 [SMILES: CC(C)(Cc1cccc(C2(C)C(=O)Nc3nc(-c4nn(CCC(F)(F)C(F)(F)F)c5cc(Cl)ccc45)nc(N)c32)c1)C(=O)O]

or a pharmaceutically acceptable salt thereof.

22. A pharmaceutically acceptable salt of the compound of claim 12.

23. A compound which is

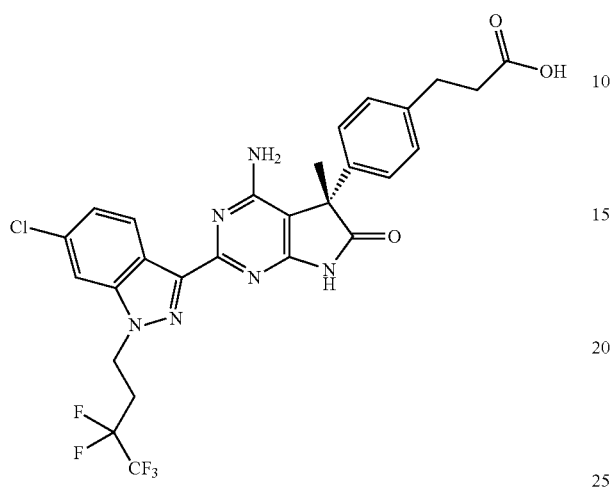

or a pharmaceutically acceptable salt thereof.

24. A pharmaceutically acceptable salt of the compound of claim 23.

25. A compound which is

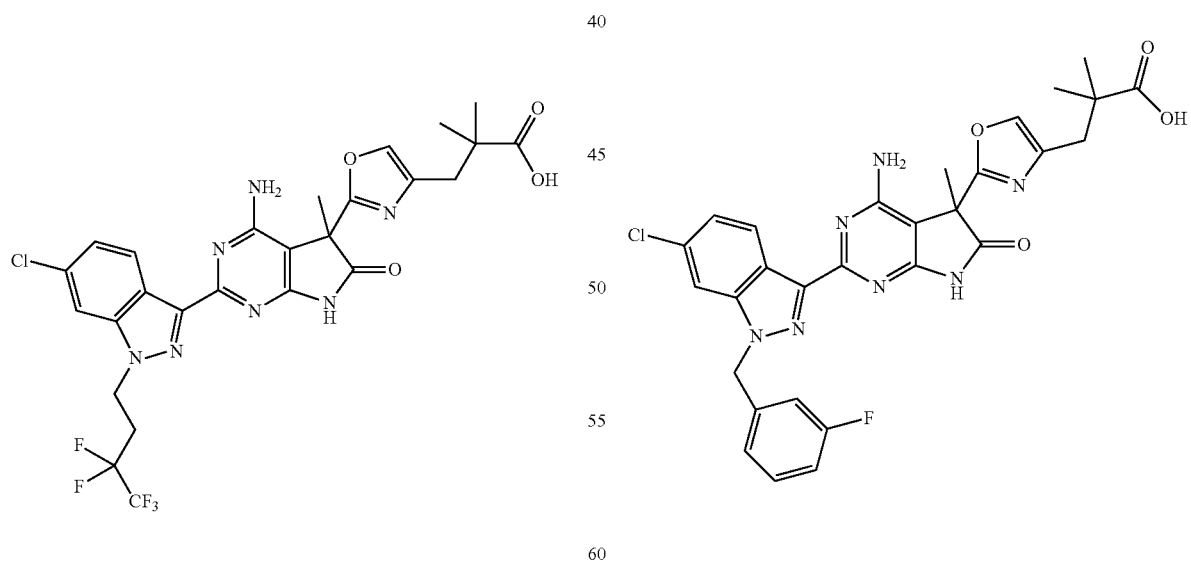

or a pharmaceutically acceptable salt thereof.

26. A pharmaceutically acceptable salt of the compound of claim 25.

27. A compound which is

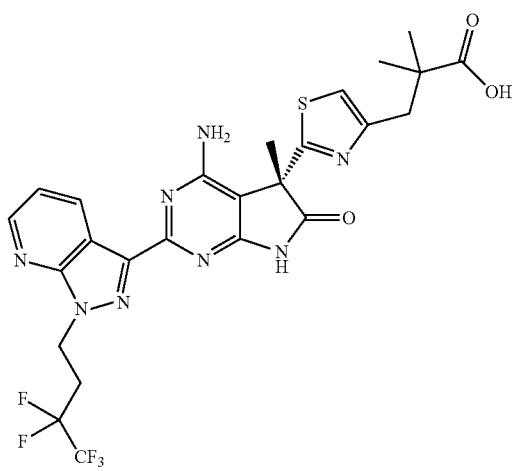 [SMILES: CC(C)(Cc1csc([C@]2(C)C(=O)Nc3nc(-c4nn(CCC(F)(F)C(F)(F)F)c5ncccc45)nc(N)c32)n1)C(=O)O]

or a pharmaceutically acceptable salt thereof.

28. A pharmaceutically acceptable salt of the compound of claim 27.

29. A compound which is or a pharmaceutically acceptable salt thereof.

30. A pharmaceutically acceptable salt of the compound of claim 29.

31. A compound which is

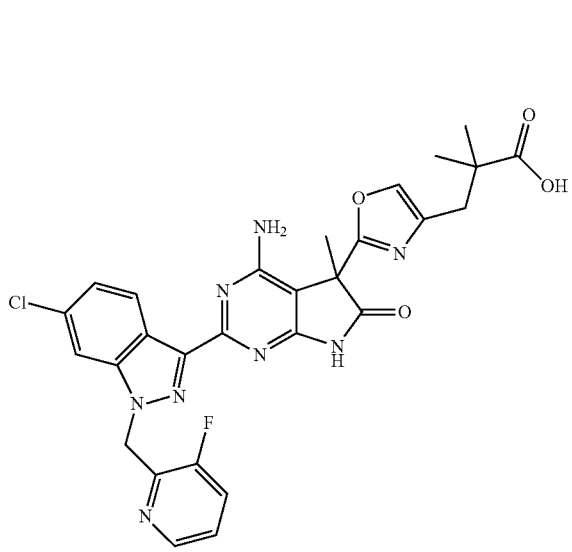 [SMILES: CC(C)(Cc1coc(C2(C)C(=O)Nc3nc(-c4nn(Cc5ncccc5F)c5cc(Cl)ccc45)nc(N)c32)n1)C(=O)O]

or a pharmaceutically acceptable salt thereof.

32. A pharmaceutically acceptable salt of the compound of claim 31.

33. A compound which is

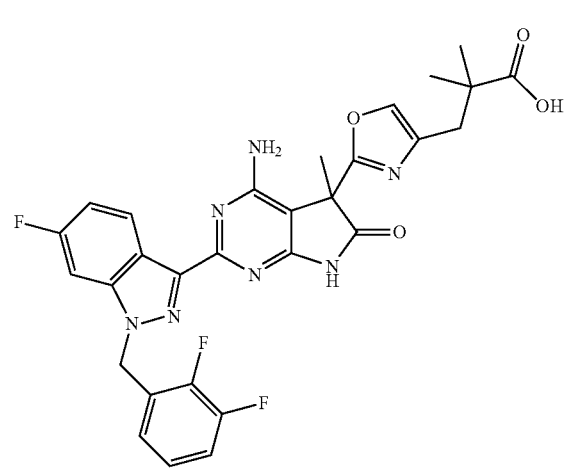 [SMILES: CC(C)(Cc1coc(C2(C)C(=O)Nc3nc(-c4nn(Cc5cccc(F)c5F)c5cc(F)ccc45)nc(N)c32)n1)C(=O)O]

or a pharmaceutically acceptable salt thereof.

34. A pharmaceutically acceptable salt of the compound of claim 33.

35. A compound which is

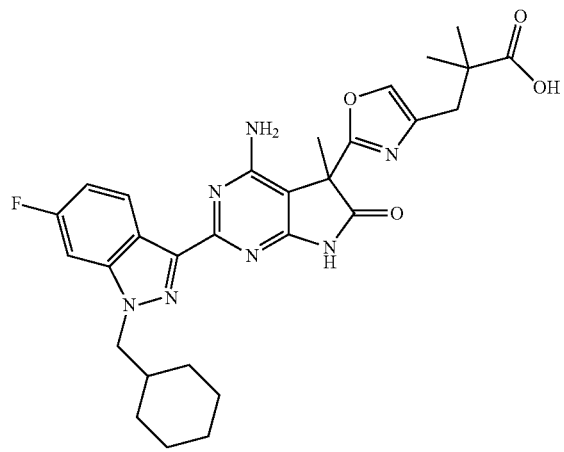 [SMILES: CC(C)(Cc1coc(C2(C)C(=O)Nc3nc(-c4nn(CC5CCCCC5)c5cc(F)ccc45)nc(N)c32)n1)C(=O)O]

or a pharmaceutically salt thereof.

36. A pharmaceutically acceptable salt of the compound of claim 35.

37. A compound which is or a pharmaceutically acceptable salt thereof.

38. A pharmaceutically acceptable salt of the compound of claim 37.

39. A pharmaceutical composition comprising the compound of claim 21 or a pharmaceutically acceptable salt thereof, and a pharmaceutically acceptable carrier.

40. A pharmaceutical composition comprising the compound of claim 23 or a pharmaceutically acceptable salt thereof, and a pharmaceutically acceptable carrier.

41. A pharmaceutical composition comprising the compound of claim 25 or a pharmaceutically acceptable salt thereof, and a pharmaceutically acceptable carrier.

42. A pharmaceutical composition comprising the compound of claim 27 or a pharmaceutically acceptable salt thereof, and a pharmaceutically acceptable carrier.

43. A pharmaceutical composition comprising the compound of claim 29 or a pharmaceutically acceptable salt thereof, and a pharmaceutically acceptable carrier.

44. A pharmaceutical composition comprising the compound of claim 31 or a pharmaceutically acceptable salt thereof, and a pharmaceutically acceptable carrier.

45. A pharmaceutical composition comprising the compound of claim 33 or a pharmaceutically acceptable salt thereof, and a pharmaceutically acceptable carrier.

46. A pharmaceutical composition comprising the compound of claim 35 or a pharmaceutically acceptable salt thereof, and a pharmaceutically acceptable carrier.

47. A pharmaceutical composition comprising the compound of claim 37 or a pharmaceutically acceptable salt thereof, and a pharmaceutically acceptable carrier.

48. A compound which is

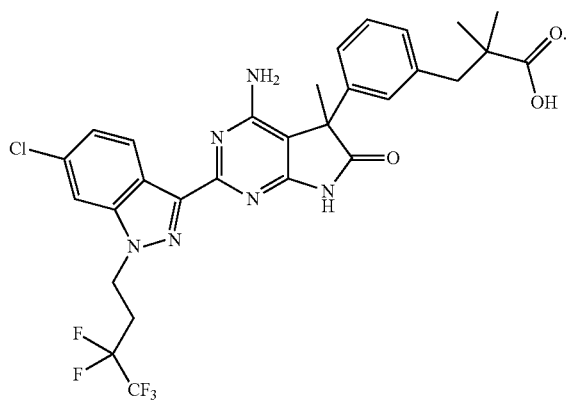 [SMILES: CC(C)(Cc1cccc(C2(C)C(=O)Nc3nc(-c4nn(CCC(F)(F)C(F)(F)F)c5cc(Cl)ccc45)nc(N)c32)c1)C(=O)O]

49. A compound which is

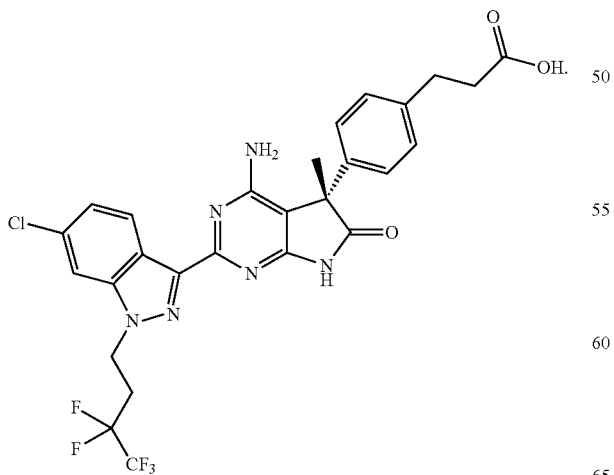

50. A compound which is

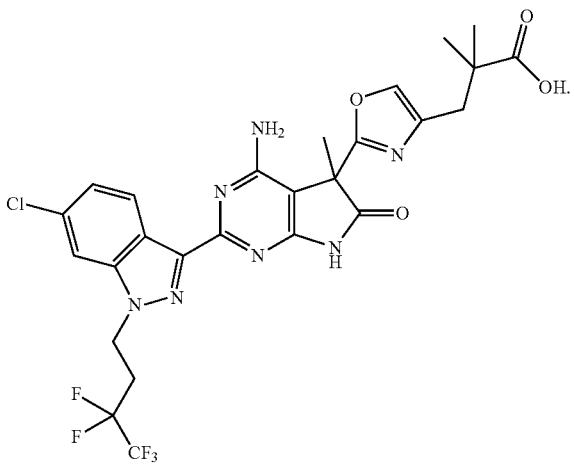 [SMILES: CC(C)(Cc1coc(C2(C)C(=O)Nc3nc(-c4nn(CCC(F)(F)C(F)(F)F)c5cc(Cl)ccc45)nc(N)c32)n1)C(=O)O]

51. A compound which is

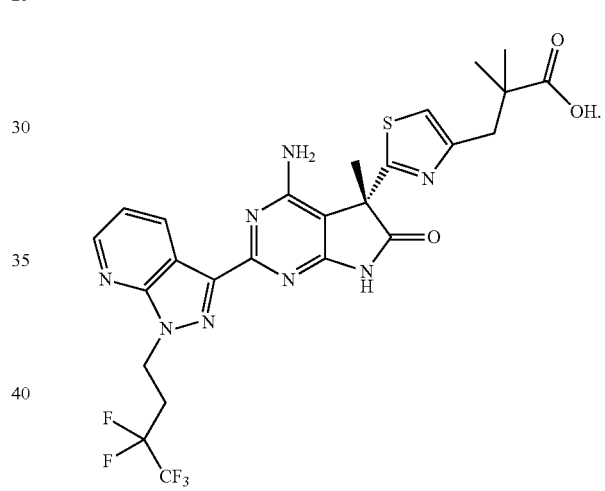

52. A compound which is

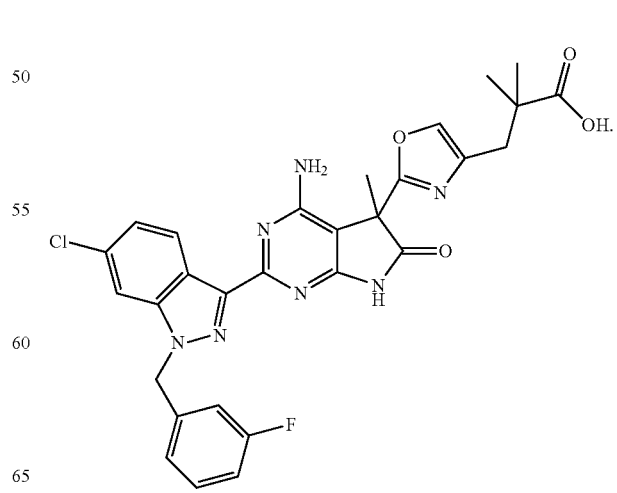

53. A compound which is
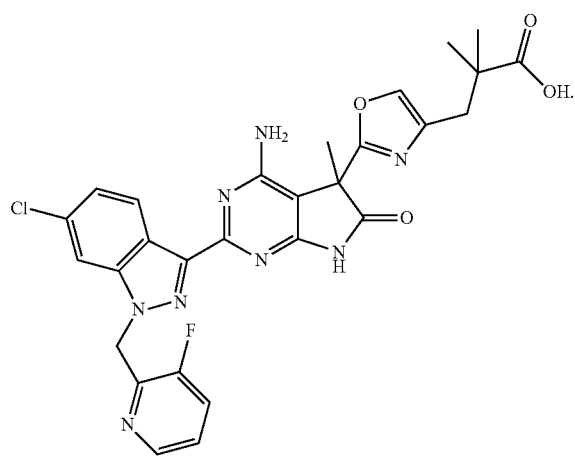 [SMILES: CC(C)(Cc1coc(C2(C)C(=O)Nc3nc(-c4nn(Cc5ncccc5F)c5cc(Cl)ccc45)nc(N)c32)n1)C(=O)O]
55. A compound which is
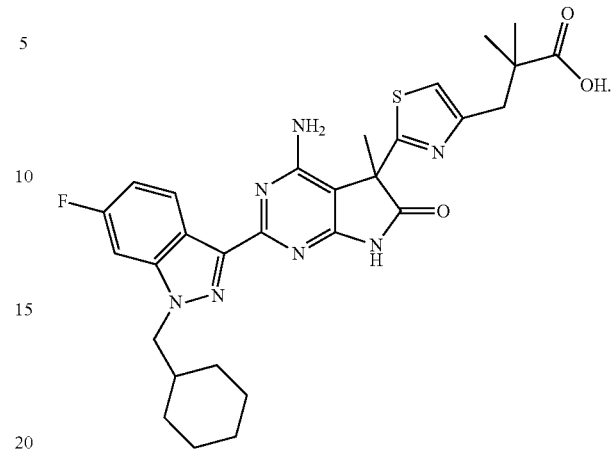
54. A compound which is
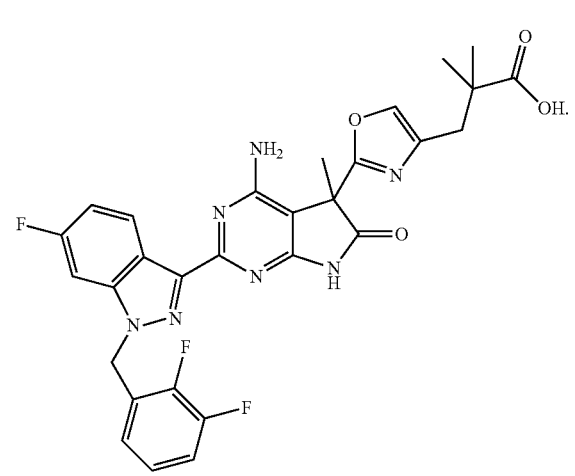 [SMILES: CC(C)(Cc1coc(C2(C)C(=O)Nc3nc(-c4nn(Cc5cccc(F)c5F)c5cc(F)ccc45)nc(N)c32)n1)C(=O)O]
56. A compound which is
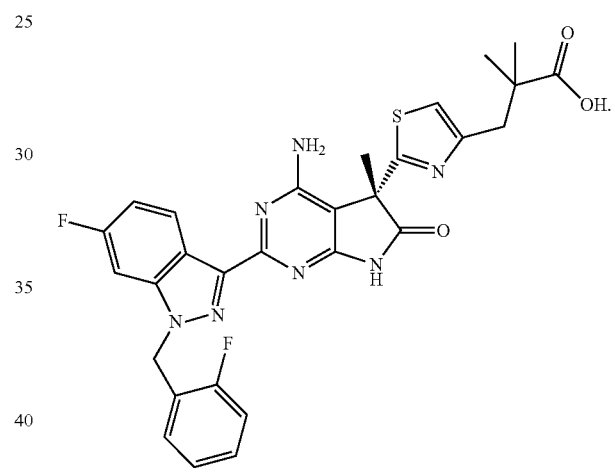
* * * * *